(12) United States Patent
Taylor et al.

(10) Patent No.: US 12,138,263 B2
(45) Date of Patent: Nov. 12, 2024

(54) PYRAZOLO[3,4-B]PYRAZINE SHP2 PHOSPHATASE INHIBITORS AND METHODS OF USE THEREOF

(71) Applicants: Relay Therapeutics, Inc., Cambridge, MA (US); D. E. Shaw Research, LLC, New York, NY (US)

(72) Inventors: Alexander M. Taylor, Cambridge, MA (US); Fabrizio Giordanetto, New York, NY (US); Jack Benjamin Greisman, New York, NY (US); Paul Maragakis, New York, NY (US); Heike Schoenherr, Ann Arbor, MI (US)

(73) Assignees: Relay Therapeutics, Inc., Cambridge, MA (US); D.E. Shaw Research, LLC, New York, NY (US)

( * ) Notice: Subject to any disclaimer, the term of this patent is extended or adjusted under 35 U.S.C. 154(b) by 979 days.

(21) Appl. No.: 16/982,395

(22) PCT Filed: Mar. 21, 2019

(86) PCT No.: PCT/US2019/023386
§ 371 (c)(1),
(2) Date: Sep. 18, 2020

(87) PCT Pub. No.: WO2019/183364
PCT Pub. Date: Sep. 26, 2019

(65) Prior Publication Data
US 2021/0069188 A1 Mar. 11, 2021

Related U.S. Application Data

(60) Provisional application No. 62/661,906, filed on Apr. 24, 2018, provisional application No. 62/649,834, (Continued)

(51) Int. Cl.
*A61K 31/4985* (2006.01)
*A61K 38/46* (2006.01)
(Continued)

(52) U.S. Cl.
CPC ........ *A61K 31/4985* (2013.01); *A61K 38/465* (2013.01); *A61K 45/06* (2013.01);
(Continued)

(58) Field of Classification Search
CPC ............................ C07D 487/04; C07D 519/00
See application file for complete search history.

(56) References Cited

U.S. PATENT DOCUMENTS

| 5,466,823 A | 11/1995 | Talley et al. |
| 10,280,171 B2 | 5/2019 | Jones et al. |

(Continued)

FOREIGN PATENT DOCUMENTS

| CN | 103570622 A | 2/2014 |
| CN | 107286150 A | 10/2017 |

(Continued)

OTHER PUBLICATIONS

Patani et al., Bioisosterism: A Rational Approach in Drug Design, 1996, Chem Rev, vol. 96, p. 3147-3176 (Year: 1996).*

(Continued)

*Primary Examiner* — Kamal A Saeed
*Assistant Examiner* — Karen Cheng
(74) *Attorney, Agent, or Firm* — Goodwin Procter LLP

(57) ABSTRACT

The present disclosure relates to novel compounds and pharmaceutical compositions thereof, and methods for inhibiting the activity of SHP2 phosphatase with the compounds and compositions of the disclosure. The present disclosure further relates to methods for treating disorders associated with SHP2 deregulation with the compounds and compositions of the disclosure.

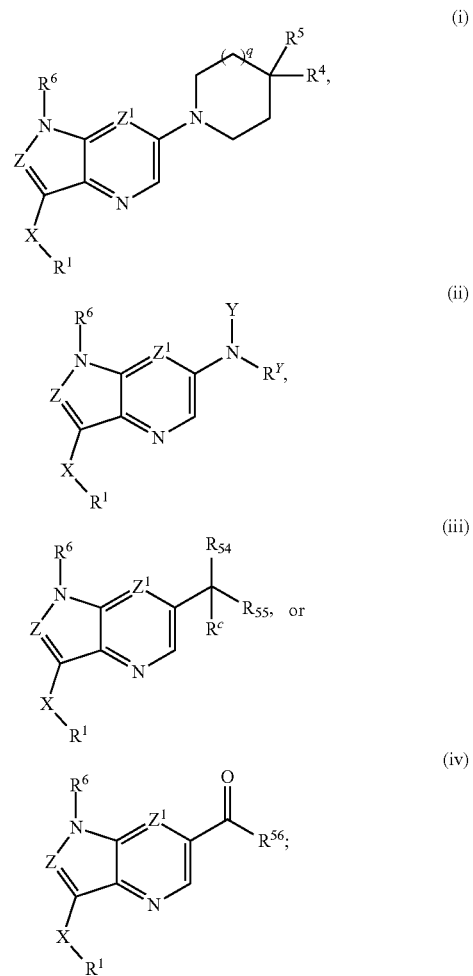

16 Claims, 1 Drawing Sheet
Specification includes a Sequence Listing.

Related U.S. Application Data filed on Mar. 29, 2018, provisional application No. 62/646,086, filed on Mar. 21, 2018, provisional application No. 62/646,080, filed on Mar. 21, 2018, provisional application No. 62/646,099, filed on Mar. 21, 2018, provisional application No. 62/646,104, filed on Mar. 21, 2018.

(51) Int. Cl.
*A61K 45/06* (2006.01)
*A61K 47/64* (2017.01)
*C07D 487/04* (2006.01)
*C07D 519/00* (2006.01)

(52) U.S. Cl.
CPC ............ *A61K 47/64* (2017.08); *C07D 487/04* (2013.01); *C07D 519/00* (2013.01)

(56) References Cited

U.S. PATENT DOCUMENTS

| | | |
|---|---|---|
| 10,934,302 B1 | 3/2021 | Taylor et al. |
| 10,988,466 B2 | 4/2021 | Ma et al. |
| 11,529,347 B2 | 12/2022 | Albrecht et al. |
| 11,591,336 B2 | 2/2023 | Taylor et al. |
| 11,629,145 B2 | 4/2023 | Giordanetto et al. |
| 11,701,354 B2 | 7/2023 | Taylor et al. |
| 2011/0130396 A1 | 6/2011 | Hoelzemann et al. |
| 2017/0001975 A1 | 1/2017 | Chen et al. |
| 2017/0015680 A1 | 1/2017 | Chen et al. |
| 2017/0204080 A1 | 7/2017 | Chen et al. |
| 2017/0342078 A1 | 11/2017 | Jones et al. |
| 2018/0186770 A1 | 7/2018 | Chen et al. |
| 2018/0251471 A1 | 9/2018 | Chen et al. |
| 2019/0077792 A1 | 3/2019 | Volkmann et al. |
| 2019/0127378 A1 | 5/2019 | Ma et al. |
| 2019/0185475 A1 | 6/2019 | Bagdanoff et al. |
| 2019/0210977 A1 | 7/2019 | Jogalekar et al. |
| 2019/0270746 A1 | 9/2019 | Jones et al. |
| 2019/0290649 A1 | 9/2019 | Xie et al. |
| 2019/0307745 A1 | 10/2019 | Albrecht et al. |
| 2019/0389867 A1 | 12/2019 | Jones et al. |
| 2020/0002330 A1 | 1/2020 | Chen et al. |
| 2020/0017511 A1 | 1/2020 | Blank et al. |
| 2020/0017517 A1 | 1/2020 | Gill et al. |
| 2020/0048249 A1 | 2/2020 | Jones et al. |
| 2020/0062760 A1 | 2/2020 | Giordanetto et al. |
| 2020/0108071 A1 | 4/2020 | Chin et al. |
| 2020/0115389 A1 | 4/2020 | Fu et al. |
| 2020/0172546 A1 | 6/2020 | Taylor et al. |
| 2020/0253969 A1 | 8/2020 | Taylor et al. |
| 2020/0392128 A1 | 12/2020 | Ma et al. |
| 2020/0392161 A1 | 12/2020 | Walters et al. |
| 2021/0085677 A1 | 3/2021 | Taylor et al. |
| 2021/0393623 A1 | 12/2021 | Han et al. |
| 2022/0340576 A1 | 10/2022 | Taylor et al. |

FOREIGN PATENT DOCUMENTS

| | | |
|---|---|---|
| CN | 110143949 A | 8/2019 |
| CN | 111153899 | 5/2020 |
| MX | 2019011330 A | 2/2020 |
| RU | 2379303 C2 | 10/2010 |
| TW | 201840553 A | 11/2018 |
| TW | 201925186 A | 7/2019 |
| WO | WO 2004/096139 | 11/2004 |
| WO | WO 2004/111060 A1 | 12/2004 |
| WO | WO 2010/011666 A2 | 1/2010 |
| WO | WO 2010/097798 A1 | 9/2010 |
| WO | WO 2010/121212 A2 | 10/2010 |
| WO | WO 2011/130396 A1 | 10/2011 |
| WO | WO 2017/156397 A1 | 9/2014 |
| WO | WO 2015/107493 A1 | 7/2015 |
| WO | WO 2015/107494 A1 | 7/2015 |
| WO | WO 2015/107495 A1 | 7/2015 |
| WO | WO 2016/203404 A1 | 12/2016 |
| WO | WO 2016/203406 A1 | 12/2016 |
| WO | WO 2017/210134 A1 | 12/2017 |
| WO | WO 2017/211303 A1 | 12/2017 |
| WO | WO 2018/013597 A1 | 1/2018 |
| WO | WO 2018/057884 A1 | 3/2018 |
| WO | WO 2018/081091 A1 | 5/2018 |
| WO | WO 2018/172984 A1 | 9/2018 |
| WO | WO 2018/218133 A1 | 11/2018 |
| WO | WO 2019/051084 A1 | 3/2019 |
| WO | WO 2019/067843 A1 | 4/2019 |
| WO | WO 2019/075265 A1 | 4/2019 |
| WO | WO 2019/118909 A1 | 6/2019 |
| WO | WO 2019/158019 A1 | 8/2019 |
| WO | WO 2019/165073 A1 | 8/2019 |
| WO | WO 2019/167000 A1 | 9/2019 |
| WO | WO 2019/183364 A1 | 9/2019 |
| WO | WO 2019/183367 A1 | 9/2019 |
| WO | WO 2019/199792 A1 | 10/2019 |
| WO | WO 2019/233810 A1 | 12/2019 |
| WO | WO 2020/022323 A1 | 1/2020 |
| WO | WO 2020/063760 A1 | 4/2020 |
| WO | WO 2020/065452 A1 | 4/2020 |
| WO | WO 2020/065453 A1 | 4/2020 |
| WO | WO 2020/073945 A1 | 4/2020 |
| WO | WO 2020/073949 A1 | 4/2020 |
| WO | WO 2020/076723 A1 | 4/2020 |
| WO | WO 2020/081848 A1 | 4/2020 |
| WO | WO 2020/094018 A1 | 5/2020 |
| WO | WO 2020/094104 A1 | 5/2020 |

OTHER PUBLICATIONS

Aceto, N. et al., "Tyrosine phosphatase SHP2 promotes breast cancer progression and maintains tumor-initiating cells via activation of key transcription factors and a positive feedback signaling loop," Nature Medicine, 18(4):529-538, (2012).

Bastin et al., "Salt selection and optimization procedures for pharmaceutical new chemical entities," Organic process research and development, 4(5):427-435, (2000) (abstract).

Bentires-Alj, M. et al., "Activating Mutations of the Noonan Syndrome-Associated SHP2/PTPN11 Gene in Human Solid Tumors and Adult Acute Myelogenous Leukemia," Cancer Res., 64:8816-8820, (2004).

Berge, et al., "Pharmaceutical Salts," J. Pharm. Sci., 66(1):1, (1977).

Cai, P. et al., "Expression and clinical significance of tyrosine phosphatase SHP-2 in colon cancer," Biomedicine & Pharmacotherapy, 68:285-290, (2014).

Chen, Y.-N.P. et al., "Allosteric inhibition of SHP2 phosphatase inhibits cancers driven by receptor tyrosine kinases," Nature, 535:158-152, (2016).

Chou, "Drug Combination studies and their synergy quantification using the Chou-Talalay method," Cancer Research, 70(2):440-446, (2010).

Dardaei et al., "SHP2 inhibition restores sensitivity in ALK-rearranged non-small-cell lung cancer resistant to ALK inhibitors," Nat Med. 24(4):512-517, (2018).

Fedele et al, "SHP2 Inhibition Abrogates MEK inhibitor Resistance in Multiple Cancer Models," BioRxiv, 307876, (2018).

Furcht, C.M. et al., "Diminished functional role and altered localization of SHP2 in non-small cell lung cancer cells with EGFR-activating mutations," Oncogene, 32:2346-2355, (2013).

Gould, P.L., "Salt selection for basic drugs," Int J. Pharmaceutics, 33:201-217, (1986).

Grossman, K.S. et al., "The tyrosine phosphatase Shp2 in development and cancer," Adv. Cancer Res., 106:53-89, (2010).

Hill et al, "PTPN11 Plays Oncogenic Roles and Is a Therapeutic Target for BRAF Wild-Type Melanomas," Mol. Cancer Res., 17:583-593, (2019).

Hu et al., "Overexpression of SHP2 tyrosine phosphatase promotes the tumorigenesis of breast carcinoma," Oncol Rep., 32(1):205-212, (2014).

(56) References Cited

OTHER PUBLICATIONS

Kümmerer, "Pharmaceuticals in the environment," Annual Review of Environment and Resources, 35:57-75, (2010).
Morissette, et al., "High-throughput crystallization: polymorphs, salts, co-crystals and solvates of pharmaceutical solids," Advanced Drug Delivery Reviews, 56:275-300, (2004).
Nichols et al., "RAS nucleotide cycling underlies the SHP2 phosphatase dependence of mutant BRAF-, NF1- and RAS-driven cancers," Nat. Cell Biol, 20:1064-1073, (2018).
Prahallad et al., "PTPN11 Is a Central Node in Intrinsic and Acquired Resistance to Targeted Cancer Drugs," Cell Rep, 12:1978-1985, (2015).
Qi et al., "Shp2 Inhibits Proliferation of Esophageal Squamous Cell Cancer via Dephosphorylation of Stat3," Int. J. Mol. Sci., 18:134, (2017).
Sausgruber et al, "Tyrosine phosphatase SHP2 increases cell motility in triple-negative breast cancer through the activation of SRC-family kinases," Oncogene, 34:2272-2278, (2015).
Schneeberger, V.E. et al., "Inhibition of Shp2 suppresses mutant EGFR-induced lung tumors in transgenic mouse model of lung adenocarcinoma," Oncotarget, 6:6191-6202, (2015).
Sun et al, Synergistic effects of SHP2 and PI3K pathway inhibitors in GAB2-overexpressing ovarian cancer,: Am J Cancer Res, 9(1):145-159, (2019).
Torres-Ayuso et al, "Shipping Out MeK Inhibitor Resistance with sHP2 Inhibitors," Cancer Discov., 8:1210-1212, (2018).
Wang, J. et al., "Inhibition of SHP2 ameliorates the pathogenesis of systemic lupus erythematosus," The Journal of Clinical Invest. 126:2077-2092, (2016).
Wong et al, "SHP-2 phosphatase contributes to KRAS-driven intestinal oncogenesis but prevents colitis-associated cancer development," Oncotarget, 7(40):65676-65695, (Oct. 4, 2016).
Yu et al., "Targeting Protein Tyrosine Phosphatase SHP2 for the Treatment of PTPN11-Associated Malignancies," Mol. Cancer Ther., 12:1738-1748, (2013).
Zhao et al., "Conditional knockout of SHP2 in ErbB2 transgenic mice or inhibition in HER2-amplified breast cancer cell lines blocks oncogene expression and tumorigenesis," Oncogene, 38:2275-2290, (2019).
CN Application No. 201980034042.8, Office Action and Search Report mailed Jan. 19, 2023.
MX Application No. MX/a/2020/009782, Office Action dated mailed Apr. 24, 2023.
ROC (Taiwan) Application No. 108109755, Office Action and Search Report mailed Jan. 4, 2023.
RU Application No. 2020134302, Official Action and Search Report dated Sep. 9, 2022.
U.S. Appl. No. 16/335,933, Non-Final Office Action mailed Sep. 16, 2021.
U.S. Appl. No. 16/335,933, Notice of Allowance mailed Apr. 15, 2022.
U.S. Appl. No. 16/335,933, Notice of Allowance mailed Aug. 25, 2022.
U.S. Appl. No. 16/335,933, Supplemental Notice of Allowability mailed Sep. 14, 2022.
U.S. Appl. No. 16/344,061, Final Office Action mailed Aug. 25, 2021.
U.S. Appl. No. 16/344,061, Non-Final Office Action mailed Mar. 31, 2022.
U.S. Appl. No. 16/344,061, Notice of Allowance mailed Nov. 16, 2022.
U.S. Appl. No. 16/616,361, Final Office Action mailed Sep. 30, 2021.
U.S. Appl. No. 16/616,361, Notice of Allowance mailed Apr. 26, 2022.
U.S. Appl. No. 16/616,361, Notice of Allowance mailed Oct. 18, 2022.
U.S. Appl. No. 16/950,576, Non-Final Office Action mailed Dec. 20, 2022.
U.S. Appl. No. 17/029,376, Non-Final Office Action mailed Jul. 27, 2022.
Bollu et al., "Molecular Pathways: Targeting Protein Tyrosine Phosphatases in Cancer," Clin Cancer Res. 23(9): 2136-2142, (May 1, 2017).
Copin et al. "Snar Versus Buchwald-Hartwig Amination/Amidation in the Imidazo[2,1-b][1,3,4]thiadiazole Series," European Journal of Organic Chemistry, vol. 2015, No. 31, pp. 6932-6942, (Sep. 29, 2015).
Fortanet et al. "Allosteric Inhibition of SHP2: Identification of a Potent, Selective, and Orally Efficacious Phosphatase Inhibitor," J. Med. Chem. 2016, 59, 17, pp. 7773-7782.
Hellmuth et al., Specific inhibitors of the protein tyrosine phosphatase Shp2 identified by high-throughput docking, PNAS, 105(20), 7275-7280, (2008).
Horig et al., "From bench to clinic and back: Perspective on the 1st IQPC Translational Research Conference" Journal of Translational Medicine, 2, 44, (Dec. 2004).
Krasavin et al. "Tert-Butyl Isocyanide Revisited as a Convertible Reagent in the Groebke-Blackburn Reaction," Tetrahedron Letters, Elsevier, Amsterdam, NL, vol. 49, No. 51, Dec. 15, 2008, pp. 7318-7321.
Larochelle et al. "Identification of An Allosteric Benzothiazolopyrimidone Inhibitor of the Oncogenic Protein Tyrosine Phosphatase SHP2," Bioorganic & Medicinal Chemistry, vol. 25, No. 24, pp. 6479-6485, (Oct. 20, 2017).
Lazo et al., "New Approaches to Difficult Drug Targets: the Phosphatase Story," SLAS Discovery, vol. 22(9), 1071-1083, (2017).
Safarov et al. "Preparation of 5-Bromo-6-phenylimidazo(2,1-b)(1,3,4) thiadiazol-2-ylamines," Journal of Heterocyclic Chemistry, Wiley-Blackwell Publishing, Inc, Us, vol. 45, No. 1, Jan. 1, 2008, pp. 299-302.
Schafer et al., "Failure is an option: learning from unsuccessful proof-of-concept trials," Drug Discovery Today, 13, 913-916, (Nov. 2018).
Shen et al. "3-Aminopyrazolopyrazine Derivatives as Spleen Tyrosine Kinase Inhibitors," Hemical Biology & Drug Design, vol. 88, No. 5, 2016, pp. 690-698.
Temple et al. "Identification of the Minimum PAR4 Inhibitor Pharmacophore and Optimization of a Series of 2-Methoxy-6-Arylimidazo[2,1-b][1,3,4]Thiadiazoles," Bioorganic & Medicinal Chemistry Letters, Pergamon, Amsterdam, NL, vol. 26, No. 22, 11, pp. 5481-5486, ( Oct. 11, 2016).
Yokoi et al. "Quantitative Structure-Activity Relationship of Substituted Imidazothiadiazoles for Their Binding Against the Ecdysone Receptor of Sf-9 Cells," Bioorganic & Medicinal Chemistry Letters, vol. 27, No. 23, pp. 5305-5309, (Oct. 13, 2017).
U.S. Appl. No. 16/335,933, Non-Final Office Action mailed Jan. 8, 2020.
U.S. Appl. No. 16/355,061, Non-Final Office Action mailed Feb. 19, 2021.
U.S. Appl. No. 16/355,061, Requirement for Restriction/Election mailed Jul. 31, 2020.
U.S. Appl. No. 16/616,361, Non-Final Office Action mailed May 13, 2021.
U.S. Appl. No. 16/616,361, Requirement for Restriction/Election mailed Oct. 30, 2020.
U.S. Appl. No. 16/886,105, Notice of Allowance mailed Sep. 9, 2020.
U.S. Appl. No. 16/886,105, Notice of Allowance mailed Nov. 4, 2020.
U.S. Appl. No. 16/335,933, Final Office Action mailed Aug. 26, 2020.
WIPO Application No. PCT/US2017/052950, PCT International Preliminary Report on Patentability mailed Mar. 26, 2019.
WIPO Application No. PCT/US2017/052950, PCT International Search Report and Written Opinion of the International Searching Authority mailed Mar. 29, 2018.
WIPO Application No. PCT/US2017/058048, PCT International Preliminary Report on Patentability mailed Apr. 30, 2019.
WIPO Application No. PCT/US2017/058048, PCT International Search Report and Written Opinion of the International Searching Authority mailed May 3, 2018.

(56) References Cited

OTHER PUBLICATIONS

WIPO Application No. PCT/US2018/034614, PCT International Preliminary Report on Patentability mailed Nov. 26, 2019.
WIPO Application No. PCT/US2018/034614, PCT International Search Report and Written Opinion of the International Searching Authority mailed Nov. 29, 2018.
WIPO Application No. PCT/US2018/053322, PCT International Preliminary Report on Patentability mailed Mar. 31, 2020.
WIPO Application No. PCT/US2018/053322, PCT International Search Report and Written Opinion of the International Searching Authority mailed Apr. 4, 2019.
WIPO Application No. PCT/US2019/023389, PCT International Search Report and Written Opinion of the International Searching Authority mailed May 10, 2019.
WIPO Application No. PCT/US2019/023389, PCT International Preliminary Report on Patentability mailed Sep. 22, 2020.
WIPO Application No. PCT/US2020/052118, PCT International Search Report and Written Opinion of the International Searching Authority mailed Dec. 14, 2020.
Hackam, et al., "Translation of Research Evidence from Animals to Humans," JAMA, 296(14):1731-1732, (2006).
Jordan, V.C., "Tamoxifen: A Most Unlikely Pioneering Medicine," Nature Reviews: Drug Discovery, 2:205-213, (2003).
U.S. Appl. No. 16/651,733, Non-Final Office Action mailed Jul. 23, 2021.

* cited by examiner

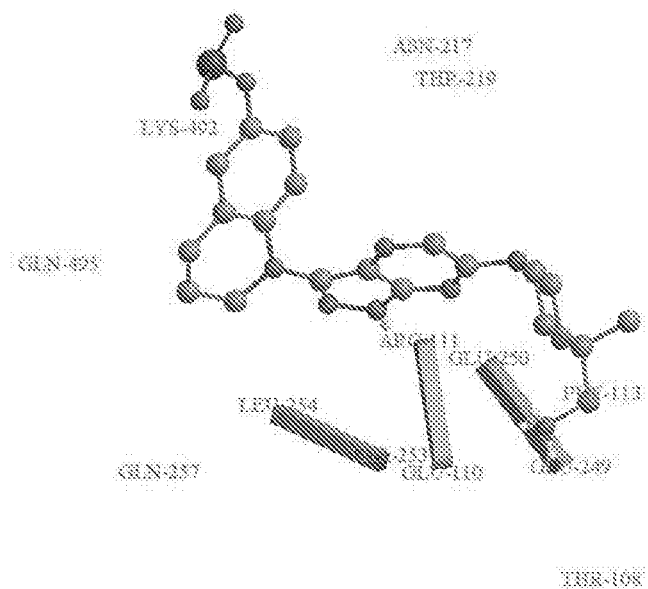

PYRAZOLO[3,4-B]PYRAZINE SHP2 PHOSPHATASE INHIBITORS AND METHODS OF USE THEREOF

CROSS REFERENCE TO RELATED APPLICATIONS

This application claims the benefit of, and priority to, U.S. provisional application Ser. No. 62/646,099, filed Mar. 21, 2018; 62/649,834, filed Mar. 29, 2018; 62/646,104, filed Mar. 21, 2018; 62/646,080, filed Mar. 21, 2018; 62/661,906, filed Apr. 24, 2018; and 62/646,086, filed Mar. 21, 2018; the contents of each of which are hereby incorporated by reference herein in their entirety.

REFERENCE TO A SEQUENCE LISTING

The Sequence Listing written in file name ST25697298SEQLISTSUB.txt is 15 kilobytes, was created on Jul. 22, 2024, and is hereby incorporated by reference.

BACKGROUND

Src homology region 2 (SH2)-containing protein tyrosine phosphatase 2 (SHP2) is a protein tyrosine phosphatase encoded by the PTPN11 gene. SHP2 contains two Src homology 2 (SH2) $NH_2$-terminal domains and a C-terminal protein-tyrosine phosphatase domain. It is ubiquitously expressed in various tissues and cell types. SHP2 plays an important role in diverse signaling pathways to regulate cellular biological processes and is involved in the signaling pathways of a variety of growth factors and cytokines. Within a single signaling pathway, SHP2 can play both positive (signal enhancing) and negative (signal diminishing) roles in intracellular signaling processes. SHP2 is believed to function by dephosphorylating its associated signaling molecules, thereby attenuating the local signaling flow. However, the main effect of SHP2 action in most signaling pathways (e.g., growth factor, cytokine, and extracellular matrix receptors) is to enhance signal transduction. For example, SHP2 is a positive regulator of the ERK/MAPK signaling pathway, playing a key role in regulating cellular proliferation and survival. (For a review of SHP2 phosphatase, see, e.g, K. S. Grossman et al., *Adv. Cancer Res.* 2010, 106, 53-89; and references cited therein.)

In the basal state, SHP2 is normally auto-inhibited due to intramolecular interactions between its N-terminal SH2 (N-SH2) domain and its catalytic (PTP) domain, which blocks access to the catalytic site. Activating proteins that interact with the SH2 domains induce a conformational change that reverses this inhibition and allows substrate access to the catalytic site. Mutations in the PTPN11 gene that affect the N-SH2 or PTP domain residues involved in basal inhibition of SHP2 result in more readily activatable forms of SHP2 protein, which can lead to unregulated or increased SHP2 activity. Such activated mutants of SHP2 have been associated with developmental disorders such as Noonan syndrome, where nearly all mutated forms of SHP2 demonstrate increased PTP activity. Thus, there is a need for SHP2 phosphatase inhibitor compounds and methods for treating cancer and other disorders with these compounds.

SUMMARY

Disclosed herein, for example, is a compound of Formula i, ii, iii, or iv, or a pharmaceutically acceptable salt or stereoisomer thereof, represented by:

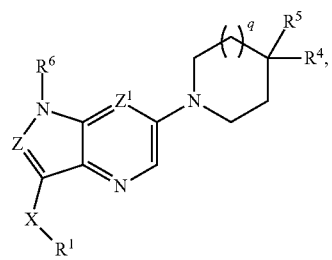
(i)

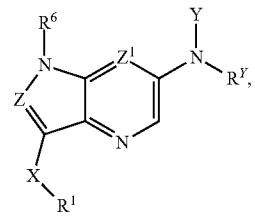
(ii)

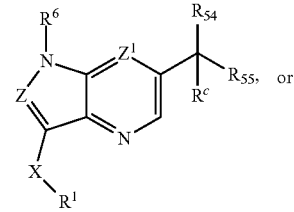
(iii)

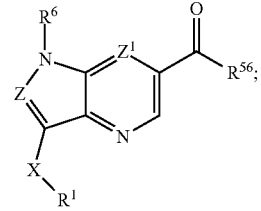
(iv)

wherein:
$Z^1$ is N or CH;
Z is N or CH;
X is selected from the group consisting of a bond, —O—, —$NR^{X1}$—, and —S(O)$_w$— (wherein w is 0, 1 or 2);
$R^{X1}$ is selected from the group consisting of hydrogen, —($C_1$-$C_6$)alkyl and phenyl;
$R^1$ is a ring moiety selected from the group consisting of a 8-12 membered bicyclic heteroaryl, a 11-15 membered tricyclic heteroaryl, phenyl, a 5-7 membered monocyclic heteroaryl, and a 4-7 membered heterocyclyl, wherein the ring moiety is optionally substituted with —O—S(O)$_2$—F or —S(O)$_2$—F, and wherein the ring moiety may additionally and optionally be substituted with one, two or more substituents each independently selected from the group consisting of $R^{10}$, —$OR^{10}$, —S(O)$_w R^{10}$ (wherein w is 0, 1 or 2), —$C_{1-6}$alkyl-S(O)$_w$—$C_{1-3}$alkyl, —N($R^{10}$)$_2$, —N(CO)$R^{10}$, —N—S(O)$_w$—$R^{10}$ (where w is 0, 1 or 2), —OS(O)$_w$—$R^{10}$ (wherein w is 0, 1, or 2), —S(O)$_w$—N($R^{10}$)$_2$ (wherein w is 0, 1 or 2), —S(O)(NH)$R^{10}$, —N(H)—SO$_2$—$C_{1-3}$alkyl, —N(SO$_2$—$C_{1-3}$alkyl)$_2$, P(O)($R^{10}$)$_2$, —C(O)$R^{10}$, —C(O)O$R^{10}$, —C(O)N($R^{10}$)$_2$, oxo, halogen, hydroxyl, cyano, nitro, —C(=N—$OR^a$)—$C_{1-3}$alkyl, —C(=N—$OR^a$)—H, —S(O)(N$R^a$)—$C_{1-3}$alkyl, phenyl (optionally substituted with one, two or three halogen, —O-phenyl, $C_{1-3}$alkyl or $C_{1-3}$haloalkyl), $C_{1-3}$alkyl, $C_{2-6}$alkynyl, $C_{1-3}$haloalkyl, $C_{3-6}$cycloalkyl, heterocyclyl (optionally substituted with one, two or three halogen, oxo, $C_{1-3}$alkyl or $C_{1-3}$haloalkyl), and heteroaryl (optionally substituted with one, two or three halogen, —C(O)N($R^{10}$)$_2$, $C_{1-3}$alkyl, $C_{1-3}$alkyl-O—$C_{1-3}$alkyl, $C_{1-3}$alkyl-OH, or $C_{1-3}$haloalkyl);

$R^{10}$ is independently selected from the group consisting of hydrogen, $C_{1-6}$alkyl, $C_{2-6}$alkenyl, $C_{2-6}$alkynyl, $C_{3-6}$cycloalkyl, $C_{5-6}$cycloalkenyl, $C_{2-6}$heteroalkyl, heterocycloalkyl, aryl, and heteroaryl; wherein $C_{1-6}$alkyl, $C_{2-6}$alkenyl, $C_{2-6}$alkynyl, $C_{3-6}$cycloalkyl, $C_{5-6}$cycloalkenyl, $C_{2-6}$heteroalkyl, heterocycloalkyl, aryl, and heteroaryl is optionally substituted by one, two, three or more substituents each independently selected from the group consisting of halogen, hydroxyl, —$NR^aC(O)$—$R^{20}$, —C(O)—$R^{20}$, —C($NR^a$)—$R^b$, —$NR^aR^b$, $C_{1-6}$alkyl, $C_{1-6}$haloalkyl and $C_{1-6}$alkoxy;

$R^{20}$ is selected from the group consisting of hydrogen, hydroxyl, halogen, —$NR^aR^b$, $C_{1-6}$alkyl and $C_{1-6}$alkoxy;

$R^a$ and $R^b$ are each independently selected from the group consisting of hydrogen and $C_{1-3}$alkyl;

$R^6$ is independently for each occurrence selected from the group consisting of H, —$(C_1-C_6)$alkyl, —C(O)O$C_{1-4}$alkyl, and phenyl;

q is 0 or 1;

$R^Y$ is selected from the group consisting of hydrogen and —$(C_1-C_6)$alkyl;

Y is selected from the group consisting of a 3-7 membered saturated carbocycle, a 4-7 membered saturated heterocycle, phenyl, and a 5-6 membered monocyclic heteroaryl; wherein Y is optionally substituted with one or more substituents each independently selected from the group consisting of $(C_1-C_6)$alkyl, —C(O)N($R^6$)$_2$, —N($R^6$)$_2$, halogen, and cyano, wherein said —$(C_1-C_6)$alkyl is optionally substituted with one or more substituents selected from the group consisting of —OH, —N($R^6$)$_2$, oxo, and halogen;

$R^{55}$ is selected from the group consisting of —$C_{1-4}$alkyl-N($R^6$)$_2$, —N($R^6$)$_2$, and heteroaryl (optionally substituted by one, two, or three substituent each independently selected from halogen, hydroxyl, cyano, —$(C_1-C_6)$alkyl, —O$(C_1-C_6)$alkyl, —C(O)N($R^6$)$_2$, —N($R^6$)$_2$, and —$(C_1-C_6)$alkyl-N($R^6$)$_2$);

$R^{54}$ is selected from the group consisting of H, and $C_{1-2}$alkyl, or $R^{54}$ and $R^{55}$ taken together with the carbon to which they are attached form a ring selected from the group consisting of $C_{3-6}$cycloalkyl and heterocyclyl, wherein the ring is optionally substituted on a carbon by one, two or three substituents each independently selected from the group consisting of $R^4$ and $R^5$ and on a nitrogen if present by $R^6$;

$R^C$ is selected from the group consisting of H, OH, —$(C_1-C_6)$alkyl, —C(O)—O—$C_{1-6}$(alkyl), —C(O)—$C_{1-6}$(alkyl), and heterocyclyl, wherein $C_{1-6}$(alkyl) is optionally substituted by one two or three substituents each selected from the group consisting of halogen, hydroxyl and N($R_6$)$_2$; or wherein $R^C$ is absent $R^{54}$ and $R^{55}$ taken together with the carbon to which they are attached form a ring selected from $C_{5-6}$cyclalkenyl and phenyl; wherein the ring is optionally substituted on a carbon by one, two or three substituents each independently selected from the group consisting of $R^4$ and $R^5$;

$R^{56}$ is N($R_6$)$_2$ or heterocycle (optionally substituted by one, two or three substituents each independently selected from halogen, hydroxyl, N($R_6$)$_2$, —$(C_1-C_6)$alkyl, —C(O)—O—$C_{1-6}$(alkyl), —C(O)—$C_{1-6}$(alkyl), wherein $C_{1-6}$(alkyl) is optionally substituted by one two or three substituents each selected from the group consisting of: halogen, hydroxyl or N($R_6$)$_2$);

$R^4$ and $R^5$ are each independently selected from the group consisting of H, —OH, —$(C_1-C_6)$alkyl, —O$(C_1-C_6)$alkyl, —$(C_1-C_6)$alkyl-O—$R^6$, —C(O)N($R^6$)$_2$, —N($R^6$)$_2$, halogen, —$(C_1-C_6)$alkyl-N($R^6$)$_2$, and cyano, wherein said —$(C_1-C_6)$alkyl, —O$(C_1-C_6)$alkyl, —$(C_1-C_6)$alkyl-O—$R^6$, or —$(C_1-C_6)$alkyl-N($R^6$)$_2$ is optionally substituted with one or more substituents selected from the group consisting of —OH, —NH$_2$, oxo, and halogen;

or $R^4$ and $R^5$, taken together with the carbon to which they are attached, form a 4-6 membered carbocyclic or heterocyclic ring B; which ring is optionally substituted with one or two substituents each independently selected from the group consisting of $(C_1-C_6)$alkyl, —O$(C_1-C_6)$alkyl, —N($R^6$)$_2$, —C(O)N($R^6$)$_2$, halogen, oxo, and cyano and/or which ring may be fused to a ring D;

D is selected from the group consisting of: phenyl, a 5- or 6-membered heteroaryl having one or two heteroatoms each independently selected from the group consisting of S, O or N, and $C_{3-6}$cycloalkyl, wherein D is optionally substituted on an available carbon with one or two substituents each independently selected from $R^{D1}$, and, optionally substituted, on nitrogen, if present, with one or two substituents each independently selected from $R^{D2}$;

B is fused to D such that the two atoms shared by D and B are both carbon or one carbon and one nitrogen;

wherein if $R^4$ and $R^5$, taken together with the carbon to which they are attached, form the 4-6 membered carbocyclic or heterocyclic ring B, which ring may be fused to the ring D; then $R^1$ is substituted with —O—S(O)$_2$—F or —S(O)$_2$—F;

$R^{D1}$ is selected from the group consisting of hydroxyl, cyano, halogen, and —N($R^6$)$_2$; and $R^{D2}$ is selected from —$(C_1-C_6)$alkyl and phenyl.

Also disclosed herein is a compound of Formula Ia, Ib or Ic, or Id, or a pharmaceutically acceptable salt or stereoisomer thereof, represented by:

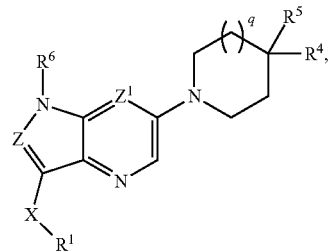

(Ia)

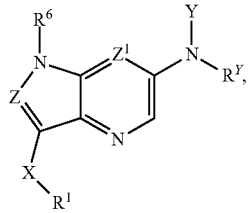

(Ib)

-continued

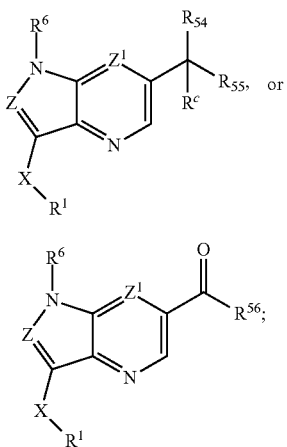

(Ic)

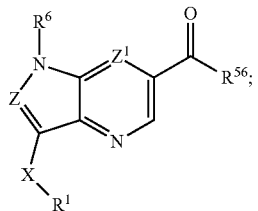

(Id)

wherein:
Z$^1$ is N or CH;
Z is N or CH;
X is selected from the group consisting of a bond, —O—, —NR$^{X1}$—, and —S(O)$_w$— (wherein w is 0, 1 or 2);
R$^{X1}$ is selected from the group consisting of hydrogen, —(C$_1$-C$_6$)alkyl and phenyl;
R$^1$ is a ring moiety substituted with —O—S(O)$_2$—F or —S(O)$_2$—F, wherein the ring moiety is selected from the group consisting of a 8-12 membered bicyclic heteroaryl, a 11-15 membered tricyclic heteroaryl, phenyl, a 5-7 membered monocyclic heteroaryl, and a 4-7 membered heterocyclyl, wherein the ring moiety is optionally substituted with one, two or more substituents each independently selected from the group consisting of R$^{10}$, —OR$^{10}$, —S(O)$_w$R$^{10}$ (wherein w is 0, 1 or 2), —C$_{1-6}$alkyl-S(O)$_w$—C$_{1-3}$alkyl, —N(R$^{10}$)$_2$, —N(CO)R$^{10}$, —N—S(O)—R$^{10}$ (where w is 0, 1 or 2), —OS(O)$_w$—R$^{10}$ (wherein w is 0, 1, or 2), —S(O)$_w$—N(R$^{10}$)$_2$ (wherein w is 0, 1, or 2), —S(O)$_2$(NH)R$^{10}$, —N(H)—SO$_2$—C$_{1-3}$alkyl, —N(SO$_2$—C$_{1-3}$alkyl)$_2$, P(O)(R$^{10}$)$_2$, —C(O)R$^{10}$, —C(O)OR$^{10}$, —C(O)N(R$^{10}$)$_2$, oxo, halogen, hydroxyl, cyano, nitro, —C(=N—OR$^a$)—C$_{1-3}$alkyl, —C(=N—OR$^a$)—H, —S(O)(NR$^a$)—C$_{1-3}$alkyl, phenyl (optionally substituted with one, two or three halogen, —O-phenyl, C$_{1-3}$alkyl or C$_{1-3}$haloalkyl), C$_{1-3}$alkyl, C$_{2-6}$alkynyl, C$_{1-3}$haloalkyl, C$_{3-6}$cycloalkyl, heterocyclyl (optionally substituted with one, two or three halogen, oxo, C$_{1-3}$alkyl or C$_{1-3}$haloalkyl), and heteroaryl (optionally substituted with one, two or three halogen, —C(O)N(R$^{10}$)$_2$, C$_{1-3}$alkyl, C$_{1-3}$alkyl-O—C$_{1-3}$alkyl, C$_{1-3}$alkyl-OH, or C$_{1-3}$haloalkyl);
R$^{10}$ is independently selected from the group consisting of hydrogen, C$_{1-6}$alkyl, C$_{2-6}$alkenyl, C$_{2-6}$alkynyl, C$_{3-6}$cycloalkyl, C$_{5-6}$cycloalkenyl, C$_{2-6}$heteroalkyl, heterocycloalkyl, aryl, and heteroaryl; wherein C$_{1-6}$alkyl, C$_{2-6}$alkenyl, C$_{2-6}$alkynyl, C$_{3-6}$cycloalkyl, C$_{5-6}$cycloalkenyl, C$_{2-6}$heteroalkyl, heterocycloalkyl, aryl, and heteroaryl is optionally substituted by one, two, three or more substituents each independently selected from the group consisting of halogen, hydroxyl, —NR$^a$C(O)—R$^{20}$, —C(O)—R$^{20}$, —C(NR$^a$)—R$^b$, —NR$^a$R$^b$, C$_{1-6}$alkyl, C$_{1-6}$haloalkyl and C$_{1-6}$alkoxy;
R$^{20}$ is selected from the group consisting of hydrogen, hydroxyl, halogen, —NR$^a$R$^b$, C$_{1-6}$alkyl and C$_{1-6}$alkoxy;

R$^a$ and R$^b$ are each independently selected from the group consisting of hydrogen and C$_{1-3}$alkyl;
R$^6$ is independently for each occurrence selected from the group consisting of H, —(C$_1$-C$_6$)alkyl, —C(O)OC$_{1-4}$alkyl, and phenyl;
q is 0 or 1;
R$^Y$ is selected from the group consisting of hydrogen and —(C$_1$-C$_6$)alkyl;
Y is selected from the group consisting of a 3-7 membered saturated carbocycle, a 4-7 membered saturated heterocycle, phenyl, and a 5-6 membered monocyclic heteroaryl; wherein Y is optionally substituted with one or more substituents each independently selected from the group consisting of (C$_1$-C$_6$)alkyl, —C(O)N(R$^6$)$_2$, —N(R$^6$)$_2$, halogen, and cyano, wherein said —(C$_1$-C$_6$) alkyl is optionally substituted with one or more substituents selected from the group consisting of —OH, —N(R$^6$)$_2$, oxo, and halogen;
R$^{55}$ is selected from the group consisting of —C$_{1-4}$alkyl-N(R$^6$)$_2$, —N(R$^6$)$_2$, and heteroaryl (optionally substituted by one, two, or three substituent each independently selected from halogen, hydroxyl, cyano, —(C$_1$-C$_6$)alkyl, —O(C$_1$-C$_6$)alkyl, —C(O)N(R$^6$)$_2$, —N(R$^6$)$_2$, and —(C$_1$-C$_6$)alkyl-N(R$^6$)$_2$);
R$^{54}$ is selected from the group consisting of H, and C$_{1-2}$alkyl, or
R$^{54}$ and R$^{55}$ taken together with the carbon to which they are attached form a ring selected from the group consisting of C$_{3-6}$cycloalkyl and heterocyclyl, wherein the ring is optionally substituted on a carbon by one, two or three substituents each independently selected from the group consisting of R$^4$ and R$^5$ and on a nitrogen if present by R$^6$;
R$^C$ is selected from the group consisting of H, OH, —(C$_1$-C$_6$)alkyl, —C(O)—O—C$_{1-6}$(alkyl), —C(O)—C$_{1-6}$(alkyl), and heterocyclyl, wherein C$_{1-6}$(alkyl) is optionally substituted by one two or three substituents each selected from the group consisting of halogen, hydroxyl and N(R$_6$)$_2$; or
wherein R$^C$ is absent R$^{54}$ and R$^{55}$ taken together with the carbon to which they are attached form a ring selected from C$_{5-6}$cyclalkenyl and phenyl; wherein the ring is optionally substituted on a carbon by one, two or three substituents each independently selected from the group consisting of R$^4$ and R$^5$;
R$^{56}$ is N(R$_6$)$_2$ or heterocycle (optionally substituted by one, two or three substituents each independently selected from halogen, hydroxyl, N(R$_6$)$_2$, —(C$_1$-C$_6$) alkyl, —C(O)—O—C$_{1-6}$(alkyl), —C(O)—C$_{1-6}$(alkyl), wherein C$_{1-6}$(alkyl) is optionally substituted by one two or three substituents each selected from the group consisting of: halogen, hydroxyl or N(R$_6$)$_2$);
R$^4$ and R$^5$ are each independently selected from the group consisting of H, —OH, —(C$_1$-C$_6$)alkyl, —O(C$_1$-C$_6$) alkyl, —(C$_1$-C$_6$)alkyl-O—R$^6$, —C(O)N(R$^6$)$_2$, —N(R$^6$)$_2$, halogen, —(C$_1$-C$_6$)alkyl-N(R$^6$)$_2$, and cyano, wherein said —(C$_1$-C$_6$)alkyl, —O(C$_1$-C$_6$)alkyl, —(C$_1$-C$_6$)alkyl-O—R$^6$, or —(C$_1$-C$_6$)alkyl-N(R$^6$)$_2$ is optionally substituted with one or more substituents selected from the group consisting of —OH, —NH$_2$, oxo, and halogen;
or R$^4$ and R$^5$, taken together with the carbon to which they are attached, form a 4-6 membered carbocyclic or heterocyclic ring B; which ring is optionally substituted with one or two substituents each independently selected from the group consisting of (C$_1$-C$_6$)alkyl, —O(C$_1$-C$_6$)alkyl, —N(R$^6$)$_2$, —C(O)N(R$^6$)$_2$, halogen, oxo, and cyano and/or which ring may be fused to a ring D;

D is selected from the group consisting of: phenyl, a 5- or 6-membered heteroaryl having one or two heteroatoms each independently selected from the group consisting of S, O or N, and C$_{3-6}$cycloalkyl, wherein D is optionally substituted on an available carbon with one or two substituents each independently selected from R$^{D1}$, and, optionally substituted, on nitrogen, if present, with one or two substituents each independently selected from R$^{D2}$;

B is fused to D such that the two atoms shared by D and B are both carbon or one carbon and one nitrogen;

R$^{D1}$ is selected from the group consisting of hydroxyl, cyano, halogen, and —N(R$^6$)$_2$; and R$^{D2}$ is selected from —(C$_1$-C$_6$)alkyl and phenyl.

Also provided herein is a compound of Formula Va or Vb, or a pharmaceutically acceptable salt or stereoisomer thereof, represented by:

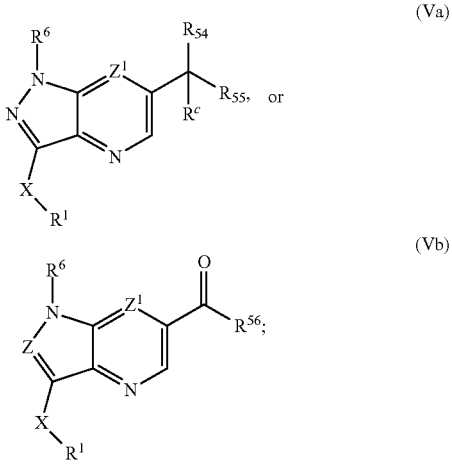

wherein.

$Z^1$ is N or CH;

Z is N or CH;

X is selected from the group consisting of a bond, —O—, —NR$^{X1}$—, and —S(O)$_w$— (wherein w is 0, 1 or 2);

R$^{X1}$ is selected from the group consisting of hydrogen, —(C$_1$-C$_6$)alkyl and phenyl;

R$^1$ is a ring moiety selected from the group consisting of a 8-12 membered bicyclic heteroaryl, phenyl, a 5-7 membered monocyclic heteroaryl, and a 4-7 membered heterocyclyl, wherein the ring moiety is optionally substituted with one, two or more substituents each independently selected from the group consisting of R$^{10}$, —OR$^{10}$, —S(O)$_w$R$^{10}$ (wherein w is 0, 1 or 2), —C$_{1-6}$alkyl-S(O)$_w$—C$_{1-3}$alkyl, —N(R$^{10}$)$_2$, —N(CO)R$^{10}$, —N—S(O)$_w$—R$^{10}$ (where w is 0, 1 or 2), —OS(O)$_w$—R$^{10}$ (wherein w is 0, 1, or 2), —S(O)$_w$—N(R$^{10}$)$_2$ (wherein w is 0, 1 or 2), —S(O)(NH)R$^{10}$, —N(H)—SO$_2$—C$_{1-3}$alkyl, —N(SO$_2$—C$_{1-3}$alkyl)$_2$, P(O)(R$^{10}$)$_2$, —C(O)R$^{10}$, —C(O)OR$^{10}$, —C(O)N(R$^{10}$)$_2$, oxo, halogen, hydroxyl, cyano, nitro, —C(=N—OR$^a$)—C$_{1-3}$alkyl, —C(=N—OR$^a$)—H, —S(O)(NR$^a$)—C$_{1-3}$alkyl, phenyl (optionally substituted with one, two or three halogen, —O-phenyl, C$_{1-3}$alkyl or C$_{1-3}$haloalkyl), C$_{1-3}$alkyl, C$_{2-3}$alkynyl, C$_{1-3}$haloalkyl, C$_{3-6}$cycloalkyl, heterocyclyl (optionally substituted with one, two or three halogen, oxo, C$_{1-3}$alkyl or C$_{1-3}$haloalkyl), and heteroaryl (optionally substituted with one, two or three halogen, —C(O)N(R$^{10}$)$_2$, C$_{1-3}$alkyl, C$_{1-3}$alkyl-O—C$_{1-3}$alkyl, C$_{1-3}$alkyl-OH, or C$_{1-3}$haloalkyl);

R$^{10}$ is independently selected from the group consisting of hydrogen, C$_{1-6}$alkyl, C$_{2-6}$alkenyl, C$_{2-6}$alkynyl, C$_{3-6}$cycloalkyl, C$_{5-6}$cycloalkenyl, C$_{2-6}$heteroalkyl, heterocycloalkyl, aryl, and heteroaryl; wherein C$_{1-6}$alkyl, C$_{2-6}$alkenyl, C$_{2-6}$alkynyl, C$_{3-6}$cycloalkyl, C$_{5-6}$cycloalkenyl, C$_{2-6}$heteroalkyl, heterocycloalkyl, aryl, and heteroaryl is optionally substituted by one, two, three or more substituents each independently selected from the group consisting of halogen, hydroxyl, —NR$^a$C(O)—R$^{20}$, —C(O)—R$^{20}$, —C(NR$^a$)—R$^b$, —NR$^a$R$^b$, C$_{1-6}$alkyl, C$_{1-6}$haloalkyl and C$_{1-6}$alkoxy;

R$^{20}$ is selected from the group consisting of hydrogen, hydroxyl, halogen, —NR$^a$R$^b$, C$_{1-6}$alkyl and C$_{1-6}$alkoxy;

R$^a$ and R$^b$ are each independently selected from the group consisting of hydrogen and C$_{1-3}$alkyl;

R$^6$ is independently for each occurrence selected from the group consisting of H, —(C$_1$-C$_6$)alkyl, —C(O)OC$_{1-4}$alkyl, and phenyl;

R$^{55}$ is selected from the group consisting of —C$_{1-4}$alkyl-N(R$^6$)$_2$, —N(R$^6$)$_2$, and heteroaryl (optionally substituted by one, two, or three substituent each independently selected from halogen, hydroxyl, cyano, —(C$_1$-C$_6$)alkyl, —O(C$_1$-C$_6$)alkyl, —C(O)N(R$^6$)$_2$, —N(R$^6$)$_2$, and —(C$_1$-C$_6$)alkyl-N(R$^6$)$_2$);

R$^{54}$ is selected from the group consisting of H, and C$_{1-2}$alkyl, or

R$^{54}$ and R$^{55}$ taken together with the carbon to which they are attached form a ring selected from the group consisting of C$_{3-6}$cycloalkyl and heterocyclyl, wherein the ring is optionally substituted on a carbon by one, two or three substituents each independently selected from the group consisting of R$^4$ and R$^5$ and on a nitrogen if present by R$^6$;

R$^C$ is selected from the group consisting of H, OH, —(C$_1$-C$_6$)alkyl, —C(O)—O—C$_{1-6}$(alkyl), —C(O)—C$_{1-6}$(alkyl), and heterocyclyl, wherein C$_{1-6}$(alkyl) is optionally substituted by one two or three substituents each selected from the group consisting of halogen, hydroxyl and N(R$_6$)$_2$; or wherein R$^C$ is absent R$^{54}$ and R$^{55}$ taken together with the carbon to which they are attached form a ring selected from C$_{5-6}$cyclalkenyl and phenyl; wherein the ring is optionally substituted on a carbon by one, two or three substituents each independently selected from the group consisting of R$^4$ and R$^5$;

R$^{56}$ is N(R$_6$)$_2$ or heterocycle (optionally substituted by one, two or three substituents each independently selected from halogen, hydroxyl, N(R$_6$)$_2$, —(C$_1$-C$_6$)alkyl, —C(O)—O—C$_{1-6}$(alkyl), —C(O)—C$_{1-6}$(alkyl), wherein C$_{1-6}$(alkyl) is optionally substituted by one two or three substituents each selected from the group consisting of: halogen, hydroxyl or N(R$_6$)$_2$);

R$^4$ and R$^5$ are each independently selected from the group consisting of H, —OH, —(C$_1$-C$_6$)alkyl, —O(C$_1$-C$_6$)alkyl, —(C$_1$-C$_6$)alkyl-O—R$^6$, —C(O)N(R$^6$)$_2$, —N(R$^6$)$_2$, halogen, —(C$_1$-C$_6$)alkyl-N(R$^6$)$_2$, and cyano, wherein said —(C$_1$-C$_6$)alkyl, —O(C$_1$-C$_6$)alkyl, —(C$_1$-C$_6$)alkyl-O—R$^6$, or —(C$_1$-C$_6$)alkyl-N(R$^6$)$_2$ is optionally substituted with one or more substituents selected from the group consisting of —OH, —NH$_2$, oxo, and halogen;

or R⁴ and R⁵, taken together with the carbon to which they are attached, form a 4-6 membered carbocyclic or heterocyclic ring B; which ring is optionally substituted with one or two substituents each independently selected from the group consisting of (C₁-C₆)alkyl, —O(C₁-C₆)alkyl, —N(R⁶)₂, —C(O)N(R⁶)₂, halogen, oxo, and cyano and/or which ring may be fused to a ring D;

D is selected from the group consisting of: phenyl, a 5- or 6-membered heteroaryl having one or two heteroatoms each independently selected from the group consisting of S, O or N, and C₃₋₆cycloalkyl, wherein D is optionally substituted on an available carbon with one or two substituents each independently selected from $R^{D1}$, and, optionally substituted, on nitrogen, if present, with one or two substituents each independently selected from $R^{D2}$;

B is fused to D such that the two atoms shared by D and B are both carbon or one carbon and one nitrogen;

$R^{D1}$ is selected from the group consisting of hydroxyl, cyano, halogen, and —N(R⁶)₂; and $R^{D2}$ is selected from the group consisting of —(C₁-C₆)alkyl and phenyl.

Further disclosed herein is a compound of Formula VIIIa, VIIIb, VIIIc, or VIIId, or a pharmaceutically acceptable salt or stereoisomer thereof, represented by:

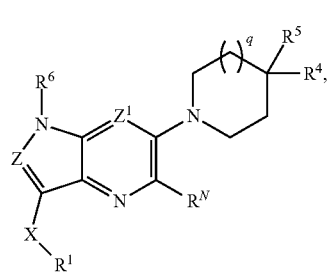
(VIIIa)

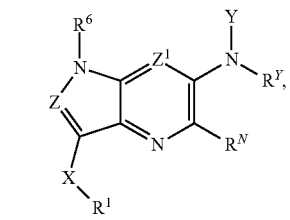
(VIIIb)

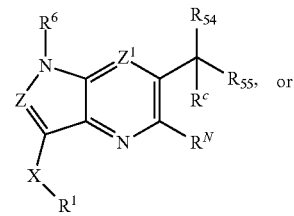
(VIIIc)

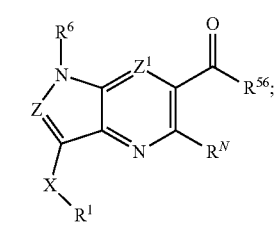
(VIIId)

wherein:

$R^N$ is selected from the group consisting of —CH₂OH, —C(H)(OH), —C(OH)(CH₃)₂, —CH₃, —CF₃, —CHF₂, —CH₂F, —CH₂OCH₃, —C₁₋₃alkyl, —C₁₋₃alkoxy, —C(O)—C₁₋₃alkoxy, —C(O)—C₁₋₃alkyl, cyclopropyl, tetrahydrofuran-3-yl, tetrahydrofuran-2-yl, oxetan-3-yl, oxetan-2-yl, azetidin-3-yl, azetidin-2-yl, hydroxyl, cyano, —C(O)—NR^aR^b, —N(R^a)—C(O)—C₁₋₃alkyl, —N(R^a)—S(O)₂—C₁₋₃alkyl, —S(O)₂—N(R^a)—C₁₋₃alkyl, —S(O)₂—C₁₋₃alkyl, CH₂NR^aR^b, —CH₂NR^aC(O)C₁₋₄alkyl, —CH₂NR^aC(O)OC₁₋₄alkyl, —CH₂NR^aC(O)NR^bC₁₋₄alkyl, —CH₂NR^aS(O)₂C₁₋₄alkyl, and

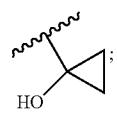 [SMILES: *C1(O)CC1];

$Z^1$ is N or CH;
Z is N or CH;
X is selected from the group consisting of a bond, —O—, —NR^{X1}—, and —S(O)_w— (wherein w is 0, 1 or 2);
$R^{X1}$ is selected from the group consisting of hydrogen, —(C₁-C₆)alkyl and phenyl;
R¹ is a ring moiety selected from the group consisting of a 8-12 membered bicyclic heteroaryl, a 11-15 membered tricyclic heteroaryl, phenyl, a 5-7 membered monocyclic heteroaryl, and a 4-7 membered heterocyclyl, wherein the ring moiety is optionally substituted with one, two or more substituents each independently selected from the group consisting of R¹⁰, —OR¹⁰, —S(O)_wR¹⁰ (wherein w is 0, 1 or 2), —C₁₋₆alkyl-S(O)_w—C₁₋₃alkyl, —N(R¹⁰)₂, —N(CO)R¹⁰, —N—S(O)_w—R¹⁰ (where w is 0, 1 or 2), —OS(O)_w—R¹⁰ (wherein w is 0, 1, or 2), —S(O)_w—N(R¹⁰)₂ (wherein w is 0, 1 or 2), —S(O)(NH)R¹⁰, —N(H)—SO₂—C₁₋₃alkyl, —N(SO₂—C₁₋₃alkyl)₂, P(O)(R¹⁰)₂, —C(O)R¹⁰, —C(O)OR¹⁰, —C(O)N(R¹⁰)₂, oxo, halogen, hydroxyl, cyano, nitro, —C(=N—OR^a)—C₁₋₃alkyl, —C(=N—OR^a)—H, —S(O)(NR^a)—C₁₋₃alkyl, phenyl (optionally substituted with one, two or three halogen, —O-phenyl, C₁₋₃alkyl or C₁₋₃haloalkyl), C₁₋₃alkyl, C₂₋₆alkynyl, C₁₋₃haloalkyl, C₃₋₆cycloalkyl, heterocyclyl (optionally substituted with one, two or three halogen, oxo, C₁₋₃alkyl or C₁₋₃haloalkyl), and heteroaryl (optionally substituted with one, two or three halogen, —C(O)N(R¹⁰)₂, C₁₋₃alkyl, C₁₋₃alkyl-O—C₁₋₃alkyl, C₁₋₃alkyl-OH, or C₁₋₃haloalkyl);

R¹⁰ is independently selected from the group consisting of hydrogen, C₁₋₆alkyl, C₂₋₆alkenyl, C₂₋₆alkynyl, C₃₋₆cycloalkyl, C₅₋₆cycloalkenyl, C₂₋₆heteroalkyl, heterocycloalkyl, aryl, and heteroaryl; wherein C₁₋₆alkyl, C₂₋₆alkenyl, C₂₋₆alkynyl, C₃₋₆cycloalkyl, C₅₋₆cycloalkenyl, C₂₋₆heteroalkyl, heterocycloalkyl, aryl, and heteroaryl is optionally substituted by one, two, three or more substituents each independently selected from the group consisting of halogen, hydroxyl, —NR^aC(O)—R²⁰, —C(O)—R²⁰, —C(NR^a)—R^b, —NR^aR^b, C₁₋₆alkyl, C₁₋₆haloalkyl and C₁₋₆alkoxy;

R²⁰ is selected from the group consisting of hydrogen, hydroxyl, halogen, —NR^aR^b, C₁₋₆alkyl and C₁₋₆alkoxy;

R^a and R^b are each independently selected from the group consisting of hydrogen and C₁₋₃alkyl;

R⁶ is independently for each occurrence selected from the group consisting of H, —(C₁-C₆)alkyl, —C(O)OC₁₋₄alkyl, and phenyl;

q is 0 or 1;

R^Y is selected from the group consisting of hydrogen and —(C₁-C₆)alkyl;

Y is selected from the group consisting of a 3-7 membered saturated carbocycle, a 4-7 membered saturated heterocycle, phenyl, and a 5-6 membered monocyclic heteroaryl; wherein Y is optionally substituted with one or more substituents each independently selected from the group consisting of (C₁-C₆)alkyl, —C(O)N(R⁶)₂, —N(R⁶)₂, halogen, and cyano, wherein said —(C₁-C₆) alkyl is optionally substituted with one or more substituents selected from the group consisting of —OH, —N(R⁶)₂, oxo, and halogen;

R⁵⁵ is selected from the group consisting of —C₁₋₄ alkyl-N(R⁶)₂, —N(R⁶)₂, and heteroaryl (optionally substituted by one, two, or three substituent each independently selected from halogen, hydroxyl, cyano, —(C₁-C₆)alkyl, —O(C₁-C₆)alkyl, —C(O)N(R⁶)₂, —N(R⁶)₂, and —(C₁-C₆)alkyl-N(R⁶)₂);

R⁵⁴ is selected from the group consisting of H, and C₁₋₂alkyl, or

R⁵⁴ and R⁵⁵ taken together with the carbon to which they are attached form a ring selected from the group consisting of C₃₋₆cycloalkyl and heterocyclyl, wherein the ring is optionally substituted on a carbon by one, two or three substituents each independently selected from the group consisting of R⁴ and R⁵ and on a nitrogen if present by R⁶;

R^C is selected from the group consisting of H, OH, —(C₁-C₆)alkyl, —C(O)—O—C₁₋₆(alkyl), —C(O)—C₁₋₆(alkyl), and heterocyclyl, wherein C₁₋₆(alkyl) is optionally substituted by one two or three substituents each selected from the group consisting of halogen, hydroxyl and N(R₆)₂; or wherein R^C is absent R⁵⁴ and R⁵⁵ taken together with the carbon to which they are attached form a ring selected from C₅₋₆cyclalkenyl and phenyl; wherein the ring is optionally substituted on a carbon by one two or three substituents each independently selected from the group consisting of R⁴ and R⁵;

R⁵⁶ is N(R₆)₂ or heterocycle (optionally substituted by one, two or three substituents each independently selected from halogen, hydroxyl, N(R₆)₂, —(C₁-C₆) alkyl, —C(O)—O—C₁₋₆(alkyl), —C(O)—C₁₋₆(alkyl), wherein C₁₋₆(alkyl) is optionally substituted by one two or three substituents each selected from the group consisting of: halogen, hydroxyl or N(R₆)₂);

R⁴ and R⁵ are each independently selected from the group consisting of H, —OH, —(C₁-C₆)alkyl, —O(C₁-C₆) alkyl, —(C₁-C₆)alkyl-O—R⁶, —C(O)N(R⁶)₂, —N(R⁶)₂, halogen, —(C₁-C₆)alkyl-N(R⁶)₂, and cyano, wherein said —(C₁-C₆)alkyl, —O(C₁-C₆)alkyl, —(C₁-C₆)alkyl-O—R⁶, or —(C₁-C₆)alkyl-N(R⁶)₂ is optionally substituted with one or more substituents selected from the group consisting of —OH, —NH₂, oxo, and halogen;

or R⁴ and R⁵, taken together with the carbon to which they are attached, form a 4-6 membered carbocyclic or heterocyclic ring B; which ring is optionally substituted with one or two substituents each independently selected from the group consisting of (C₁—C₆)alkyl, —O(C₁-C₆)alkyl, —N(R⁶)₂, —C(O)N(R⁶)₂, halogen, oxo, and cyano and/or which ring may be fused to a ring D;

D is selected from the group consisting of: phenyl, a 5- or 6-membered heteroaryl having one or two heteroatoms each independently selected from the group consisting of S, O or N, and C₃₋₆cycloalkyl, wherein D is optionally substituted on an available carbon with one or two substituents each independently selected from R^D1, and, optionally substituted, on nitrogen, if present, with one or two substituents each independently selected from R^D2;

B is fused to D such that the two atoms shared by D and B are both carbon or one carbon and one nitrogen;

R^D1 is selected from the group consisting of hydroxyl, cyano, halogen, and —N(R⁶)₂; and R^D2 is selected from —(C₁-C₆)alkyl and phenyl.

Also disclosed herein is a compound of Formula XI, or a pharmaceutically acceptable salt or stereoisomer thereof, wherein Formula XI is represented by:

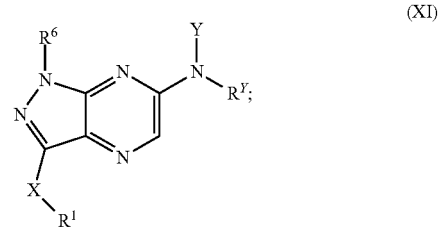

(XI)

wherein:

X is selected from the group consisting of a bond, —O—, —NR^X1—, and —S(O)_w— (wherein w is 0, 1 or 2);

R¹ is a ring moiety selected from the group consisting of a 8-12 membered bicyclic heteroaryl, phenyl, a 5-7 membered monocyclic heteroaryl, and a 4-7 membered heterocyclyl, wherein the ring moiety is optionally substituted with one, two or more substituents each independently selected from the group consisting of R¹⁰, —OR¹⁰, —S(O)_wR¹⁰ (wherein w is 0, 1 or 2), —C₁₋₆alkyl-S(O)_w—C₁₋₃alkyl, —N(R¹⁰)₂, —N(CO)R¹⁰, —N—S(O)_w—R¹⁰ (where w is 0, 1 or 2), —OS(O)_w—R¹⁰ (wherein w is 0, 1, or 2), —S(O)_w—N(R¹⁰)₂ (wherein w is 0, 1 or 2), —S(O)(NH)R¹⁰, —N(H)—SO₂—C₁₋₃alkyl, —N(SO₂—C₁₋₃alkyl)₂, P(O)(R¹⁰)₂, —C(O)R¹⁰, —C(O)OR¹⁰, —C(O)N(R¹⁰)₂, oxo, halogen, hydroxyl, cyano, nitro, —C(=N—OR^a)—C₁₋₃alkyl, —C(=N—OR^a)—H, —S(O)(NR^a)—C₁₋₃alkyl, phenyl (optionally substituted with one, two or three halogen, —O-phenyl, C₁₋₃alkyl or C₁₋₃haloalkyl), C₁₋₃alkyl, C₂₋₆alkynyl, C₁₋₃haloalkyl, C₃₋₆cycloalkyl, heterocyclyl (optionally substituted with one, two or three halogen, oxo, C₁₋₃alkyl or C₁₋₃haloalkyl), and heteroaryl (optionally substituted with one, two or three halogen, —C(O)N(R¹⁰)₂, C₁₋₃alkyl, C₁₋₃alkyl-O—C₁₋₃alkyl, C₁₋₃alkyl-OH, or C₁₋₃haloalkyl);

R¹⁰ is independently selected from the group consisting of hydrogen, C₁₋₆alkyl, C₂₋₆alkenyl, C₂₋₆alkynyl, C₃₋₆cycloalkyl, C₅₋₆cycloalkenyl, C₂₋₆heteroalkyl, heterocycloalkyl, aryl, and heteroaryl; wherein C₁₋₆alkyl, C₂₋₆alkenyl, C₂₋₆alkynyl, C₃₋₆cycloalkyl, C₅₋₆cycloalkenyl, C₂₋₆heteroalkyl, heterocycloalkyl, aryl, and heteroaryl is optionally substituted by one, two, three or more substituents each independently selected from the group consisting of halogen, hydroxyl, —NR^aC(O)—R²⁰, —C(O)—R²⁰, —C(NR^a)—R^b, —NR^aR^b, C₁₋₆alkyl, C₁₋₆haloalkyl and C₁₋₆alkoxy;

$R^{20}$ is selected from the group consisting of hydrogen, hydroxyl, halogen, —NR$^a$R$^b$, C$_{1-6}$alkyl and C$_{1-6}$alkoxy;

Y is selected from the group consisting of phenyl and a 5-6 membered monocyclic heteroaryl; wherein Y is optionally substituted with one or more substituents each independently selected from the group consisting of (C$_1$-C$_6$)alkyl, —C(O)N(R$^6$)$_2$, —N(R$^6$)$_2$, halogen, and cyano, wherein said —(C$_1$-C$_6$)alkyl is optionally substituted with one or more substituents selected from the group consisting of —OH, —N(R$^6$)$_2$, oxo, and halogen;

$R^6$ is independently for each occurrence selected from the group consisting of H, —(C$_1$-C$_6$)alkyl, —C(O)OC$_{1-4}$alkyl, and phenyl;

$R^{X1}$ is selected from the group consisting of hydrogen, —(C$_1$-C$_6$)alkyl and phenyl;

$R^Y$ is selected from the group consisting of hydrogen and —(C$_1$-C$_6$)alkyl; and $R^a$ and $R^b$ are each independently selected from the group consisting of hydrogen and C$_{1-3}$alkyl.

The present disclosure also provides, for example, pharmaceutical compositions containing the compounds described herein. Further, the disclosure provides a method of inhibiting SHP2 phosphatase activity in a subject by administering a therapeutically effective amount of a compound or composition described herein, to a subject, e.g., a human, in need.

The present disclosure further provides, for example, a method of treating a disorder in a subject by administering a therapeutically effective amount of a compound or composition described herein, to a subject in need thereof. Examples of disorders include Noonan syndrome, neutropenia, diabetes, neuroblastoma, melanoma, acute myeloid leukemia, juvenile leukemia, juvenile myelomonocytic leukemia, breast cancer, lung cancer, and colorectal cancer. In addition to the compound or composition described herein, such method may include administration of a therapeutically effective amount of an antibody, an antibody-drug conjugate, an immunomodulator, or a histone deacetylase inhibitor.

The present disclosure is based, in part, on certain discoveries which are described more fully in the Examples section of the present application. For example, the present disclosure is based, in part, on the discovery of compounds disclosed herein and the SHP2 phosphatase inhibition exhibited by such compounds.

These and other embodiments of the disclosure are further described in the following sections of the application, including the Detailed Description, Examples, and Claims. Still other objects and advantages of the disclosure will become apparent by those of skill in the art from the disclosure herein, which are simply illustrative and not restrictive. Thus, other embodiments will be recognized by the ordinarily skilled artisan without departing from the spirit and scope of the disclosure.

BRIEF DESCRIPTION OF THE DRAWING

The FIGURE depicts a disclosed compound bound to a lysine of SHP2 as described herein.

DETAILED DESCRIPTION

Activating SHP2 mutations have been detected in juvenile myelomonocytic leukemia (e.g., Q506P), chronic myelomonocytic leukemia (e.g., Y63C), neuroblastoma (e.g., T507K), melanoma (e.g., R138Q), acute myeloid leukemia (e.g., G503V), breast cancer, lung cancer (e.g., E76V), colorectal cancer (e.g., E76G). (M. Bentires-Alj et al., in *Cancer Res.* 2004, 64, 8816-8820; and references cited therein.

SHP2 phosphatase inhibitors are disclosed, e.g., in WO 2015/107493; WO 2015/107494; WO 2015/107495; and J. G. Fortanet et al., in *J. Med. Chem.* 2016, DOI: 10.1021/acs.jmedchem.6b00680; and references cited therein. The effects of SHP2 phsophatase inhibition are described, e.g., Y.-N. P. Chen et al., in *Nature,* 2016, doi:10.1038/nature18621; J. Wang et al., in *J. Clin. Invest.* 2016, 126, 2077-2092; and references cited therein.

The compounds and/or compositions of the disclosure, alone or in combination with other treatments, may be effective in treating, reducing, and/or suppressing disorders related to SHP2 phosphatase activity such as, e.g., Noonan syndrome, Leopard Syndrome, diabetes, neuroblastoma, melanoma, juvenile leukemia, juvenile myelomonocytic leukemia (JMML), chronic myelomonocytic leukemia, acute myeloid leukemia, HER2-positive breast cancer, triple-negative breast cancer, ductal carcinoma of the breast, invasive ductal carcinoma of the breast, non-small cell lung cancer (including adenocarcinoma of the lung), colorectal cancer, esophageal cancer, gastric cancer, squamous-cell carcinoma of the head and neck (SCCHN), neutropenia (Kostmann's syndrome), and systemic lupus erythematosus. See, e.g, N. Aceto et al. *Nature Medicine,* 2012, 28, 529-538; C. M. Furcht et al. *Oncogene,* 2013, 32, 2346-2355; V. E. Schneeberger et al. *Oncotarget,* 2015, 6, 6191-6202; P. Cai et al., *Biomedicine & Pharmacotherapy* 2014, 68, 285-290; and references cited therein.

The methods described herein may also include additionally administering a therapeutically effective amount of an antibody, an antibody-drug conjugate, an immunomodulator, or a histone deacetylase inhibitor.

Abbreviations and Definitions

The term "isomer" as used herein refers to a compound having the identical chemical formula but different structural or optical configurations. The term "stereoisomer" as used herein refers to and includes isomeric molecules that have the same molecular formula but differ in positioning of atoms and/or functional groups in the space. All stereoisomers of the present compounds (e.g., those which may exist due to asymmetric carbons on various substituents), including enantiomeric forms and diastereomeric forms, are contemplated within the scope of this disclosure.

The term "tautomer" as used herein refers to one of two or more structural isomers which exist in equilibrium and which are readily converted from one isomeric form to another. It is understood that tautomers encompass valence tautomers and proton tautomers (also known as prototropic tautomers). Valence tautomers include interconversions by reorganization of some of the bonding electrons. Proton tautomers include interconversions via migration of a proton, such as keto-enol and imine-enamine isomerizations.

The term "isotopic substitution" as used herein refers to the substitution of an atom with its isotope. The term "isotope" as used herein refers to an atom having the same atomic number as that of atoms dominant in nature but having a mass number (neutron number) different from the mass number of the atoms dominant in nature. It is understood that a compound with an isotopic substitution refers to a compound in which at least one atom contained therein is substituted with its isotope. Atoms that can be substituted with its isotope include, but are not limited to, hydrogen, carbon, and oxygen. Examples of the isotope of a hydrogen atom include $^2$H (also represented as D) and $^3$H. Examples of the isotope of a carbon atom include $^{13}$C and $^{14}$C. Examples of the isotope of an oxygen atom include $^{18}$O.

The term "alkyl", as used herein, unless otherwise indicated, refers to a monovalent aliphatic hydrocarbon radical having a straight chain, branched chain, monocyclic moiety, or polycyclic moiety or combinations thereof, wherein the radical is optionally substituted at one or more carbons of the straight chain, branched chain, monocyclic moiety, or polycyclic moiety or combinations thereof with one or more substituents at each carbon, wherein the one or more substituents are independently $C_1$-$C_{10}$ alkyl. Examples of "alkyl" groups include methyl, ethyl, propyl, isopropyl, butyl, iso-butyl, sec-butyl, tert-butyl, pentyl, hexyl, heptyl, cyclopropyl, cyclobutyl, cyclopentyl, cyclohexyl, cycloheptyl, norbornyl, and the like.

The terms "heteroaryl" or "heteroaromatic group" as used herein refers to a monocyclic aromatic 5-6 membered ring system containing one or more heteroatoms, for example one to three heteroatoms, such as nitrogen, oxygen, and sulfur, or a 8-10 membered bicyclic unsaturated or partially unsaturated ring system containing one or more heteroatoms, for example one to three heteroatoms, such as nitrogen, oxygen, and sulfur. Where possible, said heteroaryl ring may be linked to the adjacent radical though carbon or nitrogen. Examples of heteroaryl rings include but are not limited to furan, thiophene, pyrrole, thiazole, oxazole, isothiazole, isoxazole, imidazole, pyrazole, triazole, pyridine or pyrimidine, tetrahydroquinoline, etc.

The terms "heterocyclyl" or "heterocyclic group" are art-recognized and refer to saturated 4-10 membered monocyclic and bicyclic ring structures, including bridged or fused rings, and whose ring structures include one to three heteroatoms, such as nitrogen, oxygen, and sulfur. Where possible, heterocyclyl rings may be linked to the adjacent radical through carbon or nitrogen.

The term "pharmaceutically acceptable salt" is intended to include salts derived from inorganic or organic acids including, e.g., hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluroacetic, trichloroacetic, naphthalene-2 sulfonic and other acids; and salts derived from inorganic or organic bases including, e.g., sodium, potassium, calcium, magnesium, zinc, ammonia, lysine, arginine, histidine, polyhydroxylated amines or tetrafluoroborate. Exemplary pharmaceutically acceptable salts are found, e.g., in Berge, et al. (J. Pharm. Sci. 1977, 66(1), 1; and Gould, P. L., Int. J. Pharmaceutics 1986, 33, 201-217; (each hereby incorporated by reference in its entirety). Pharmaceutically acceptable salts are also intended to encompass hemi-salts, wherein the ratio of compound:acid is respectively 2:1. Exemplary hemi-salts are those salts derived from acids comprising two carboxylic acid groups, such as malic acid, fumaric acid, maleic acid, succinic acid, tartaric acid, glutaric acid, oxalic acid, adipic acid and citric acid. Other exemplary hemi-salts are those salts derived from diprotic mineral acids such as sulfuric acid. Exemplary preferred hemi-salts include, but are not limited to, hemimaleate, hemifumarate, and hemisuccinate.

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

An "effective amount", "sufficient amount" or "therapeutically effective amount" as used herein is an amount of a compound that is sufficient to effect beneficial or desired results, including clinical results. As such, the effective amount may be sufficient, e.g., to reduce or ameliorate the severity and/or duration of afflictions related to SHP2 phosphatase, or one or more symptoms thereof, prevent the advancement of conditions or symptoms related to afflictions related to SHP2 phosphatase, or enhance or otherwise improve the prophylactic or therapeutic effect(s) of another therapy. An effective amount also includes the amount of the compound that avoids or substantially attenuates undesirable side effects.

As used herein and as well understood in the art, "treatment" is an approach for obtaining beneficial or desired results, including clinical results. Beneficial or desired clinical results may include, but are not limited to, alleviation or amelioration of one or more symptoms or conditions, diminution of extent of disease or affliction, a stabilized (i.e., not worsening) state of disease or affliction, preventing spread of disease or affliction, delay or slowing of disease or affliction progression, amelioration or palliation of the disease or affliction state and remission (whether partial or total), whether detectable or undetectable. "Treatment" can also mean prolonging survival as compared to expected survival if not receiving treatment.

The phrase "in need thereof" refers to the need for symptomatic or asymptomatic relief from conditions related to SHP2 phosphatase activity or that may otherwise be relieved by the compounds and/or compositions of the disclosure.

Disclosed herein, for example, is a compound of Formula i, ii, iii, or iv, or a pharmaceutically acceptable salt or stereoisomer thereof, represented by:

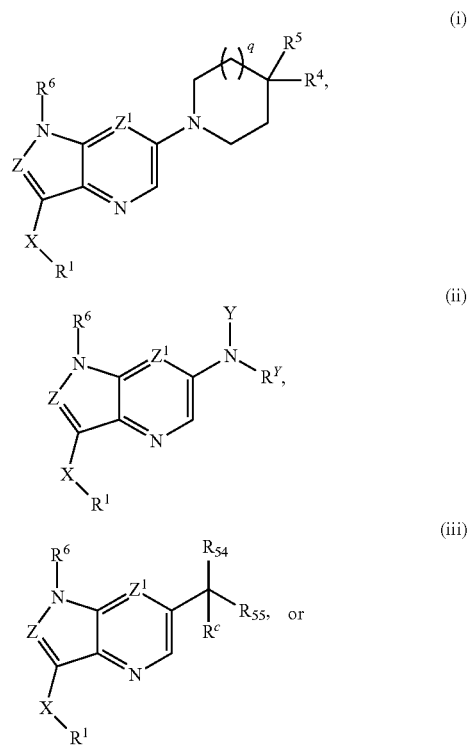

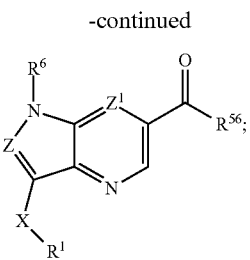

(iv)

wherein:
- $Z^1$ is N or CH;
- Z is N or CH;
- X is selected from the group consisting of a bond, —O—, —NR$^{X1}$—, and —S(O)$_w$— (wherein w is 0, 1 or 2);
- R$^{X1}$ is selected from the group consisting of hydrogen, —(C$_1$-C$_6$)alkyl and phenyl;
- R$^1$ is a ring moiety selected from the group consisting of a 8-12 membered bicyclic heteroaryl, a 11-15 membered tricyclic heteroaryl, phenyl, a 5-7 membered monocyclic heteroaryl, and a 4-7 membered heterocyclyl, wherein the ring moiety is optionally substituted with —O—S(O)$_2$—F or —S(O)$_2$—F, and wherein the ring moiety may additionally and optionally be substituted with one, two or more substituents each independently selected from the group consisting of R$^{10}$, —OR$^{10}$, —S(O)$_w$R$^{10}$ (wherein w is 0, 1 or 2), —C$_{1-6}$alkyl-S(O)$_w$—C$_{1-3}$alkyl, —N(R$^{10}$)$_2$, —N(CO)R$^{10}$, —N—S(O)$_w$—R$^{10}$ (where w is 0, 1 or 2), —OS(O)$_w$—R$^{10}$ (wherein w is 0, 1, or 2), —S(O)$_w$—N(R$^{10}$)$_2$ (wherein w is 0, 1 or 2), —S(O)(NH)R$^{10}$, —N(H)—SO$_2$—C$_{1-3}$alkyl, —N(SO$_2$—C$_{1-3}$alkyl)$_2$, P(O)(R$^{10}$)$_2$, —C(O)R$^{10}$, —C(O)OR$^{10}$, —C(O)N(R$^{10}$)$_2$, oxo, halogen, hydroxyl, cyano, nitro, —C(=N—OR$^a$)—C$_{1-3}$alkyl, —C(=N—OR$^a$)—H, —S(O)(NR$^a$)—C$_{1-3}$alkyl, phenyl (optionally substituted with one, two or three halogen, —O-phenyl, C$_{1-3}$alkyl or C$_{1-3}$haloalkyl), C$_{1-3}$alkyl, C$_{2-6}$alkynyl, C$_{1-3}$haloalkyl, C$_{3-6}$cycloalkyl, heterocyclyl (optionally substituted with one, two or three halogen, oxo, C$_{1-3}$alkyl or C$_{1-3}$haloalkyl), and heteroaryl (optionally substituted with one, two or three halogen, —C(O)N(R$^{10}$)$_2$, C$_{1-3}$alkyl, C$_{1-3}$alkyl-O—C$_{1-3}$alkyl, C$_{1-3}$alkyl-OH, or C$_{1-3}$haloalkyl);
- R$^{10}$ is independently selected from the group consisting of hydrogen, C$_{1-6}$alkyl, C$_{2-6}$alkenyl, C$_{2-6}$alkynyl, C$_{3-6}$cycloalkyl, C$_{5-6}$cycloalkenyl, C$_{2-6}$heteroalkyl, heterocycloalkyl, aryl, and heteroaryl; wherein C$_{1-6}$alkyl, C$_{2-6}$alkenyl, C$_{2-6}$alkynyl, C$_{3-6}$cycloalkyl, C$_{5-6}$cycloalkenyl, C$_{2-6}$heteroalkyl, heterocycloalkyl, aryl, and heteroaryl is optionally substituted by one, two, three or more substituents each independently selected from the group consisting of halogen, hydroxyl, —NR$^a$C(O)—R$^{20}$, —C(O)—R$^{20}$, —C(NR$^a$)—R$^b$, —NR$^a$R$^b$, C$_{1-6}$alkyl, C$_{1-6}$haloalkyl and C$_{1-6}$alkoxy;
- R$^{20}$ is selected from the group consisting of hydrogen, hydroxyl, halogen, —NR$^a$R$^b$, C$_{1-6}$alkyl and C$_{1-6}$alkoxy;
- R$^a$ and R$^b$ are each independently selected from the group consisting of hydrogen and C$_{1-3}$alkyl;
- R$^6$ is independently for each occurrence selected from the group consisting of H, —(C$_1$-C$_6$)alkyl, —C(O)OC$_{1-4}$alkyl, and phenyl;
- q is 0 or 1;
- R$^Y$ is selected from the group consisting of hydrogen and —(C$_1$-C$_6$)alkyl;
- Y is selected from the group consisting of a 3-7 membered saturated carbocycle, a 4-7 membered saturated heterocycle, phenyl, and a 5-6 membered monocyclic heteroaryl; wherein Y is optionally substituted with one or more substituents each independently selected from the group consisting of (C$_1$-C$_6$)alkyl, —C(O)N(R$^6$)$_2$, —N(R$^6$)$_2$, halogen, and cyano, wherein said —(C$_1$-C$_6$)alkyl is optionally substituted with one or more substituents selected from the group consisting of —OH, —N(R$^6$)$_2$, oxo, and halogen;
- R$^{55}$ is selected from the group consisting of —C$_{1-4}$alkyl-N(R$^6$)$_2$, —N(R$^6$)$_2$, and heteroaryl (optionally substituted by one, two, or three substituent each independently selected from halogen, hydroxyl, cyano, —(C$_1$-C$_6$)alkyl, —O(C$_1$-C$_6$)alkyl, —C(O)N(R$^6$)$_2$, —N(R$^6$)$_2$, and —(C$_1$-C$_6$)alkyl-N(R$^6$)$_2$);
- R$^{54}$ is selected from the group consisting of H, and C$_{1-2}$alkyl, or
- R$^{54}$ and R$^{55}$ taken together with the carbon to which they are attached form a ring selected from the group consisting of C$_{3-6}$cycloalkyl and heterocyclyl, wherein the ring is optionally substituted on a carbon by one, two or three substituents each independently selected from the group consisting of R$^4$ and R$^5$ and on a nitrogen if present by R$^6$;
- R$^C$ is selected from the group consisting of H, OH, —(C$_1$-C$_6$)alkyl, —C(O)—O—C$_{1-6}$(alkyl), —C(O)—C$_{1-6}$(alkyl), and heterocyclyl, wherein C$_{1-6}$(alkyl) is optionally substituted by one two or three substituents each selected from the group consisting of halogen, hydroxyl and N(R$_6$)$_2$; or
- wherein R$^C$ is absent R$^{54}$ and R$^{55}$ taken together with the carbon to which they are attached form a ring selected from C$_{5-6}$cyclalkenyl and phenyl; wherein the ring is optionally substituted on a carbon by one, two or three substituents each independently selected from the group consisting of R$^4$ and R$^5$;
- R$^{56}$ is N(R$_6$)$_2$ or heterocycle (optionally substituted by one, two or three substituents each independently selected from halogen, hydroxyl, N(R$_6$)$_2$, —(C$_1$-C$_6$)alkyl, —C(O)—O—C$_{1-6}$(alkyl), —C(O)—C$_{1-6}$(alkyl), wherein C$_{1-6}$(alkyl) is optionally substituted by one two or three substituents each selected from the group consisting of: halogen, hydroxyl or N(R$_6$)$_2$);
- R$^4$ and R$^5$ are each independently selected from the group consisting of H, —OH, —(C$_1$-C$_6$)alkyl, —O(C$_1$-C$_6$)alkyl, —(C$_1$-C$_6$)alkyl-O—R$^6$, —C(O)N(R$^6$)$_2$, —N(R$^6$)$_2$, halogen, —(C$_1$-C$_6$)alkyl-N(R$^6$)$_2$, and cyano, wherein said —(C$_1$-C$_6$)alkyl, —O(C$_1$-C$_6$)alkyl, —(C$_1$-C$_6$)alkyl-O—R$^6$, or —(C$_1$-C$_6$)alkyl-N(R$^6$)$_2$ is optionally substituted with one or more substituents selected from the group consisting of —OH, —NH$_2$, oxo, and halogen;
- or R$^4$ and R$^5$, taken together with the carbon to which they are attached, form a 4-6 membered carbocyclic or heterocyclic ring B; which ring is optionally substituted with one or two substituents each independently selected from the group consisting of (C$_1$-C$_6$)alkyl, —O(C$_1$-C$_6$)alkyl, —N(R$^6$)$_2$, —C(O)N(R$^6$)$_2$, halogen, oxo, and cyano and/or which ring may be fused to a ring D;
- D is selected from the group consisting of: phenyl, a 5- or 6-membered heteroaryl having one or two heteroatoms each independently selected from the group consisting of S, O or N, and C$_{3-6}$cycloalkyl, wherein D is optionally substituted on an available carbon with one or two substituents each independently selected from R$^{D1}$, and, optionally substituted, on nitrogen, if present, with one or two substituents each independently selected from $R^{D2}$;

B is fused to D such that the two atoms shared by D and B are both carbon or one carbon and one nitrogen;

wherein if $R^4$ and $R^5$, taken together with the carbon to which they are attached, form the 4-6 membered carbocyclic or heterocyclic ring B, which ring may be fused to the ring D; then $R^1$ is substituted with —O—S(O)$_2$—F or —S(O)$_2$—F;

$R^{D1}$ is selected from the group consisting of hydroxyl, cyano, halogen, and —N(R$^6$)$_2$; and $R^{D2}$ is selected from —(C$_1$-C$_6$)alkyl and phenyl.

Also disclosed herein is a compound of Formula Ia, Ib or Ic, or Id, or a pharmaceutically acceptable salt or stereoisomer thereof, represented by:

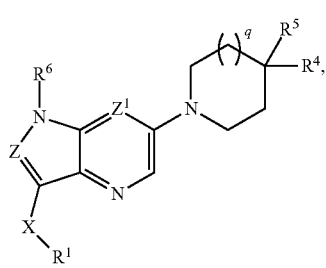

(Ia)

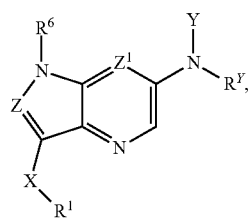

(Ib)

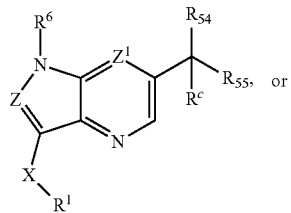

(Ic)

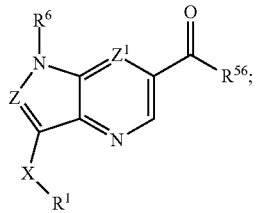

(Id)

wherein:
$Z^1$ is N or CH;
Z is N or CH;
X is selected from the group consisting of a bond, —O—, —NR$^{X1}$—, and —S(O)$_w$— (wherein w is 0, 1 or 2);
$R^{X1}$ is selected from the group consisting of hydrogen, —(C$_1$-C$_6$)alkyl and phenyl;
$R^1$ is a ring moiety substituted with —O—S(O)$_2$—F or —S(O)$_2$—F, wherein the ring moiety is selected from the group consisting of a 8-12 membered bicyclic heteroaryl, a 11-15 membered tricyclic heteroaryl, phenyl, a 5-7 membered monocyclic heteroaryl, and a 4-7 membered heterocyclyl, wherein the ring moiety is optionally substituted with one, two or more substituents each independently selected from the group consisting of $R^{10}$, —OR$^{10}$, —S(O)$_w$R$^{10}$ (wherein w is 0, 1 or 2), —C$_{1-6}$alkyl-S(O)$_w$—C$_{1-3}$alkyl, —N(R$^{10}$)$_2$, —N(CO)R$^{10}$, —N—S(O)$_w$—R$^{10}$ (where w is 0, 1 or 2), —OS(O)$_w$—R$^{10}$ (wherein w is 0, 1, or 2), —S(O)$_w$—N(R$^{10}$)$_2$ (wherein w is 0, 1 or 2), —S(O)(NH)R$^{10}$, —N(H)—SO$_2$—C$_{1-3}$alkyl, —N(SO$_2$—C$_{1-3}$alkyl)$_2$, P(O)(R$^{10}$)$_2$, —C(O)R$^{10}$, —C(O)OR$^{10}$, —C(O)N(R$^{10}$)$_2$, oxo, halogen, hydroxyl, cyano, nitro, —C(=N—OR$^a$)—C$_{1-3}$alkyl, —C(=N—OR$^a$)—H, —S(O)(NR$^a$)—C$_{1-3}$alkyl, phenyl (optionally substituted with one, two or three halogen, —O-phenyl, C$_{1-3}$alkyl or C$_{1-3}$haloalkyl), C$_{1-3}$alkyl, C$_{2-6}$alkynyl, C$_{1-3}$haloalkyl, C$_{3-6}$cycloalkyl, heterocyclyl (optionally substituted with one, two or three halogen, oxo, C$_{1-3}$alkyl or C$_{1-3}$haloalkyl), and heteroaryl (optionally substituted with one, two or three halogen, —C(O)N(R$^{10}$)$_2$, C$_{1-3}$alkyl, C$_{1-3}$alkyl-O—C$_{1-3}$alkyl, C$_{1-3}$alkyl-OH, or C$_{1-3}$haloalkyl);

$R^{10}$ is independently selected from the group consisting of hydrogen, C$_{1-6}$alkyl, C$_{2-6}$alkenyl, C$_{2-6}$alkynyl, C$_{3-6}$cycloalkyl, C$_{5-6}$cycloalkenyl, C$_{2-6}$heteroalkyl, heterocycloalkyl, aryl, and heteroaryl; wherein C$_{1-6}$alkyl, C$_{2-6}$alkenyl, C$_{2-6}$alkynyl, C$_{3-6}$cycloalkyl, C$_{5-6}$cycloalkenyl, C$_{2-6}$heteroalkyl, heterocycloalkyl, aryl, and heteroaryl is optionally substituted by one, two, three or more substituents each independently selected from the group consisting of halogen, hydroxyl, —NR$^a$C(O)—R$^{20}$, —C(O)—R$^{20}$, —C(NR$^a$)—R$^b$, —NR$^a$R$^b$, C$_{1-6}$alkyl, C$_{1-6}$haloalkyl and C$_{1-6}$alkoxy;

$R^{20}$ is selected from the group consisting of hydrogen, hydroxyl, halogen, —NR$^a$R$^b$, C$_{1-6}$alkyl and C$_{1-6}$alkoxy;

$R^a$ and $R^b$ are each independently selected from the group consisting of hydrogen and C$_{1-3}$alkyl;

$R^6$ is independently for each occurrence selected from the group consisting of H, —(C$_1$-C$_6$)alkyl, —C(O)OC$_{1-4}$alkyl, and phenyl;

q is 0 or 1;

$R^Y$ is selected from the group consisting of hydrogen and —(C$_1$-C$_6$)alkyl;

Y is selected from the group consisting of a 3-7 membered saturated carbocycle, a 4-7 membered saturated heterocycle, phenyl, and a 5-6 membered monocyclic heteroaryl; wherein Y is optionally substituted with one or more substituents each independently selected from the group consisting of (C$_1$-C$_6$)alkyl, —C(O)N(R$^6$)$_2$, —N(R$^6$)$_2$, halogen, and cyano, wherein said —(C$_1$-C$_6$)alkyl is optionally substituted with one or more substituents selected from the group consisting of —OH, —N(R$^6$)$_2$, oxo, and halogen;

$R^{55}$ is selected from the group consisting of —C$_{1-4}$alkyl-N(R$^6$)$_2$, —N(R$^6$)$_2$, and heteroaryl (optionally substituted by one, two, or three substituent each independently selected from halogen, hydroxyl, cyano, —(C$_1$-C$_6$)alkyl, —O(C$_1$-C$_6$)alkyl, —C(O)N(R$^6$)$_2$, —N(R$^6$)$_2$, and —(C$_1$-C$_6$)alkyl-N(R$^6$)$_2$);

$R^{54}$ is selected from the group consisting of H, and C$_{1-2}$alkyl, or $R^{54}$ and $R^{55}$ taken together with the carbon to which they are attached form a ring selected from the group consisting of C$_{3-6}$cycloalkyl and heterocyclyl, wherein the ring is optionally substituted on a carbon by one, two or three substituents each independently selected from the group consisting of $R^4$ and $R^5$ and on a nitrogen if present by $R^6$;

$R^C$ is selected from the group consisting of H, OH, —($C_1$-$C_6$)alkyl, —C(O)—O—$C_{1-6}$(alkyl), —C(O)—$C_{1-6}$(alkyl), and heterocyclyl, wherein $C_{1-6}$(alkyl) is optionally substituted by one two or three substituents each selected from the group consisting of halogen, hydroxyl and N($R_6$)$_2$; or wherein $R^C$ is absent $R^{54}$ and $R^{55}$ taken together with the carbon to which they are attached form a ring selected from $C_{5-6}$cyclalkenyl and phenyl; wherein the ring is optionally substituted on a carbon by one, two or three substituents each independently selected from the group consisting of $R^4$ and $R^5$;

$R^{56}$ is N($R_6$)$_2$ or heterocycle (optionally substituted by one, two or three substituents each independently selected from halogen, hydroxyl, N($R_6$)$_2$, —($C_1$-$C_6$)alkyl, —C(O)—O—$C_{1-6}$(alkyl), —C(O)—$C_{1-6}$(alkyl), wherein $C_{1-6}$(alkyl) is optionally substituted by one two or three substituents each selected from the group consisting of: halogen, hydroxyl or N($R_6$)$_2$);

$R^4$ and $R^5$ are each independently selected from the group consisting of H, —OH, —($C_1$-$C_6$)alkyl, —O($C_1$-$C_6$)alkyl, —($C_1$-$C_6$)alkyl-O—$R^6$, —C(O)N($R^6$)$_2$, —N($R^6$)$_2$, halogen, —($C_1$-$C_6$)alkyl-N($R^6$)$_2$, and cyano, wherein said —($C_1$-$C_6$)alkyl, —O($C_1$-$C_6$)alkyl, —($C_1$-$C_6$)alkyl-O—$R^6$, or —($C_1$-$C_6$)alkyl-N($R^6$)$_2$ is optionally substituted with one or more substituents selected from the group consisting of —OH, —NH$_2$, oxo, and halogen;

or $R^4$ and $R^5$, taken together with the carbon to which they are attached, form a 4-6 membered carbocyclic or heterocyclic ring B; which ring is optionally substituted with one or two substituents each independently selected from the group consisting of ($C_1$-$C_6$)alkyl, —O($C_1$-$C_6$)alkyl, —N($R^6$)$_2$, —C(O)N($R^6$)$_2$, halogen, oxo, and cyano and/or which ring may be fused to a ring D;

D is selected from the group consisting of: phenyl, a 5- or 6-membered heteroaryl having one or two heteroatoms each independently selected from the group consisting of S, O or N, and $C_{3-6}$cycloalkyl, wherein D is optionally substituted on an available carbon with one or two substituents each independently selected from $R^{D1}$ and, optionally substituted, on nitrogen, if present, with one or two substituents each independently selected from $R^{D2}$;

B is fused to D such that D and B are both carbon or one carbon and one nitrogen;

$R^{D1}$ is selected from the group consisting of hydroxyl, cyano, halogen, and —N($R^6$)$_2$; and $R^{D2}$ is selected from —($C_1$-$C_6$)alkyl and phenyl.

In some embodiments, X is a bond, $R^1$ is a nitrogen containing ring moiety and $R^1$ is bound through the nitrogen.

In some embodiments, $R^1$ is selected from the group consisting of 1,2,3,4-tetrahydroquinolin-1-yl, 1,2,3,4-tetrahydro-1,5-naphthyridin-1-yl, 1,2,3,4-tetrahydroquinolin-1-yl, 1,2,3,4-tetrahydroquinoxalin-1-yl, 1,2,3,4-tetrahydropyrido[2,3-b]pyrazin-1-yl, 1H-benzo[d]imidazol-1-yl, indolin-1-yl, 2,3-dihydro-1H-pyrrolo[3,2-b]pyridin-1-yl, 2,3-dihydro-1H-pyrrolo[3,2-c]pyridin-1-yl, isoindolin-2-yl, 2,3,4,5-tetrahydrobenzo[f][1,4]oxazepin-4-yl, 2-(3,4-dihydroisoquinolin-1(2H)-one), 2-(3,4-dihydroisoquinolin-1(2H)-one), 2,3-dihydro-1H-pyrido[2,3-b][1,4]oxazin-1-yl, piperidin-1-yl, 1-(1,2,3,4-tetrahydro-6H-pyrido[1,2-a]pyrimidin-6-one), 1,2,3,4-tetrahydro-1,8-naphthyridin-1-yl, 1-(3,4-dihydro-1,5-naphthyridin-2(1H)-one), 2,3,4,5-tetrahydro-1H-benzo[b]azepin-1-yl, 1-(2,3-dihydroquinolin-4(1H)-one), 2,3-dihydro-1H-pyrido[2,3-b][1,4]oxazin-1-yl, 1,2,3,4-tetrahydro-1,6-naphthyridin-1-yl, 5,6,7,8-tetrahydro-4H-pyrazolo[1,5-a][1,3]diazepin-4-yl, 3,4-dihydroquinoxalin-1-yl-2(1H)-one, 2,3,4,6-tetrahydro-1,6-naphthyridin-1-yl-5(1H)-one, 1,2,3,4-tetrahydroisoquinolin-2-yl, 1,2,3,4-tetrahydro-2,7-naphthyridin-2-yl, 1,2,3,4-tetrahydro-2,6-naphthyridin-2-yl, 3,4-dihydro-2H-benzo[b][1,4]thiazin-4-yl 1 1-dioxide, 1,2,3,4-tetrahydropyrazino[2,3-d]pyridazin-1-yl, 1,4-dihydropyrido[3,4-b]pyrazin-1-yl-3(2H)-one, 5,6,7,8-tetrahydro-1,6-naphthyridin-6-yl, 5,6,7,8-tetrahydro-1,7-naphthyridin-7-yl, 1,2,3,4-tetrahydropyrido[3,4-b]pyrazin-1-yl, 5,8-dihydropteridin-5-yl-7(6H)-one, 4,5,6,7-tetrahydrothieno[3,2-b]pyridin-4-yl, or 5,6,7,8-tetrahydropyrazino[2,3-c]pyridazin-5-yl wherein the nitrogen ring moiety may be optionally substituted with one or two substituents each independently selected from the group consisting of Cl, F, —CN, $C_{1-4}$alkyl, —O$C_{1-4}$alkyl, $C_{2-6}$alkenyl, $C_{2-4}$alkynyl, $C_{3-6}$cycloalkyl, $C_{5-6}$cycloalkenyl, —C(H)=N—OCH$_3$, —C(H)=N—OH, —C(CH$_3$)=N—OH, —(CH$_2$)$_{0-1}$C(O)NH$_2$, —(CH$_2$)$_{0-1}$C(O)NHC$_{1-4}$alkyl, —(CH$_2$)$_{0-1}$C(O)N(C$_{1-4}$alkyl)$_2$, —(CH$_2$)$_{0-1}$C(O)OC$_{1-4}$alkyl, —(CH$_2$)$_{0-1}$C(O)OH, —S(O)$_2$C$_{1-4}$alkyl, —(CH$_2$)$_{0-1}$NH$_2$, —(CH$_2$)$_{0-1}$NHC$_{1-4}$alkyl, —(CH$_2$)$_{0-1}$(C$_{1-4}$alkyl)$_2$, —(CH$_2$)$_{0-1}$NH(CO)C$_{1-4}$alkyl, phenyl, optionally substituted heteroaryl and optionally substituted heterocyclyl, wherein $C_{1-4}$alkyl or $C_{3-6}$cycloalkyl may be optionally substituted with one, two or three fluorine atoms, one or two hydroxyl groups, or one or two —OC$_{1-2}$alkyl groups.

In some embodiments, heteroaryl is selected from the group consisting of 2-pyridyl, 3-pyridyl, 4-pyridyl, 1,2,4-triazol-3-yl, thiazol-2-yl, pyrazol-1-yl, pyrazol-3-yl, pyrazol-4-yl, imidazol-2-yl, oxazol-2-yl, oxazol-5-yl, isoxazol-5-yl, thiazol-2-yl, thiazol-5-yl, 1,3,4-thiadiazol-2-yl, and 1,2,4-oxadiazol-3-yl, 1,3,4-oxadiazol-2-yl, 1,2,4-triazol-2-yl, 1,3,4-triazol-2-yl; wherein heteroaryl may be optionally substituted with $C_{1-2}$alkyl (optionally substituted with one, two or three fluorine atoms, one or two 2 hydroxyl groups, or one or two —OC$_{1-2}$alkyl groups).

In some embodiments, heterocyclyl is selected from the group consisting of tetrahydrofuran-3-yl, pyrrolidine-1-yl, piperazin-1-yl, piperidin-4-yl, piperidin-1-yl, 1,2,3,6-tetrahydropyridin-4-yl, 2,5-dihydrofuran-3-yl, piperazin-1-yl-3-one, morpholino, tetrahydropyran-2-yl, or 1,2,4-oxadiazo-3-yl-5-one, wherein heterocyclyl may be optionally substituted with hydroxyl or $C_{1-2}$alkyl (optionally substituted with one, two or three fluorine atoms, one or two 2 hydroxyl groups, or one or two —OC$_{1-2}$alkyl groups).

In some embodiments, $R^1$ is a 1,2,3,4-tetrahydroquinoline moiety optionally substituted with one, two or three halo, —C(O)N($R^{10}$)$_2$, $C_{1-3}$alkyl, $C_{1-3}$haloalkyl, and heteroaryl (optionally substituted with one, two or three halogen, —C(O)N($R^{10}$)$_2$, $C_{1-3}$alkyl, $C_{1-3}$alkyl-O—$C_{1-3}$alkyl, $C_{1-3}$alkyl-OH, or $C_{1-3}$haloalkyl).

In some embodiments, $R^1$ is a 1,2,3,4-tetrahydro-1,5-naphthyridine moiety optionally substituted with one, two or three halo, —C(O)N($R^{10}$)$_2$, $C_{1-3}$alkyl, $C_{1-3}$haloalkyl, and heteroaryl (optionally substituted with one, two or three halogen, —C(O)N($R^{10}$)$_2$, $C_{1-3}$alkyl, $C_{1-3}$alkyl-O—$C_{1-3}$alkyl, $C_{1-3}$alkyl-OH, or $C_{1-3}$haloalkyl).

In some embodiments, $R^1$ is phenyl; wherein phenyl is optionally substituted by one, two, or three substituents each independently selected from the group consisting of —OR$^{10}$, —N($R^{10}$)$_2$, halogen, and cyano.

In some embodiments, $R^1$ is pyridyl; wherein pyridyl is optionally substituted by one, two, or three substituents each independently selected from the group consisting of —OR$^{10}$, —N(R$^{10}$)$_2$, halogen, and cyano.

In some embodiments, R$^1$ is indolyl or indolinyl, wherein indolyl or indolinyl is optionally substituted with one, two, or three substituents each independently selected from the group consisting of —OR$^{10}$, —N(R$^{10}$)$_2$, halogen, and cyano; and wherein indolyl or indolinyl is bound through carbon.

In some embodiments, the compound is represented by:

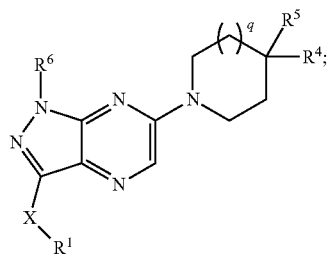

wherein q is 0 or 1.

In some embodiments, R$^4$ and R$^5$ are each independently selected from the group consisting of H, —OH, —(C$_1$-C$_6$)alkyl, —O(C$_1$-C$_6$)alkyl, —(C$_1$-C$_6$)alkyl-O—R$^6$, —C(O)N(R$^6$)$_2$, —N(R$^6$)$_2$, halogen, —(C$_1$-C$_6$)alkyl-N(R$^6$)$_2$, and cyano, wherein said —(C$_1$-C$_6$)alkyl, —O(C$_1$-C$_6$)alkyl, —(C$_1$-C$_6$)alkyl-O—R$^6$, or —(C$_1$-C$_6$)alkyl-N(R$^6$)$_2$ is optionally substituted with one or more substituents selected from the group consisting of —OH, —NH$_2$, oxo, and halogen.

In some embodiments, R$^4$ and R$^5$ are independently selected from the group consisting of fluorine, —NH$_2$, —CH$_3$, —OCH$_3$, —CH$_2$H, —CH$_2$NH$_2$ and —CH(NH)$_2$CH$_3$.

In some embodiments, R$^4$ and R$^5$, taken together with the carbon to which they are attached, form a 4-6 membered carbocyclic or heterocyclic ring, which ring is optionally substituted with one or two substituents each independently selected from the group consisting of (C$_1$-C$_6$)alkyl, —O(C$_1$-C$_6$)alkyl, —N(R$^6$)$_2$, —C(O)N(R$^6$)$_2$, halogen, oxo, and cyano.

In some embodiments, R$^4$ and R$^5$ taken together, are selected from the group consisting of:

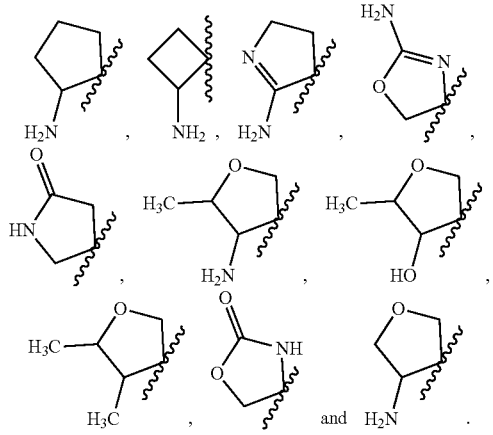

In some embodiments, q is 1.

In some embodiments, the compound is represented by:

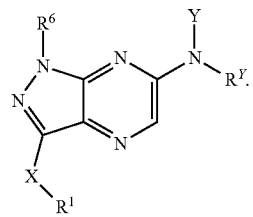

In some embodiments, Y is cyclopentyl, wherein Y is optionally substituted with one or more substituents each independently selected from the group consisting of (C$_1$-C$_6$)alkyl, —C(O)N(R$^6$)$_2$, —N(R$^6$)$_2$, halogen, and cyano, wherein said —(C$_1$-C$_6$)alkyl is optionally substituted with one or more substituents selected from the group consisting of —OH, —N(R$^6$)$_2$, oxo, and halogen.

In some embodiments, Y is cyclohexyl, wherein Y is optionally substituted with one or more substituents each independently selected from the group consisting of (C$_1$-C$_6$)alkyl, —C(O)N(R$^6$)$_2$, —N(R$^6$)$_2$, halogen, and cyano, wherein said —(C$_1$-C$_6$)alkyl is optionally substituted with one or more substituents selected from the group consisting of —OH, —N(R$^6$)$_2$, oxo, and halogen.

In some embodiments, Y is tetrahydrofuranyl, wherein Y is optionally substituted with one or more substituents each independently selected from the group consisting of (C$_1$-C$_6$)alkyl, —C(O)N(R$^6$)$_2$, —N(R$^6$)$_2$, halogen, and cyano, wherein said —(C$_1$-C$_6$)alkyl is optionally substituted with one or more substituents selected from the group consisting of —OH, —N(R$^6$)$_2$, oxo, and halogen.

In some embodiments, wherein Y is tetrahydropyranyl, wherein Y is optionally substituted with one or more substituents each independently selected from the group consisting of (C$_1$-C$_6$)alkyl, —C(O)N(R$^6$)$_2$, —N(R$^6$)$_2$, halogen, and cyano, wherein said —(C$_1$-C$_6$)alkyl is optionally substituted with one or more substituents selected from the group consisting of —OH, —N(R$^6$)$_2$, oxo, and halogen.

In some embodiments, Y is substituted on an available carbon by a substituent selected from the group consisting of —NH$_2$ and —CH$_2$NH$_2$.

In some embodiments, Y is selected from the group consisting of:

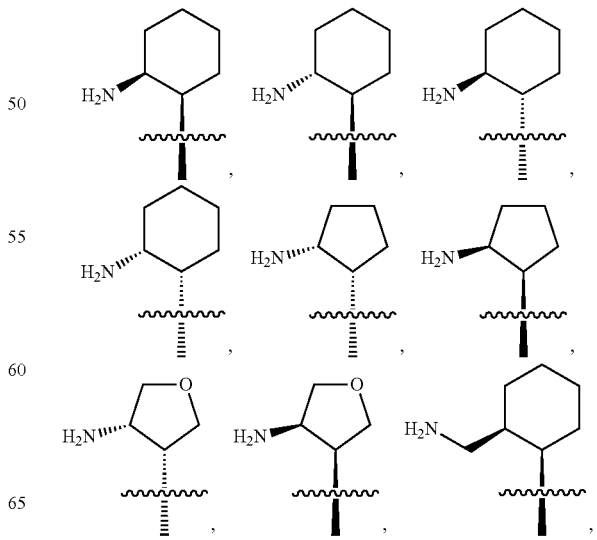

-continued

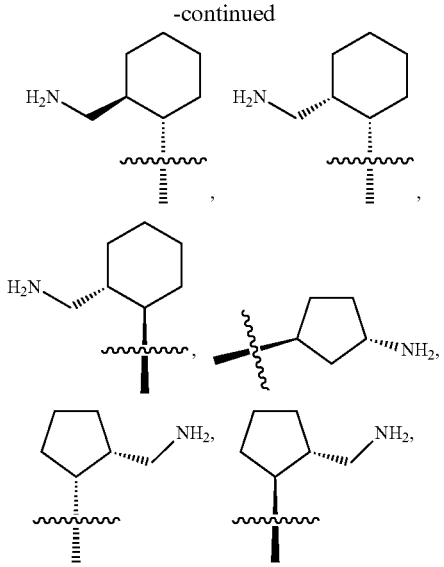

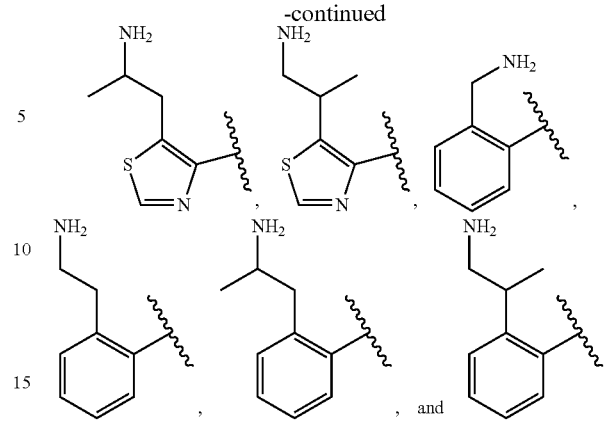

and stereoisomers thereof.

In some embodiments, Y is phenyl or 5-6 membered heteroaryl, wherein Y is optionally substituted with one or more substituents each independently selected from the group consisting of $(C_1$-$C_6)$alkyl, —C(O)N(R$^6$)$_2$, —N(R$^6$)$_2$, halogen, and cyano, wherein said —$(C_1$-$C_6)$alkyl is optionally substituted with one or more substituents selected from the group consisting of —OH, —N(R$^6$)$_2$, oxo, and halogen.

In some embodiments, Y is selected from the group consisting of:

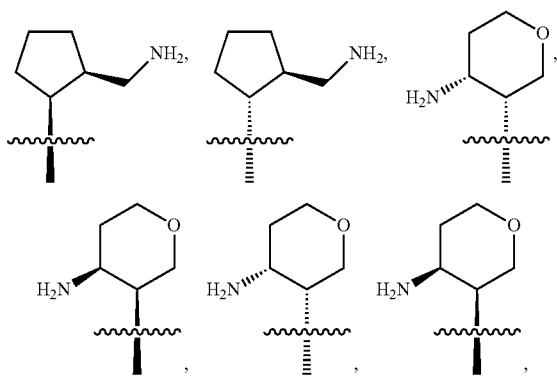

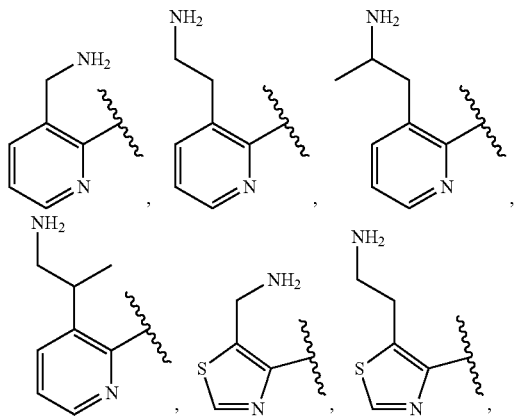

In some embodiments, R$^Y$ is —H or —CH$_3$.
In some embodiments, the compound is represented by:

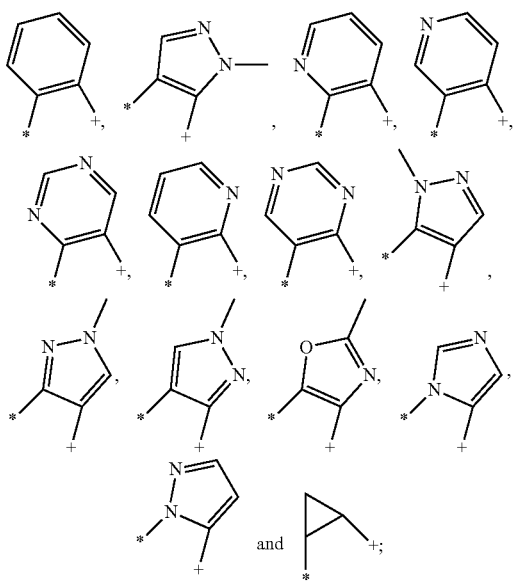

wherein R$^B$ is independently selected from the group consisting of hydrogen, —C(O)N(R$^6$)$_2$, —N(R$^6$)$_2$, and —$C_{1-3}$alkyl-N(R$^6$)$_2$;

U is selected from the group consisting of C, CH and N;
V is selected from the group consisting of C, CH and N;
wherein at least one of U or V is not N.

In some embodiments, D is selected from the group consisting of:

wherein * and + represent fusion points of attachment to ring B.

In some embodiments, the compound is represented by:

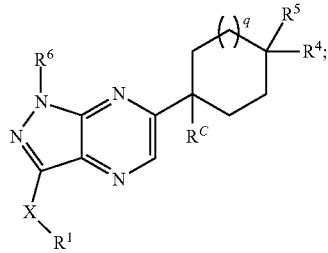

wherein q is 0 or 1.

In some embodiments, the compound is represented by:

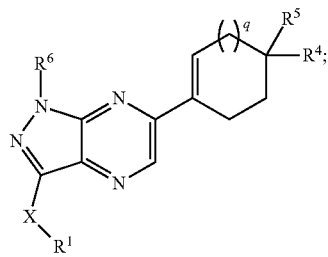

wherein q is 0 or 1.

In some embodiments, $R^4$ and $R^5$ are independently selected from the group consisting of hydrogen, halogen, hydroxyl, —($C_1$-$C_3$)alkyl, —($C_1$-$C_3$)alkoxy, and —N($R^6$)$_2$, wherein said —($C_1$-$C_3$)alkyl is optionally substituted with one or more substituents selected from the group consisting of —OH, —N($R^6$)$_2$, and halogen.

In some embodiments, $R^4$ and $R^5$ are independently selected from the group consisting of fluorine, —NH$_2$, —CH$_3$, —OCH$_3$, —CH$_2$H, —CH$_2$NH$_2$ and —CH(NH)$_2$CH$_3$.

In some embodiments, $R^4$ and $R^5$, taken together with the carbon to which they are attached, form a 4-6 membered carbocyclic or heterocyclic ring, which ring is optionally substituted with one or two substituents each independently selected from the group consisting of ($C_1$-$C_6$)alkyl, —O($C_1$-$C_6$)alkyl, —N($R^6$)$_2$, —C(O)N($R^6$)$_2$, halogen, oxo, and cyano.

In some embodiments, $R^4$ and $R^5$ taken together, are selected from the group consisting of:

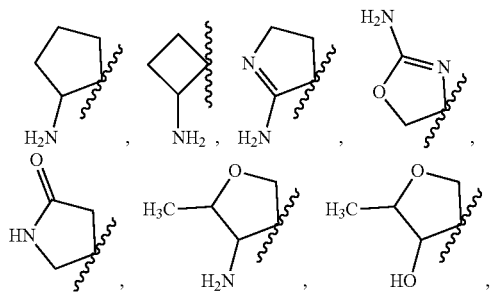

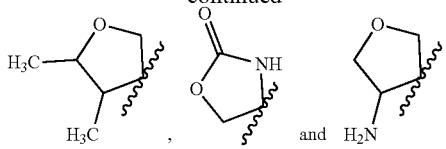

In some embodiments, the compound is represented by:

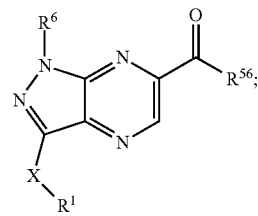

wherein $R^{56}$ is selected from the group consisting of piperidin-1-yl and pyrrolidine-1-yl, wherein $R^{56}$ is optionally substituted by one or two substituents each selected from the group consisting of $C_{1-2}$alkylNH$_2$, NH$_2$, and $C_{1-2}$alkyl.

In some embodiments, the compound is represented by:

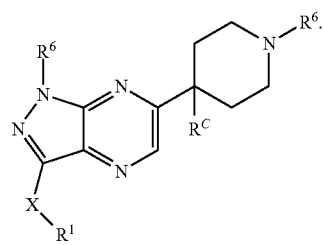

In some embodiments, the compound is represented by:

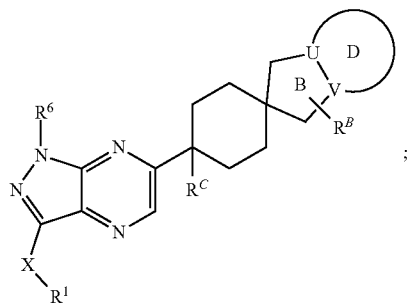

wherein:
$R^B$ is independently selected from the group consisting of hydrogen, —C(O)N($R^6$)$_2$, —N($R^6$)$_2$, and —C$_{1-3}$alkyl-N($R^6$)$_2$;
U is selected from the group consisting of C, CH and N;
V is selected from the group consisting of C, CH and N;
wherein at least one of U or V is not N.

In some embodiments, D is selected from the group consisting of:

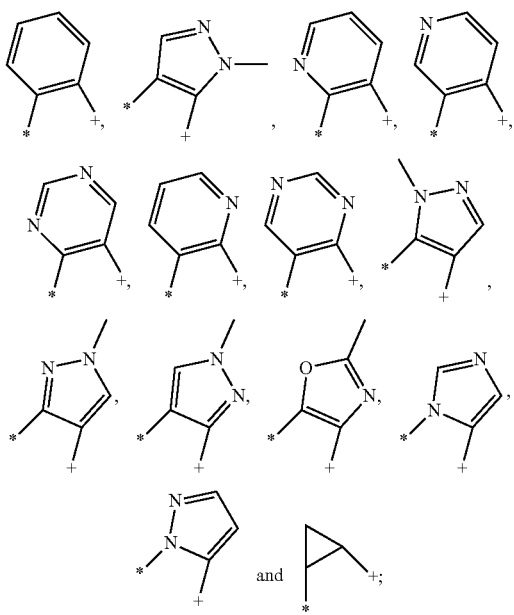

wherein * and + represent fusion points of attachment to ring B.

Also disclosed herein, for example, is a compound of Formula IIa, IIb, or Ic, or a pharmaceutically acceptable salt or stereoisomer thereof, represented by:

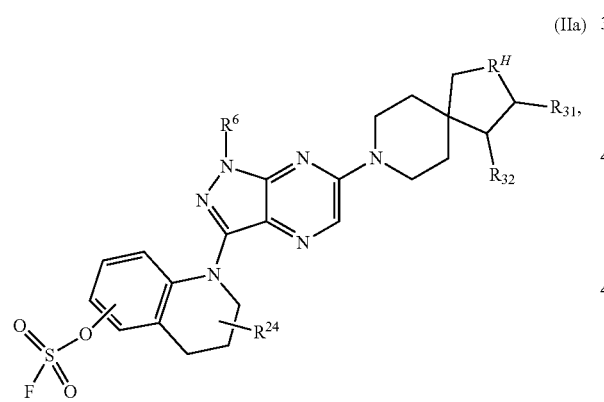

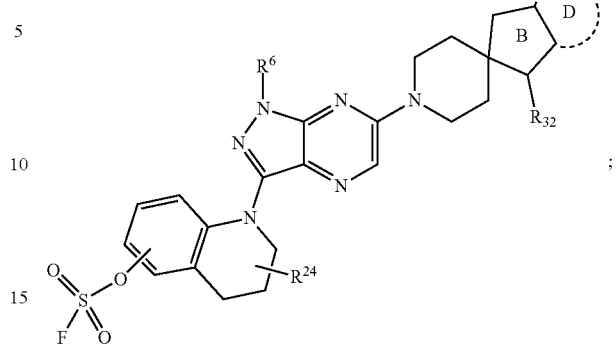

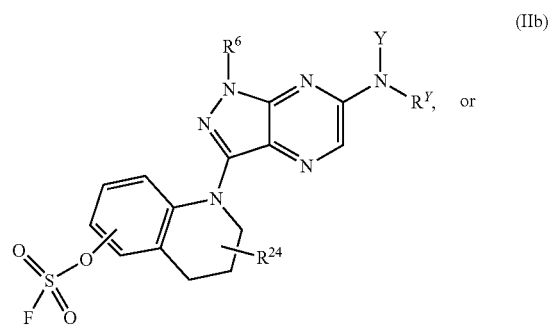

wherein:
$R^H$ is O or $C(R^{25})_2$;
$R^{31}$ is hydrogen or $C_{1-6}$alkyl;
$R^{32}$ is $N(R^6)_2$;
$R^{24}$ is selected from the group consisting of hydrogen, halogen, and $C_1$-$C_6$alkyl;
$R^{25}$ is independently selected for each occurrence from the group consisting of hydrogen, hydroxyl, halogen, and $C_1$-$C_6$alkyl (optionally substituted by hydroxyl or halogen);
$R^6$ is independently for each occurrence selected from the group consisting of H, —$(C_1$-$C_6)$alkyl, —$C(O)OC_{1-4}$alkyl, and phenyl;
Y is selected from the group consisting of a 3-7 membered saturated carbocycle, a 4-7 membered saturated heterocycle, phenyl, and a 5-6 membered monocyclic heteroaryl; wherein Y is optionally substituted with one or more substituents each independently selected from the group consisting of $(C_1$-$C_6)$alkyl, —$C(O)N(R^6)_2$, —$N(R^6)_2$, halogen, and cyano, wherein said —$(C_1$-$C_6)$alkyl is optionally substituted with one or more substituents selected from the group consisting of —OH, —$N(R^6)_2$, oxo, and halogen;
$R^Y$ is selected from the group consisting of hydrogen and —$(C_1$-$C_6)$alkyl;
D is an optional ring moiety selected from the group consisting of: phenyl, a 5- or 6-membered heteroaryl having one or two heteroatoms each independently selected from the group consisting of S, O or N, and $C_{3-6}$cycloalkyl, wherein D is optionally substituted on an available carbon with one or two substituents each independently selected from $R^{D1}$,and, optionally substituted, on nitrogen, if present, with one or two substituents each independently selected from $R^{D2}$; B is fused to D such that the two atoms shared by D and B are both carbon or one carbon and one nitrogen;
$R^B$ is independently selected from the group consisting of hydrogen, —$C(O)N(R^6)_2$, —$N(R^6)_2$, and —$C_{1-3}$alkyl-$N(R^6)_2$;
$R^{D1}$ is selected from the group consisting of hydroxyl, cyano, halogen, and —$N(R^6)_2$; and
$R^{D2}$ is selected from the group consisting of —$(C_1$-$C_6)$alkyl and phenyl.

Also disclosed herein, for example, is a compound of Formula IIIa, IIIb, or IIIc, or a pharmaceutically acceptable salt or stereoisomer thereof, represented by:

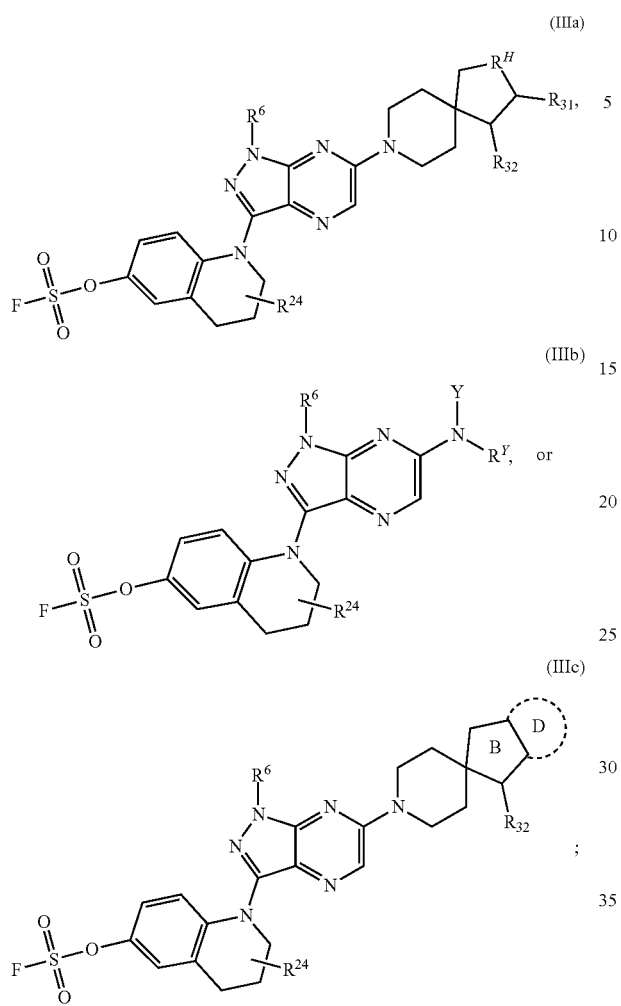

wherein:
R$^H$ is O or C(R$^{25}$)$_2$;
R$^{31}$ is hydrogen or C$_{1-6}$alkyl;
R$^{32}$ is N(R$^6$)$_2$;
R$^{24}$ is selected from the group consisting of hydrogen, halogen, and C$_1$-C$_6$alkyl;
R$^{25}$ is independently selected for each occurrence from the group consisting of hydrogen, hydroxyl, halogen, and C$_1$-C$_6$alkyl (optionally substituted by hydroxyl or halogen);
R$^6$ is independently selected, for each occurrence, from the group consisting of hydrogen, —(C$_1$-C$_6$)alkyl and phenyl;
Y is selected from the group consisting of a 3-7 membered saturated carbocycle, a 4-7 membered saturated heterocycle, phenyl, and a 5-6 membered monocyclic heteroaryl; wherein Y is optionally substituted with one or more substituents each independently selected from the group consisting of (C$_1$-C$_6$)alkyl, —C(O)N(R$^6$)$_2$, —N(R$^6$)$_2$, halogen, and cyano, wherein said —(C$_1$-C$_6$) alkyl is optionally substituted with one or more substituents selected from the group consisting of —OH, —N(R$^6$)$_2$, oxo, and halogen;
R$^Y$ is selected from the group consisting of hydrogen and —(C$_1$-C$_6$)alkyl;
D is an optional ring moiety selected from the group consisting of: phenyl, a 5- or 6-membered heteroaryl having one or two heteroatoms each independently selected from the group consisting of S, O or N, and C$_{3-6}$cycloalkyl, wherein D is optionally substituted on an available carbon with one or two substituents each independently selected from R$^{D1}$, and, optionally substituted, on nitrogen, if present, with one or two substituents each independently selected from R$^{D2}$;
B is fused to D such that the two atoms shared by D and B are both carbon or one carbon and one nitrogen;
R$^B$ is independently selected from the group consisting of hydrogen, —C(O)N(R$^6$)$_2$, —N(R$^6$)$_2$, and —C$_{1-3}$alkyl-N(R$^6$)$_2$;
R$^{D1}$ is selected from the group consisting of hydroxyl, cyano, halogen, and —N(R$^6$)$_2$; and
R$^{D2}$ is selected from the group consisting of —(C$_1$-C$_6$) alkyl and phenyl.

Also contemplated herein are conjugates that include a disclosed compound covalently bonded to a lysine residue of a SHP2 protein (for Example SEQ ID NO:1 or SEQ ID NO:2), e.g., though a —O—S(O)$_2$F via a reaction of the —O—S(O)$_2$F moiety with the lysine. For example, a conjugate is provided herein that is represented by:

K492-CL-SI; wherein K492 is the lysine residue K492 of SHP2;

CL is a bivalent binding moiety formed from the interaction of the —O—S(O)$_2$F moiety with the lysine; and SI is a disclosed compound or a contemplated compound of Formula IVa, IVb, or IVc, or a pharmaceutically acceptable salt or stereoisomer thereof, or for example, a compound represented by:

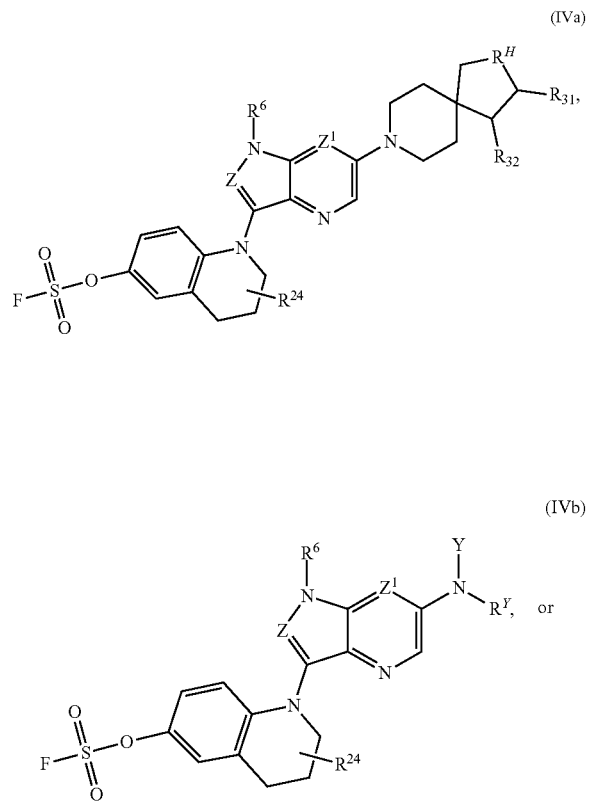

(IVc)

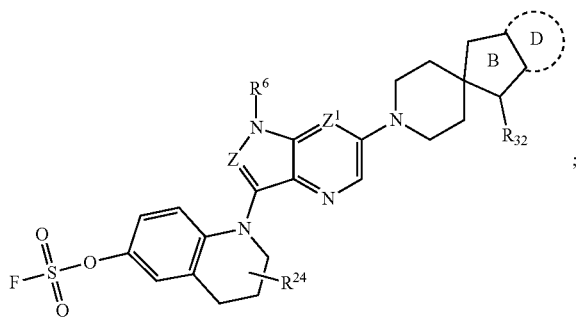

wherein:
$Z^1$ is N or CH;
Z is N or CH;
$R^H$ is O or $C(R^{25})_2$;
$R^{31}$ is hydrogen or $C_{1-6}$alkyl;
$R^{32}$ is $N(R^6)_2$;
$R^{24}$ is selected from the group consisting of hydrogen, halogen, and $C_1$-$C_6$alkyl;
$R^2$ is selected from the group consisting of hydrogen, hydroxyl, halogen, and $C_1$-$C_6$alkyl (optionally substituted by hydroxyl or halogen);
$R^6$ is independently for each occurrence selected from the group consisting of H, —($C_1$-$C_6$)alkyl, —C(O)O$C_{1-4}$alkyl, and phenyl;
Y is selected from the group consisting of a 3-7 membered saturated carbocycle, a 4-7 membered saturated heterocycle, phenyl, and a 5-6 membered monocyclic heteroaryl; wherein Y is optionally substituted with one or more substituents each independently selected from the group consisting of ($C_1$-$C_6$)alkyl, —C(O)N($R^6$)$_2$, —N($R^6$)$_2$, halogen, and cyano, wherein said —($C_1$-$C_6$)alkyl is optionally substituted with one or more substituents selected from the group consisting of —OH, —N($R^6$)$_2$, oxo, and halogen;
$R^Y$ is selected from the group consisting of hydrogen and —($C_1$-$C_6$)alkyl;
D is an optional ring moiety selected from the group consisting of: phenyl, a 5- or 6-membered heteroaryl having one or two heteroatoms each independently selected from the group consisting of S, O or N, and $C_{3-6}$cycloalkyl, wherein D is optionally substituted on an available carbon with one or two substituents each independently selected from $R^{D1}$, and, optionally substituted, on nitrogen, if present, with one or two substituents each independently selected from $R^{D2}$; B is fused to D such that the two atoms shared by D and B are both carbon or one carbon and one nitrogen;
$R^B$ is independently selected from the group consisting of hydrogen, —C(O)N($R^6$)$_2$, —N($R^6$)$_2$, and —$C_{1-3}$alkyl-N($R^6$)$_2$;
$R^{D1}$ is selected from the group consisting of hydroxyl, cyano, halogen, and —N($R^6$)$_2$; and
$R^{D2}$ is selected from the group consisting of —($C_1$-$C_6$)alkyl and phenyl.

For example, disclosed herein is a conjugate represented by:
K492-CL-SI; wherein
K492 is the lysine residue K492 of SHP2 (e.g. K492 of SEQ ID NO:2);

SI is represented by a disclosed compound; and
CL is a bivalent binding moiety formed from the interaction of the —O—S(O)$_2$—F moiety with the lysine.

The SHP2 protein may be e.g. SEQ ID NO:1 (isoform 1), SEQ ID NO:2 (isoform 2) or SEQ ID NO:3 (isoform 3):

```
SEQ ID NO: 1:
>sp|Q06124|PTN11_HUMAN Tyrosine-protein
phosphatase non-receptor type 11 OS = Homo sapiens
OX = 9606 GN = PTPN11 PE = 1 SV = 2
MTSRRWFHPNITGVEAENLLLTRGVDGSFLARPSKSNPGDFTLSVRRNGA

VTHIKIQNTGDYYDLYGGEKFATLAELVQYYMEHHGQLKEKNGDVIELKY

PLNCADPTSERWFHGHLSGKEAEKLLTEKGKHGSFLVRESQSHPGDFVLS

VRTGDDKGESNDGKSKVTHVMIRCQELKYDVGGGERFDSLTDLVEHYKKN

PMVETLGTVLQLKQPLNTTRINAAEIESRVRELSKLAETTDKVKQGFWEE

FETLQQQECKLLYSRKEGQRQENKNKNRYKNILPFDHTRVVLHDGDPNEP

VSDYINANIIMPEFETKCNNSKPKKSYIATQGCLQNTVNDFWRMVFQENS

RVIVMTTKEVERGKSKCVKYWPDEYALKEYGVMRVRNVKESAAHDYTLRE

LKLSKVGQALLQGNTERTVWQYHFRTWPDHGVPSDPGGVLDFLEEVHHKQ

ESIMDAGPVVVHCSAGIGRTGTFIVIDILIDIIREKGVDCDIDVPKTIQM

VRSQRSGMVQTEAQYRFIYMAVQHYIETLQRRIEEEQKSKRKGHEYTNIK

YSLADQTSGDQSPLPPCTPTPPCAEMREDSARVYENVGLMQQQKSFR

SEQ ID NO: 2:
>sp|Q06124-2|PTN11_HUMAN Isoform 2 of Tyrosine-
protein phosphatase non-receptor type 11 OS =
Homo sapiens OX = 9606 GN = PTPN11
MTSRRWFHPNITGVEAENLLLTRGVDGSFLARPSKSNPGDFTLSVRRNGA

VTHIKIQNTGDYYDLYGGEKFATLAELVQYYMEHHGQLKEKNGDVIELKY

PLNCADPTSERWFHGHLSGKEAEKLLTEKGKHGSFLVRESQSHPGDFVLS

VRTGDDKGESNDGKSKVTHVMIRCQELKYDVGGGERFDSLTDLVEHYKKN

PMVETLGTVLQLKQPLNTTRINAAEIESRVRELSKLAETTDKVKQGFWEE

FETLQQQECKLLYSRKEGQRQENKNKNRYKNILPFDHTRVVLHDGDPNEP

VSDYINANIIMPEFETKCNNSKPKKSYIATQGCLQNTVNDFWRMVFQENS

RVIVMTTKEVERGKSKCVKYWPDEYALKEYGVMRVRNVKESAAHDYTLRE

LKLSKVGQGNTERTVWQYHFRTWPDHGVPSDPGGVLDFLEEVHHKQESIM

DAGPVVVHCSAGIGRTGTFIVIDILIDIIREKGVDCDIDVPKTIQMVRSQ

RSGMVQTEAQYRFIYMAVQHYIETLQRRIEEEQKSKRKGHEYTNIKYSLA

DQTSGDQSPLPPCTPTPPCAEMREDSARVYENVGLMQQQKSFR

SEQ ID NO: 3:
sp|Q06124-3|PTN11_HUMAN Isoform 3 of Tyrosine-
protein phosphatase non-receptor type 11 OS =
Homo sapiens OX = 9606 GN = PTPN11
MTSRRWFHPNITGVEAENLLLTRGVDGSFLARPSKSNPGDFTLSVRRNGA

VTHIKIQNTGDYYDLYGGEKFATLAELVQYYMEHHGQLKEKNGDVIELKY

PLNCADPTSERWFHGHLSGKEAEKLLTEKGKHGSFLVRESQSHPGDFVLS

VRTGDDKGESNDGKSKVTHVMIRCQELKYDVGGGERFDSLTDLVEHYKKN

PMVETLGTVLQLKQPLNTTRINAAEIESRVRELSKLAETTDKVKQGFWEE

FETLQQQECKLLYSRKEGQRQENKNKNRYKNILPFDHTRVVLHDGDPNEP

VSDYINANIIMPEFETKCNNSKPKKSYIATQGCLQNTVNDFWRMVFQENS
```

-continued
RVIVMTTKEVERGKSKCVKYWPDEYALKEYGVMRVRNVKESAAHDYTLRE
LKLSKVGQGNTERTVWQYHFRTWPDHGVPSDPGGVLDFLEEVHHKQESIM
DAGPVVVHCR
Also disclosed herein is a compound selected from the group consisting of:
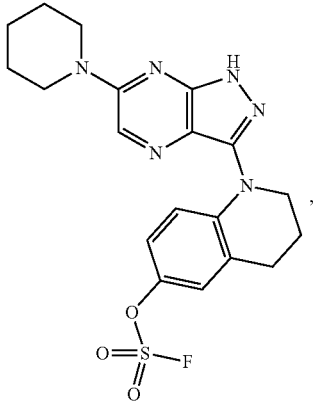
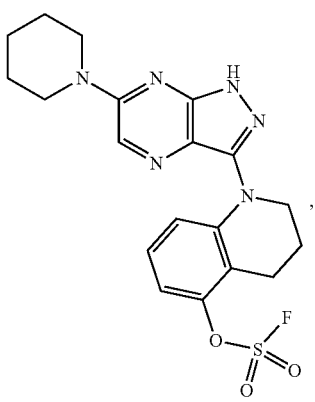
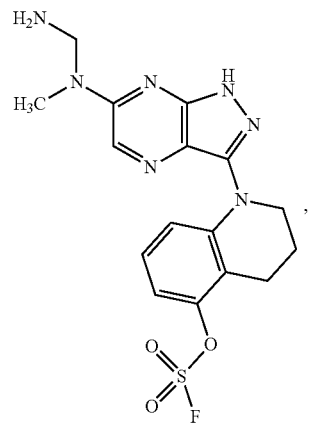
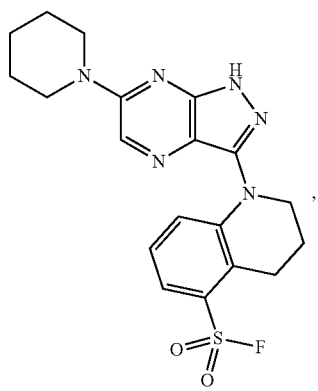
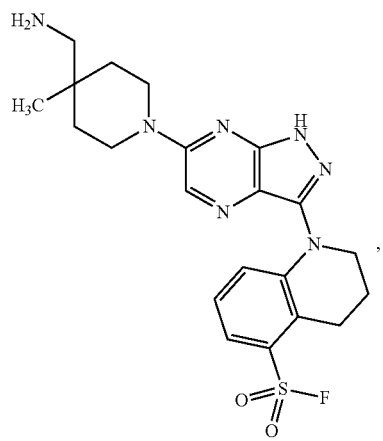
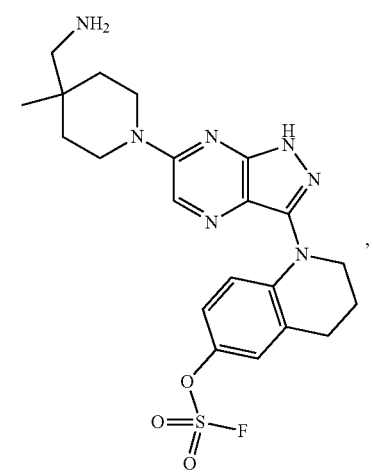

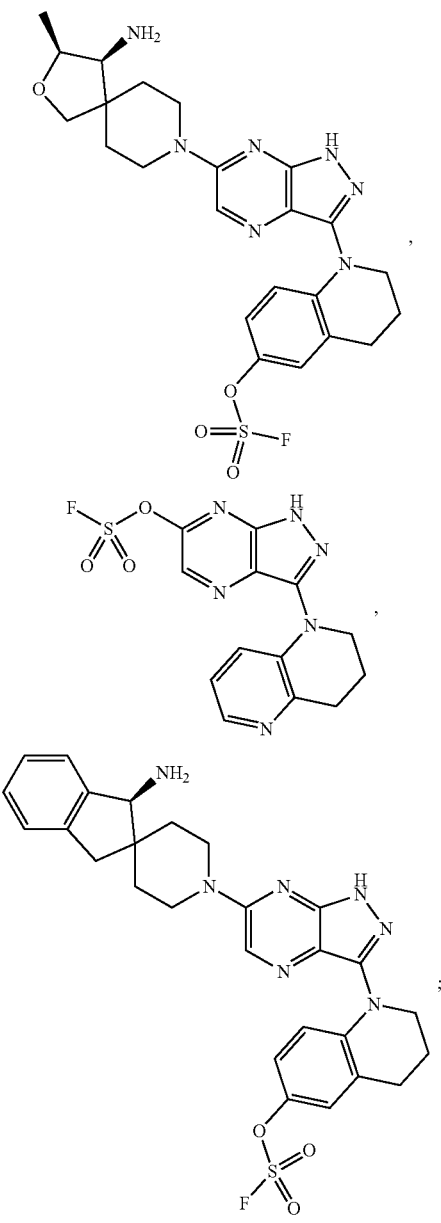

and a pharmaceutically acceptable salt or stereoisomer thereof.

Also disclosed herein is a compound of Formula Va or Vb, or a pharmaceutically acceptable salt or stereoisomer thereof, represented by:

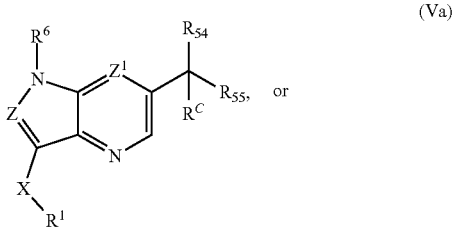

wherein:
$Z^1$ is N or CH;
Z is N or CH;
X is selected from the group consisting of a bond, —O—, —NR$^{X1}$—, and —S(O)$_w$— (wherein w is 0, 1 or 2);
R$^{X1}$ is selected from the group consisting of hydrogen, —(C$_1$-C$_6$)alkyl and phenyl;
R$^1$ is a ring moiety selected from the group consisting of a 8-12 membered bicyclic heteroaryl, phenyl, a 5-7 membered monocyclic heteroaryl, and a 4-7 membered heterocyclyl, wherein the ring moiety is optionally substituted with one, two or more substituents each independently selected from the group consisting of R$^{10}$, —OR$^{10}$, —S(O)$_w$R$^{10}$ (wherein w is 0, 1 or 2), —C$_{1-6}$alkyl-S(O)$_w$—C$_{1-3}$alkyl, —N(R$^{10}$)$_2$, —N(CO)R$^{10}$, —N—S(O)$_w$—R$^{10}$ (where w is 0, 1 or 2), —OS(O)$_w$—R$^{10}$ (wherein w is 0, 1, or 2), —S(O)$_w$—N(R$^{10}$)$_2$ (wherein w is 0, 1 or 2), —S(O)(NH)R$^{10}$, —N(H)—SO$_2$—C$_{1-3}$alkyl, —N(SO$_2$—C$_{1-3}$alkyl)$_2$, P(O)(R$^{10}$)$_2$, —C(O)R$^{10}$, —C(O)OR$^{10}$, —C(O)N(R$^{10}$)$_2$, oxo, halogen, hydroxyl, cyano, nitro, —C(=N—OR$^a$)—C$_{1-3}$alkyl, —C(=N—OR$^a$)—H, —S(O)(NR$^a$)—C$_{1-3}$alkyl, phenyl (optionally substituted with one, two or three halogen, —O-phenyl, C$_{1-3}$alkyl or C$_{1-3}$haloalkyl), C$_{1-3}$alkyl, C$_{2-6}$alkynyl, C$_{1-3}$haloalkyl, C$_{3-6}$cycloalkyl, heterocyclyl (optionally substituted with one, two or three halogen, oxo, C$_{1-3}$alkyl or C$_{1-3}$haloalkyl), and heteroaryl (optionally substituted with one, two or three halogen, —C(O)N(R$^{10}$)$_2$, C$_{1-3}$alkyl, C$_{1-3}$alkyl-O—C$_{1-3}$alkyl, C$_{1-3}$alkyl-OH, or C$_{1-3}$haloalkyl);
R$^{10}$ is independently selected from the group consisting of hydrogen, C$_{1-6}$alkyl, C$_{2-6}$alkenyl, C$_{2-6}$alkynyl, C$_{3-6}$cycloalkyl, C$_{5-6}$cycloalkenyl, C$_{2-6}$heteroalkyl, heterocycloalkyl, aryl, and heteroaryl; wherein C$_{1-6}$alkyl, C$_{2-6}$alkenyl, C$_{2-6}$alkynyl, C$_{3-6}$cycloalkyl, C$_{5-6}$cycloalkenyl, C$_{2-6}$heteroalkyl, heterocycloalkyl, aryl, and heteroaryl is optionally substituted by one, two, three or more substituents each independently selected from the group consisting of halogen, hydroxyl, —NR$^a$C(O)—R$^{20}$, —C(O)—R$^{20}$, —C(NR$^a$)—R$^b$, —NR$^a$R$^b$, C$_{1-6}$alkyl, C$_{1-6}$haloalkyl and C$_{1-6}$alkoxy;
R$^{20}$ is selected from the group consisting of hydrogen, hydroxyl, halogen, —NR$^a$R$^b$, C$_{1-6}$alkyl and C$_{1-6}$alkoxy;
R$^a$ and R$^b$ are each independently selected from the group consisting of hydrogen and C$_{1-3}$alkyl;
R$^6$ is independently for each occurrence selected from the group consisting of H, —(C$_1$-C$_6$)alkyl, —C(O)OC$_{1-4}$alkyl, and phenyl;
R$^{55}$ is selected from the group consisting of —C$_{1-4}$alkyl-N(R$^6$)$_2$, —N(R$^6$)$_2$, and heteroaryl (optionally substituted by one, two, or three substituent each independently selected from halogen, hydroxyl, cyano, —(C$_1$-C$_6$)alkyl, —O(C$_1$-C$_6$)alkyl, —C(O)N(R$^6$)$_2$, —N(R$^6$)$_2$, and —(C$_1$-C$_6$)alkyl-N(R$^6$)$_2$);

$R^{54}$ is selected from the group consisting of H, and $C_{1-2}$alkyl, or $R^{54}$ and $R^{55}$ taken together with the carbon to which they are attached form a ring selected from the group consisting of $C_{3-6}$cycloalkyl and heterocyclyl, wherein the ring is optionally substituted on a carbon by one, two or three substituents each independently selected from the group consisting of $R^4$ and $R^5$ and on a nitrogen if present by $R^6$;

$R^C$ is selected from the group consisting of H, OH, —$(C_1$-$C_6)$alkyl, —C(O)—O—$C_{1-6}$(alkyl), —C(O)—$C_{1-6}$(alkyl), and heterocyclyl, wherein $C_{1-6}$(alkyl) is optionally substituted by one two or three substituents each selected from the group consisting of halogen, hydroxyl and $N(R_6)_2$; or wherein $R^C$ is absent $R^{54}$ and $R^{55}$ taken together with the carbon to which they are attached form a ring selected from $C_{5-6}$cyclalkenyl and phenyl; wherein the ring is optionally substituted on a carbon by one, two or three substituents each independently selected from the group consisting of $R^4$ and $R^5$;

$R^{56}$ is $N(R_6)_2$ or heterocycle (optionally substituted by one, two or three substituents each independently selected from halogen, hydroxyl, $N(R_6)_2$, —$(C_1$-$C_6)$ alkyl, —C(O)—O—$C_{1-6}$(alkyl), —C(O)—$C_{1-6}$(alkyl), wherein $C_{1-6}$(alkyl) is optionally substituted by one two or three substituents each selected from the group consisting of: halogen, hydroxyl or $N(R_6)_2$);

$R^4$ and $R^5$ are each independently selected from the group consisting of H, —OH, —$(C_1$-$C_6)$alkyl, —O$(C_1$-$C_6)$ alkyl, —$(C_1$-$C_6)$alkyl-O—$R^6$, —C(O)N$(R^6)_2$, —N$(R^6)_2$, halogen, —$(C_1$-$C_6)$alkyl-N$(R^6)_2$, and cyano, wherein said —$(C_1$-$C_6)$alkyl, —O$(C_1$-$C_6)$alkyl, —$(C_1$-$C_6)$alkyl-O—$R^6$, or —$(C_1$-$C_6)$alkyl-N$(R^6)_2$ is optionally substituted with one or more substituents selected from the group consisting of —OH, —$NH_2$, oxo, and halogen;

or $R^4$ and $R^5$, taken together with the carbon to which they are attached, form a 4-6 membered carbocyclic or heterocyclic ring B; which ring is optionally substituted with one or two substituents each independently selected from the group consisting of $(C_1$-$C_6)$alkyl, —O$(C_1$-$C_6)$alkyl, —N$(R^6)_2$, —C(O)N$(R^6)_2$, halogen, oxo, and cyano and/or which ring may be fused to a ring D;

D is selected from the group consisting of phenyl, a 5- or 6-membered heteroaryl having one or two heteroatoms each independently selected from the group consisting of S, O or N, and $C_{3-6}$cycloalkyl, wherein D is optionally substituted on an available carbon with one or two substituents each independently selected from $R^{D1}$, and, optionally substituted, on nitrogen, if present, with one or two substituents each independently selected from $R^{D2}$;

B is fused to D such that the two atoms shared by D and B are both carbon or one carbon and one nitrogen;

$R^{D1}$ is selected from the group consisting of hydroxyl, cyano, halogen, and —N$(R^6)_2$; and $R^{D2}$ is selected from the group consisting of —$(C_1$-$C_6)$ alkyl and phenyl.

In some embodiments, X is a bond, $R^1$ is a nitrogen containing ring moiety and $R^1$ is bound through the nitrogen.

In some embodiments, $R^1$ is selected from the group consisting of 1,2,3,4-tetrahydroquinolin-1-yl, 1,2,3,4-tetrahydro-1,5-naphthyridin-1-yl, 1,2,3,4-tetrahydroquinolin-1-yl, 1,2,3,4-tetrahydroquinoxalin-1-yl, 1,2,3,4-tetrahydropyrido[2,3-b]pyrazin-1-yl, 1H-benzo[d]imidazol-1-yl, indolin-1-yl, 2,3-dihydro-1H-pyrrolo[3,2-b]pyridin-1-yl, 2,3-dihydro-1H-pyrrolo[3,2-c]pyridin-1-yl, isoindolin-2-yl, 2,3,4,5-tetrahydrobenzo[f][1,4]oxazepin-4-yl, 2-(3,4-dihydroisoquinolin-1(2H)-one), 2-(3,4-dihydroisoquinolin-1 (2H)-one), 2,3-dihydro-1H-pyrido[2,3-b][1,4]oxazin-1-yl, piperidin-1-yl, 1-(1,2,3,4-tetrahydro-6H-pyrido[1,2-a]pyrimidin-6-one), 1,2,3,4-tetrahydro-1,8-naphthyridin-1-yl, 1-(3,4-dihydro-1,5-naphthyridin-2(1H)-one), 2,3,4,5-tetrahydro-1H-benzo[b]azepin-1-yl, 1-(2,3-dihydroquinolin-4 (1H)-one), 2,3-dihydro-1H-pyrido[2,3-b][1,4]oxazin-1-yl, 1,2,3,4-tetrahydro-1,6-naphthyridin-1-yl, 5,6,7,8-tetrahydro-4H-pyrazolo[1,5-a][1,3]diazepin-4-yl, 3,4-dihydroquinoxalin-1-yl-2(1H)-one, 2,3,4,6-tetrahydro-1,6-naphthyridin-1-yl-5(1H)-one, 1,2,3,4-tetrahydroisoquinolin-2-yl, 1,2,3,4-tetrahydro-2,7-naphthyridin-2-yl, 1,2,3,4-tetrahydro-2,6-naphthyridin-2-yl, 3,4-dihydro-2H-benzo[b][1,4]thiazin-4-yl 1 1-dioxide, 1,2,3,4-tetrahydropyrazino[2,3-d]pyridazin-1-yl, 1,4-dihydropyrido[3,4-b]pyrazin-1-yl-3 (2H)-one, 5,6,7,8-tetrahydro-1,6-naphthyridin-6-yl, 5,6,7,8-tetrahydro-1,7-naphthyridin-7-yl, 1,2,3,4-tetrahydropyrido [3,4-b]pyrazin-1-yl, 5,8-dihydropteridin-5-yl-7(6H)-one, 4,5,6,7-tetrahydrothieno[3,2-b]pyridin-4-yl, or 5,6,7,8-tetrahydropyrazino[2,3-c]pyridazin-5-yl wherein the nitrogen ring moiety may be optionally substituted with one or two substituents each independently selected from the group consisting of Cl, F, —CN, $C_{1-4}$alkyl, —O$C_{1-4}$alkyl, $C_{2-6}$alkenyl, $C_{2-4}$alkynyl, $C_{3-6}$cycloalkyl, $C_{5-6}$cycloalkenyl, —C(H)=N—OCH_3, —C(H)=N—OH, —C(CH_3)=N—OH, —$(CH_2)_{0-1}$C(O)NH_2, —$(CH_2)_{0-1}$C(O)NHC_{1-4}alkyl, —$(CH_2)_{0-1}$C(O)N$(C_{1-4}$alkyl$)_2$, —$(CH_2)_{0-1}$C(O)O$C_{1-4}$alkyl, —$(CH_2)_{0-1}$C(O)OH, —S(O)_2$C_{1-4}$alkyl, —$(CH_2)_{0-1}$NH_2, —$(CH_2)_{0-1}$NH$C_{1-4}$alkyl, —$(CH_2)_{0-1}$(C_{1-4}$alkyl$)_2$, —$(CH_2)_{0-1}$NH(CO)$C_{1-4}$alkyl, phenyl, optionally substituted heteroaryl and optionally substituted heterocyclyl, wherein $C_{1-4}$alkyl or $C_{3-6}$cycloalkyl may be optionally substituted with one, two or three fluorine atoms, one or two hydroxyl groups, or one or two —O$C_{1-2}$alkyl groups.

In some embodiments, heteroaryl is selected from the group consisting of 2-pyridyl, 3-pyridyl, 4-pyridyl, 1,2,4-triazol-3-yl, thiazol-2-yl, pyrazol-1-yl, pyrazol-3-yl, pyrazol-4-yl, imidazol-2-yl, oxazol-2-yl, oxazol-5-yl, isoxazol-5-yl, thiazol-2-yl, thiazol-5-yl, 1,3,4-thiadiazol-2-yl, and 1,2,4-oxadiazol-3-yl, 1,3,4-oxadiazol-2-yl, 1,2,4-triazol-2-yl, 1,3,4-triazol-2-yl; wherein heteroaryl may be optionally substituted with $C_{1-2}$alkyl (optionally substituted with one, two or three fluorine atoms, one or two 2 hydroxyl groups, or one or two —O$C_{1-2}$alkyl groups).

In some embodiments, heterocyclyl is selected from the group consisting of tetrahydrofuran-3-yl, pyrrolidine-1-yl, piperazin-1-yl, piperidin-4-yl, piperidin-1-yl, 1,2,3,6-tetrahydropyridin-4-yl, 2,5-dihydrofuran-3-yl, piperazin-1-yl-3-one, morpholino, tetrahydropyran-2-yl, or 1,2,4-oxadiazo-3-yl-5-one, wherein heterocyclyl may be optionally substituted with hydroxyl or $C_{1-2}$alkyl (optionally substituted with one, two or three fluorine atoms, one or two 2 hydroxyl groups, or one or two —O$C_{1-2}$alkyl groups).

In some embodiments, $R^1$ is a 1,2,3,4-tetrahydroquinoline moiety optionally substituted with one, two or three halo, $C_{1-3}$alkyl, $C_{1-3}$haloalkyl, and heteroaryl (optionally substituted with one, two or three halogen, —C(O)N$(R^{10})_2$, $C_{1-3}$alkyl, $C_{1-3}$alkyl-O—$C_{1-3}$alkyl, $C_{1-3}$alkyl-OH, or $C_{1-3}$haloalkyl).

In some embodiments, $R^1$ is a 1,2,3,4-tetrahydro-1,5-naphthyridine moiety optionally substituted with one, two or three halo, $C_{1-3}$alkyl, $C_{1-3}$haloalkyl, and heteroaryl (optionally substituted with one, two or three halogen, —C(O)N(R$^{10}$)$_2$, C$_{1-3}$alkyl, C$_{1-3}$alkyl-O—C$_{1-3}$alkyl, C$_{1-3}$alkyl-OH, or C$_{1-3}$haloalkyl).

In some embodiments, R$^1$ is phenyl; wherein phenyl is optionally substituted by one, two, or three substituents each independently selected from the group consisting of —OR$^{10}$, —N(R$^{10}$)$_2$, halogen, and cyano.

In some embodiments, R$^1$ is pyridyl; wherein pyridyl is optionally substituted by one, two, or three substituents each independently selected from the group consisting of —OR$^{10}$, —N(R$^{10}$)$_2$, halogen, and cyano.

In some embodiments, R$^1$ is indolyl or indolinyl, wherein indolyl or indolinyl is optionally substituted with one, two, or three substituents each independently selected from the group consisting of —OR$^{10}$, —N(R$^{10}$)$_2$, halogen, and cyano; and wherein indolyl or indolinyl is bound through carbon.

In some embodiments, the compound is represented by:

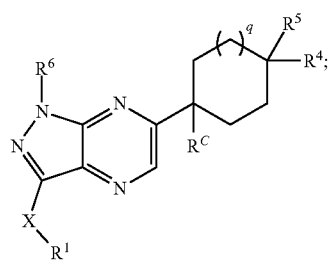

wherein q is 0 or 1.

In some embodiments, the compound is represented by:

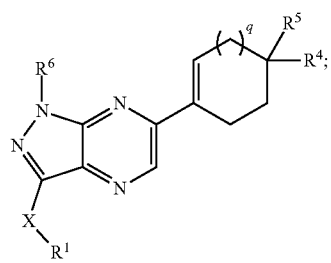

wherein q is 0 or 1.

In some embodiments, R$^4$ and R$^5$ are independently selected from the group consisting of hydrogen, halogen, hydroxyl, —(C$_1$-C$_3$)alkyl, —(C$_1$-C$_3$)alkoxy, and —N(R$^6$)$_2$, wherein said —(C$_1$-C$_3$)alkyl is optionally substituted with one or more substituents selected from the group consisting of —OH, —N(R$^6$)$_2$, and halogen.

In some embodiments, R$^4$ and R$^5$ are independently selected from the group consisting of fluorine, —NH$_2$, —CH$_3$, —OCH$_3$, —CH$_2$H, —CH$_2$NH$_2$ and —CH(NH)$_2$CH$_3$.

In some embodiments, R$^4$ and R$^5$, taken together with the carbon to which they are attached, form a 4-6 membered carbocyclic or heterocyclic ring, which ring is optionally substituted with one or two substituents each independently selected from the group consisting of (C$_1$-C$_6$)alkyl, —O(C$_1$-C$_6$)alkyl, —N(R$^6$)$_2$, —C(O)N(R$^6$)$_2$, halogen, oxo, and cyano.

In some embodiments, R$^4$ and R$^5$ taken together, are selected from the group consisting of:

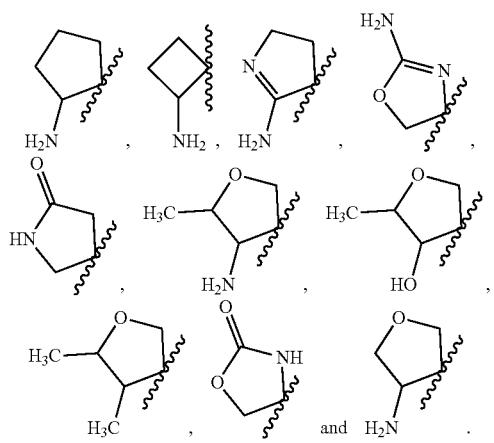

In some embodiments, the compound is represented by:

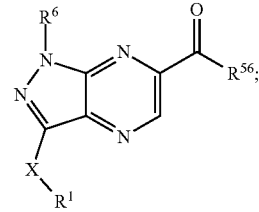

wherein

R$^{56}$ is selected from the group consisting of piperidin-1-yl and pyrrolidine-1-yl, wherein R$^{56}$ is optionally substituted by one or two substituents each selected from the group consisting of C$_{1-2}$alkylNH$_2$, NH$_2$, and C$_{1-2}$alkyl.

In some embodiments, the compound is represented by:

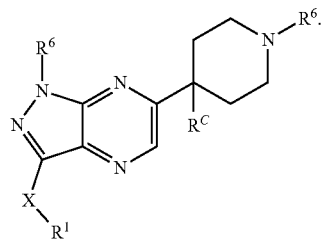

In some embodiments, the compound is represented by:

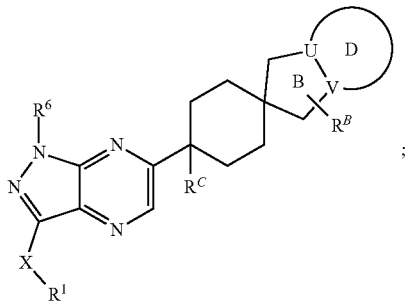

wherein:
R$^B$ is independently selected from the group consisting of hydrogen, —C(O)N(R$^6$)$_2$, —N(R$^6$)$_2$, and —C$_{1-3}$alkyl-N(R$^6$)$_2$;
U is selected from the group consisting of C, CH and N;
V is selected from the group consisting of C, CH and N;
wherein at least one of U or V is not N.

In some embodiments, D is selected from the group consisting of:

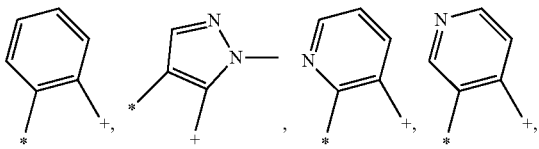

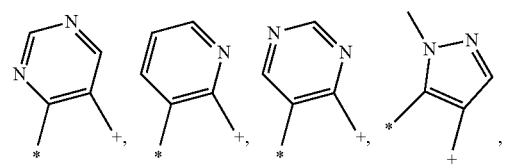

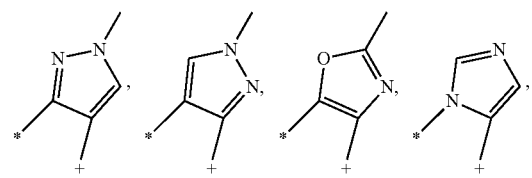

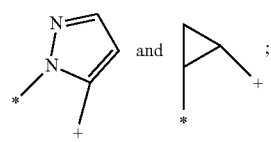 and 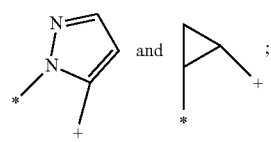;

wherein * and + represent fusion points of attachment to ring B.

Also disclosed herein, for example, is a compound of Formula VIa, VIb, VIc or VId, or a pharmaceutically acceptable salt or stereoisomer thereof, represented by:

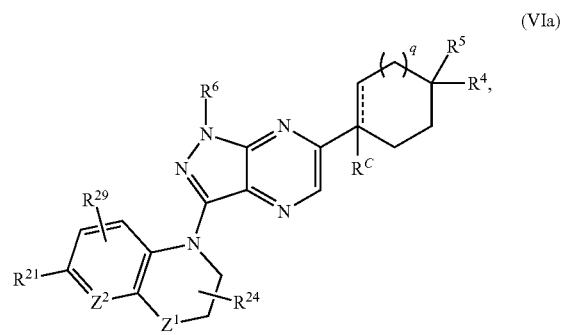 (VIa)

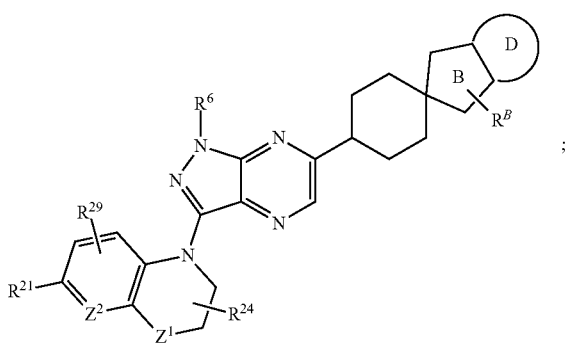 (VIb)

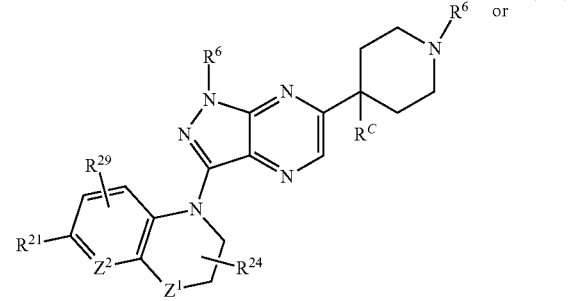 (VIc) or

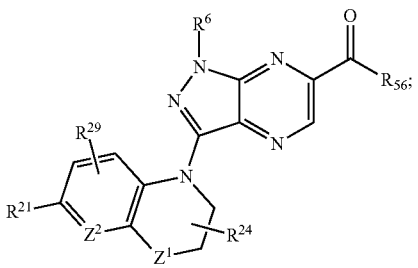 (VId)

wherein:
the dashed bond represents an optional double bond;
wherein R$^C$ is absent when the dashed bond represents a double bond;
Z$^2$ is selected from the group consisting of N and CR$^{22}$;
Z$^1$ is selected from the group consisting of: NR$^{61}$, C(R$^{23}$)$_2$, C(O), and O;
R$^{21}$ is selected from the group consisting of hydrogen, halogen, cyano, hydroxyl, N(R$^6$)$_2$, C$_1$-C$_6$alkyl, C$_3$-C$_6$cycloalkyl, C$_1$-C$_6$alkyoxy, —C(O)N(R$^6$)$_2$, heterocycloalkyl, phenyl, and heteroaryl, wherein C$_1$-C$_6$alkyl, C$_3$-C$_6$cycloalkyl, C$_1$-C$_6$alkyoxy, heterocycloalkyl, phenyl, and heteroaryl may each be substituted by one, two or three or more substituents each selected from the group consisting of halo, —C(O)—OR$^{26}$, —C(O)R$^{26}$, —C(O)N(R$^6$)$_2$, —N(R$^6$)$_2$, C$_{1-3}$alkyl (optionally substituted by hydroxyl or methoxy), C$_1$-C$_3$alkyoxy, and C$_{1-3}$haloalkyl;
R$^{22}$ is selected from the group consisting of hydrogen, halogen, cyano, N(R$^6$)$_2$, C$_1$-C$_6$alkyl, C$_3$-C$_6$cycloalkyl, C$_1$-C$_6$alkyoxy, —C(O)N(R$^6$)$_2$, heterocycloalkyl, phenyl, and heteroaryl, wherein C$_1$-C$_6$alkyl, C$_3$-C$_6$cycloalkyl, C$_1$-C$_6$alkyoxy, heterocycloalkyl, phenyl, and heteroaryl may each be substituted by one, two or three or more substituents each selected from the group consisting of halo, —C(O)R$^{26}$, C(O)—OR$^{26}$, —C(O)N(R$^6$)$_2$, N(R$^6$)$_2$, C$_{1-3}$ alkyl (optionally substituted with hydroxyl or methoxy) and C$_3$haloalkyl;

R²⁹ is selected from the group consisting of hydrogen, halogen, N(R⁶)₂, C₁-C₆alkyl, C₃-C₆cycloalkyl, C₁-C₆alkyoxy, —C(O)N(R⁶)₂, heterocycloalkyl, phenyl, and heteroaryl; wherein C₁-C₆alkyl, C₃-C₆cycloalkyl, C₁-C₆alkyoxy, heterocycloalkyl, phenyl, and heteroaryl may each be substituted by one, two or three or more substituents each selected from the group consisting of halo, —C(O)R²⁶, —C(O)—OR²⁶, —C(O)N(R⁶)₂, —N(R⁶)₂, C₁₋₃alkyl (optionally substituted by hydroxyl or methoxy) and C₁₋₃haloalkyl;

R²³ independently, for each occurrence, is selected from the group consisting of H, halogen, and C₁-C₆alkyl;

R²⁴ is selected from the group consisting of H, halogen, and C₁-C₆alkyl;

R²⁶ is hydrogen or C₁₋₃alkyl;

R⁶¹ is selected from the group consisting of hydrogen, —(C₁-C₆)alkyl, —C(O)—(C₁-C₆)alkyl and phenyl;

R⁶ is independently for each occurrence selected from the group consisting of H, —(C₁-C₆)alkyl, —C(O)OC₁₋₄alkyl, and phenyl;

R^C is selected from the group consisting of H, OH, —(C₁-C₆)alkyl, —C(O)—O—C₁₋₆(alkyl), —C(O)—C₁₋₆(alkyl), and heterocyclyl, wherein C₁₋₆(alkyl) is optionally substituted by one two or three substituents each selected from the group consisting of halogen, hydroxyl and N(R₆)₂;

R⁴ and R⁵ are each independently selected from the group consisting of hydrogen, (C₁-C₆)alkyl, —C(O)N(R⁶)₂, —N(R⁶)₂, halogen, and cyano, wherein said —(C₁-C₆)alkyl is optionally substituted with one or more substituents selected from the group consisting of —OH, —N(R⁶)₂, oxo, and halogen;

or R⁴ and R⁵, taken together with the carbon to which they are attached, form a 4-6 membered carbocyclic or heterocyclic ring, which ring is optionally substituted with one or two substituents each independently selected from the group consisting of (C₁-C₆)alkyl, —O(C₁-C₆)alkyl, —N(R⁶)₂, —C(O)N(R⁶)₂, halogen, oxo, and cyano;

q is 0 or 1;

R⁵⁶ is heterocyclyl, wherein R⁵⁶ is optionally substituted by one or two substituents each selected from the group consisting of C₁₋₂alkylNH₂, NH₂, and C₁₋₂alkyl;

D is selected from the group consisting of: phenyl, a 5- or 6-membered heteroaryl having one or two heteroatoms independently selected from the group consisting of S, O or N, and C₃₋₆cycloalkyl, wherein D is optionally substituted on a carbon with one or two substituents each independently selected from R^D1, and, optionally substituted, on nitrogen, if present, with one or two substituents each independently selected from R^D2;

B is fused to D such that the two atoms shared by D and B are both carbon;

R^B is independently selected from the group consisting of hydrogen, —C(O)N(R⁶)₂, and —N(R⁶)₂;

R^D1 is selected from the group consisting of hydroxyl, cyano, halogen, and, —N(R⁶)₂; and R^D2 is selected from —(C₁-C₆)alkyl and phenyl.

In some embodiments, the compound is represented by:

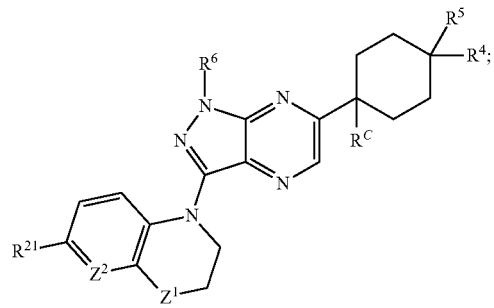

wherein q is 0 or 1.

In some embodiments, the compound is represented by:

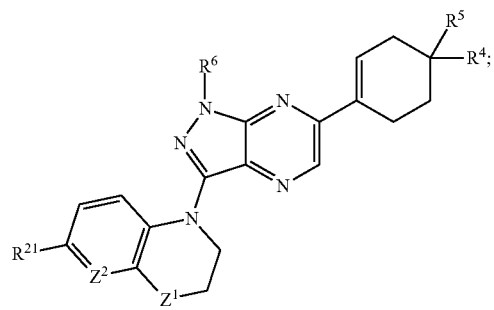

wherein q is 0 or 1.

In some embodiments, R⁴ and R⁵ are independently selected from the group consisting of hydrogen, halogen, hydroxyl, —(C₁-C₃)alkyl, —(C₁-C₃)alkoxy, and —N(R⁶)₂, wherein said —(C₁-C₃)alkyl is optionally substituted with one or more substituents selected from the group consisting of —OH, —N(R⁶)₂, and halogen.

In some embodiments, R⁴ and R⁵ are independently selected from the group consisting of fluorine, —NH₂, —CH₃, —OCH₃, —CH₂H, —CH₂NH₂ and —CH(NH)₂CH₃.

In some embodiments, R⁴ and R⁵, taken together with the carbon to which they are attached, form a 4-6 membered carbocyclic or heterocyclic ring, which ring is optionally substituted with one or two substituents each independently selected from the group consisting of (C₁-C₆)alkyl, —O(C₁-C₆)alkyl, —N(R⁶)₂, —C(O)N(R⁶)₂, halogen, oxo, and cyano.

In some embodiments, R⁴ and R⁵ taken together, are selected from the group consisting of:

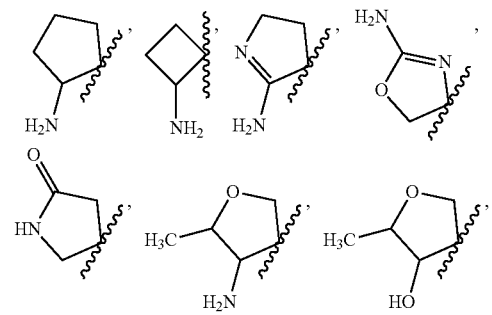

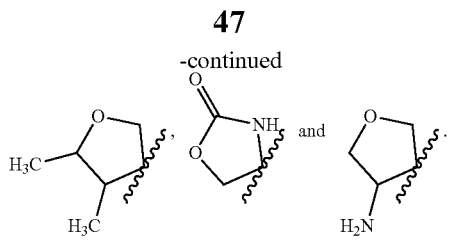

In some embodiments, the compound is represented by:

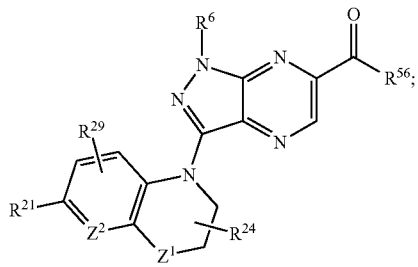

wherein $R^{56}$ is selected from the group consisting of piperidin-1-yl and pyrrolidine-1-yl, wherein $R^{56}$ is optionally substituted by one or two substituents each selected from the group consisting of $C_{1-2}$alkylNH$_2$, NH$_2$, and $C_{1-2}$alkyl.

In some embodiments, the compound is represented by:

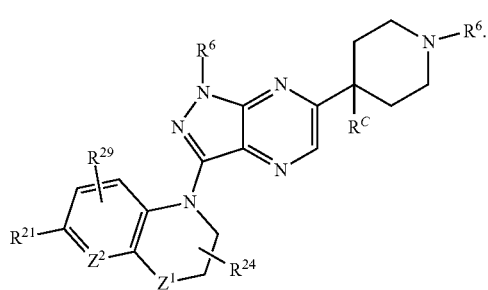

In some embodiments, the compound is represented by:

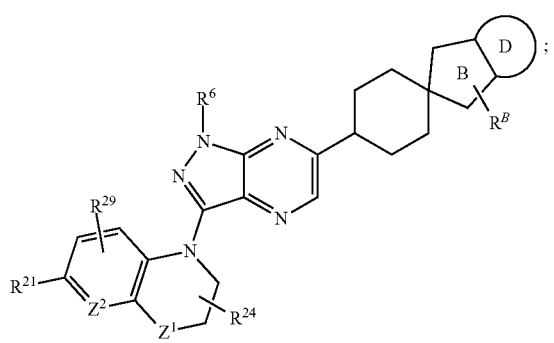

wherein $R^B$ is independently selected from the group consisting of hydrogen, —C(O)N(R$^6$)$_2$, —N(R$^6$)$_2$, and —C$_{1-3}$alkyl-N(R$^6$)$_2$.

In some embodiments, D is selected from the group consisting of:

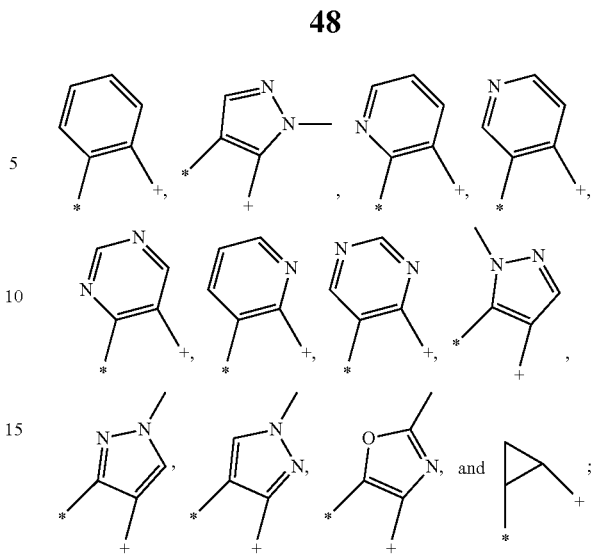

wherein * and + represent fusion points of attachment to ring B.

In some embodiments, $Z^2$ is N. In some embodiments, $Z^2$ is CH. In some embodiments, $Z^1$ is C(R$^{23}$)$_2$.

In some embodiments, $R^{23}$ for each occurrence is hydrogen. In some embodiments, $R^{23}$ for each occurrence is methyl.

In some embodiments, $R^{22}$ and $R^{24}$, for each occurrence, is hydrogen.

In some embodiments, $R^{21}$ is selected from the group consisting of hydrogen, halogen, CF$_3$, N(R$^6$)$_2$, C(O)N(R$^6$)$_2$, heteroaryl, and phenyl. In some embodiments, $R^{21}$ is C(O)NHCH$_3$.

In some embodiments, $R^{21}$ is heteroaryl. In some embodiments, $R^{21}$ is selected from the group consisting of selected from the group consisting of:

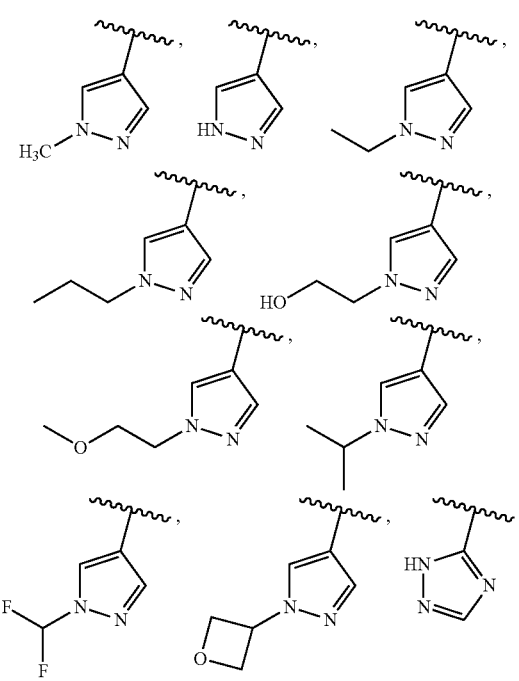

49

-continued

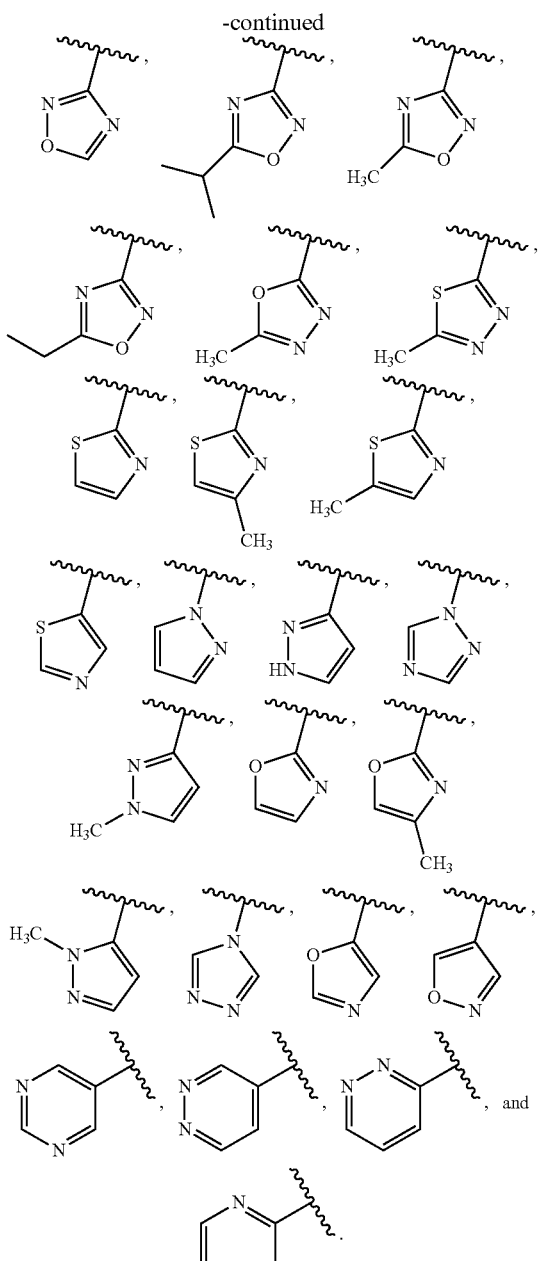

In some embodiments, $R^{21}$ is hydrogen.

Also disclosed herein, for example, is a compound of Formula VIIa, VIIb, VIIc or VId, or a pharmaceutically acceptable salt or stereoisomer thereof, represented by:

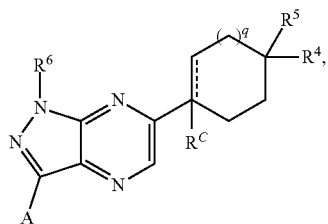
(VIIa)

50

-continued

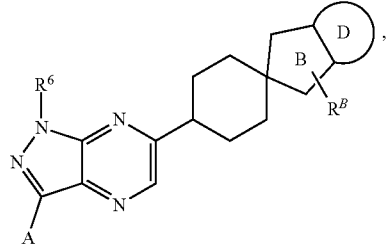
(VIIb)

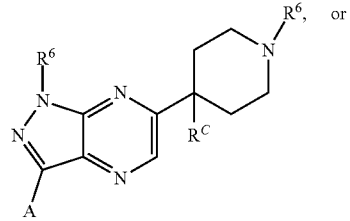
(VIIc)

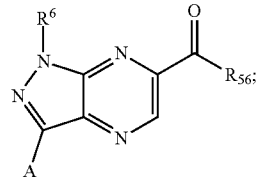
(VIId)

wherein:
A is selected from the group consisting of:

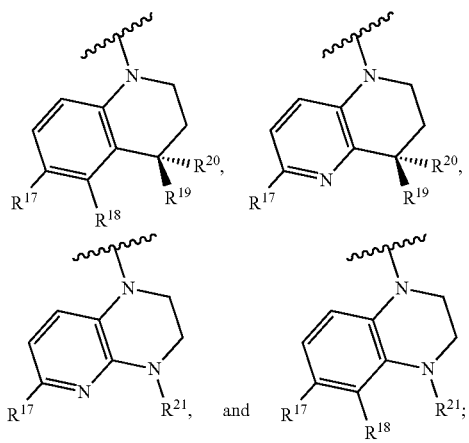

wherein:
$R^7$ is selected from the group consisting of H, Cl, F, $CHF_2$, $CF_3$, —CN, $C_{1-4}$alkyl, $C_{3-6}$cycloalkyl, $C_{5-6}$cycloalkenyl, —$OC_{1-4}$alkyl, —O-heteroaryl, $C_{2-4}$alkenyl, $C_{2-4}$alkynyl, —C≡N—$OC_{1-4}$alkyl, —C≡N—OH, —C($C_{1-4}$alkyl)=N—OH, —$(CH_2)_{0-1}$C(O)$NH_2$, —$(CH_2)_{0-1}$C(O)$NHC_{1-4}$alkyl, —$(CH_2)_{0-1}$C(O)$NHC_{1-4}$alkyl-heteroaryl, —$(CH_2)_{0-1}$C(O)N($C_{1-4}$alkyl)$_2$, —$(CH_2)_{0-1}$C(O)O$C_{1-4}$alkyl, —$(CH_2)_{0-1}$C(O)OH, —$(CH_2)_{0-1}$S(O)$_2$$C_{1-4}$alkyl, —$(CH_2)_{0-1}$$NH_2$, —$(CH_2)_{0-1}$$NHC_{1-4}$alkyl, —$(CH_2)$—$_1$($C_{1-4}$alkyl)$_2$, —$(CH_2)_{0-1}$NH(CO)$C_{1-4}$alkyl, phenyl, heteroaryl, and heterocyclyl,
wherein heteroaryl and O-heteroaryl is optionally substituted with one or more $C_{1-2}$ alkyl (optionally substituted with one, two or three fluorine atoms, one or two hydroxyl groups, or one or two —OC$_{1-2}$alkyl groups); and wherein heterocyclyl is optionally substituted with one or more hydroxyl or C$_{1-2}$alkyl (optionally substituted with one, two or three fluorine atoms, one or two hydroxyl groups, or one or two —OC$_{1-2}$alkyl groups);

R$^{18}$ is selected from the group consisting of H, Cl, F, —CN, NO$_2$, C$_{1-4}$alkyl, C$_{3-4}$cycloalkyl, C$_{2-4}$alkenyl, C$_{2-4}$alkynyl, —OC$_{1-4}$alkyl, —(CH$_2$)$_{0-1}$C(O)NH$_2$, —(CH$_2$)$_{0-1}$C(O)NHC$_{1-4}$alkyl, —(CH$_2$)$_{0-1}$C(O)N(C$_{1-4}$alkyl)$_2$, —(CH$_2$)$_{0-1}$C(O)OC$_{1-4}$alkyl, —(CH$_2$)$_{0-1}$C(O)OH, NH$_2$, —NHC(O)C$_{1-4}$alkyl, —NHS(O)$_2$C$_{1-4}$alkyl, —N(S(O)$_2$C$_{1-4}$alkyl)$_2$, —N(C$_{1-4}$alkyl)S(O)$_2$C$_{1-4}$alkyl, —N=S(O)(C$_{1-4}$alkyl)$_2$, —(CH$_2$)$_{0-1}$SC$_{1-4}$alkyl, —(CH$_2$)$_{0-1}$S(O)C$_{1-4}$alkyl, —(CH$_2$)$_{0-1}$S(O)$_2$C$_{1-4}$alkyl, —S(O)$_2$C$_{3-4}$cycloalkyl, —S(O)$_2$heteroaryl, —S(O)(=NH)C$_{1-4}$alkyl, —S(O)(=NC$_{1-4}$alkyl)C$_{1-4}$alkyl, phenyl, heteroaryl, and heterocyclyl;

wherein phenyl, heteroaryl and heterocyclyl is optionally substituted with one or more groups independently selected from the group consisting of F, C$_{1-2}$alkyl (optionally substituted with one, two or three fluorine atoms, one or two hydroxyl groups, or one or two —OC$_{1-2}$alkyl groups), cyclopropyl, —C(O)NH$_2$, —C(O)NHC$_{1-4}$alkyl, —C(O)N(C$_{1-4}$alkyl)$_2$, —C(O)OC$_{1-4}$alkyl, and —C(O)OH;

each of R$^{19}$ and R$^{20}$ is independently selected from the group consisting of H and —C$_{1-4}$alkyl; or R$^{19}$ and R$^{20}$ together with the carbon atom to which they are attached form a C$_{2-4}$ alkenyl moiety which is optionally substituted with one or two fluorine atoms;

R$^{21}$ is selected from the group consisting of H, C$_{1-4}$alkyl, —C$_{3-4}$cycloalkyl, —(CH$_2$)$_{0-4}$C(O)C$_{1-4}$alkyl, —(CH$_2$)$_{0-4}$C(O)OC$_{1-4}$alkyl, —(CH$_2$)$_{0-4}$C(O)NH$_2$, —(CH$_2$)$_{0-4}$C(O)NHC$_{1-4}$alkyl, —(CH$_2$)$_{0-4}$C(O)N(C$_{1-4}$alkyl)$_2$, —(CH$_2$)$_{0-4}$S(O)$_2$C$_{1-4}$alkyl, and heterocyclyl;

wherein each C$_{1-4}$alkyl, C$_{2-4}$alkenyl, C$_{2-4}$alkynyl, C$_{3-4}$cycloalkyl, C$_{3-6}$cycloalkyl, or C$_{5-6}$cycloalkenyl of R$^{17}$, R$^{18}$, R$^{19}$, R$^{20}$, or R$^{21}$ is optionally substituted with one, two or three fluorine atoms, one or two hydroxyl groups, or one or two —OC$_{1-2}$alkyl groups;

R$^6$ is independently for each occurrence selected from the group consisting of H, —(C$_1$-C$_6$)alkyl, —C(O)OC$_{1-4}$alkyl, and phenyl;

the dashed bond represents an optional double bond;

wherein R$^C$ is absent when the dashed bond represents a double bond;

R$^C$ is selected from the group consisting of H, OH, —(C$_1$-C$_6$)alkyl, —C(O)—O—C$_{1-6}$(alkyl), —C(O)—C$_{1-6}$(alkyl), and heterocyclyl, wherein C$_{1-6}$(alkyl) is optionally substituted by one two or three substituents each selected from the group consisting of halogen, hydroxyl and N(R$_6$)$_2$;

R$^4$ and R$^5$ are each independently selected from the group consisting of hydrogen, (C$_1$-C$_6$)alkyl, —C(O)N(R$^6$)$_2$, —N(R$^6$)$_2$, halogen, and cyano, wherein said —(C$_1$-C$_6$) alkyl is optionally substituted with one or more substituents selected from the group consisting of —OH, —N(R$^6$)$_2$, oxo, and halogen;

or R$^4$ and R$^5$, taken together with the carbon to which they are attached, form a 4-6 membered carbocyclic or heterocyclic ring, which ring is optionally substituted with one or two substituents each independently selected from the group consisting of (C$_1$-C$_6$)alkyl, —O(C$_1$-C$_6$)alkyl, —N(R$^6$)$_2$, —C(O)N(R$^6$)$_2$, halogen, oxo, and cyano;

q is 0 or 1;

R$^{56}$ is a heterocycle, wherein R$^{56}$ is optionally substituted by one or two substituents each selected from the group consisting of C$_{1-2}$alkylNH$_2$, NH$_2$, and C$_{1-2}$alkyl;

D is selected from the group consisting of: phenyl, a 5- or 6-membered heteroaryl having one or two heteroatoms independently selected from the group consisting of S, O or N, and C$_{3-6}$cycloalkyl, wherein D is optionally substituted on a carbon with one or two substituents each independently selected from R$^{D1}$, and, optionally substituted, on nitrogen, if present, with one or two substituents each independently selected from R$^{D2}$;

B is fused to D such that the two atoms shared by D and B are both carbon;

R$^B$ is independently selected from the group consisting of hydrogen, —C(O)N(R$^6$)$_2$, and —N(R$^6$)$_2$;

R$^{D1}$ is selected from the group consisting of hydroxyl, cyano, halogen, and, —N(R$^6$)$_2$; and R$^{D2}$ is selected from —(C$_1$-C$_6$)alkyl and phenyl.

In some embodiments, the compound is represented by:

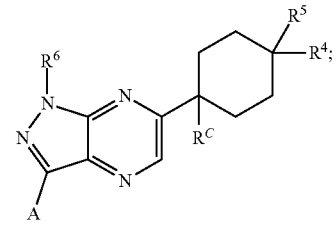

wherein q is 0 or 1.

In some embodiments, the compound is represented by:

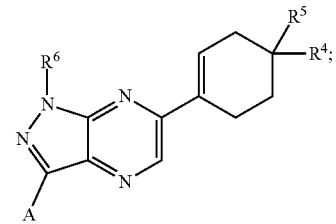

wherein q is 0 or 1.

In some embodiments, R$^4$ and R$^5$ are independently selected from the group consisting of hydrogen, halogen, hydroxyl, —(C$_1$-C$_3$)alkyl, —(C$_1$-C$_3$)alkoxy, and —N(R$^6$)$_2$, wherein said —(C$_1$-C$_3$)alkyl is optionally substituted with one or more substituents selected from the group consisting of —OH, —N(R$^6$)$_2$, and halogen.

In some embodiments, R$^4$ and R$^5$ are independently selected from the group consisting of fluorine, —NH$_2$, —CH$_3$, —OCH$_3$, —CH$_2$H, —CH$_2$NH$_2$ and —CH(NH)$_2$CH$_3$.

In some embodiments, R$^4$ and R$^5$, taken together with the carbon to which they are attached, form a 4-6 membered carbocyclic or heterocyclic ring, which ring is optionally substituted with one or two substituents each independently selected from the group consisting of (C$_1$-C$_6$)alkyl, —O(C$_1$-C$_6$)alkyl, —N(R$^6$)$_2$, —C(O)N(R$^6$)$_2$, halogen, oxo, and cyano.

In some embodiments, R$^4$ and R$^5$ taken together, are selected from the group consisting of:

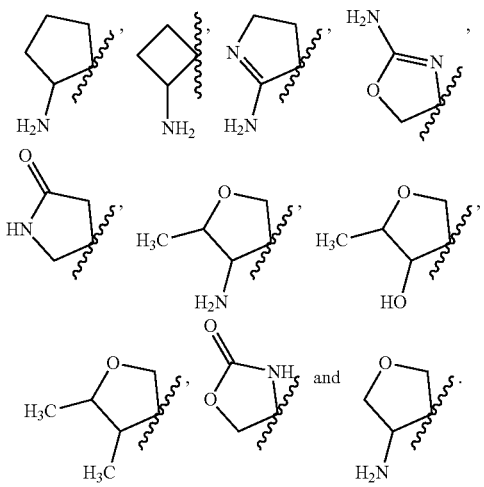

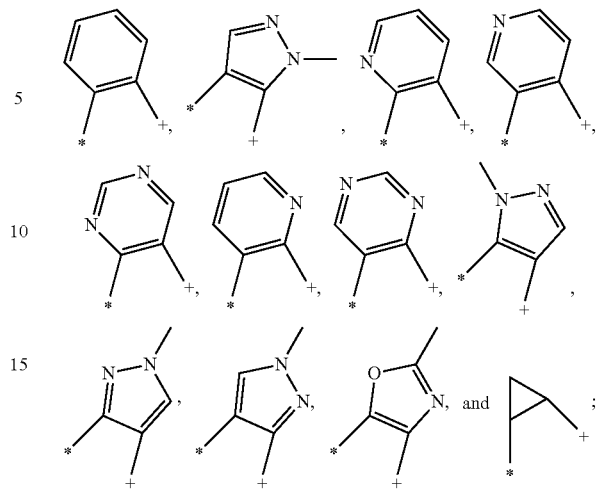

wherein * and + represent fusion points of attachment to ring B.

In some embodiments, the compound is represented by:

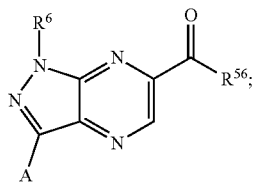

wherein $R^{56}$ is selected from the group consisting of piperidin-1-yl and pyrrolidine-1-yl, wherein $R^{56}$ is optionally substituted by one or two substituents each selected from the group consisting of $C_{1-2}$alkylNH$_2$, NH$_2$, and $C_{1-2}$alkyl.

In some embodiments, the compound is represented by:

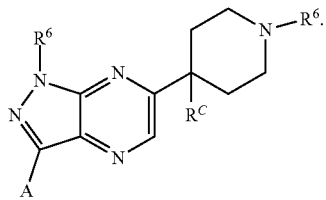

In some embodiments, the compound is represented by:

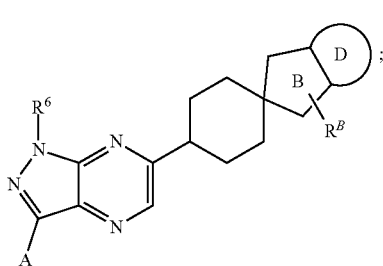

wherein $R^B$ is independently selected from the group consisting of hydrogen, —C(O)N(R$^6$)$_2$, —N(R$^6$)$_2$, and —C$_{1-3}$alkyl-N(R$^6$)$_2$.

In some embodiments, D is selected from the group consisting of

In some embodiments, $R^7$ is selected from the group consisting of 2-pyridyl, 3-pyridyl, 4-pyridyl, 1,2,4-triazol-3-yl, thiazol-2-yl, pyrazol-1-yl, pyrazol-3-yl, pyrazol-4-yl, imidazol-2-yl, oxazol-2-yl, oxazol-5-yl, isoxazol-5-yl, thiazol-2-yl, thiazol-5-yl, 1,3,4-thiadiazol-2-yl, 1,2,4-oxadiazol-3-yl, 1,3,4-oxadiazol-2-yl, 1,2,4-triazol-2-yl, and 1,3,4-triazol-2-yl; wherein $R^{17}$ is optionally substituted with one, two or three fluorine atoms, one or two hydroxyl groups, or one or two —OC$_{1-2}$alkyl groups.

In some embodiments, $R^{17}$ is selected from the group consisting of tetrahydrofuran-3-yl, pyrrolidine-1-yl, piperazin-1-yl, piperidin-4-yl, piperidin-1-yl, 1,2,3,6-tetrahydropyridin-4-yl, 2,5-dihydrofuran-3-yl, piperazin-1-yl-3-one, morpholino, tetrahydropyran-2-yl, and 1,2,4-oxadiazo-3-yl-5-one; wherein $R^{17}$ is optionally substituted with one or more hydroxyl or $C_{1-2}$alkyl (optionally substituted with one, two or three fluorine atoms, one or two hydroxyl groups, or one or two —OC$_{1-2}$alkyl groups).

In some embodiments, $R^{18}$ is selected from the group consisting of phenyl, 2-pyridyl, 3-pyridyl, 4-pyridyl, pyrazol-3-yl, pyrazol-4-yl, thiazol-2-yl, 1,2,4-oxadiazol-3-yl, and 1,3,4-oxadiazol-2-yl; wherein $R^{18}$ is optionally substituted with one or more groups independently selected from the group consisting of F, $C_{1-2}$alkyl (optionally substituted with one, two or three fluorine atoms, one or two hydroxyl groups, or one or two —OC$_{1-2}$alkyl groups), cyclopropyl, —C(O)NH$_2$, —C(O)NHC$_{1-4}$alkyl, —C(O)N(C$_{1-4}$alkyl)$_2$, —C(O)OC$_{1-4}$alkyl, and —C(O)OH.

In some embodiments, $R^{18}$ is selected from the group consisting of —(CH$_2$)$_{0-1}$-morpholino, tetrahydropyranyl, tetrahydrofuranyl, oxiranyl, isothiazolidin-2-yl-1,1-dioxide, and —(CH$_2$)$_{0-1}$-oxazolidin-3-yl-2-one; wherein $R^{18}$ $R^{18}$ is optionally substituted with one or more groups independently selected from the group consisting of F, $C_{1-2}$alkyl (optionally substituted with one, two or three fluorine atoms, one or two hydroxyl groups, or one or two —OC$_{1-2}$alkyl groups), cyclopropyl, —C(O)NH$_2$, —C(O)NHC$_{1-4}$alkyl, —C(O)N(C$_{1-4}$alkyl)$_2$, —C(O)OC$_{1-4}$alkyl, and —C(O)OH.

In some embodiments, $R^{19}$ is —CH$_3$ or —CHF$_2$, $R^{20}$ is H, and the carbon to which $R^{19}$ and $R^{20}$ are attached has an (R)-configuration. In some embodiments, $R^{19}$ is H, $R^{20}$ is —CH$_3$ or —CHF$_2$, and the carbon to which $R^{19}$ and $R^{20}$ are attached has an (S)-configuration.

Also disclosed herein is a compound selected from the group consisting of:
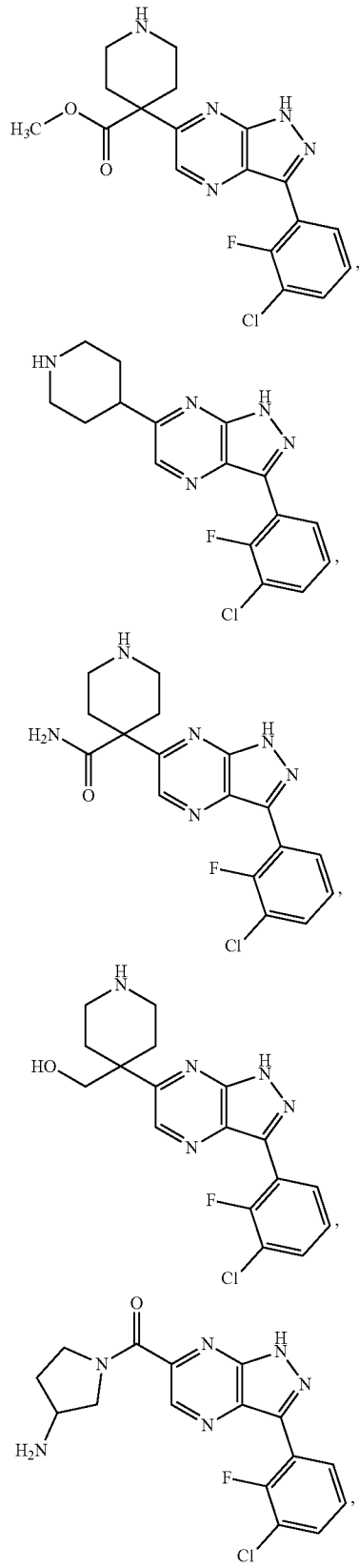
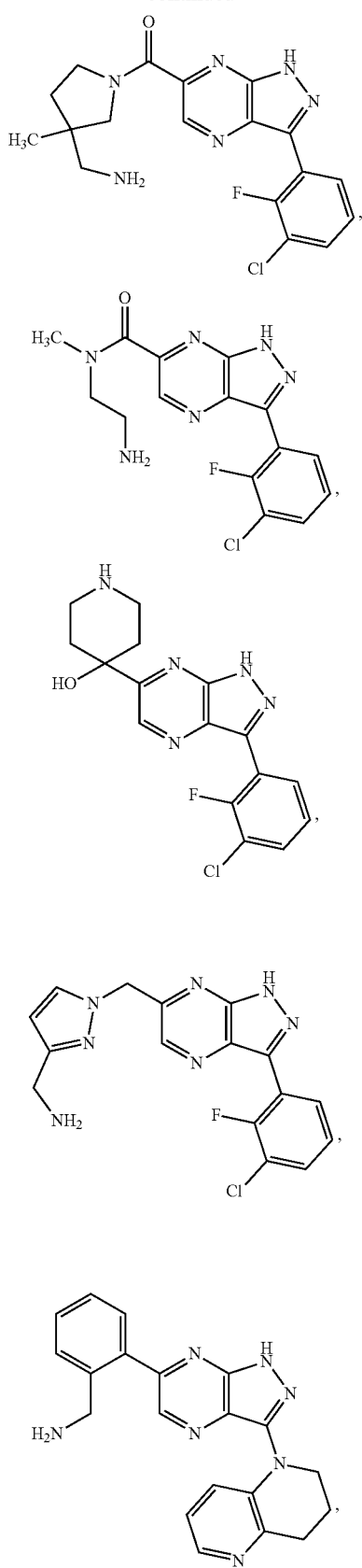

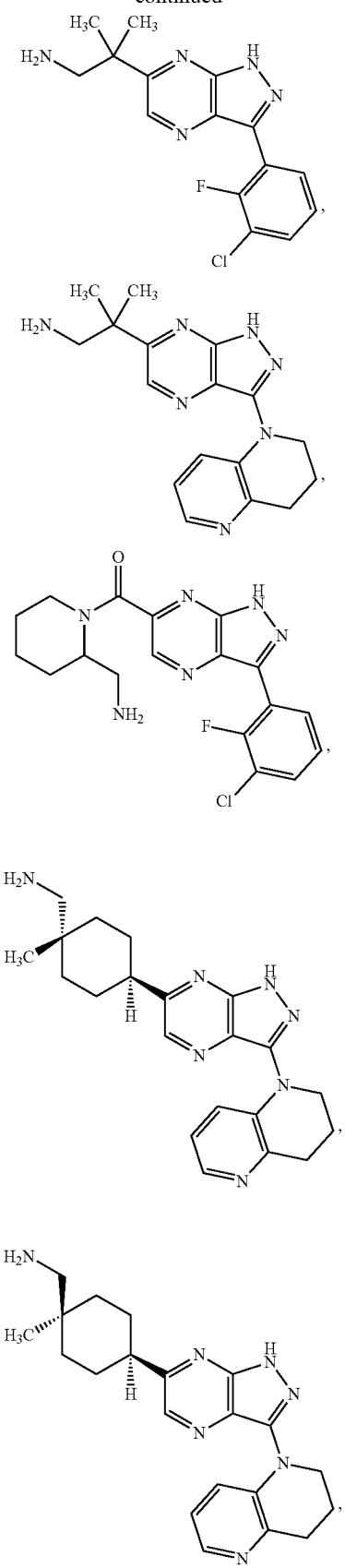
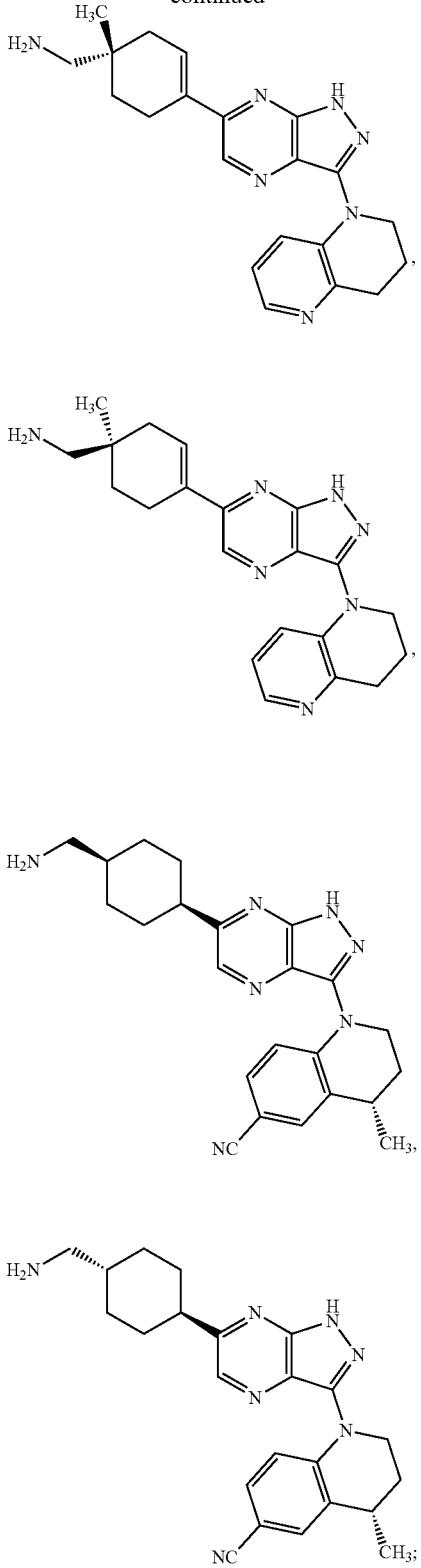
and a pharmaceutically acceptable salt or stereoisomer thereof.
Further disclosed herein is a compound of Formula VIIIa, VIIIb, VIIIc, or VIIId, or a pharmaceutically acceptable salt or stereoisomer thereof, represented by:

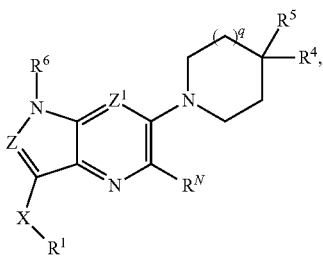

(VIIIa)

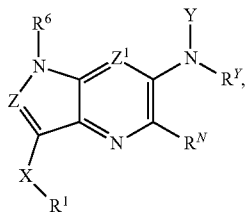

(VIIIb)

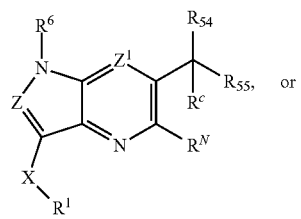

(VIIIc)

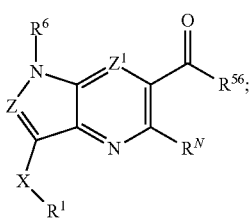

(VIIId)

wherein:

$R^N$ is selected from the group consisting of —CH$_2$OH, —C(H)(OH), —C(OH)(CH$_3$)$_2$, —CH$_3$, —CF$_3$, —CHF$_2$, —CH$_2$F, —CH$_2$OCH$_3$, —C$_{1-3}$alkyl, —C$_{1-3}$alkoxy, —C(O)—C$_{1-3}$alkoxy, —C(O)—C$_{1-3}$alkyl, cyclopropyl, tetrahydrofuran-3-yl, tetrahydrofuran-2-yl, oxetan-3-yl, oxetan-2-yl, azetidin-3-yl, azetidin-2-yl, hydroxyl, cyano, —C(O)—NR$^a$R$^b$, —N(R$^a$)—C(O)—C$_{1-3}$alkyl, —N(R$^a$)—S(O)$_2$—C$_{1-3}$alkyl, —S(O)$_2$—N(R$^a$)—C$_{1-3}$alkyl, —S(O)$_2$—C$_{1-3}$alkyl, CH$_2$NR$^a$R$^b$, —CH$_2$NR$^a$C(O)C$_{1-4}$alkyl, —CH$_2$NR$^a$C(O)OC$_{1-4}$alkyl, —CH$_2$NR$^a$C(O)NR$^b$C$_{1-4}$alkyl, —CH$_2$NR$^a$S(O)$_2$C$_{1-4}$alkyl, and

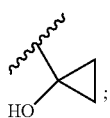;

$Z^1$ is N or CH;
Z is N or CH;
X is selected from the group consisting of a bond, —O—, —NR$^{X1}$—, and —S(O)$_w$— (wherein w is 0, 1 or 2);
$R^{X1}$ is selected from the group consisting of hydrogen, —(C$_1$-C$_6$)alkyl and phenyl;
$R^1$ is a ring moiety selected from the group consisting of a 8-12 membered bicyclic heteroaryl, a 11-15 membered tricyclic heteroaryl, phenyl, a 5-7 membered monocyclic heteroaryl, and a 4-7 membered heterocyclyl, wherein the ring moiety is optionally substituted with one, two or more substituents each independently selected from the group consisting of R$^{10}$, —OR$^{10}$, —S(O)$_w$R$^{10}$ (wherein w is 0, 1 or 2), —C$_{1-6}$alkyl-S(O)$_w$—C$_{1-3}$alkyl, —N(R$^{10}$)$_2$, —N(CO)R$^{10}$, —N—S(O)$_w$—R$^{10}$ (where w is 0, 1 or 2), —OS(O)$_w$—R$^{10}$ (wherein w is 0, 1, or 2), —S(O)$_w$—N(R$^{10}$)$_2$ (wherein w is 0, 1 or 2), —S(O)(NH)R$^{10}$, —N(H)—SO$_2$—C$_{1-3}$alkyl, —N(SO$_2$—C$_{1-3}$alkyl)$_2$, P(O)(R$^{10}$)$_2$, —C(O)R$^{10}$, —C(O)OR$^{10}$, —C(O)N(R$^{10}$)$_2$, oxo, halogen, hydroxyl, cyano, nitro, —C(=N—OR$^a$)—C$_{1-3}$alkyl, —C(=N—OR$^a$)—H, —S(O)(NR$^a$)—C$_{1-3}$alkyl, phenyl (optionally substituted with one, two or three halogen, —O-phenyl, C$_{1-3}$alkyl or C$_{1-3}$haloalkyl), C$_{1-3}$alkyl, C$_{2-6}$alkynyl, C$_{1-3}$haloalkyl, C$_{3-6}$cycloalkyl, heterocyclyl (optionally substituted with one, two or three halogen, oxo, C$_{1-3}$alkyl or C$_{1-3}$haloalkyl), and heteroaryl (optionally substituted with one, two or three halogen, —C(O)N(R$^{10}$)$_2$, C$_{1-3}$alkyl, C$_{1-3}$alkyl-O—C$_{1-3}$alkyl, C$_{1-3}$alkyl-OH, or C$_{1-3}$haloalkyl);

$R^{10}$ is independently selected from the group consisting of hydrogen, C$_{1-6}$alkyl, C$_{2-6}$alkenyl, C$_{2-6}$alkynyl, C$_{3-6}$cycloalkyl, C$_{5-6}$cycloalkenyl, C$_{2-6}$heteroalkyl, heterocycloalkyl, aryl, and heteroaryl; wherein C$_{1-6}$alkyl, C$_{2-6}$alkenyl, C$_{2-6}$alkynyl, C$_{3-6}$cycloalkyl, C$_{5-6}$cycloalkenyl, C$_{2-6}$heteroalkyl, heterocycloalkyl, aryl, and heteroaryl is optionally substituted by one, two, three or more substituents each independently selected from the group consisting of halogen, hydroxyl, —NR$^a$C(O)—R$^{20}$, —C(O)—R$^{20}$, —C(NR$^a$)—R$^b$, —NR$^a$R$^b$, C$_{1-6}$alkyl, C$_{1-6}$haloalkyl and C$_{1-6}$alkoxy;

$R^{20}$ is selected from the group consisting of hydrogen, hydroxyl, halogen, —NR$^a$R$^b$, C$_{1-6}$alkyl and C$_{1-6}$alkoxy;

$R^a$ and $R^b$ are each independently selected from the group consisting of hydrogen and C$_{1-3}$alkyl;

$R^6$ is independently for each occurrence selected from the group consisting of H, —(C$_1$-C$_6$)alkyl, —C(O)OC$_{1-4}$alkyl, and phenyl;

q is 0 or 1;

$R^Y$ is selected from the group consisting of hydrogen and —(C$_1$-C$_6$)alkyl;

Y is selected from the group consisting of a 3-7 membered saturated carbocycle, a 4-7 membered saturated heterocycle, phenyl, and a 5-6 membered monocyclic heteroaryl; wherein Y is optionally substituted with one or more substituents each independently selected from the group consisting of (C$_1$-C$_6$)alkyl, —C(O)N(R$^6$)$_2$, —N(R$^6$)$_2$, halogen, and cyano, wherein said —(C$_1$-C$_6$)alkyl is optionally substituted with one or more substituents selected from the group consisting of —OH, —N(R$^6$)$_2$, oxo, and halogen;

$R^{55}$ is selected from the group consisting of —C$_{1-4}$alkyl-N(R$^6$)$_2$, —N(R$^6$)$_2$, and heteroaryl (optionally substituted by one, two, or three substituent each independently selected from halogen, hydroxyl, cyano, —(C$_1$-C$_6$)alkyl, —O(C$_1$-C$_6$)alkyl, —C(O)N(R$^6$)$_2$, —N(R$^6$)$_2$, and —(C$_1$-C$_6$)alkyl-N(R$^6$)$_2$);

$R^{54}$ is selected from the group consisting of H, and C$_{1-2}$alkyl, or $R^{54}$ and $R^{55}$ taken together with the carbon to which they are attached form a ring selected from the group consisting of C$_{3-6}$cycloalkyl and heterocyclyl, wherein the ring is optionally substituted on a carbon by one, two or three substituents each independently selected from the group consisting of $R^4$ and $R^5$ and on a nitrogen if present by $R^6$;

$R^C$ is selected from the group consisting of H, OH, —($C_1$-$C_6$)alkyl, —C(O)—O—$C_{1-6}$(alkyl), —C(O)—$C_{1-6}$(alkyl), and heterocyclyl, wherein $C_{1-6}$(alkyl) is optionally substituted by one two or three substituents each selected from the group consisting of halogen, hydroxyl. —C(O)N($R^{10}$)$_2$, and N($R_6$)$_2$; or wherein $R^C$ is absent $R^{54}$ and $R^{55}$ taken together with the carbon to which they are attached form a ring selected from $C_{5-6}$cyclalkenyl and phenyl; wherein the ring is optionally substituted on a carbon by one, two or three substituents each independently selected from the group consisting of $R^4$ and $R^5$;

$R^{56}$ is N($R_6$)$_2$ or heterocycle (optionally substituted by one, two or three substituents each independently selected from halogen, hydroxyl, N($R_6$)$_2$, —($C_1$-$C_6$)alkyl, —C(O)—O—$C_{1-6}$(alkyl), —C(O)—$C_{1-6}$(alkyl), wherein $C_{1-6}$(alkyl) is optionally substituted by one two or three substituents each selected from the group consisting of: halogen, hydroxyl or N($R_6$)$_2$);

$R^4$ and $R^5$ are each independently selected from the group consisting of H, —OH, —($C_1$-$C_6$)alkyl, —O($C_1$-$C_6$)alkyl, —($C_1$-$C_6$)alkyl-O—$R^6$, —C(O)N($R^6$)$_2$, —N($R^6$)$_2$, halogen, —($C_1$-$C_6$)alkyl-N($R^6$)$_2$, and cyano, wherein said —($C_1$-$C_6$)alkyl, —O($C_1$-$C_6$)alkyl, —($C_1$-$C_6$)alkyl-O—$R^6$, or —($C_1$-$C_6$)alkyl-N($R^6$)$_2$ is optionally substituted with one or more substituents selected from the group consisting of —OH, —NH$_2$, oxo, and halogen;

or $R^4$ and $R^5$, taken together with the carbon to which they are attached, form a 4-6 membered carbocyclic or heterocyclic ring B; which ring is optionally substituted with one or two substituents each independently selected from the group consisting of ($C_1$-$C_6$)alkyl, —O($C_1$-$C_6$)alkyl, —N($R^6$)$_2$, —C(O)N($R^6$)$_2$, halogen, oxo, and cyano and/or which ring may be fused to a ring D;

D is selected from the group consisting of: phenyl, a 5- or 6-membered heteroaryl having one or two heteroatoms each independently selected from the group consisting of S, O or N, and $C_{3-6}$cycloalkyl, wherein D is optionally substituted on an available carbon with one or two substituents each independently selected from $R^{D1}$, and, optionally substituted, on nitrogen, if present, with one or two substituents each independently selected from $R^{D2}$;

B is fused to D such that the two atoms shared by D and B are both carbon or one carbon and one nitrogen;

$R^{D1}$ is selected from the group consisting of hydroxyl, cyano, halogen, and —N($R^6$)$_2$; and $R^{D2}$ is selected from —($C_1$-$C_6$)alkyl and phenyl.

In some embodiments, X is a bond, $R^1$ is a nitrogen containing ring moiety and $R^1$ is bound through the nitrogen.

In some embodiments, $R^1$ is selected from the group consisting of 1,2,3,4-tetrahydroquinolin-1-yl, 1,2,3,4-tetrahydro-1,5-naphthyridin-1-yl, 1,2,3,4-tetrahydroquinolin-1-yl, 1,2,3,4-tetrahydroquinoxalin-1-yl, 1,2,3,4-tetrahydropyrido[2,3-b]pyrazin-1-yl, 1H-benzo[d]imidazol-1-yl, indolin-1-yl, 2,3-dihydro-1H-pyrrolo[3,2-b]pyridin-1-yl, 2,3-dihydro-1H-pyrrolo[3,2-c]pyridin-1-yl, isoindolin-2-yl, 2,3,4,5-tetrahydrobenzo[f][1,4]oxazepin-4-yl, 2-(3,4-dihydroisoquinolin-1(2H)-one), 2-(3,4-dihydroisoquinolin-1(2H)-one), 2,3-dihydro-1H-pyrido[2,3-b][1,4]oxazin-1-yl, piperidin-1-yl, 1-(1,2,3,4-tetrahydro-6H-pyrido[1,2-a]pyrimidin-6-one), 1,2,3,4-tetrahydro-1,8-naphthyridin-1-yl, 1-(3,4-dihydro-1,5-naphthyridin-2(1H)-one), 2,3,4,5-tetrahydro-1H-benzo[b]azepin-1-yl, 1-(2,3-dihydroquinolin-4(1H)-one), 2,3-dihydro-1H-pyrido[2,3-b][1,4]oxazin-1-yl, 1,2,3,4-tetrahydro-1,6-naphthyridin-1-yl, 5,6,7,8-tetrahydro-4H-pyrazolo[1,5-a][1,3]diazepin-4-yl, 3,4-dihydroquinoxalin-1-yl-2(1H)-one, 2,3,4,6-tetrahydro-1,6-naphthyridin-1-yl-5(1H)-one, 1,2,3,4-tetrahydroisoquinolin-2-yl, 1,2,3,4-tetrahydro-2,7-naphthyridin-2-yl, 1,2,3,4-tetrahydro-2,6-naphthyridin-2-yl, 3,4-dihydro-2H-benzo[b][1,4]thiazin-4-yl 1 1-dioxide, 1,2,3,4-tetrahydropyrazino[2,3-d]pyridazin-1-yl, 1,4-dihydropyrido[3,4-b]pyrazin-1-yl-3(2H)-one, 5,6,7,8-tetrahydro-1,6-naphthyridin-6-yl, 5,6,7,8-tetrahydro-1,7-naphthyridin-7-yl, 1,2,3,4-tetrahydropyrido[3,4-b]pyrazin-1-yl, 5,8-dihydropteridin-5-yl-7(6H)-one, 4,5,6,7-tetrahydrothieno[3,2-b]pyridin-4-yl, or 5,6,7,8-tetrahydropyrazino[2,3-c]pyridazin-5-yl wherein the nitrogen ring moiety may be optionally substituted with one or two substituents each independently selected from the group consisting of Cl, F, —CN, $C_{1-4}$alkyl, —O$C_{1-4}$alkyl, $C_{2-6}$alkenyl, $C_{2-4}$alkynyl, $C_{3-6}$cycloalkyl, $C_{5-6}$cycloalkenyl, —C(H)=N—OCH$_3$, —C(H)=N—OH, —C(CH$_3$)=N—OH, —(CH$_2$)$_{0-1}$C(O)NH$_2$, —(CH$_2$)$_{0-1}$C(O)NHC$_{1-4}$alkyl, —(CH$_2$)$_{0-1}$C(O)N(C$_{1-4}$alkyl)$_2$, —(CH$_2$)$_{0-1}$C(O)OC$_{1-4}$alkyl, —(CH$_2$)$_{0-1}$C(O)OH, —S(O)$_2$C$_{1-4}$alkyl, —(CH$_2$)$_{0-1}$NH$_2$, —(CH$_2$)$_{0-1}$NHC$_{1-4}$alkyl, —(CH$_2$)$_{0-1}$(C$_{1-4}$alkyl)$_2$, —(CH$_2$)$_{0-1}$NH(CO)C$_{1-4}$alkyl, phenyl, optionally substituted heteroaryl and optionally substituted heterocyclyl, wherein $C_{1-4}$alkyl or $C_{3-6}$cycloalkyl may be optionally substituted with one, two or three fluorine atoms, one or two hydroxyl groups, or one or two —OC$_{1-2}$alkyl groups.

In some embodiments, heteroaryl is selected from the group consisting of 2-pyridyl, 3-pyridyl, 4-pyridyl, 1,2,4-triazol-3-yl, thiazol-2-yl, pyrazol-1-yl, pyrazol-3-yl, pyrazol-4-yl, imidazol-2-yl, oxazol-2-yl, oxazol-5-yl, isoxazol-5-yl, thiazol-2-yl, thiazol-5-yl, 1,3,4-thiadiazol-2-yl, and 1,2,4-oxadiazol-3-yl, 1,3,4-oxadiazol-2-yl, 1,2,4-triazol-2-yl, 1,3,4-triazol-2-yl; wherein heteroaryl may be optionally substituted with $C_{1-2}$alkyl (optionally substituted with one, two or three fluorine atoms, one or two 2 hydroxyl groups, or one or two —OC$_{1-2}$alkyl groups).

In some embodiments, heterocyclyl is selected from the group consisting of tetrahydrofuran-3-yl, pyrrolidine-1-yl, piperazin-1-yl, piperidin-4-yl, piperidin-1-yl, 1,2,3,6-tetrahydropyridin-4-yl, 2,5-dihydrofuran-3-yl, piperazin-1-yl-3-one, morpholino, tetrahydropyran-2-yl, or 1,2,4-oxadiazo-3-yl-5-one, wherein heterocyclyl may be optionally substituted with hydroxyl or $C_{1-2}$alkyl (optionally substituted with one, two or three fluorine atoms, one or two 2 hydroxyl groups, or one or two —OC$_{1-2}$alkyl groups).

In some embodiments, $R^1$ is a 1,2,3,4-tetrahydroquinoline moiety optionally substituted with one, two or three halo, $C_{1-3}$alkyl, $C_{1-3}$haloalkyl, and heteroaryl (optionally substituted with one, two or three halogen, —C(O)N($R^{10}$)$_2$, $C_{1-3}$alkyl, $C_{1-3}$alkyl-O—$C_{1-3}$alkyl, $C_{1-3}$alkyl-OH, or $C_{1-3}$haloalkyl).

In some embodiments, $R^1$ is a 1,2,3,4-tetrahydro-1,5-naphthyridine moiety optionally substituted with one, two or three halo, $C_{1-3}$alkyl, $C_{1-3}$haloalkyl, and heteroaryl (optionally substituted with one, two or three halogen, —C(O)N($R^{10}$)$_2$, $C_{1-3}$alkyl, $C_{1-3}$alkyl-O—$C_{1-3}$alkyl, $C_{1-3}$alkyl-OH, or $C_{1-3}$haloalkyl).

In some embodiments, $R^1$ is phenyl; wherein phenyl is optionally substituted by one, two, or three substituents each independently selected from the group consisting of —O$R^{10}$, —N($R^{10}$)$_2$, halogen, and cyano.

In some embodiments, $R^1$ is pyridyl; wherein pyridyl is optionally substituted by one, two, or three substituents each independently selected from the group consisting of —OR$^{10}$, —N(R$^{10}$)$_2$, halogen, and cyano.

In some embodiments, R$^1$ is indolyl or indolinyl, wherein indolyl or indolinyl is optionally substituted with one, two, or three substituents each independently selected from the group consisting of —OR$^{10}$, —N(R$^{10}$)$_2$, halogen, and cyano; and wherein indolyl or indolinyl is bound through carbon.

In some embodiments, the compound is represented by:

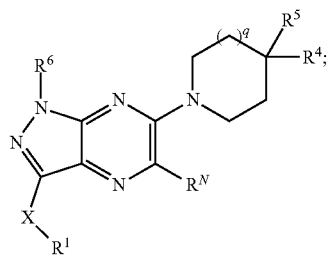

wherein q is 0 or 1.

In some embodiments, R$^4$ and R$^5$ are each independently selected from the group consisting of H, —OH, —(C$_1$-C$_6$) alkyl, —O(C$_1$-C$_6$)alkyl, —(C$_1$-C$_6$)alkyl-O—R$^6$, —C(O)N(R$^6$)$_2$, —N(R$^6$)$_2$, halogen, —(C$_1$-C$_6$)alkyl-N(R$^6$)$_2$, and cyano, wherein said —(C$_1$-C$_6$)alkyl, —O(C$_1$-C$_6$)alkyl, —(C$_1$-C$_6$)alkyl-O—R$^6$, or —(C$_1$-C$_6$)alkyl-N(R$^6$)$_2$ is optionally substituted with one or more substituents selected from the group consisting of —OH, —NH$_2$, oxo, and halogen.

In some embodiments, R$^4$ and R$^5$ are independently selected from the group consisting of fluorine, —NH$_2$, —CH$_3$, —OCH$_3$, —CH$_2$OH, —CH$_2$NH$_2$ and —CH(NH)$_2$CH$_3$.

In some embodiments, R$^4$ and R$^5$, taken together with the carbon to which they are attached, form a 4-6 membered carbocyclic or heterocyclic ring, which ring is optionally substituted with one or two substituents each independently selected from the group consisting of (C$_1$-C$_6$)alkyl, —O(C$_1$-C$_6$)alkyl, —N(R$^6$)$_2$, —C(O)N(R$^6$)$_2$, halogen, oxo, and cyano.

In some embodiments, R$^4$ and R$^5$ taken together, are selected from the group consisting of:

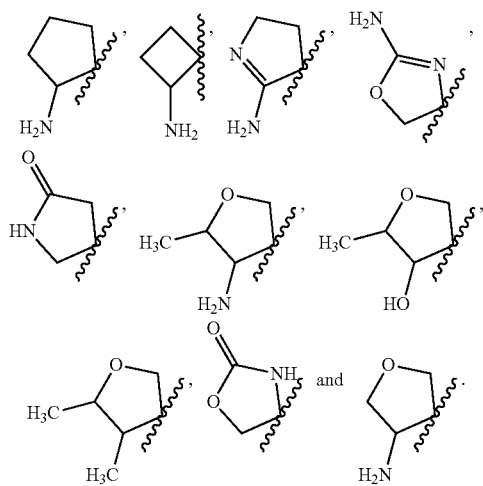

In some embodiments, q is 1.

In some embodiments, the compound is represented by:

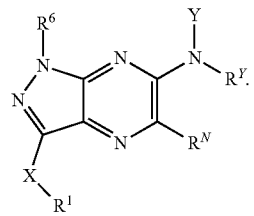

In some embodiments, Y is cyclopentyl, wherein Y is optionally substituted with one or more substituents each independently selected from the group consisting of (C$_1$-C$_6$)alkyl, —C(O)N(R$^6$)$_2$, —N(R$^6$)$_2$, halogen, and cyano, wherein said —(C$_1$-C$_6$)alkyl is optionally substituted with one or more substituents selected from the group consisting of —OH, —N(R$^6$)$_2$, oxo, and halogen.

In some embodiments, Y is cyclohexyl, wherein Y is optionally substituted with one or more substituents each independently selected from the group consisting of (C$_1$-C$_6$)alkyl, —C(O)N(R$^6$)$_2$, —N(R$^6$)$_2$, halogen, and cyano, wherein said —(C$_1$-C$_6$)alkyl is optionally substituted with one or more substituents selected from the group consisting of —OH, —N(R$^6$)$_2$, oxo, and halogen.

In some embodiments, Y is tetrahydrofuranyl, wherein Y is optionally substituted with one or more substituents each independently selected from the group consisting of (C$_1$-C$_6$)alkyl, —C(O)N(R$^6$)$_2$, —N(R$^6$)$_2$, halogen, and cyano, wherein said —(C$_1$-C$_6$)alkyl is optionally substituted with one or more substituents selected from the group consisting of —OH, —N(R$^6$)$_2$, oxo, and halogen.

In some embodiments, Y is tetrahydropyranyl, wherein Y is optionally substituted with one or more substituents each independently selected from the group consisting of (C$_1$-C$_6$)alkyl, —C(O)N(R$^6$)$_2$, —N(R$^6$)$_2$, halogen, and cyano, wherein said —(C$_1$-C$_6$)alkyl is optionally substituted with one or more substituents selected from the group consisting of —OH, —N(R$^6$)$_2$, oxo, and halogen.

In some embodiments, Y is substituted on an available carbon by a substituent selected from the group consisting of —NH$_2$ and —CH$_2$NH$_2$.

In some embodiments, Y is selected from the group consisting of:

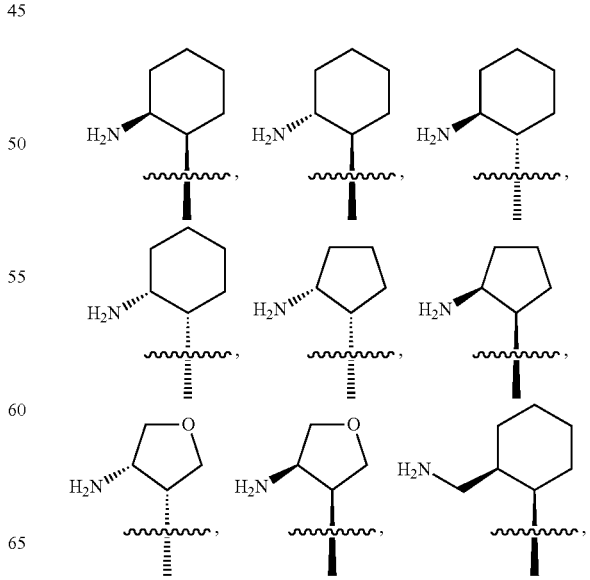

-continued

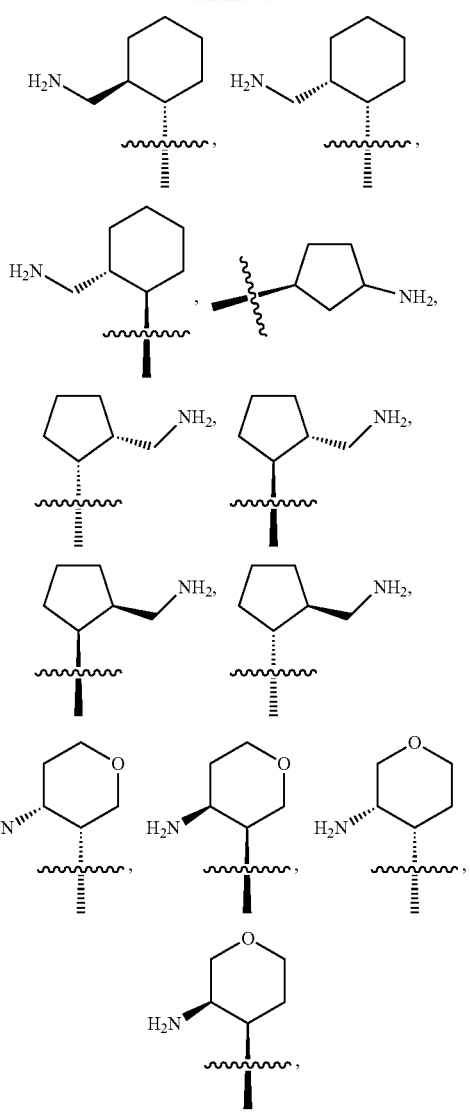

and stereoisomers thereof.

In some embodiments, Y is phenyl or 5-6 membered heteroaryl, wherein Y is optionally substituted with one or more substituents each independently selected from the group consisting of $(C_1$-$C_6)$alkyl, —C(O)N(R$^6$)$_2$, —N(R$^6$)$_2$, halogen, and cyano, wherein said —$(C_1$-$C_6)$alkyl is optionally substituted with one or more substituents selected from the group consisting of —OH, —N(R$^6$)$_2$, oxo, and halogen.

In some embodiments, Y is selected from the group consisting of:

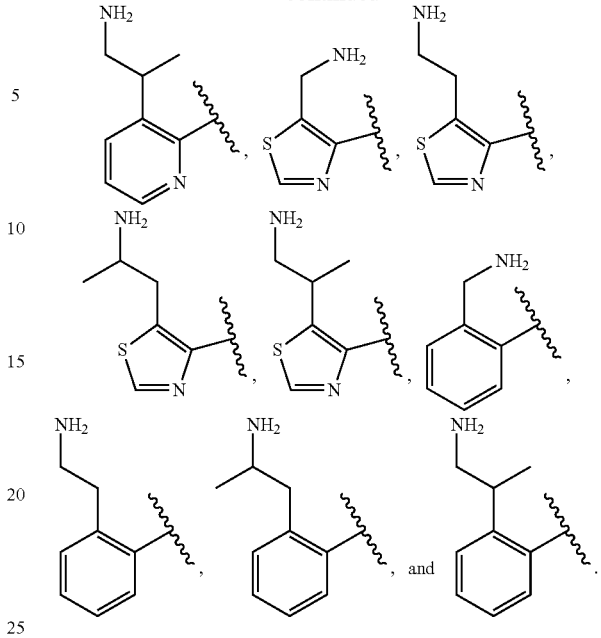

In some embodiments, R$^Y$ is —H or —CH$_3$.

In some embodiments, the compound is represented by:

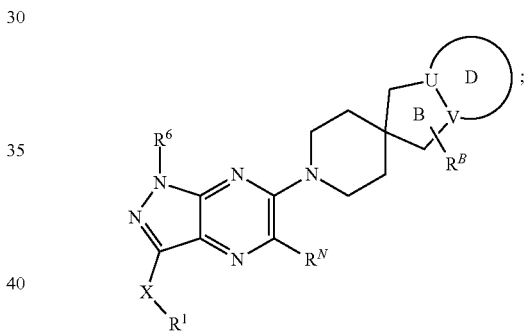

wherein R$^B$ is independently selected from the group consisting of hydrogen, —C(O)N(R$^6$)$_2$, —N(R$^6$)$_2$, and —C$_{1-3}$alkyl-N(R$^6$)$_2$;

U is selected from the group consisting of C, CH and N;

V is selected from the group consisting of C, CH and N;

wherein at least one of U or V is not N.

In some embodiments, D is selected from the group consisting of:

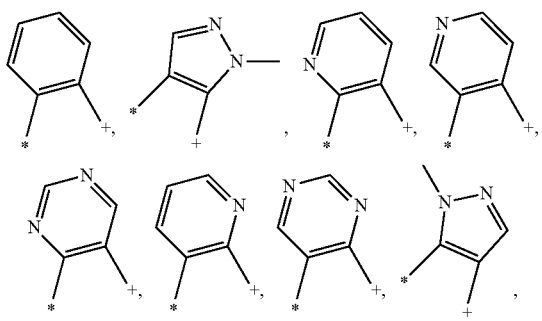

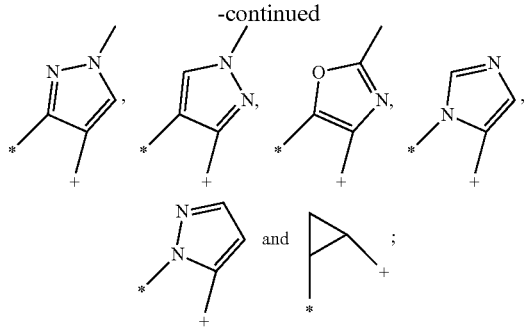

wherein * and + represent fusion points of attachment to ring B.

In some embodiments, the compound is represented by:

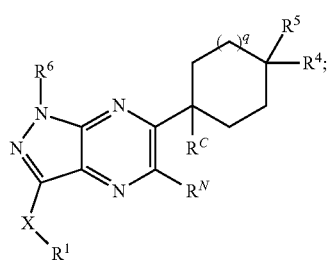

wherein q is 0 or 1.

In some embodiments, the compound is represented by:

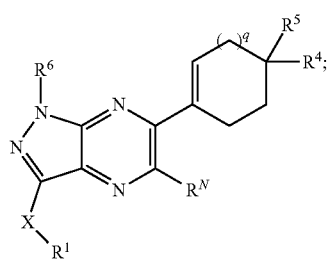

wherein q is 0 or 1.

In some embodiments, $R^4$ and $R^5$ are independently selected from the group consisting of hydrogen, halogen, hydroxyl, —$(C_1-C_3)$alkyl, —$(C_1-C_3)$alkoxy, and —$N(R^6)_2$, wherein said —$(C_1-C_3)$alkyl is optionally substituted with one or more substituents selected from the group consisting of —OH, —$N(R^6)_2$, and halogen.

In some embodiments, $R^4$ and $R^5$ are independently selected from the group consisting of fluorine, —$NH_2$, —$CH_3$, —$OCH_3$, —$CH_2H$, —$CH_2NH_2$ and —$CH(NH)_2CH_3$.

In some embodiments, $R^4$ and $R^5$, taken together with the carbon to which they are attached, form a 4-6 membered carbocyclic or heterocyclic ring, which ring is optionally substituted with one or two substituents each independently selected from the group consisting of $(C_1-C_6)$alkyl, —$O(C_1-C_6)$alkyl, —$N(R^6)_2$, —$C(O)N(R^6)_2$, halogen, oxo, and cyano.

In some embodiments, $R^4$ and $R^5$ taken together, are selected from the group consisting of:

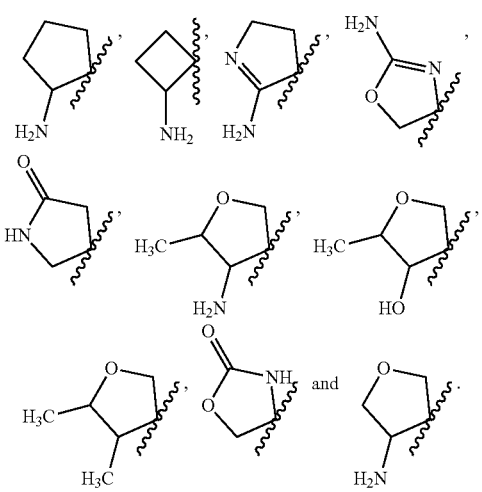

In some embodiments, the compound is represented by:

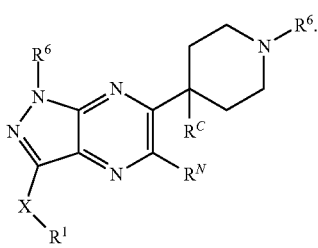

wherein
$R^{56}$ is selected from the group consisting of piperidin-1-yl and pyrrolidine-1-yl, wherein $R^{56}$ is optionally substituted by one or two substituents each selected from the group consisting of $C_{1-2}$alkyl$NH_2$, $NH_2$, and $C_{1-2}$alkyl.

In some embodiments, the compound is represented by:

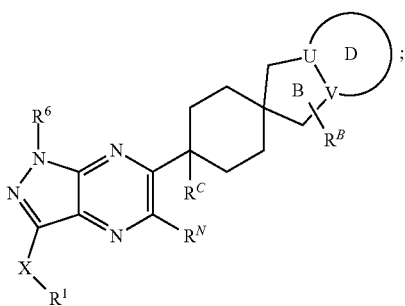

In some embodiments, the compound is represented by:

wherein:
$R^B$ is independently selected from the group consisting of hydrogen, —C(O)N($R^6$)$_2$, —N($R^6$)$_2$, and —C$_{1-3}$alkyl-N($R^6$)$_2$;
U is selected from the group consisting of C, CH and N;
V is selected from the group consisting of C, CH and N;
wherein at least one of U or V is not N.

In some embodiments, D is selected from the group consisting of:

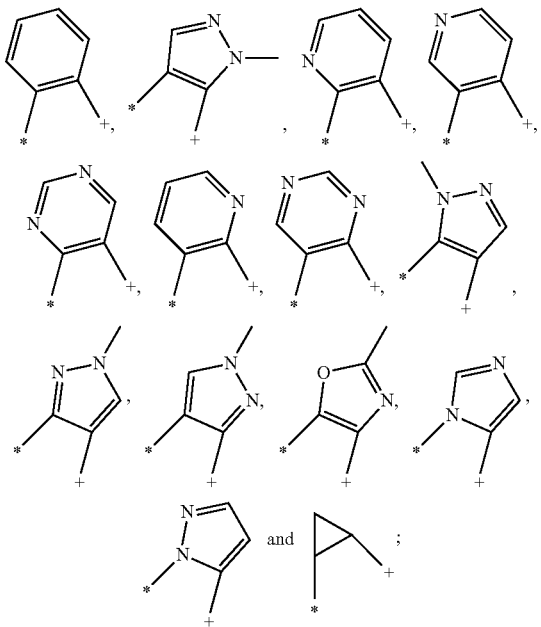

wherein * and + represent fusion points of attachment to ring B.

Also disclosed herein is, for example, a compound of Formula IX, or a pharmaceutically acceptable salt or stereoisomer thereof, represented by:

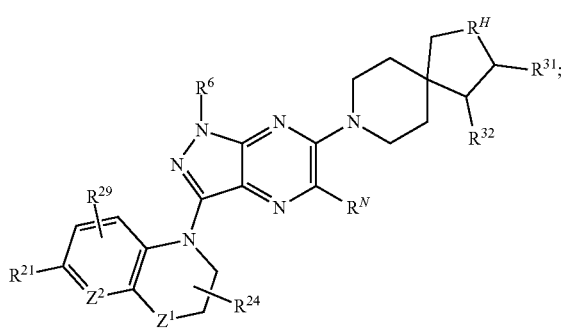

(IX)

wherein:
$R^N$ is selected from the group consisting of —CH$_2$OH, —C(H)(OH), —C(OH)(CH$_3$)$_2$, —CH$_3$, —CF$_3$, —CHF$_2$, —CH$_2$F, —CH$_2$OCH$_3$, —C$_{1-3}$alkyl, —C$_{1-3}$alkoxy, —C(O)—C$_{1-3}$alkoxy, —C(O)—C$_{1-3}$alkyl, cyclopropyl, tetrahydrofuran-3-yl, tetrahydrofuran-2-yl, oxetan-3-yl, oxetan-2-yl, azetidin-3-yl, azetidin-2-yl, hydroxyl, cyano, —C(O)—NR$^a$R$^b$, —N(R$^a$)—C(O)—C$_{1-3}$alkyl, —N(R$^a$)—S(O)$_2$—C$_{1-3}$alkyl, —S(O)$_2$—N(R$^a$)—C$_{1-3}$alkyl, —S(O)$_2$—C$_{1-3}$alkyl, CH$_2$NR$^a$R$^b$, —CH$_2$NR$^a$C(O)C$_{1-4}$alkyl, —CH$_2$NR$^a$C(O)OC$_{1-4}$alkyl, —CH$_2$NR$^a$C(O)NR$^b$C$_{1-4}$alkyl, —CH$_2$NR$^a$S(O)$_2$C$_{1-4}$alkyl, and

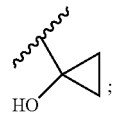;

$R^H$ is O or C($R^{25}$)$_2$;
$R^{31}$ is hydrogen or C$_{1-6}$alkyl;
$R^{32}$ is N($R^6$)$_2$;
$Z^2$ is selected from the group consisting of N and CR$^{22}$;
$Z^1$ is selected from the group consisting of: NR$^{61}$, C($R^{23}$)$_2$; C(O), or O;
$R^{21}$ is selected from the group consisting of hydrogen, halogen, cyano, N($R^6$)$_2$, C$_1$-C$_6$alkyl, C$_3$-C$_6$cycloalkyl, C$_1$-C$_6$alkyoxy, —C(O)N($R^6$)$_2$, heterocycloalkyl, phenyl, and heteroaryl, wherein C$_1$-C$_6$alkyl, C$_3$-C$_6$cycloalkyl, C$_1$-C$_6$alkyoxy, heterocycloalkyl, phenyl, and heteroaryl may each be substituted by one, two or three or more substituents each selected from the group consisting of halo, —C(O)R$^{26}$, C(O)—OR$^{26}$, —C(O)N($R^6$)$_2$, N($R^6$)$_2$, C$_{1-3}$ alkyl (optionally substituted with hydroxyl or methoxy) and C$_3$haloalkyl;
$R^{22}$ is independently selected from the group consisting of hydrogen, halogen, cyano, hydroxyl, N($R^6$)$_2$, C$_1$-C$_6$alkyl, C$_3$-C$_6$cycloalkyl, C$_1$-C$_6$alkyoxy, —C(O)N($R^6$)$_2$, heterocycloalkyl, phenyl, and heteroaryl, wherein C$_1$-C$_6$alkyl, C$_3$-C$_6$cycloalkyl, C$_1$-C$_6$alkyoxy, heterocycloalkyl, phenyl, and heteroaryl may each be substituted by one, two or three or more substituents each selected from the group consisting of halo, —C(O)—OR$^{26}$, —C(O)R$^{26}$, —C(O)N($R^6$)$_2$, —N($R^6$)$_2$, C$_{1-3}$alkyl (optionally substituted by hydroxyl or methoxy), C$_1$-C$_3$alkyoxy, and C$_{1-3}$haloalkyl;
$R^{29}$ is selected from the group consisting of hydrogen, halogen, N($R^6$)$_2$, C$_1$-C$_6$alkyl, C$_3$-C$_6$cycloalkyl, C$_1$-C$_6$alkyoxy, —C(O)N($R^6$)$_2$, heterocycloalkyl, phenyl, and heteroaryl; wherein C$_1$-C$_6$alkyl, C$_3$-C$_6$cycloalkyl, C$_1$-C$_6$alkyoxy, heterocycloalkyl, phenyl, and heteroaryl may each be substituted by one, two or three or more substituents each selected from the group consisting of halo, —C(O)R$^{26}$, —C(O)—OR$^{26}$, —C(O)N($R^6$)$_2$, —N($R^6$)$_2$, C$_{1-3}$alkyl (optionally substituted by hydroxyl or methoxy) and C$_{1-3}$haloalkyl;
$R^{23}$ independently, for each occurrence, is selected from the group consisting of H, halogen, and C$_1$-C$_6$alkyl;
$R^{24}$ is selected from the group consisting of H, halogen, and C$_1$-C$_6$alkyl;
$R^{25}$ is independently selected for each occurrence from the group consisting of hydrogen, hydroxyl, halogen, and C$_1$-C$_6$alkyl (optionally substituted by hydroxyl or halogen);
$R^{26}$ is hydrogen or C$_{1-3}$alkyl;
$R^{61}$ is selected from the group consisting of hydrogen, —(C$_1$-C$_6$)alkyl, —C(O)—(C$_1$-C$_6$)alkyl, C$_{3-6}$cycloalkyl (optionally substituted with one or two hydroxyl, C$_{1-2}$alkyl, or C$_{1-2}$alkoxy), and phenyl;
$R^6$ is independently for each occurrence selected from the group consisting of H, —(C$_1$-C$_6$)alkyl, —C(O)OC$_{1-4}$alkyl, and phenyl; and $R^a$ and $R^b$ are each independently selected from the group consisting of hydrogen and $C_{1-3}$alkyl.

In some embodiments, $Z^2$ is N. In some embodiments, $Z^2$ is CH. In some embodiments, $Z^1$ is $C(R^{23})_2$.

In some embodiments, $R^{23}$ for each occurrence is hydrogen. In some embodiments, $R^{23}$ for each occurrence is methyl.

In some embodiments, $R^{22}$ and $R^{24}$, for each occurrence, is hydrogen.

In some embodiments, $R^{21}$ is selected from the group consisting of hydrogen, halogen, $CF_3$, $N(R^6)_2$, $C(O)N(R^6)_2$, heteroaryl, and phenyl. In some embodiments, wherein $R^{21}$ is $C(O)NHCH_3$.

In some embodiments, $R^{21}$ is heteroaryl. In some embodiments, $R^{21}$ is selected from the group consisting of selected from the group consisting of:

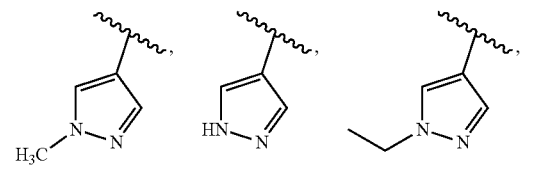

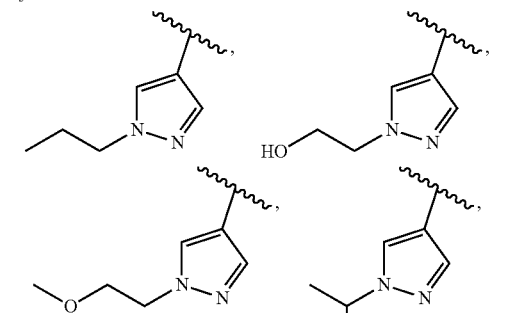

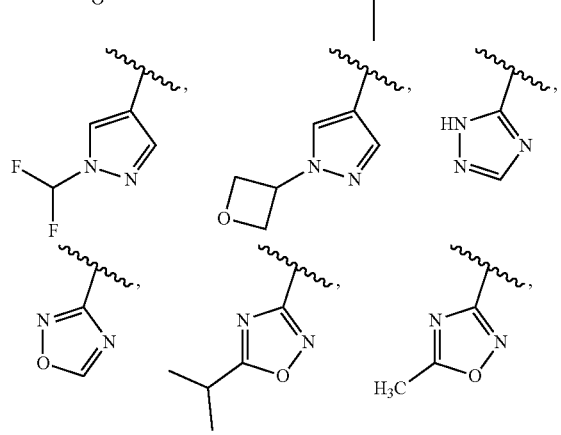

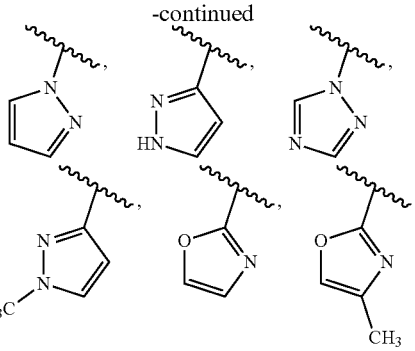

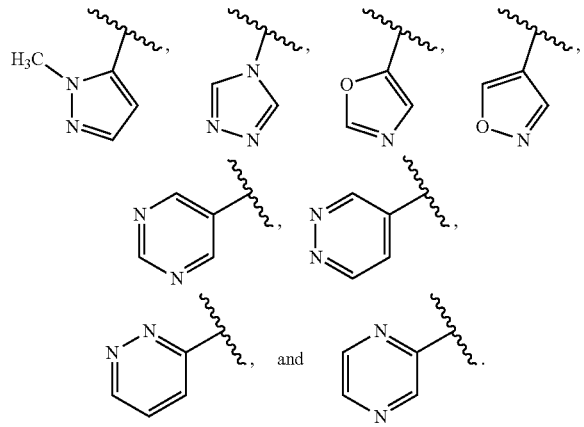

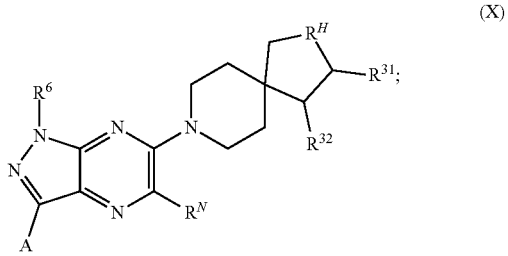

In some embodiments, $R^{21}$ is hydrogen.

Also disclosed herein, for example, is a compound of Formula X, or a pharmaceutically acceptable salt or stereoisomer thereof, wherein Formula X is represented by:

$$\text{(X)}$$

wherein:

$R^N$ is selected from the group consisting of —$CH_2OH$, —$C(H)(OH)$, —$C(OH)(CH_3)_2$, —$CH_3$, —$CF_3$, —$CHF_2$, —$CH_2F$, —$CH_2OCH_3$, —$C_{1-3}$alkyl, —$C_{1-3}$alkoxy, —$C(O)$—$C_{1-3}$alkoxy, —$C(O)$—$C_{1-3}$alkyl, cyclopropyl, tetrahydrofuran-3-yl, tetrahydrofuran-2-yl, oxetan-3-yl, oxetan-2-yl, azetidin-3-yl, azetidin-2-yl, hydroxyl, cyano, —$C(O)$—$NR^aR^b$, —$N(R^a)$—$C(O)$—$C_{1-3}$alkyl, —$N(R^a)$—$S(O)_2$—$C_{1-3}$alkyl, —$S(O)_2$—$N(R^a)$—$C_{1-3}$alkyl, —$S(O)_2$—$C_{1-3}$alkyl, $CH_2NR^aR^b$, —$CH_2NR^aC(O)C_{1-4}$alkyl, —$CH_2NR^aC(O)OC_{1-4}$alkyl, —$CH_2NR^aC(O)NR^b$ $C_{1-4}$alkyl, —$CH_2NR^aS(O)_2C_{1-4}$alkyl, and

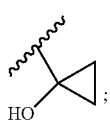

A is selected from the group consisting of:

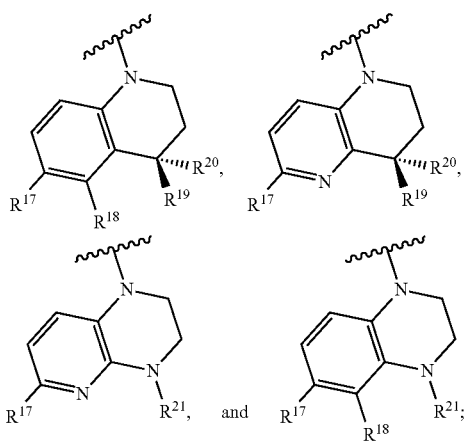

wherein:
R$^{17}$ is selected from the group consisting of H, Cl, F, CHF$_2$, CF$_3$, —CN, C$_{1-4}$alkyl, C$_{3-6}$cycloalkyl, C$_{5-6}$cycloalkenyl, —OC$_{1-4}$alkyl, —O-heteroaryl, C$_{2-4}$alkenyl, C$_{2-4}$alkynyl, —C=N—OC$_{1-4}$alkyl, —C=N—OH, —C(C$_{1-4}$alkyl)=N—OH, —(CH$_2$)$_{0-1}$C(O)NH$_2$, —(CH$_2$)$_{0-1}$C(O)NHC$_{1-4}$alkyl, —(CH$_2$)$_{0-1}$C(O)NHC$_{1-4}$alkyl-heteroaryl, —(CH$_2$)$_{0-1}$C(O)N(C$_{1-4}$alkyl)$_2$, —(CH$_2$)$_{0-1}$C(O)OC$_{1-4}$alkyl, —(CH$_2$)$_{0-1}$C(O)OH, —(CH$_2$)$_{0-1}$S(O)$_2$C$_{1-4}$alkyl, —(CH$_2$)$_{0-1}$NH$_2$, —(CH$_2$)$_{0-1}$NHC$_{1-4}$alkyl, —(CH$_2$)—$_1$(C$_{1-4}$alkyl)$_2$, —(CH$_2$)$_{0-1}$NH(CO)C$_{1-4}$alkyl, phenyl, heteroaryl, and heterocyclyl;
wherein heteroaryl and O-heteroaryl is optionally substituted with one or more C$_{1-2}$ alkyl (optionally substituted with one, two or three fluorine atoms, one or two hydroxyl groups, or one or two —OC$_{1-2}$alkyl groups); and
wherein heterocyclyl is optionally substituted with one or more hydroxyl or C$_{1-2}$alkyl (optionally substituted with one, two or three fluorine atoms, one or two hydroxyl groups, or one or two —OC$_{1-2}$alkyl groups);
R$^{18}$ is selected from the group consisting of H, Cl, F, —CN, NO$_2$, C$_{1-4}$alkyl, C$_{3-4}$cycloalkyl, C$_{2-4}$alkenyl, C$_{2-4}$alkynyl, —OC$_{1-4}$alkyl, —(CH$_2$)$_{0-1}$C(O)NH$_2$, —(CH$_2$)$_{0-1}$C(O)NHC$_{1-4}$alkyl, —(CH$_2$)$_{0-1}$C(O)N(C$_{1-4}$alkyl)$_2$, —(CH$_2$)$_{0-1}$C(O)OC$_{1-4}$alkyl, —(CH$_2$)$_{0-1}$C(O)OH, NH$_2$, —NHC(O)C$_{1-4}$alkyl, —NHS(O)$_2$C$_{1-4}$alkyl, —N(S(O)$_2$C$_{1-4}$alkyl)$_2$, —N(C$_{1-4}$alkyl)S(O)$_2$C$_{1-4}$alkyl, —N=S(O)(C$_{1-4}$alkyl)$_2$, —(CH$_2$)$_{0-1}$SC$_{1-4}$alkyl, —(CH$_2$)$_{0-1}$S(O)C$_{1-4}$alkyl, —(CH$_2$)$_{0-1}$S(O)$_2$C$_{1-4}$alkyl, —S(O)$_2$C$_{3-4}$cycloalkyl, —S(O)$_2$heteroaryl, —S(O)(=NH)C$_{1-4}$alkyl, —S(O)(=NC$_{1-4}$alkyl)C$_{1-4}$alkyl, phenyl, heteroaryl, and heterocyclyl;
wherein phenyl, heteroaryl and heterocyclyl is optionally substituted with one or more groups independently selected from the group consisting of F, C$_{1-2}$alkyl (optionally substituted with one, two or three fluorine atoms, one or two hydroxyl groups, or one or two —OC$_{1-2}$alkyl groups), cyclopropyl, —C(O)NH$_2$, —C(O)NHC$_{1-4}$alkyl, —C(O)N(C$_{1-4}$alkyl)$_2$, —C(O)OC$_{1-4}$alkyl, and —C(O)OH;
each of R$^{19}$ and R$^{20}$ is independently selected from the group consisting of H and —C$_{1-4}$alkyl; or
R$^{19}$ and R$^{20}$ together with the carbon atom to which they are attached form a C$_{2-4}$ alkenyl moiety which is optionally substituted with one or two fluorine atoms;
R$^{21}$ is selected from the group consisting of H, C$_{1-4}$alkyl, —C$_{3-4}$cycloalkyl, —(CH$_2$)$_{0-4}$C(O)C$_{1-4}$alkyl, —(CH$_2$)$_{0-4}$C(O)OC$_{1-4}$alkyl, —(CH$_2$)$_{0-4}$C(O)NH$_2$, —(CH$_2$)$_{0-4}$C(O)NHC$_{1-4}$alkyl, —(CH$_2$)$_{0-4}$C(O)N(C$_{1-4}$alkyl)$_2$, —(CH$_2$)$_{0-4}$S(O)$_2$C$_{1-4}$alkyl, and heterocyclyl;
wherein each C$_{1-4}$alkyl, C$_{2-4}$alkenyl, C$_{2-4}$alkynyl, C$_{3-4}$cycloalkyl, C$_{3-6}$cycloalkyl, or C$_{5-6}$cycloalkenyl of R$^{17}$, R$^{18}$, R$^{19}$, R$^{20}$, or R$^{21}$ is optionally substituted with one, two or three fluorine atoms, one or two hydroxyl groups, or one or two —OC$_{1-2}$alkyl groups;
R$^6$ is independently for each occurrence selected from the group consisting of H, —(C$_1$-C$_6$)alkyl, —C(O)OC$_{1-4}$alkyl, and phenyl;
R$^H$ is O or C(R$^{25}$)$_2$;
R$^{25}$ is independently selected for each occurrence from the group consisting of hydrogen, hydroxyl, halogen, and C$_1$-C$_6$alkyl (optionally substituted by hydroxyl or halogen);
R$^{31}$ is hydrogen or C$_{1-6}$alkyl; and
R$^{32}$ is N(R$^6$)$_2$.

In some embodiments, R$^{17}$ is selected from the group consisting of 2-pyridyl, 3-pyridyl, 4-pyridyl, 1,2,4-triazol-3-yl, thiazol-2-yl, pyrazol-1-yl, pyrazol-3-yl, pyrazol-4-yl, imidazol-2-yl, oxazol-2-yl, oxazol-5-yl, isoxazol-5-yl, thiazol-2-yl, thiazol-5-yl, 1,3,4-thiadiazol-2-yl, 1,2,4-oxadiazol-3-yl, 1,3,4-oxadiazol-2-yl, 1,2,4-triazol-2-yl, and 1,3,4-triazol-2-yl; wherein R$^{17}$ is optionally substituted with one, two or three fluorine atoms, one or two hydroxyl groups, or one or two —OC$_{1-2}$alkyl groups.

In some embodiments, R$^{17}$ is selected from the group consisting of tetrahydrofuran-3-yl, pyrrolidine-1-yl, piperazin-1-yl, piperidin-4-yl, piperidin-1-yl, 1,2,3,6-tetrahydropyridin-4-yl, 2,5-dihydrofuran-3-yl, piperazin-1-yl-3-one, morpholino, tetrahydropyran-2-yl, and 1,2,4-oxadiazo-3-yl-5-one; wherein R$^{17}$ is optionally substituted with one or more hydroxyl or C$_{1-2}$alkyl (optionally substituted with one, two or three fluorine atoms, one or two hydroxyl groups, or one or two —OC$_{1-2}$alkyl groups).

In some embodiments, R$^{18}$ is selected from the group consisting of phenyl, 2-pyridyl, 3-pyridyl, 4-pyridyl, pyrazol-3-yl, pyrazol-4-yl, thiazol-2-yl, 1,2,4-oxadiazol-3-yl, and 1,3,4-oxadiazol-2-yl; wherein R$^{18}$ is optionally substituted with one or more groups independently selected from the group consisting of F, C$_{1-2}$alkyl (optionally substituted with one, two or three fluorine atoms, one or two hydroxyl groups, or one or two —OC$_{1-2}$alkyl groups), cyclopropyl, —C(O)NH$_2$, —C(O)NHC$_{1-4}$alkyl, —C(O)N(C$_{1-4}$alkyl)$_2$, —C(O)OC$_{1-4}$alkyl, and —C(O)OH.

In some embodiments, R$^{18}$ is selected from the group consisting of —(CH$_2$)$_{0-1}$-morpholino, tetrahydropyranyl, tetrahydrofuranyl, oxiranyl, isothiazolidin-2-yl-1,1-dioxide, and —(CH$_2$)$_{0-1}$-oxazolidin-3-yl-2-one; wherein R$^{18}$ R$^{18}$ is optionally substituted with one or more groups independently selected from the group consisting of F, C$_{1-2}$alkyl (optionally substituted with one, two or three fluorine atoms, one or two hydroxyl groups, or one or two —OC$_{1-2}$alkyl groups), cyclopropyl, —C(O)NH$_2$, —C(O)NHC$_{1-4}$alkyl, —C(O)N(C$_{1-4}$alkyl)$_2$, —C(O)OC$_{1-4}$alkyl, and —C(O)OH.

In some embodiments, R$^{19}$ is —CH$_3$ or —CHF$_2$, R$^{20}$ is H, and the carbon to which R$^{19}$ and R$^{20}$ are attached has an (R)-configuration. In some embodiments, $R^{19}$ is H, $R^{20}$ is —$CH_3$ or —$CHF_2$, and the carbon to which $R^{19}$ and $R^{20}$ are attached has an (S)-configuration.
Also disclosed herein is a compound selected from the group consisting of:
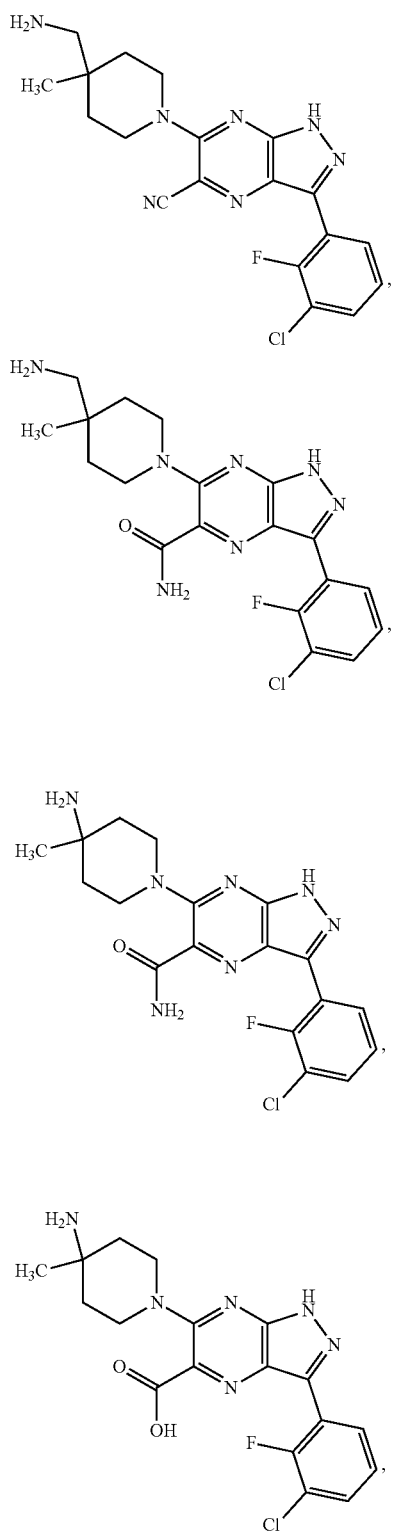
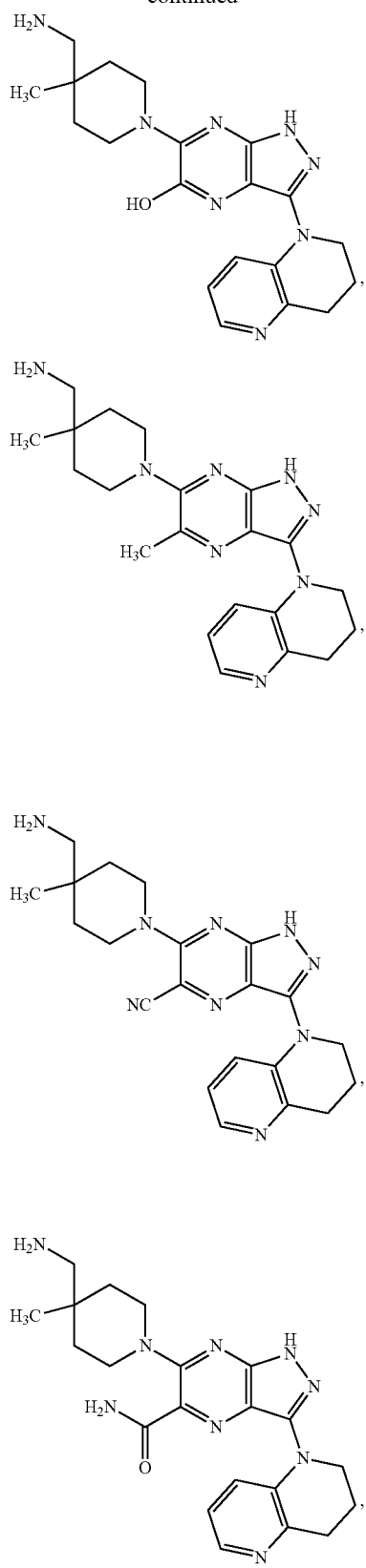

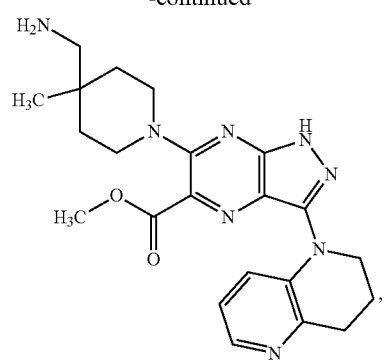
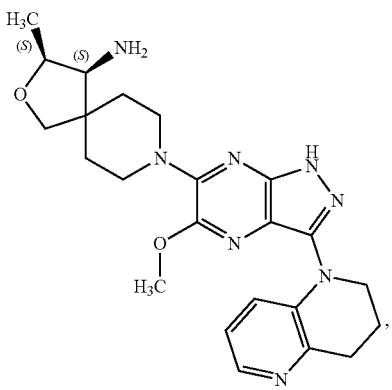
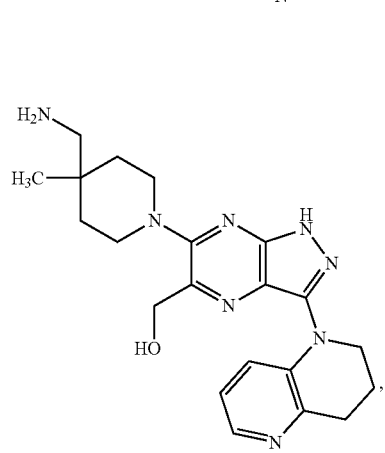
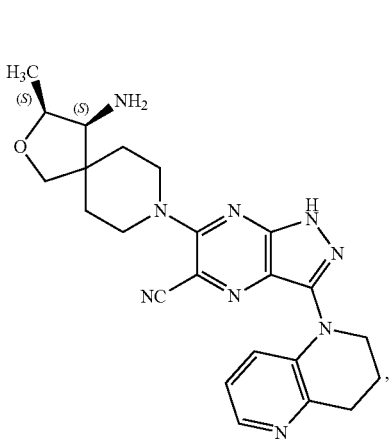
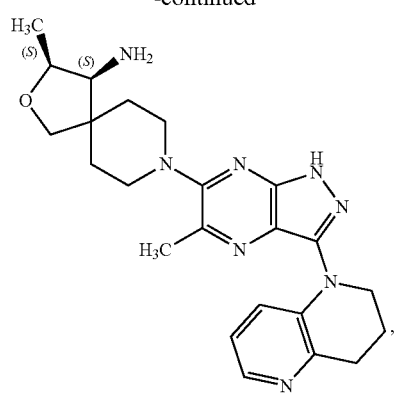
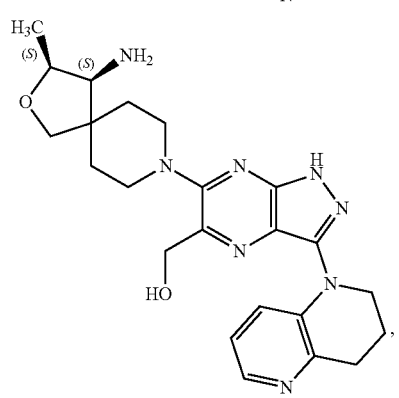
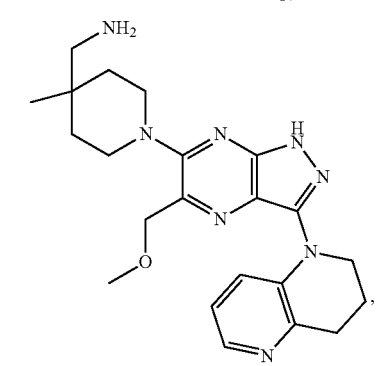
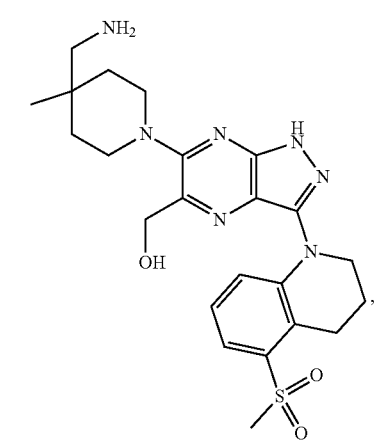

79
-continued
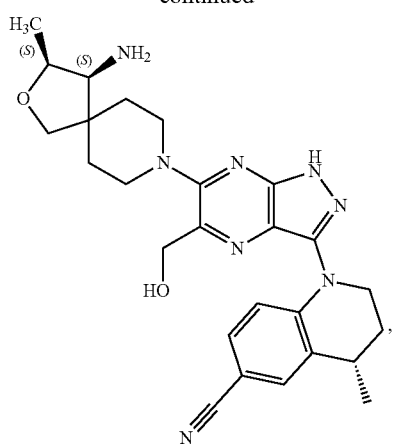
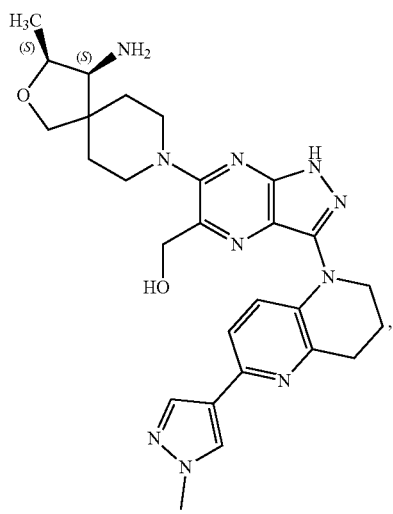
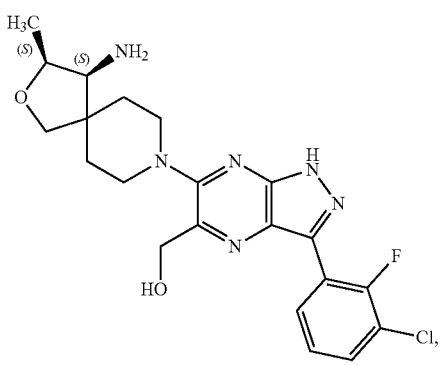
80
-continued
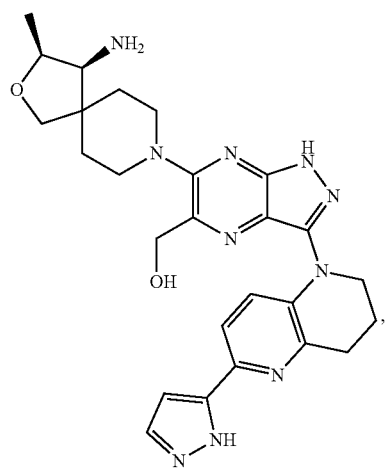
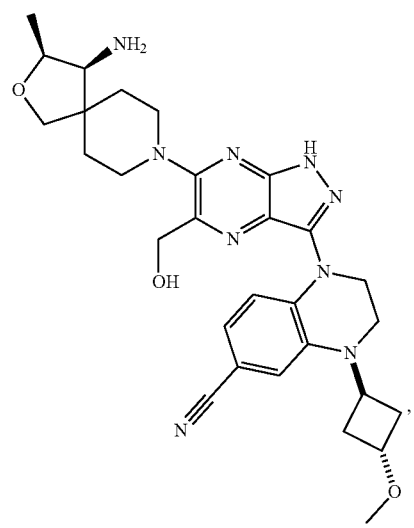
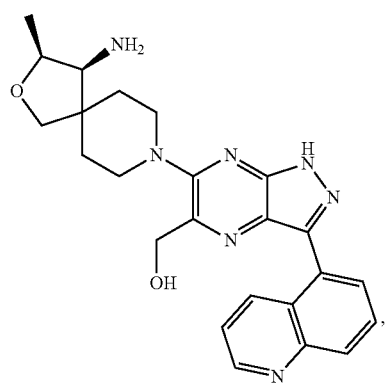

-continued

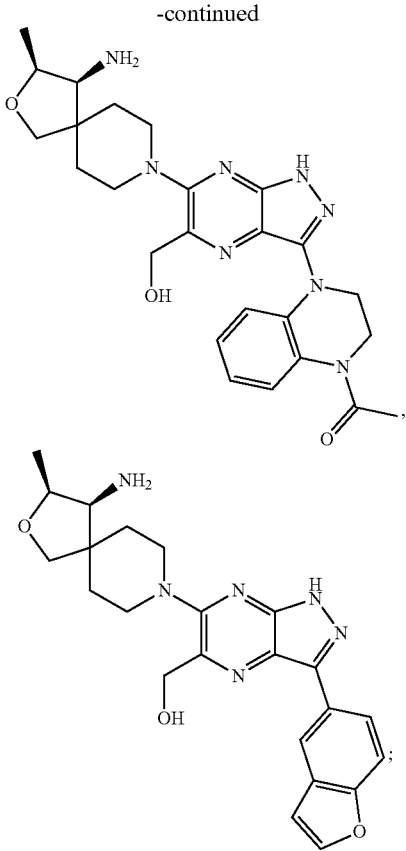

and a pharmaceutically acceptable salt or stereoisomer thereof.

Further disclosed herein is compound of Formula XI, or a pharmaceutically acceptable salt or stereoisomer thereof, wherein Formula XI is represented by:

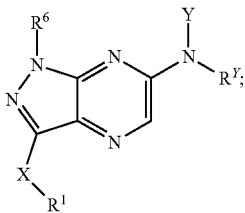

(XI)

wherein:
X is selected from the group consisting of a bond, —O—, —NR$^{X1}$—, and —S(O)$_w$— (wherein w is 0, 1, or 2);
R$^1$ is a ring moiety selected from the group consisting of a 8-12 membered bicyclic heteroaryl, phenyl, a 5-7 membered monocyclic heteroaryl, and a 4-7 membered heterocyclyl, wherein the ring moiety is optionally substituted with one, two or more substituents each independently selected from the group consisting of R$^{10}$, —OR$^{10}$, —S(O)$_w$R$^{10}$ (wherein w is 0, 1 or 2), —C$_{1-6}$alkyl-S(O)$_w$—C$_{1-3}$alkyl, —N(R$^{10}$)$_2$, —N(CO)R$^{10}$, —N—S(O)$_w$—R$^{10}$ (where w is 0, 1 or 2), —OS(O)$_w$—R$^{10}$ (wherein w is 0, 1, or 2), —S(O)$_w$—N(R$^{10}$)$_2$ (wherein w is 0, 1 or 2), —S(O)(NH)R$^{10}$, —N(H)—SO$_2$—C$_{1-3}$alkyl, —N(SO$_2$—C$_{1-3}$alkyl)$_2$, P(O)(R$^{10}$)$_2$, —C(O)R$^{10}$, —C(O)OR$^{10}$, —C(O)N(R$^{10}$)$_2$, oxo, halogen, hydroxyl, cyano, nitro, —C(=N—OR$^a$)—C$_{1-3}$alkyl, —C(=N—OR$^a$)—H, —S(O)(NR$^a$)—C$_{1-3}$alkyl, phenyl (optionally substituted with one, two or three halogen, —O-phenyl, C$_{1-3}$alkyl or C$_{1-3}$haloalkyl), C$_{1-3}$alkyl, C$_{2-6}$alkynyl, C$_{1-3}$haloalkyl, C$_{3-6}$cycloalkyl, heterocyclyl (optionally substituted with one, two or three halogen, oxo, C$_{1-3}$alkyl or C$_{1-3}$haloalkyl), and heteroaryl (optionally substituted with one, two or three halogen, —C(O)N(R$^{10}$)$_2$, C$_{1-3}$alkyl, C$_{1-3}$alkyl-O—C$_{1-3}$alkyl, C$_{1-3}$alkyl-OH, or C$_{1-3}$haloalkyl);
R$^{10}$ is independently selected from the group consisting of hydrogen, C$_{1-6}$alkyl, C$_{2-6}$alkenyl, C$_{2-6}$alkynyl, C$_{3-6}$cycloalkyl, C$_{5-6}$cycloalkenyl, C$_{2-6}$heteroalkyl, heterocycloalkyl, aryl, and heteroaryl; wherein C$_{1-6}$alkyl, C$_{2-6}$alkenyl, C$_{2-6}$alkynyl, C$_{3-6}$cycloalkyl, C$_{5-6}$cycloalkenyl, C$_{2-6}$heteroalkyl, heterocycloalkyl, aryl, and heteroaryl is optionally substituted by one, two, three or more substituents each independently selected from the group consisting of halogen, hydroxyl, —NR$^a$C(O)—R$^{20}$, —C(O)—R$^{20}$, —C(NR$^a$)—R$^b$, —NR$^a$R$^b$, C$_{1-6}$alkyl, C$_{1-6}$haloalkyl and C$_{1-6}$alkoxy;
R$^{20}$ is selected from the group consisting of hydrogen, hydroxyl, halogen, —NR$^a$R$^b$, C$_{1-6}$alkyl and C$_{1-6}$alkoxy;
Y is selected from the group consisting of phenyl and a 5-6 membered monocyclic heteroaryl; wherein Y is optionally substituted with one or more substituents each independently selected from the group consisting of (C$_1$-C$_6$)alkyl, —C(O)N(R$^6$)$_2$, —N(R$^6$)$_2$, halogen, and cyano, wherein said —(C$_1$-C$_6$)alkyl is optionally substituted with one or more substituents selected from the group consisting of —OH, —N(R$^6$)$_2$, oxo, and halogen;
R$^6$ is independently for each occurrence selected from the group consisting of H, —(C$_1$-C$_6$)alkyl, —C(O)OC$_{1-4}$alkyl, and phenyl;
R$^{X1}$ is selected from the group consisting of hydrogen, —(C$_1$-C$_6$)alkyl and phenyl;
R$^Y$ is selected from the group consisting of hydrogen and —(C$_1$-C$_6$)alkyl; and
R$^a$ and R$^b$ are each independently selected from the group consisting of hydrogen and C$_{1-3}$alkyl.

In some embodiments, X is a bond, R$^1$ is a nitrogen containing ring moiety and R$^1$ is bound through the nitrogen.

In some embodiments, R$^1$ is selected from the group consisting of 1,2,3,4-tetrahydroquinolin-1-yl, 1,2,3,4-tetrahydro-1,5-naphthyridin-1-yl, 1,2,3,4-tetrahydroquinolin-1-yl, 1,2,3,4-tetrahydroquinoxalin-1-yl, 1,2,3,4-tetrahydropyrido[2,3-b]pyrazin-1-yl, 1H-benzo[d]imidazol-1-yl, indolin-1-yl, 2,3-dihydro-1H-pyrrolo[3,2-b]pyridin-1-yl, 2,3-dihydro-1H-pyrrolo[3,2-c]pyridin-1-yl, isoindolin-2-yl, 2,3,4,5-tetrahydrobenzo[f][1,4]oxazepin-4-yl, 2-(3,4-dihydroisoquinolin-1(2H)-one), 2-(3,4-dihydroisoquinolin-1(2H)-one), 2,3-dihydro-1H-pyrido[2,3-b][1,4]oxazin-1-yl, piperidin-1-yl, 1-(1,2,3,4-tetrahydro-6H-pyrido[1,2-a]pyrimidin-6-one), 1,2,3,4-tetrahydro-1,8-naphthyridin-1-yl, 1-(3,4-dihydro-1,5-naphthyridin-2(1H)-one), 2,3,4,5-tetrahydro-1H-benzo[b]azepin-1-yl, 1-(2,3-dihydroquinolin-4(1H)-one), 2,3-dihydro-1H-pyrido[2,3-b][1,4]oxazin-2-yl, 1,2,3,4-tetrahydro-1,6-naphthyridin-1-yl, 5,6,7,8-tetrahydro-4H-pyrazolo[1,5-a][1,3]diazepin-4-yl, 3,4-dihydroquinoxalin-1-yl-2(1H)-one, 2,3,4,6-tetrahydro-1,6-naphthyridin-1-yl-5(1H)-one, 1,2,3,4-tetrahydroisoquinolin-2-yl, 1,2,3,4-tetrahydro-2,7-naphthyridin-2-yl, 1,2,3,4-tetrahydro-2,6-naphthyridin-2-yl, 3,4-dihydro-2H-benzo[b][1,4]thiazin-4-yl 1 1-dioxide, 1,2,3,4-tetrahydropyrazino[2,3-d]pyridazin-1-yl, 1,4-dihydropyrido[3,4-b]pyrazin-1-yl-3

(2H)-one, 5,6,7,8-tetrahydro-1,6-naphthyridin-6-yl, 5,6,7,8-tetrahydro-1,7-naphthyridin-7-yl, 1,2,3,4-tetrahydropyrido[3,4-b]pyrazin-1-yl, 5,8-dihydropteridin-5-yl-7(6H)-one, 4,5,6,7-tetrahydrothieno[3,2-b]pyridin-4-yl, or 5,6,7,8-tetrahydropyrazino[2,3-c]pyridazin-5-yl wherein the nitrogen ring moiety may be optionally substituted with one or two substituents each independently selected from the group consisting of Cl, F, —CN, $C_{1-4}$alkyl, —$OC_{1-4}$alkyl, $C_{2-6}$alkenyl, $C_{2-4}$alkynyl, $C_{3-6}$cycloalkyl, $C_{5-6}$cycloalkenyl, —C(H)=N—OCH$_3$, —C(H)=N—OH, —C(CH$_3$)=N—OH, —(CH$_2$)$_{0-1}$C(O)NH$_2$, —(CH$_2$)$_{0-1}$C(O)NHC$_{1-4}$alkyl, —(CH$_2$)$_{0-1}$C(O)N(C$_{1-4}$alkyl)$_2$, —(CH$_2$)$_{0-1}$C(O)OC$_{1-4}$alkyl, —(CH$_2$)$_{0-1}$C(O)OH, —S(O)$_2$C$_{1-4}$alkyl, —(CH$_2$)$_{0-1}$NH$_2$, —(CH$_2$)$_{0-1}$NHC$_{1-4}$alkyl, —(CH$_2$)$_{0-1}$(C$_{1-4}$alkyl)$_2$, —(CH$_2$)$_{0-1}$NH(CO)C$_{1-4}$alkyl, phenyl, optionally substituted heteroaryl and optionally substituted heterocyclyl, wherein $C_{1-4}$alkyl or $C_{3-6}$cycloalkyl may be optionally substituted with one, two or three fluorine atoms, one or two hydroxyl groups, or one or two —$OC_{1-2}$alkyl groups.

In some embodiments, the nitrogen ring moiety is optionally substituted with one or two substituents each independently selected from the group consisting of Cl, F, —CN, $C_{1-4}$alkyl, —$OC_{1-4}$alkyl, $C_{2-6}$alkenyl, $C_{2-4}$alkynyl, $C_{3-6}$cycloalkyl, $C_{5-6}$cycloalkenyl, —C=N—OCH$_3$, —C(H)=N—OH, —C(CH$_3$)=N—OH, —(CH$_2$)$_{0-1}$C(O)NH$_2$, —(CH$_2$)$_{0-1}$C(O)NHC$_{1-4}$alkyl, —(CH$_2$)$_{0-1}$C(O)N(C$_{1-4}$alkyl)$_2$, —(CH$_2$)$_{0-1}$C(O)OC$_{1-4}$alkyl, —(CH$_2$)$_{0-1}$C(O)OH, —S(O)$_2$C$_{1-4}$alkyl, —(CH$_2$)$_{0-1}$NH$_2$, —(CH$_2$)$_{0-1}$NHC$_{1-4}$alkyl, —(CH$_2$)$_{0-1}$(C$_{1-4}$alkyl)$_2$, —(CH$_2$)$_{0-1}$NH(CO)C$_{1-4}$alkyl, phenyl, optionally substituted heteroaryl and optionally substituted heterocyclyl, wherein $C_{1-4}$alkyl, or $C_{3-6}$cycloalkyl may be optionally substituted with one, two or three fluorine atoms, one or two hydroxyl groups, or one or two —$OC_{1-2}$alkyl groups.

In some embodiments, heteroaryl is selected from the group consisting of 2-pyridyl, 3-pyridyl, 4-pyridyl, 1,2,4-triazol-3-yl, thiazol-2-yl, pyrazol-1-yl, pyrazol-3-yl, pyrazol-4-yl, imidazol-2-yl, oxazol-2-yl, oxazol-5-yl, isoxazol-5-yl, thiazol-2-yl, thiazol-5-yl, 1,3,4-thiadiazol-2-yl, and 1,2,4-oxadiazol-3-yl, 1,3,4-oxadiazol-2-yl, 1,2,4-triazol-2-yl, 1,3,4-triazol-2-yl; wherein heteroaryl may be optionally substituted with $C_{1-2}$alkyl (optionally substituted with one, two or three fluorine atoms, one or two 2 hydroxyl groups, or one or two —$OC_{1-2}$alkyl groups).

In some embodiments, heterocyclyl is selected from the group consisting of tetrahydrofuran-3-yl, pyrrolidine-1-yl, piperazin-1-yl, piperidin-4-yl, piperidin-1-yl, 1,2,3,6-tetrahydropyridin-4-yl, 2,5-dihydrofuran-3-yl, piperazin-1-yl-3-one, morpholino, tetrahydropyran-2-yl, or 1,2,4-oxadiazo-3-yl-5-one, wherein heterocyclyl may be optionally substituted with hydroxyl or $C_{1-2}$alkyl (optionally substituted with one, two or three fluorine atoms, one or two 2 hydroxyl groups, or one or two —$OC_{1-2}$alkyl groups).

In some embodiments, $R^1$ is a 1,2,3,4-tetrahydroquinoline moiety optionally substituted with one, two or three halo, $C_{1-3}$alkyl, $C_{1-3}$haloalkyl, and heteroaryl (optionally substituted with one, two or three halogen, —C(O)N($R^{10}$)$_2$, $C_{1-3}$alkyl, $C_{1-3}$alkyl-O—$C_{1-3}$alkyl, $C_{1-3}$alkyl-OH, or $C_{1-3}$haloalkyl).

In some embodiments, $R^1$ is a 1,2,3,4-tetrahydro-1,5-naphthyridine moiety optionally substituted with one, two or three halo, $C_{1-3}$haloalkyl), $C_{1-3}$alkyl, $C_{1-3}$haloalkyl, and heteroaryl (optionally substituted with one, two or three halogen, —C(O)N($R^{10}$)$_2$, $C_{1-3}$alkyl, $C_{1-3}$alkyl-O—$C_{1-3}$alkyl, $C_{1-3}$alkyl-OH, or $C_{1-3}$haloalkyl).

In some embodiments, $R^1$ is phenyl; wherein phenyl is optionally substituted by one, two, or three substituents each independently selected from the group consisting of —$OR^{10}$, —N($R^{10}$)$_2$, halogen, and cyano.

In some embodiments, $R^1$ is pyridyl; wherein pyridyl is optionally substituted by one, two, or three substituents each independently selected from the group consisting of —$OR^{10}$, —N($R^{10}$)$_2$, halogen, and cyano.

In some embodiments, $R^1$ is indolyl or indolinyl, wherein indolyl or indolinyl is optionally substituted with one, two, or three substituents each independently selected from the group consisting of —$OR^{10}$, —N($R^{10}$)$_2$, halogen, and cyano; and wherein indolyl or indolinyl is bound through carbon.

In some embodiments, Y is a 5-6 membered heteroaryl, wherein Y is optionally substituted with one or more substituents each independently selected from the group consisting of ($C_1$-$C_6$)alkyl, —C(O)N($R^6$)$_2$, —N($R^6$)$_2$, halogen, and cyano, wherein said —($C_1$-$C_6$)alkyl is optionally substituted with one or more substituents selected from the group consisting of —OH, —N($R^6$)$_2$, oxo, and halogen.

In some embodiments, Y is pyridyl or thiazolyl, wherein Y is optionally substituted with one or more substituents each independently selected from the group consisting of ($C_1$-$C_6$)alkyl, —C(O)N($R^6$)$_2$, —N($R^6$)$_2$, halogen, and cyano, wherein said —($C_1$-$C_6$)alkyl is optionally substituted with one or more substituents selected from the group consisting of —OH, —N($R^6$)$_2$, oxo, and halogen.

In some embodiments, Y is phenyl, wherein Y is optionally substituted with one or more substituents each independently selected from the group consisting of ($C_1$-$C_6$)alkyl, —C(O)N($R^6$)$_2$, —N($R^6$)$_2$, halogen, and cyano, wherein said —($C_1$-$C_6$)alkyl is optionally substituted with one or more substituents selected from the group consisting of —OH, —N($R^6$)$_2$, oxo, and halogen.

In some embodiments, Y is substituted on an available carbon by a substituent selected from the group consisting of $C_{1-3}$alkyl, $C_{1-3}$alkyl-NH$_2$, and —NH$_2$.

In some embodiments, Y is selected from the group consisting of:

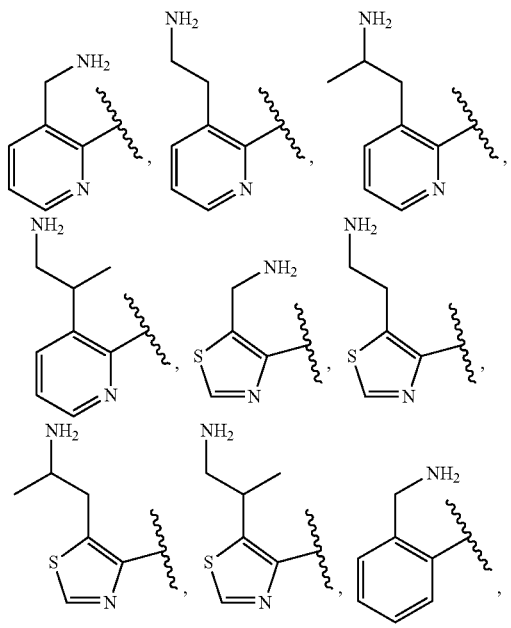

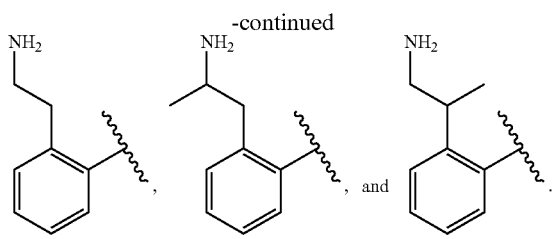

In some embodiments, $R^Y$ is —H or —CH$_3$.

Also disclosed herein, for example, is a compound of Formula XII, or a pharmaceutically acceptable salt or stereoisomer thereof, represented by:

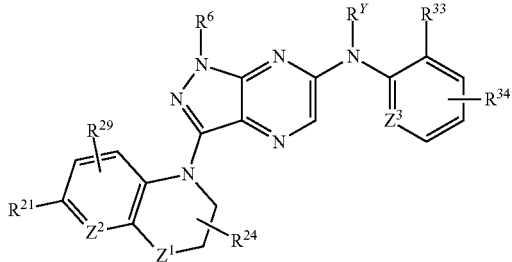

(XII)

wherein:
- $Z^2$ is selected from the group consisting of N and CR$^{22}$;
- $Z^1$ is selected from the group consisting of: NR$^{61}$, C(R$^{23}$)$_2$; C(O), and O;
- $Z^3$ is selected from the group consisting of N and CR$^{25}$;
- $R^{21}$ is selected from the group consisting of hydrogen, halogen, cyano, hydroxyl, N(R$^6$)$_2$, C$_1$-C$_6$alkyl, C$_3$-C$_6$cycloalkyl, C$_1$-C$_6$alkyoxy, —C(O)N(R$^6$)$_2$, heterocycloalkyl, phenyl, and heteroaryl, wherein C$_1$-C$_6$alkyl, C$_3$-C$_6$cycloalkyl, C$_1$-C$_6$alkyoxy, heterocycloalkyl, phenyl, and heteroaryl may each be substituted by one, two or three or more substituents each selected from the group consisting of halo, —C(O)—OR$^{26}$, —C(O)R$^{26}$, —C(O)N(R$^6$)$_2$, —N(R$^6$)$_2$, C$_{1-3}$ alkyl (optionally substituted by hydroxyl or methoxy), C$_1$-C$_3$alkyoxy, and C$_{1-3}$haloalkyl;
- $R^{22}$ is selected from the group consisting of hydrogen, halogen, cyano, N(R$^6$)$_2$, C$_1$-C$_6$alkyl, C$_3$-C$_6$cycloalkyl, C$_1$-C$_6$alkyoxy, —C(O)N(R$^6$)$_2$, heterocycloalkyl, phenyl, and heteroaryl, wherein C$_1$-C$_6$alkyl, C$_3$-C$_6$cycloalkyl, C$_1$-C$_6$alkyoxy, heterocycloalkyl, phenyl, and heteroaryl may each be substituted by one, two or three or more substituents each selected from the group consisting of halo, —C(O)R$^{26}$, C(O)—OR$^{26}$, —C(O)N(R$^6$)$_2$, N(R$^6$)$_2$, C$_{1-3}$ alkyl (optionally substituted with hydroxyl or methoxy) and C$_3$haloalkyl;
- $R^{29}$ is selected from the group consisting of hydrogen, halogen, N(R$^6$)$_2$, C$_1$-C$_6$alkyl, C$_3$-C$_6$cycloalkyl, C$_1$-C$_6$alkyoxy, —C(O)N(R$^6$)$_2$, heterocycloalkyl, phenyl, and heteroaryl; wherein C$_1$-C$_6$alkyl, C$_3$-C$_6$cycloalkyl, C$_1$-C$_6$alkyoxy, heterocycloalkyl, phenyl, and heteroaryl may each be substituted by one, two or three or more substituents each selected from the group consisting of halo, —C(O)R$^{26}$, —C(O)—OR$^{26}$, —C(O)N(R$^6$)$_2$, —N(R$^6$)$_2$, C$_{1-3}$alkyl (optionally substituted by hydroxyl or methoxy) and C$_{1-3}$haloalkyl;
- $R^{23}$ independently, for each occurrence, is selected from the group consisting of H, halogen, and C$_1$-C$_6$alkyl;
- $R^{24}$ is selected from the group consisting of H, halogen, and C$_1$-C$_6$alkyl;
- $R^{25}$ is selected from the group consisting of hydrogen, halogen, cyano, hydroxyl, N(R$^6$)$_2$, C$_1$-C$_6$alkyl, C$_3$-C$_6$cycloalkyl, C$_1$-C$_6$alkyoxy, and —C(O)N(R$^6$)$_2$; wherein C$_1$-C$_6$alkyl, C$_3$-C$_6$cycloalkyl, and C$_1$-C$_6$alkyoxy may each be substituted by one, two or three or more substituents each selected from the group consisting of halo, —C(O)—OR$^{26}$, C(O)R$^{26}$, —C(O)N(R$^6$)$_2$, N(R$^6$)$_2$, C$_{1-3}$alkyl (optionally substituted with hydroxyl or methoxy), C$_1$-C$_2$alkyoxy, and C$_{1-2}$haloalkyl;
- $R^{26}$ is hydrogen or C$_{1-3}$alkyl;
- $R^{33}$ is C$_{1-6}$alkyl-N(R$^6$)$_2$;
- $R^{34}$ is selected from the group consisting of hydrogen, halogen, cyano, hydroxyl, N(R$^6$)$_2$, C$_1$-C$_6$alkyl, C$_3$-C$_6$cycloalkyl, C$_1$-C$_6$alkyoxy, and —C(O)N(R$^6$)$_2$; wherein C$_1$-C$_6$alkyl, C$_3$-C$_6$cycloalkyl, and C$_1$-C$_6$alkyoxy may each be substituted by one, two or three or more substituents each selected from the group consisting of halo, —C(O)—OR$^{26}$, C(O)R$^{26}$, —C(O)N(R$^6$)$_2$, N(R$^6$)$_2$, C$_{1-3}$alkyl (optionally substituted with hydroxyl or methoxy), C$_1$-C$_2$alkyoxy, and C$_{1-2}$haloalkyl;
- $R^6$ is independently for each occurrence selected from the group consisting of H, —(C$_1$-C$_6$)alkyl, —C(O)OC$_{1-4}$alkyl, and phenyl;
- $R^{61}$ is selected from the group consisting of hydrogen, —(C$_1$-C$_6$)alkyl, —C(O)—(C$_1$-C$_6$)alkyl and phenyl; and
- $R^Y$ is selected from the group consisting of hydrogen and —(C$_1$-C$_6$)alkyl.

In some embodiments, $Z^2$ is N. In some embodiments, $Z^2$ is CH. In some embodiments, $Z^1$ is C(R$^{23}$)$_2$.

In some embodiments, $R^{23}$ for each occurrence is hydrogen. In some embodiments, $R^{23}$ for each occurrence is methyl.

In some embodiments, $R^{22}$ and $R^{24}$, for each occurrence, is hydrogen.

In some embodiments, $R^{21}$ is selected from the group consisting of hydrogen, halogen, CF$_3$, N(R$^6$)$_2$, C(O)N(R$^6$)$_2$, heteroaryl, and phenyl. In some embodiments, $R^{21}$ is C(O)NHCH$_3$.

In some embodiments, $R^{21}$ is heteroaryl.

In some embodiments, $R^{21}$ is selected from the group consisting of selected from the group consisting of:

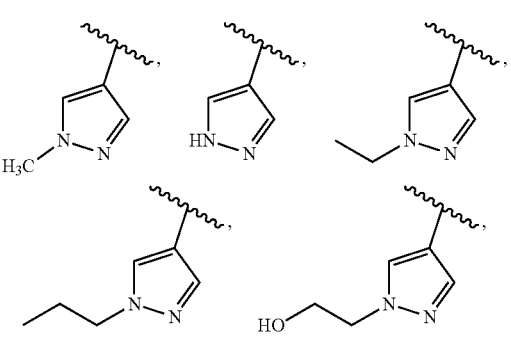

87
-continued

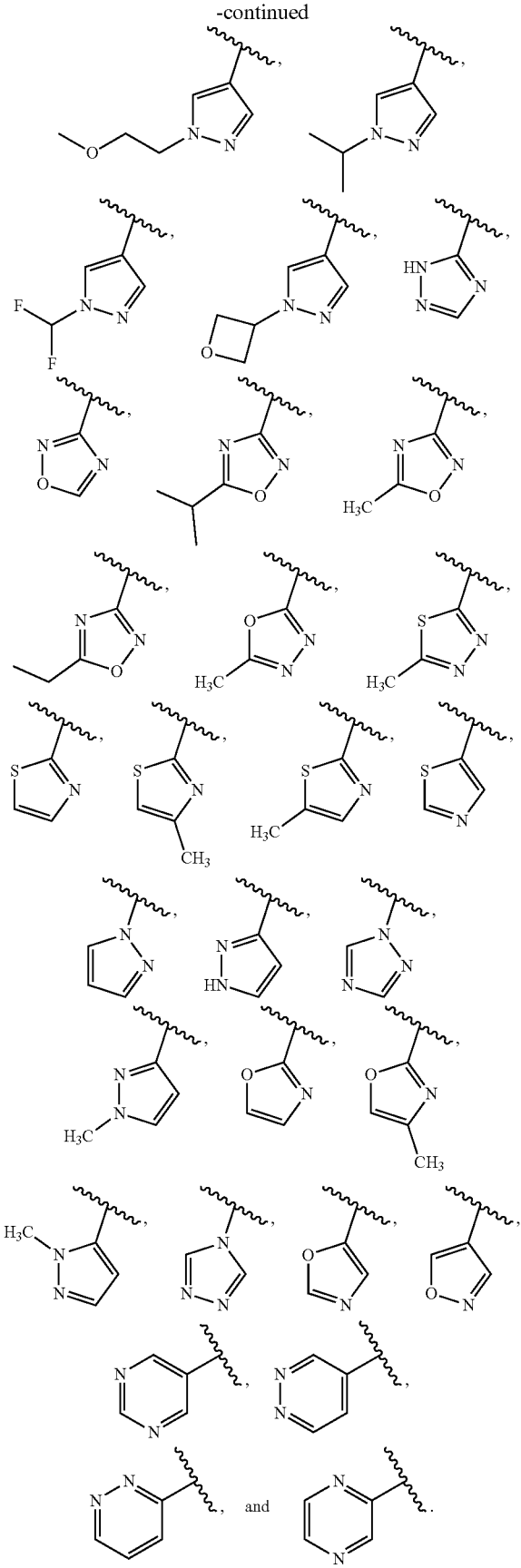

In some embodiments, $R^{21}$ is hydrogen.
In some embodiments, $Z^3$ is N. In some embodiments, wherein $Z^3$ is CH.
In some embodiments, $R^Y$ is —H or —CH$_3$.

Also disclosed herein, for example, is a compound of Formula XIII, or a pharmaceutically acceptable salt or stereoisomer thereof, represented by:

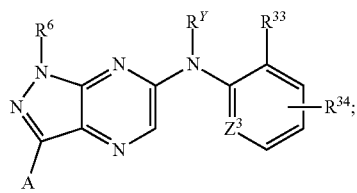

(XIII)

wherein:
A is selected from the group consisting of:

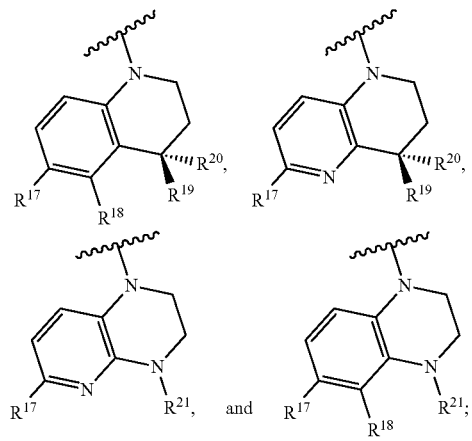

wherein:
R$^{17}$ is selected from the group consisting of H, Cl, F, CHF$_2$, CF$_3$, —CN, C$_{1-4}$alkyl, C$_{3-6}$cycloalkyl, C$_{5-6}$cycloalkenyl, —OC$_{1-4}$alkyl, —O-heteroaryl, C$_{2-4}$alkenyl, C$_{2-4}$alkynyl, —C≡N—OC$_{1-4}$alkyl, —C≡N—OH, —C(C$_{1-4}$alkyl)=N—OH, —(CH$_2$)$_{0-1}$C(O)NH$_2$, —(CH$_2$)$_{0-1}$C(O)NHC$_{1-4}$alkyl, —(CH$_2$)$_{0-1}$C(O)NHC$_{1-4}$alkyl-heteroaryl, —(CH$_2$)$_{0-1}$C(O)N(C$_{1-4}$alkyl)$_2$, —(CH$_2$)$_{0-1}$C(O)OC$_{1-4}$alkyl, —(CH$_2$)$_{0-1}$C(O)OH, —(CH$_2$)$_{0-1}$S(O)$_2$C$_{1-4}$alkyl, —(CH$_2$)$_{0-1}$NH$_2$, —(CH$_2$)$_{0-1}$NHC$_{1-4}$alkyl, —(CH$_2$)—1(C$_{1-4}$alkyl)$_2$, —(CH$_2$)$_{0-1}$NH(CO)C$_{1-4}$alkyl, phenyl, heteroaryl, and heterocyclyl,
wherein heteroaryl and O-heteroaryl is optionally substituted with one or more C$_{1-2}$ alkyl (optionally substituted with one, two or three fluorine atoms, one or two hydroxyl groups, or one or two —OC$_{1-2}$alkyl groups); and
wherein heterocyclyl is optionally substituted with one or more hydroxyl or C$_{1-2}$ alkyl (optionally substituted with one, two or three fluorine atoms, one or two hydroxyl groups, or one or two —OC$_{1-2}$alkyl groups);
R$^{18}$ is selected from the group consisting of H, Cl, F, —CN, NO$_2$, C$_{1-4}$alkyl, C$_{3-4}$cycloalkyl, C$_{2-4}$alkenyl, C$_{2-4}$alkynyl, —OC$_{1-4}$alkyl, —(CH$_2$)$_{0-1}$C(O)NH$_2$, —(CH$_2$)$_{0-1}$C(O)NHC$_{1-4}$alkyl, —(CH$_2$)$_{0-1}$C(O)N(C$_{1-4}$alkyl)$_2$, —(CH$_2$)$_{0-1}$C(O)OC$_{1-4}$alkyl, —(CH$_2$)$_{0-1}$C(O)OH, NH$_2$, —NHC(O)C$_{1-4}$alkyl, —NHS(O)$_2$C$_{1-4}$alkyl, —N(S(O)$_2$C$_{1-4}$alkyl)$_2$, —N(C$_{1-4}$alkyl)S(O)$_2$C$_{1-4}$alkyl, —N=S(O)(C$_{1-4}$alkyl)$_2$, —(CH$_2$)$_{0-1}$SC$_{1-4}$alkyl, —(CH$_2$)$_{0-1}$S(O)C$_{1-4}$alkyl, —(CH$_2$)$_{0-1}$S(O)$_2$C$_{1-4}$alkyl, —S(O)$_2$C$_{3-4}$cycloalkyl, —S(O)$_2$heteroaryl, —S(O)(=NH)C$_{1-4}$alkyl, —S(O)(=NC$_{1-4}$alkyl)C$_{1-4}$alkyl, phenyl, heteroaryl, and heterocyclyl;

wherein phenyl, heteroaryl and heterocyclyl is optionally substituted with one or more groups independently selected from the group consisting of F, C$_{1-2}$alkyl (optionally substituted with one, two or three fluorine atoms, one or two hydroxyl groups, or one or two —OC$_{1-2}$alkyl groups), cyclopropyl, —C(O)NH$_2$, —C(O)NHC$_{1-4}$alkyl, —C(O)N(C$_{1-4}$alkyl)$_2$, —C(O)OC$_{1-4}$alkyl, and —C(O)OH;

each of R$^{19}$ and R$^{20}$ is independently selected from the group consisting of H and —C$_{1-4}$alkyl; or R$^{19}$ and R$^{20}$ together with the carbon atom to which they are attached form a C$_{2-4}$ alkenyl moiety which is optionally substituted with one or two fluorine atoms;

R$^{21}$ is selected from the group consisting of H, C$_{1-4}$alkyl, —C$_{3-4}$cycloalkyl, —(CH$_2$)$_{0-4}$C(O)C$_{1-4}$alkyl, —(CH$_2$)$_{0-4}$C(O)OC$_{1-4}$alkyl, —(CH$_2$)$_{0-4}$C(O)NH$_2$, —(CH$_2$)$_{0-4}$C(O)NHC$_{1-4}$alkyl, —(CH$_2$)$_{0-4}$C(O)N(C$_{1-4}$alkyl)$_2$, —(CH$_2$)$_{0-4}$S(O)$_2$C$_{1-4}$alkyl, and heterocyclyl;

wherein each C$_{1-4}$alkyl, C$_{2-4}$alkenyl, C$_{2-4}$alkynyl, C$_{3-4}$cycloalkyl, C$_{3-6}$cycloalkyl, or C$_{5-6}$cycloalkenyl of R$^{17}$, R$^{18}$, R$^{19}$, R$^{20}$, or R$^{21}$ is optionally substituted with one, two or three fluorine atoms, one or two hydroxyl groups, or one or two —OC$_{1-2}$alkyl groups;

R$^6$ is independently for each occurrence selected from the group consisting of H, —(C$_1$-C$_6$)alkyl, —C(O)OC$_{1-4}$alkyl, and phenyl;

R$^Y$ is selected from the group consisting of hydrogen and —(C$_1$-C$_6$)alkyl;

R$^{33}$ is C$_{1-6}$alkyl-N(R$^6$)$_2$; and

R$^{34}$ is selected from the group consisting of hydrogen, halogen, cyano, hydroxyl, N(R$^6$)$_2$, C$_1$-C$_6$alkyl, C$_3$-C$_6$cycloalkyl, C$_1$-C$_6$alkyoxy, and —C(O)N(R$^6$)$_2$; wherein C$_1$-C$_6$alkyl, C$_3$-C$_6$cycloalkyl, and C$_1$-C$_6$alkyoxy may each be substituted by one, two or three or more substituents each selected from the group consisting of halo, —C(O)—OR$^{26}$, C(O)R$^{26}$, C(O)N(R$^6$)$_2$, N(R$^6$)$_2$, C$_{1-3}$alkyl (optionally substituted with hydroxyl or methoxy), C$_1$-C$_2$alkyoxy, and C$_{1-2}$haloalkyl.

In some embodiments, R$^{17}$ is selected from the group consisting of 2-pyridyl, 3-pyridyl, 4-pyridyl, 1,2,4-triazol-3-yl, thiazol-2-yl, pyrazol-1-yl, pyrazol-3-yl, pyrazol-4-yl, imidazol-2-yl, oxazol-2-yl, oxazol-5-yl, isoxazol-5-yl, thiazol-2-yl, thiazol-5-yl, 1,3,4-thiadiazol-2-yl, 1,2,4-oxadiazol-3-yl, 1,3,4-oxadiazol-2-yl, 1,2,4-triazol-2-yl, and 1,3,4-triazol-2-yl; wherein R$^{17}$ is optionally substituted with one, two or three fluorine atoms, one or two hydroxyl groups, or one or two —OC$_{1-2}$alkyl groups.

In some embodiments, R$^{17}$ is selected from the group consisting of tetrahydrofuran-3-yl, pyrrolidine-1-yl, piperazin-1-yl, piperidin-4-yl, piperidin-1-yl, 1,2,3,6-tetrahydropyridin-4-yl, 2,5-dihydrofuran-3-yl, piperazin-1-yl-3-one, morpholino, tetrahydropyran-2-yl, and 1,2,4-oxadiazo-3-yl-5-one; wherein R$^{17}$ is optionally substituted with one or more hydroxyl or C$_{1-2}$alkyl (optionally substituted with one, two or three fluorine atoms, one or two hydroxyl groups, or one or two —OC$_{1-2}$alkyl groups).

In some embodiments, R$^{18}$ is selected from the group consisting of phenyl, 2-pyridyl, 3-pyridyl, 4-pyridyl, pyrazol-3-yl, pyrazol-4-yl, thiazol-2-yl, 1,2,4-oxadiazol-3-yl, and 1,3,4-oxadiazol-2-yl; wherein R$^{18}$ is optionally substituted with one or more groups independently selected from the group consisting of F, C$_{1-2}$alkyl (optionally substituted with one, two or three fluorine atoms, one or two hydroxyl groups, or one or two —OC$_{1-2}$alkyl groups), cyclopropyl, —C(O)NH$_2$, —C(O)NHC$_{1-4}$alkyl, —C(O)N(C$_{1-4}$alkyl)$_2$, —C(O)OC$_{1-4}$alkyl, and —C(O)OH.

In some embodiments, R$^{18}$ is selected from the group consisting of —(CH$_2$)$_{0-1}$-morpholino, tetrahydropyranyl, tetrahydrofuranyl, oxiranyl, isothiazolidin-2-yl-1,1-dioxide, and —(CH$_2$)$_{0-1}$-oxazolidin-3-yl-2-one; wherein R$^{18}$ R$^{18}$ is optionally substituted with one or more groups independently selected from the group consisting of F, C$_{1-2}$alkyl (optionally substituted with one, two or three fluorine atoms, one or two hydroxyl groups, or one or two —OC$_{1-2}$alkyl groups), cyclopropyl, —C(O)NH$_2$, —C(O)NHC$_{1-4}$alkyl, —C(O)N(C$_{1-4}$alkyl)$_2$, —C(O)OC$_{1-4}$alkyl, and —C(O)OH.

In some embodiments, R$^{19}$ is —CH$_3$ or —CHF$_2$, R$^{20}$ is H, and the carbon to which R$^{19}$ and R$^{20}$ are attached has an (R)-configuration. In some embodiments, R$^{19}$ is H, R$^{20}$ is —CH$_3$ or —CHF$_2$, and the carbon to which R$^{19}$ and R$^{20}$ are attached has an (S)-configuration.

In some embodiments, Z$^3$ is N. In some embodiments, Z$^3$ is CH.

In some embodiments, R$^Y$ is —H or —CH$_3$.

Also disclosed herein is a compound selected from the group consisting of:

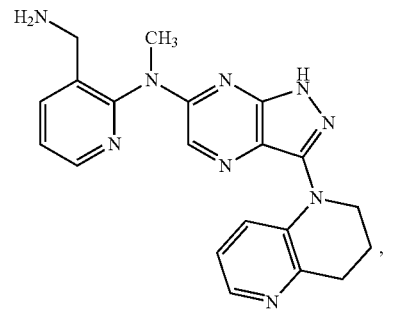

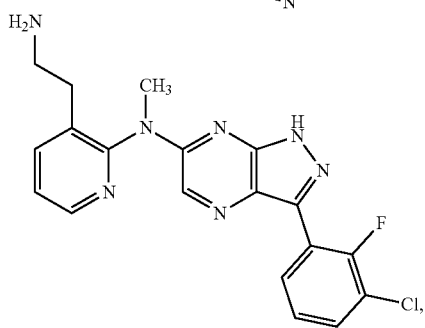

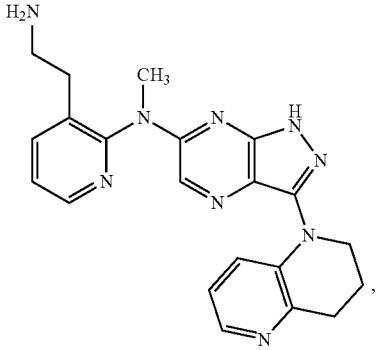

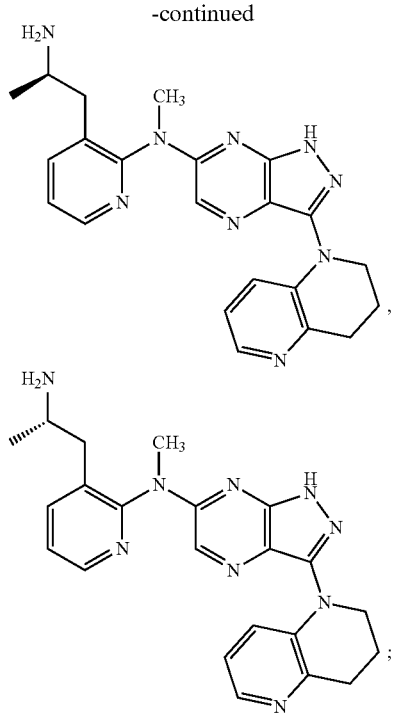

and a pharmaceutically acceptable salt or stereoisomer thereof.

Compounds or compositions of the disclosure can be useful in applications that benefit from inhibition of SHP2 phosphatase enzymes. For example, inhibition of SHP2 phosphatase may offer a therapeutic approach for the treatment of cancer. (See, e.g., Y.-N. P. Chen et al., in *Nature*, 2016, doi:10.1038/nature18621; and references cited therein; each of which hereby incorporated by reference in its entirety.) Inhibition of SHP2 phosphatase also has been found to ameliorate the pathogensis of systemic lupus erythematosus. (See, e.g., J. Wang et al., in *J. Clin. Invest.* 2016, 126, 2077-2092; and references cited therein; each of which hereby incorporated by reference in its entirety.)

In some embodiments, compounds or compositions of the disclosure can be useful in suppressing tumor cell growth. In some embodiments, compounds or compositions of the disclosure can be useful in ameliorating the pathogenesis of systemic lupus erythematosus. In some embodiments, compounds or compositions of the disclosure can be useful in the treatment of various other disorders, including Noonan syndrome (NS), diabetes, neuroblastoma, melanoma, juvenile leukemia, juvenile myelomonocytic leukemia (JMML), chronic myelomonocytic leukemia, acute myeloid leukemia, HER2-positive breast cancer, triple-negative breast cancer, ductal carcinoma of the breast, invasive ductal carcinoma of the breast, non-small cell lung cancer (including adenocarcinoma of the lung), colorectal cancer (SW480, SW620, CACO2, HCT116, HT29 colon cancer cell lines), esophageal cancer, gastric cancer, squamous-cell carcinoma of the head and neck (SCCHN), and neutropenia (Kostmann's syndrome).

In some embodiments, compounds or compositions of the disclosure can be used in combination with other treatments and/or cancer therapies. For example, compounds or compositions of the disclosure can be used in combination with, but are not limited to, antibodies, antibody-drug conjugates, kinase inhibitors, immunomodulators, and histone deacetylase inhibitors. The compounds or compositions of the disclosure can also be used in combination with other treatments and/or cancer therapies as disclosed in WO 2015/107495; and references cited therein; each of which is hereby incorporated by reference in its entirety.

For example, the compounds disclosed herein (or pharmaceutical compositions containing them) can be used in the treatment of one or more of the diseases mentioned herein, alone or in combination with another therapeutic agent. For example, a disclosed compound can be used in combination with the following agents: BCR-ABL inhibitors: imatinib mesylate; inilotinib hydrochloride; nilotinib; dasatinib; bosutinib; ponatinib; bafetinib; danusertib; saracatinib; N-[2-[((1S,4R)-6-[[4-(Cyclobutylamino)-5-(tjifluoromethyl)-2-pyrimidinyl]amino]-1,2,3,4-tetrahydronaphthalen-1,4-imin-9-yl]-2-oxoethyl]-acetamide. ALK inhibitors: crizotinib; 5-chloro-N4-(2-(isopropylsulfonyl)phenyl)-N2-(2-methoxy-4-(4-(4-methylpiperazin-1-yl)piperidin-1-yl)phenyl)pyrimidine-2,4-diamine, ceritinib, alectinib, brigatinib, entrecinib. BRAF inhibitors: vemurafenib and dabrafenib. FGFR inhibitors: infigratinib, dovitinib, erdafitinib, BLU-554, AZD4547. FLT3 inhibitors: sunitinib malate; midostaurin; tanutinib; sorafenib, lestaurtinib, quizartinib and crenolanib. MEK Inhibitors—trametinib, combimetinib, binimetinib, selumetinib. VEGF receptor inhibitors: bevacizumab, axitinib, Aflibercept, (N-methyl-2-[[3-[(E)-2-pyridin-2-ylethenyl]-H-indazol-6-yl]sulfanyl]benzamide, brivanib alaninate ((S)—((R)-1-(4-(4-Fluoro-2-methyl-1H-indol-5-yloxy)-5-methylpyrrolo[2,1-f][1,2,4]triazin-6-yloxy)propan-2-yl)$_2$-aminopropanoate, motesanib (N-(2,3-dihydro-3,3-dimethyl-1H-indol-6-yl)-2-[(4-pyridinylmethyl)amino]-3-pyridinecarboxamide, pasireotide, sorafenib. Tyrosine kinase inhibitors: erlotinib hydrochloride, linifanib, sunitinib malate, pazopanib. Epidermal growth factor receptor (EGFR) inhibitors: Gefitnib, osimertinib, cetuximab, panitumumab. HER2 receptor inhibitors: trastuzumab, neratinib, lapatinib or lapatinib ditosylate. MET inhibitors: crizotinib, cabozantinib. CD20 antibodies: rituximab, tositumomab, ofatumumab. DNA Synthesis inhibitors: capecitabine, gemcitabine hydrochloride, nelarabine, hydroxycarbamide. Antineoplastic agents: oxaliplatin. HER dimerization inhibitors: pertuzumab. Human Granulocyte colony-stimulating factor (G-CSF) modulators: Filgrastim. Immunomodulators: Afutuzumab, lenalidomide, thalidomide. CD40 inhibitors: Dacetuzumab. Pro-apoptotic receptor agonists (PARAs): Dulanermin. Heat Shock Protein (HSP) inhibitors: Tanespimycin (17-allylamino-17-demethoxygeldanamycin). Hedgehog antagonists: 2-chloro-N-[4-chloro-3-(2-pyridinyl)phenyl]-4-(methylsulfonyl)-benzamide. Proteasome inhibitors: Bortezomib. PI3K inhibitors: 4-[2-(H-Indazol-4-yl)-6-[[4-(methylsulfonyl)piperazin-1-yl]methyl]thieno[3,2-d]pyrimidin-4-yl]mo choline, 2-Methyl-2-[4-[3-methyl-2-oxo-8-(quinolin-3-yl)-2,3-dihydroimidazo[4,5-c]quinolin-1-yl]phenyl]propiocyano, buparlisib, taselisib, idelalisib, duvelisib, TGR 1202. Phospholipase A2 inhibitors: Anagrelide. BCL-2 inhibitors: 4-[4-[[2-(4-chlorophenyl)-5,5-dimethyl-1-cyclohexen-1-yl]methyl]-1-piperazinyl]-N-[[4-[[(1R)-3-(4-morpholinyl)-1-[(phenylthio)methyl]propyl]amino]-3-[(trifluoromethyl)sulfonyl]phenyl]sulfonyl]benzamide. Mitogen-activated protein kinase kinase (MEK) inhibitors: XL-518. Aromatase inhibitors: Exemestane, letrozole, anastrozole, faslodex, tamoxifen. Topoisomerase I inhibitors: Irinotecan, topotecan hydrochloride. Topoisomerase II inhibitors: etoposide, teniposide. mTOR inhibitors: Temsirolimus, ridaforolimus, everolimus. Osteoclastic bone resorption inhibitors: 1-Hydroxy-2-imidazol-1-yl-phosphonoethyl) phosphonic acid monohydrate. CD33 Antibody Drug Conjugates: Gemtuzumab ozogamicin. CD22 Antibody Drug Conjugates: Inotuzumab ozogamicin. CD20 Antibody Drug Conjugates: Ibritumomab tiuxetan. Somatostain analogs: octreotide. Synthetic Interleukin-11 (IL-11): oprelvekin. Synthetic erythropoietin: Darbepoetin alfa. Receptor Activator for Nuclear Factor κ B (RANK) inhibitors: Denosumab. Thrombopoietin mimetic peptides: Romiplostim. Cell growth stimulators: Palifermin. Anti-Insulin-like Growth Factor-1 receptor (IGF-1R) antibodies: Figitumumab. Anti-CSl antibodies: Elotuzumab. CD52 antibodies: Alemtuzumab. CTLA-4 inhibitors: Tremelimumab, ipilimumab. PD1 inhibitors: Nivolumab; pembrolizumab; an immunoadhesin; Pidilizumab; and AMP-224. PDL1 inhibitors: MSB0010718C; YW243.55.S70, MPDL3280A; MEDI-4736, MSB-0010718C, orMDX-1105. LAG-3 inhibitors: BMS-986016. GITR agonists: GITR fusion proteins and anti-GITR antibodies. Histone deacetylase inhibitors (HDI): Voninostat. Anti-CTLA4 antibodies: Tremelimumab; and Ipilimumab. Alkylating agents: Temozolomide, dactinomycin, melphalan, altretamine carmustine, bendamustine, busulfan, carboplatin, lomustine, cisplatin, chlorambucil, cyclophosphamide, dacarbazine, altretamine, ifosfamide, procarbazine, mechlorethamine, mustine and mechloroethamine hydrochloride, streptozocin, thiotepa. Biologic response modifiers: bacillus calmette-guerin, denileukin diftitox. Anti-tumor antibiotics: doxorubicin, bleomycin, daunorubicin, daunorubicin liposomal, mitoxantrone, epirubicin, idarubicin, mitomycin C. Anti-microtubule agents: Estramustine. Cathepsin K inhibitors: Odanacatib. Epothilone B analogs: Ixabepilone. TpoR agonists: Eltrombopag. Anti-mitotic agents: Docetaxel. Adrenal steroid inhibitors: aminoglutethimide. Anti-androgens: Nilutamide, Androgen Receptor inhibitors: enzalutamide, abiraterone acetate, orteronel, galeterone, and seviteronel, bicalutamide, flutamide. Androgens: Fluoxymesterone. CDK1 inhibitors: Alvocidib, palbociclib, ribociclib, trilaciclib, abemaciclib. Gonadotropin-releasing hormone (GnRH) receptor agonists: Leuprolide or leuprolide acetate. Taxane anti-neoplastic agents: Cabazitaxel (1-hydroxy^, 10-dimethoxy-9-oxo-5,20-epoxytax-1 1-ene-2a,4,13a-triyl-4-acetate-2-benzoate-13-[(2R,3S)-3-{[(tert-butoxy)carbonyl]amino}-2-hydroxy-3-phenylpropanoate), larotaxel ((2α,3ξ, 4α,5β,7α,10β,13α)-4,10-bis(acetyloxy)-13-({(2R,3S)-3-[(tert-butoxycarbonyl) amino]-2-hydroxy-3-phenylpropanoyl}oxy)-1-hydroxy-9-oxo-5,20-epoxy-7,19-cyclotax-11-en-2-yl benzoate). 5HT1a receptor agonists: Xaliproden (also known as SR57746, 1-[2-(2-naphthyl)ethyl]-4-[3-(trifluoromethyl)phenyl]-1,2,3,6-tetrahydropyridine. HPC vaccines: Cervarix® sold by GlaxoSmithKline, Gardasil® sold by Merck; Iron Chelating agents: Deferasinox. Anti-metabolites: Claribine (2-chlorodeoxyadenosine), 5-fluorouracil, 6-thioguanine, pemetrexed, cytarabine, cytarabine liposomal, decitabine, hydroxyurea, fludarabine, floxuridine, cladribine, methotrexate, pentostatin. Bisphosphonates: Pamidronate. Demethylating agents: 5-azacitidine, decitabine. Plant Alkaloids: Paclitaxel protein-bound; vinblastine, vincristine, vinorelbine, paclitaxel. Retinoids: Alitretinoin (sold under the tradename Panretin®), tretinoin (all-trans retinoic acid, also known as ATRA, sold under the tradename Vesanoid®), Isotretinoin (13-cis-retinoic acid, sold under the tradenames Accutane®, Amnesteem®, Claravis®, Claras®, Decutan®, Isotane®, Izotech®, Oratane®, Isotret®, and Sotret®), bexarotene (sold under the tradename Targretin®). Glucocorticosteroids: Hydrocortisone (also known as cortisone, hydrocortisone sodium succinate, hydrocortisone sodium phosphate, and sold under the tradenames Ala-Cort®, Hydrocortisone Phosphate, Solu-Cortef®, Hydrocort Acetate® and Lanacort®), dexamethazone ((8S,9R,10S,11 S,13S,14S,16R,17R)-9-fluoro-11,17-dihydroxy-17-(2-hydroxy acetyl)-10,13,16-trimethyl-6,7,8,9,10, 11,12, 13, 14,15, 16,17-dodecahydro-3H-cyclopenta[a]phenanthren-3-one), prednisolone (sold under the tradenames Delta-Cortel®, Orapred®, Pediapred® and Prelone®), prednisone (sold under the tradenames Deltasone®, Liquid Red®, Meticorten® and Orasone®), methylprednisolone (also known as 6-Methylprednisolone, Methylprednisolone Acetate, Methylprednisolone Sodium Succinate, sold under the tradenames Duralone®, Medralone®, Medrol®, M-Prednisol® and Solu-Medrol®). Cytokines: interleukin-2 (also known as aldesleukin and IL-2, sold under the tradename Proleukin®), interleukin-11 (also known as oprevelkin, sold under the tradename Neumega®), alpha interferon alfa (also known as IFN-alpha, sold under the tradenames Intron® A, and Roferon-A®). Estrogen receptor downregulators: Fulvestrant (sold under the tradename Faslodex®). Anti-estrogens: tamoxifen (sold under the tradename Novaldex®). Toremifene (sold under the tradename Fareston®). Selective estrogen receptor modulators (SERMs): Raloxifene (sold under the tradename Evista®). Leutinizing hormone releasing hormone (LHRH) agonists: Goserelin (sold under the tradename Zoladex®); Progesterones: megestrol (also known as megestrol acetate, sold under the tradename Megace®); Miscellaneous cytotoxic agents: Arsenic trioxide (sold under the tradename Trisenox®), asparaginase (also known as L-asparaginase, Erwinia L-asparaginase, sold under the tradenames Elspar® and Kidrolase®). Anti-nausea drugs: NK-1 receptor antagonists: Casopitant (sold under the tradenames Rezonic® and Zunrisa® by GlaxoSmithKline); and Cytoprotective agents: Amifostine (sold under the tradename Ethyol®), leucovorin (also known as calcium leucovorin, citrovorum factor and folinic acid). Immune checkpoint inhibitors: The term "immune checkpoints" refers to a group of molecules on the cell surface of CD4 and CD8 T cells. Immune checkpoint molecules include, but are not limited to, Programmed Death 1 (PD-1), Cytotoxic T-Lymphocyte Antigen 4 (CTLA-4), B7H1, B7H4, OX-40, CD 137, CD40, and LAG3. Immunotherapeutic agents which can act as immune checkpoint inhibitors useful in the methods of the present disclosure, include, but are not limited to, inhibitors of PD-L1, PD-L2, CTLA4, TIM3, LAG3, VISTA, BTLA, TIGIT, LAIR1, CD 160, 2B4 and/or TGFR beta.

The compounds described herein can function as allosteric inhibitors and block the activation of SHP2 by targeting the auto-inhibited conformation of SHP2.

The compounds described herein can also inhibit SHP2 function through incorporation into agents that catalyze the destruction of SHP2. For example, the compounds can be incorporated into proteolysis targeting chimeras (PROTACs). A PROTAC is a bifunctional molecule, with one portion capable of engaging an E3 ubiquitin ligase, and the other portion having the ability to bind to a target protein meant for degradation by the cellular protein quality control machinery. Recruitment of the target protein to the specific E3 ligase results in its tagging for destruction (i.e., ubiquitination) and subsequent degradation by the proteasome. Any E3 ligase can be used. The portion of the PROTAC that engages the E3 ligase is connected to the portion of the PROTAC that engages the target protein via a linker which consists of a variable chain of atoms. Recruitment of SHP2 to the E3 ligase will thus result in the destruction of the SHP2 protein. The variable chain of atoms can include, for example, rings, heteroatoms, and/or repeating polymeric units. It can be rigid or flexible. It can be attached to the two portions described above using standard techniques.

The compounds described herein can be linked to one end of a variable chain, while the other end of the variable chain can be bound to the E3 ligase. Recruitment of SHP2 to the ligase will thus result in the destruction of the SHP2 protein.

In some embodiments, compounds or compositions of the disclosure can be used in combination with an antibody. In some embodiments, compounds or compositions of the disclosure can be used in combination with an antibody-drug conjugate. In some embodiments, compounds or compositions of the disclosure can be used in combination with a kinase inhibitor. In some embodiments, compounds or compositions of the disclosure can be used in combination with an immunomodulator. In some embodiments, compounds or compositions of the disclosure can be used in combination with a histone deacetylase inhibitor.

In some embodiments, a disclosed compound can be administered to a subject in need of treatment at dosages ranging from about 0.0001 mg to about 100 mg/kg body weight of the subject to be treated per day, such as from about 1.0 to 10 mg/kg. However, additional variations are within the scope of the disclosure.

A disclosed compound can be administered alone or in combination with pharmaceutically acceptable carriers, such as diluents, fillers, aqueous solution, and even organic solvents. The compound and/or compositions of the disclosure can be administered as a tablet, powder, lozenge, syrup, injectable solution, and the like. Additional ingredients, such as flavoring, binder, excipients, and the like are within the scope of the disclosure.

In some embodiments, pharmaceutically acceptable compositions can contain a disclosed compound and/or a pharmaceutically acceptable salt thereof at a concentration ranging from about 0.01 to about 2.0 wt %, such as 0.01 to about 1 wt % or about 0.05 to about 0.5 wt %. The composition can be formulated as a solution, suspension, ointment, or a capsule, and the like. The pharmaceutical composition can be prepared as an aqueous solution and can contain additional components, such as preservatives, buffers, tonicity agents, antioxidants, stabilizers, viscosity-modifying ingredients and the like.

In some embodiments, the present disclosure provides for the use of pharmaceutical compositions and/or medicaments comprised of a disclosed compound, or a pharmaceutically acceptable salt thereof, in a method of treating a disease state, and/or condition caused by or related to SHP2 phosphatase. For example, provided herein are methods of treating subjects in need thereof (e.g., subjects suffering from cancer (e.g., leukemia, breast, lung and/or colorectal cancer) an effective amount of a disclosed compound, and optionally an effective amount of an additional compound (e.g., therapeutic agent) such as disclosed herein.

In some embodiments, the method of treatment comprises the steps of: i) identifying a subject in need of such treatment; (ii) providing a disclosed compound, or a pharmaceutically acceptable salt thereof; and (iii) administering said disclosed compound in a therapeutically effective amount to treat, suppress and/or prevent the disease state or condition in a subject in need of such treatment.

In some embodiments, the method of treatment comprises the steps of: i) identifying a subject in need of such treatment; (ii) providing a composition comprising a disclosed compound, or a pharmaceutically acceptable salt thereof; and (iii) administering said composition in a therapeutically effective amount to treat, suppress and/or prevent the disease state or condition in a subject in need of such treatment.

In some embodiments, the subject is an animal. Animals include all members of the animal kingdom, but are not limited to humans, mice, rats, cats, monkeys, dogs, horses, and swine. In some embodiments, the subject is a human. In some embodiments, the subject is a mouse, a rat, a cat, a monkey, a dog, a horse, or a pig.

In some embodiments, the compound or composition is administered orally. In some embodiments, the compound or composition is administered intravenously.

In some embodiments, the methods comprise administering to the subject an effective amount of a disclosed compound, or a pharmaceutically acceptable salt thereof; or a composition comprising a disclosed compound, or a pharmaceutically acceptable salt thereof, and a pharmaceutically acceptable carrier.

Pharmaceutically acceptable carriers are well-known to those skilled in the art, and include, e.g., adjuvants, diluents, excipients, fillers, lubricants and vehicles. In some embodiments, the carrier is a diluent, adjuvant, excipient, or vehicle. In some embodiments, the carrier is a diluent, adjuvant, or excipient. In some embodiments, the carrier is a diluent or adjuvant. In some embodiments, the carrier is an excipient. Often, the pharmaceutically acceptable carrier is chemically inert toward the active compounds and is non-toxic under the conditions of use. Examples of pharmaceutically acceptable carriers may include, e.g., water or saline solution, polymers such as polyethylene glycol, carbohydrates and derivatives thereof, oils, fatty acids, or alcohols. Non-limiting examples of oils as pharmaceutical carriers include oils of petroleum, animal, vegetable or synthetic origin, such as peanut oil, soybean oil, mineral oil, sesame oil and the like. The pharmaceutical carriers may also be saline, gum acacia, gelatin, starch paste, talc, keratin, colloidal silica, urea, and the like. In addition, auxiliary, stabilizing, thickening, lubricating and coloring agents may be used. Other examples of suitable pharmaceutical carriers are described in e.g., Remington's: The Science and Practice of Pharmacy, 22nd Ed. (Allen, Loyd V., Jr ed., Pharmaceutical Press (2012)); Modern Pharmaceutics, $5^{th}$ Ed. (Alexander T. Florence, Juergen Siepmann, CRC Press (2009)); Handbook of Pharmaceutical Excipients, $7^{th}$ Ed. (Rowe, Raymond C.; Sheskey, Paul J.; Cook, Walter G.; Fenton, Marian E. eds., Pharmaceutical Press (2012)) (each of which hereby incorporated by reference in its entirety).

In some embodiments, the method of treatment, prevention and/or suppression of a condition related to SHP2 phosphatase comprises the steps of: i) identifying a subject in need of such treatment; (ii) providing a disclosed compound, or a pharmaceutically acceptable salt thereof, or a composition comprising a disclosed compound, or a pharmaceutically acceptable salt thereof, and a pharmaceutically acceptable carrier; and (iii) administering said compound or composition in a therapeutically effective amount to treat, prevent and/or suppress the disease state or condition related to SHP2 phosphatase in a subject in need of such treatment.

In some embodiments, the compounds of the disclosure are formulated into pharmaceutical compositions for administration to subjects in a biologically compatible form suitable for administration in vivo. According to another aspect, the present disclosure provides a pharmaceutical composition comprising a disclosed compound in admixture with a pharmaceutically acceptable diluent and/or carrier. The pharmaceutically-acceptable carrier is "acceptable" in the sense of being compatible with the other ingredients of the composition and not deleterious to the recipient thereof. The pharmaceutically-acceptable carriers employed herein may be selected from various organic or inorganic materials that are used as materials for pharmaceutical formulations and which are incorporated as analgesic agents, buffers, binders, disintegrants, diluents, emulsifiers, excipients, extenders, glidants, solubilizers, stabilizers, suspending agents, tonicity agents, vehicles and viscosity-increasing agents. Pharmaceutical additives, such as antioxidants, aromatics, colorants, flavor-improving agents, preservatives, and sweeteners, may also be added. Examples of acceptable pharmaceutical carriers include carboxymethyl cellulose, crystalline cellulose, glycerin, gum arabic, lactose, magnesium stearate, methyl cellulose, powders, saline, sodium alginate, sucrose, starch, talc and water, among others. In some embodiments, the term "pharmaceutically acceptable" means approved by a regulatory agency of the Federal or a state government or listed in the U.S. Pharmacopeia or other generally recognized pharmacopeia for use in animals, and more particularly in humans.

Surfactants such as, e.g., detergents, are also suitable for use in the formulations. Specific examples of surfactants include polyvinylpyrrolidone, polyvinyl alcohols, copolymers of vinyl acetate and of vinylpyrrolidone, polyethylene glycols, benzyl alcohol, mannitol, glycerol, sorbitol or polyoxyethylenated esters of sorbitan; lecithin or sodium carboxymethylcellulose; or acrylic derivatives, such as methacrylates and others, anionic surfactants, such as alkaline stearates, in particular sodium, potassium or ammonium stearate; calcium stearate or triethanolamine stearate; alkyl sulfates, in particular sodium lauryl sulfate and sodium cetyl sulfate; sodium dodecylbenzenesulphonate or sodium dioctyl sulphosuccinate; or fatty acids, in particular those derived from coconut oil, cationic surfactants, such as water-soluble quaternary ammonium salts of formula $N^+R'R''R'''R''''Y^-$, in which the R radicals are identical or different optionally hydroxylated hydrocarbon radicals and $Y^-$ is an anion of a strong acid, such as halide, sulfate and sulfonate anions; cetyltrimethylammonium bromide is one of the cationic surfactants which can be used, amine salts of formula $N^+R'R''R'''$, in which the R radicals are identical or different optionally hydroxylated hydrocarbon radicals; octadecylamine hydrochloride is one of the cationic surfactants which can be used, non-ionic surfactants, such as optionally polyoxyethylenated esters of sorbitan, in particular Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide, amphoteric surfactants, such as substituted lauryl compounds of betaine.

When administered to a subject, a disclosed compound and pharmaceutically acceptable carriers can be sterile. Suitable pharmaceutical carriers may also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, polyethylene glycol 300, water, ethanol, polysorbate 20, and the like. The present compositions, if desired, may also contain minor amounts of wetting or emulsifying agents, or pH buffering agents.

The pharmaceutical formulations of the present disclosure are prepared by methods well-known in the pharmaceutical arts. Optionally, one or more accessory ingredients (e.g., buffers, flavoring agents, surface active agents, and the like) also are added. The choice of carrier is determined by the solubility and chemical nature of the compounds, chosen route of administration and standard pharmaceutical practice.

Additionally, the compounds and/or compositions of the present disclosure are administered to a human or animal subject by known procedures including oral administration, sublingual or buccal administration. In some embodiments, the compound and/or composition is administered orally.

For oral administration, a formulation of the compounds of the disclosure may be presented in dosage forms such as capsules, tablets, powders, granules, or as a suspension or solution. Capsule formulations may be gelatin, soft-gel or solid. Tablets and capsule formulations may further contain one or more adjuvants, binders, diluents, disintegrants, excipients, fillers, or lubricants, each of which are known in the art. Examples of such include carbohydrates such as lactose or sucrose, dibasic calcium phosphate anhydrous, corn starch, mannitol, xylitol, cellulose or derivatives thereof, microcrystalline cellulose, gelatin, stearates, silicon dioxide, talc, sodium starch glycolate, acacia, flavoring agents, preservatives, buffering agents, disintegrants, and colorants. Orally administered compositions may contain one or more optional agents such as, e.g., sweetening agents such as fructose, aspartame or saccharin; flavoring agents such as peppermint, oil of wintergreen, or cherry; coloring agents; and preservative agents, to provide a pharmaceutically palatable preparation.

In some embodiments, the composition is in unit dose form such as a tablet, capsule or single-dose vial. Suitable unit doses, i.e., therapeutically effective amounts, may be determined during clinical trials designed appropriately for each of the conditions for which administration of a chosen compound is indicated and will, of course, vary depending on the desired clinical endpoint.

In accordance with the methods of the present disclosure, the compounds of the disclosure are administered to the subject in a therapeutically effective amount, e.g., to reduce or ameliorate symptoms related to SHP2 phosphatase activity in the subject. This amount is readily determined by the skilled artisan, based upon known procedures, including analysis of titration curves established in vivo and methods and assays disclosed herein.

In some embodiments, the methods comprise administration of a therapeutically effective dosage of the compounds of the disclosure. In some embodiments, the therapeutically effective dosage is at least about 0.0001 mg/kg body weight, at least about 0.001 mg/kg body weight, at least about 0.01 mg/kg body weight, at least about 0.05 mg/kg body weight, at least about 0.1 mg/kg body weight, at least about 0.25 mg/kg body weight, at least about 0.3 mg/kg body weight, at least about 0.5 mg/kg body weight, at least about 0.75 mg/kg body weight, at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, at least about 100 mg/kg body weight, at least about 200 mg/kg body weight, at least about 250 mg/kg body weight, at least about 300 mg/kg body weight, at least about 350 mg/kg body weight, at least about 400 mg/kg body weight, at least about 450 mg/kg body weight, at least about 500 mg/kg body weight, at least about 550 mg/kg body weight, at least about 600 mg/kg body weight, at least about 650 mg/kg body weight, at least about 700 mg/kg body weight, at least about 750 mg/kg body weight, at least about 800 mg/kg body weight, at least about 900 mg/kg body weight, or at least about 1000 mg/kg body weight. It will be recognized that any of the dosages listed herein may constitute an upper or lower dosage range, and may be combined with any other dosage to constitute a dosage range comprising an upper and lower limit.

In some embodiments, the therapeutically effective dosage is in the range of about 0.1 mg to about 10 mg/kg body weight, about 0.1 mg to about 6 mg/kg body weight, about 0.1 mg to about 4 mg/kg body weight, or about 0.1 mg to about 2 mg/kg body weight.

In some embodiments the therapeutically effective dosage is in the range of about 1 to 500 mg, about 2 to 150 mg, about 2 to 120 mg, about 2 to 80 mg, about 2 to 40 mg, about 5 to 150 mg, about 5 to 120 mg, about 5 to 80 mg, about 10 to 150 mg, about 10 to 120 mg, about 10 to 80 mg, about 10 to 40 mg, about 20 to 150 mg, about 20 to 120 mg, about 20 to 80 mg, about 20 to 40 mg, about 40 to 150 mg, about 40 to 120 mg or about 40 to 80 mg.

In some embodiments, the methods comprise a single dosage or administration (e.g., as a single injection or deposition). Alternatively, the methods comprise administration once daily, twice daily, three times daily or four times daily to a subject in need thereof for a period of from about 2 to about 28 days, or from about 7 to about 10 days, or from about 7 to about 15 days, or longer. In some embodiments, the methods comprise chronic administration. In yet other embodiments, the methods comprise administration over the course of several weeks, months, years or decades. In still other embodiments, the methods comprise administration over the course of several weeks. In still other embodiments, the methods comprise administration over the course of several months. In still other embodiments, the methods comprise administration over the course of several years. In still other embodiments, the methods comprise administration over the course of several decades.

The dosage administered can vary depending upon known factors such as the pharmacodynamic characteristics of the active ingredient and its mode and route of administration; time of administration of active ingredient; age, sex, health and weight of the recipient; nature and extent of symptoms; kind of concurrent treatment, frequency of treatment and the effect desired; and rate of excretion. These are all readily determined and may be used by the skilled artisan to adjust or titrate dosages and/or dosing regimens.

The precise dose to be employed in the compositions will also depend on the route of administration, and should be decided according to the judgment of the practitioner and each subject's circumstances. In specific embodiments of the disclosure, suitable dose ranges for oral administration of the compounds of the disclosure are generally about 1 mg/day to about 1000 mg/day. In some embodiments, the oral dose is about 1 mg/day to about 800 mg/day. In some embodiments, the oral dose is about 1 mg/day to about 500 mg/day. In some embodiments, the oral dose is about 1 mg/day to about 250 mg/day. In some embodiments, the oral dose is about 1 mg/day to about 100 mg/day. In some embodiments, the oral dose is about 5 mg/day to about 50 mg/day. In some embodiments, the oral dose is about 5 mg/day. In some embodiments, the oral dose is about 10 mg/day. In some embodiments, the oral dose is about 20 mg/day. In some embodiments, the oral dose is about 30 mg/day. In some embodiments, the oral dose is about 40 mg/day. In some embodiments, the oral dose is about 50 mg/day. In some embodiments, the oral dose is about 60 mg/day. In some embodiments, the oral dose is about 70 mg/day. In some embodiments, the oral dose is about 100 mg/day. It will be recognized that any of the dosages listed herein may constitute an upper or lower dosage range, and may be combined with any other dosage to constitute a dosage range comprising an upper and lower limit.

Any of the compounds and/or compositions of the disclosure may be provided in a kit comprising the compounds and/or compositions. Thus, in some embodiments, the compound and/or composition of the disclosure is provided in a kit.

Those skilled in the art will recognize, or be able to ascertain using no more than routine experimentation, many equivalents to the specific embodiments of the disclosure described herein. Such equivalents are intended to be within the scope of the present disclosure.

The disclosure is further described by the following non-limiting Examples.

EXAMPLES

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

At least some of the compounds identified as "Intermediates" herein are contemplated as compounds of the disclosure.

Examples are provided herein to facilitate a more complete understanding of the disclosure. The following examples serve to illustrate the exemplary modes of making and practicing the subject matter of the disclosure. However, the scope of the disclosure is not to be construed as limited to specific embodiments disclosed in these examples, which are illustrative only.

Reactions were monitored and final products were characterized using one of the following methods. LCMS standard conditions were: Waters HPLC system equipped with an Alliance 2695 main module, Waters 996 diode array detector and ZQ micromass ESI-MS detector. Mobile phase A: $H_2O$ (10.0 mM $NH_4HCO_2$), mobile phase B: $CH_3CN$. HPLC conditions were: XBridge C18 column, 4.6×30 mm, 3.5 μm, 0.0-0.2 min. isocratic (5% B), 0.2-2.0 min. gradient (5-100% B), 3.0-3.0 min. isocratic (100% B); flow rate: 3.0 mL/min; UV channel: 254 nm.

Purification of some racemic products was performed using semi preparative HPLC A, semi preparative HPLC B, or semi preparative SFC. Semi preparative HPLC A: Gilson 215 system equipped with a Waters 996 diode array detector and a Waters 2525 pump. Semi preparative HPLC B: Waters 2767 system equipped with a Waters 996 diode array detector, 2×Waters 515 pumps, a Waters 2525 pump and a ZQ micromass ESI-MS detector. Semi preparative SFC: Mettler Toledo Minigram SFC equipped with a Knauer K-2501 UV detector and an Alcott Model 1719 Autosampler.

Product homogeneity and enantiomeric excess determination were performed using Analytical HPLC A: Agilent 1100 HPLC system equipped with an Agilent G1315A diode array detector.

The compounds of Formula (Ia), for example, can generally be prepared according to exemplary Scheme 1:

Scheme 1

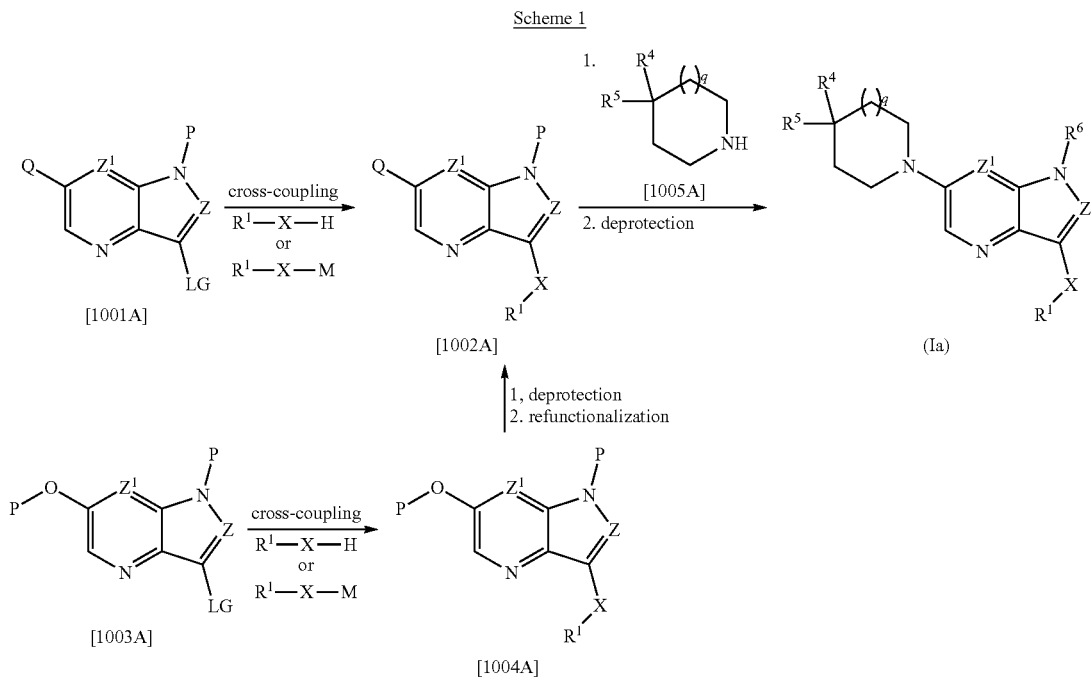

wherein X, Z, $Z^1$, $R^1$, $R^6$, $R^4$ $R^5$ and q are as defined as elsewhere herein, Q is independently a halogen, such as Cl, Br, I, and the like, or any other leaving group, such as $OSO_2Me$, OMs, OTs, OTf, and the like. LG is a leaving group, such as Cl, Br, I, OTs, OTf, and the like, and P is a protecting group, such as 4-methoxybenzyl and the like. Alternative protecting groups that can be used are described, e.g., in Greene et al., Protective Groups in Organic Synthesis (4$^{th}$ ed. 2006).

As shown in Scheme 1, an aryl compound such as a compound of Formula 1001A undergoes a cross-coupling reaction with a metalated or otherwise activated moiety to provide a compound of Formula 1002A. The compound of Formula 1002A then undergoes a substitution reaction with an amine such as Compound 1005A, followed by removal of the protecting group to provide a compound of Formula (I). In some embodiments, LG is I. In some embodiments, LG is Cl. In some embodiments, LG is OTf or OTs. Alternatively, a protected heteroaryl ether, such as a compound of Formula 1003A, undergoes a cross-coupling reaction to provide a compound of Formula 1004A. The ether protecting group is subsequently removed and the resulting hydroxyl group activated to form a Q group, such as $OSO_2Me$, OMs, OTs, OTf, and the like, to form a compound of Formula 1002A, which can then be carried forward to prepare compounds having the Formula (Ia).

Alternatively, compounds of the disclosure can generally be prepared according to exemplary Scheme 2:

Scheme 2

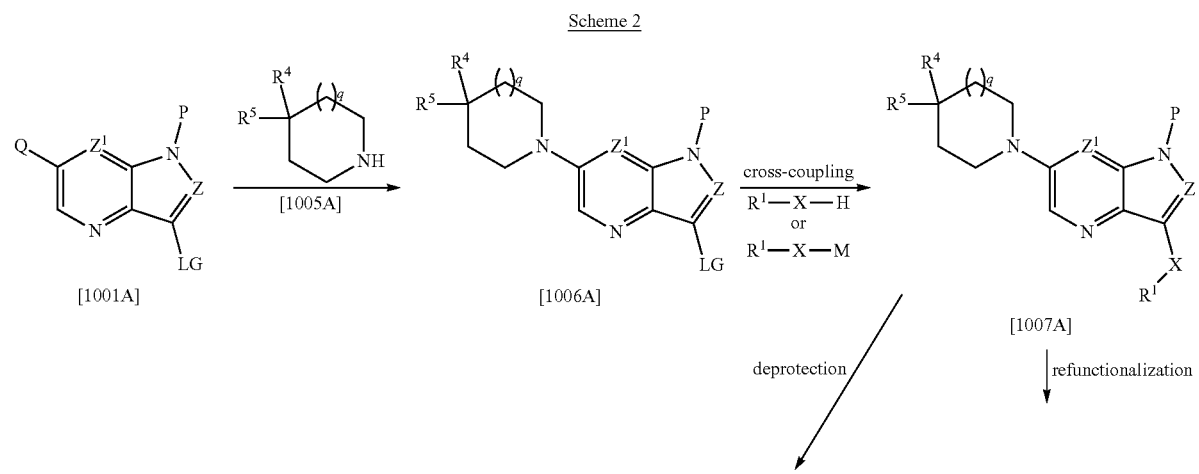

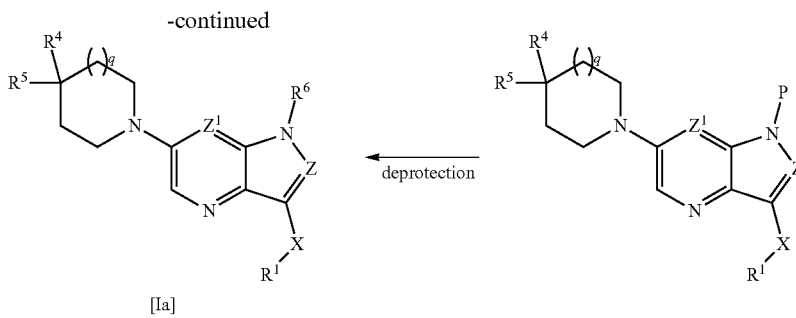

wherein X, $R^1$, $R^6$, $R^4$ $R^5$ and q are as defined as elsewhere herein, Q is independently a halogen, such as Cl, Br, I, and the like, or any other leaving group, such as $OSO_2Me$, OMs, OTs, OTf, and the like. LG is a leaving group, such as Cl, Br, I, OTs, OTf, and the like, and P is a protecting group, such as 4-methoxybenzyl and the like. Alternative protecting groups that can be used are described, e.g., in Greene et al., Protective Groups in Organic Synthesis ($4^{th}$ ed. 2006).

As shown in Scheme 2, an aryl compound such as a compound of Formula 1001A undergoes a undergoes a substitution reaction with an amine such as 1005A to provide a compound of Formula 1006A. The compound of Formula 1006A then undergoes a cross-coupling reaction with a metalated or otherwise activated moiety to provide a compound of Formula 1007A. In some embodiments, the compound of Formula 1007A can be deprotected to produce a compound of Formula (Ia). In other embodiments, the compound of Formula 1007A can be left protected and functional groups on the $R^1$ moiety refunctionalized by methods known to those of ordinary skill in the art.

In some embodiments, the cross-coupling reaction is a Buchwald-Hartwig reaction. In some embodiments, the cross-coupling reaction is a Chan-Lam coupling reaction. In some embodiments, the cross-coupling reaction is an Ullmann reaction. In some embodiments, the cross-coupling reaction is a Suzuki reaction. In some embodiments, the cross-coupling reaction is a Stille reaction. In some embodiments, the cross-coupling reaction is a Negishi reaction. In some embodiments, the cross-coupling reaction is a Hiyama reaction. Other cross-coupling reactions may be employed as would be apparent to one of ordinary skill in the art.

In some embodiments, the protecting group is removed under acidic conditions, such as HBr in AcOH. Conditions for removal of the protecting group will depend on the nature of the protecting group. Conditions for the removal of various protecting groups can be found, e.g., in Greene et al., Protective Groups in Organic Synthesis ($4^{th}$ ed. 2006).

Compound 7A: Preparation of 1-(6-((3S,4S)-4-amino-3-methyl-2-oxa-8-azaspiro[4.5]decan-8-yl)-1H-pyrazolo[3,4-b]pyrazin-3-yl)-1,2,3,4-tetrahydroquinolin-6-yl Sulfurofluoridate

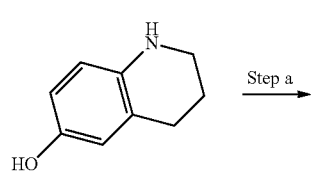 Step a

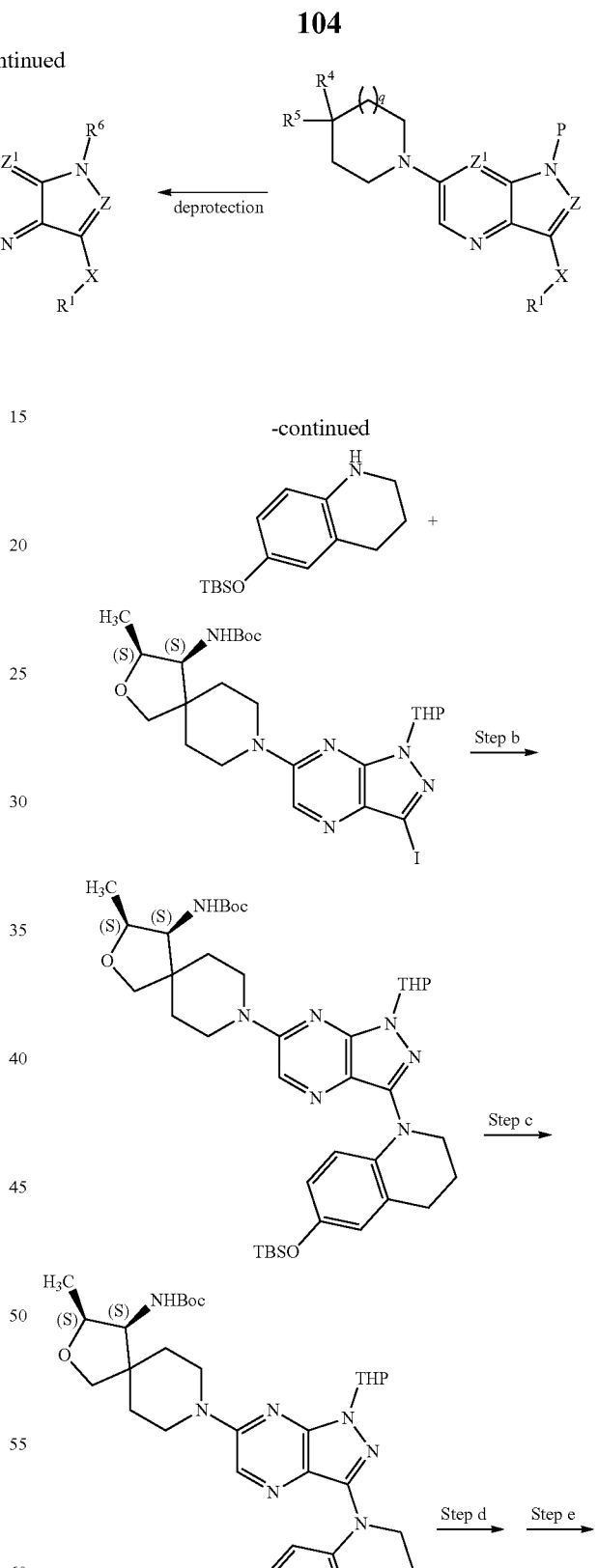

-continued

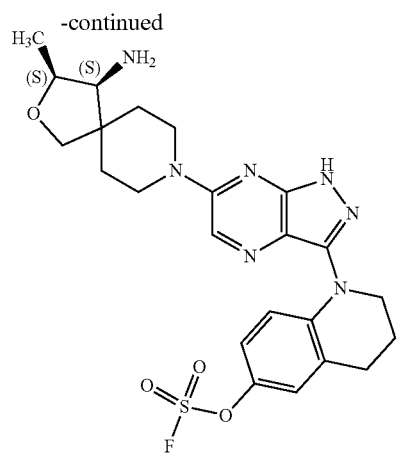

Step a: A 100-mL round-bottom flask was charged with 1,2,3,4-tertrahydroquinolin-6-ol (1.5 g, 10 mmol), DMF (20 mL), TBSCl (1.8 g, 12 mmol) and imidazole (1.36 g, 20 mmol). The resulting solution was stirred for 2 hours at 25° C., quenched with water (30 mL), and extracted with EtOAc (3×50 mL). The organics were washed with brine (2×50 mL), dried over anhydrous sodium sulfate, filtered, concentrated under reduced pressure, and purified by silica gel chromatography (25% EtOAc/petroleum ether) to give 6-((tert-butyldimethylsilyl)oxy)-1,2,3,4-tetrahydroquinoline (2.1 g, 80% yield) as a yellow oil: LCMS [M+H]$^+$=264.1.

Step b: A 50-mL round-bottom flask was charged with tert-butyl ((3S,4S)-8-(3-iodo-1-(tetrahydro-2H-pyran-2-yl)-1H-pyrazolo[3,4-b]pyrazin-6-yl-3-methyl-2-oxa-8-azaspiro[4.5]decan-4yl)carbamate (600 mg, 1 mmol), 6-((tert-butyldimethylsilyl)oxy)-1,2,3,4-tetrahydroquinoline (789 mg, 3 mmol), 1,4-dioxane (20 mL), RuPhos (93.4 mg, 0.2 mmol), 2$^{nd}$ RuPhos Precatalyst (77.6 mg, 0.1 mmol), and Cs$_2$CO$_3$ (652 mg, 2 mmol). The resulting solution was purged with N$_2$ three times then heated at 80° C. for 4 hours. After cooling, water (10 mL) was added and the resulting solution extracted with EtOAc (3×20 mL). The organics were washed with brine (2×20 mL), dried over anhydrous sodium sulfate, filtered, concentrated under reduced pressure, and purified by silica gel chromatography (50% EtOAc/petroleum ether) to give tert-butyl ((3S,4S)-8-(3-(6-((tert-butyldimethylsilyl)oxy)-3,4-dihydroquinolin-1(2H)-yl)-1-(tetrahydro-2H-pyran-2-yl)-1H-pyrazolo[3,4-b]pyrazin-6-yl)-3-methyl-2-oxa-8-azaspiro[4.5]decan-4-yl)carbamate (360 mg, 49% yield) as a yellow solid: LCMS [M+H]$^+$=734.2.

Step c: A 50-mL round-bottom flask was charged with tert-butyl ((3S,4S)-8-(3-(6-((tert-butyldimethylsilyl)oxy)-3,4-dihydroquinolin-1(2H)-yl)-1-(tetrahydro-2H-pyran-2-yl)-1H-pyrazolo[3,4-b]pyrazin-6-yl)-3-methyl-2-oxa-8-azaspiro[4.5]decan-4-yl)carbamate (360 mg, 0.5 mmol), THF (10 mL), and TBAF (260 mg, 1 mmol). The reaction mixture was stirred for 1 hour at 25° C. and water (10 mL) was added. The mixture was extracted with EtOAc (3×10 mL) and the organics combined, dried over anhydrous sodium sulfate, filtered, concentrated under reduced pressure, and purified by silica gel chromatography (75% EtOAc/petroleum ether) to give the tert-butyl ((3S,4S)-8-(3-(6-hydroxy-3,4-dihydroquinolin-1(2H)-yl)-1-(tetrahydro-2H-pyran-2-yl)-1H-pyrazolo[3,4-b]pyrazin-6-yl)-3-methyl-2-oxa-8-azaspiro[4.5]decan-4-yl)carbamate (200 mg, 65% yield) as a yellow solid: LCMS [M+H]$^+$=620.15.

Step d: A 50-mL round-bottom flask was charged with tert-butyl ((3S,4S)-8-(3-(6-hydroxy-3,4-dihydroquinolin-1(2H)-yl)-1-(tetrahydro-2H-pyran-2-yl)-1H-pyrazolo[3,4-b]pyrazin-6-yl)-3-methyl-2-oxa-8-azaspiro[4.5]decan-4-yl)carbamate (200 mg, 0.32 mmol), DCM (10 mL), and Et$_3$N (64.6 mg, 0.64 mmol). The resulting solution was purged with SO$_2$F$_2$ twice then stirred for 1 hour at 25° C. Water (10 mL) was added and the resulting solution was extracted with DCM (3×10 mL). The organics were combined, dried over anhydrous sodium sulfate, filtered, and concentrated under reduced pressure to give 1-(6-((3S,4S)-4-((tert-butoxycarbonyl)amino)-3-methyl-2-oxa-8-azaspiro[4.5]decan-8-yl)-1-(tetrahydro-2H-pyran-2-yl)-1H-pyrazolo[3,4-b]pyrazin-3-yl)-1,2,3,4-tetrahydroquinolin-6-yl sulfurofluoridate (157 mg, 70% yield) as a yellow solid: LCMS [M+H]$^+$=702.2.

Step e: A 50-mL round-bottom flask was charged with 1-(6-((3S,4S)-4-((tert-butoxycarbonyl)amino)-3-methyl-2-oxa-8-azaspiro[4.5]decan-8-yl)-1-(tetrahydro-2H-pyran-2-yl)-1H-pyrazolo[3,4-b]pyrazin-3-yl)-1,2,3,4-tetrahydroquinolin-6-yl sulfurofluoridate (157 mg, 0.22 mmol), 1,4-dioxane (5 mL) and 4M HCl in 1,4-dioxane (0.2 mL) was added. The reaction mixture was stirred for 2 hours at 25° C., concentrated under reduced pressure, and purified by preparative reversed phase HPLC (23% B to 34% CH$_3$CN/H$_2$O, 0.1% TFA) to give 1-(6-((3S,4S)-4-amino-3-methyl-2-oxa-8-azaspiro[4.5]decan-8-yl)-1H-pyrazolo[3,4-b]pyrazin-3-yl)-1,2,3,4-tetrahydroquinolin-6-yl sulfurofluoridate as a yellow solid (56 mg, 48% yield): LCMS [M+H]$^+$=518.2; $^1$H-NMR (400 MHz, DMSO-d$_6$) δ 12.68 (s, 1H), 8.33 (s, 1H), 7.27 (d, J=2.4 Hz, 1H), 7.09 (d, J=3.3 Hz, 2H), 5.75-5.25 (m, 2H), 4.18-3.93 (m, 3H), 3.90 (t, J=5.7 Hz, 2H), 3.74 (d, J=8.6 Hz, 1H), 3.54 (d, J=8.6 Hz, 1H), 3.46-3.37 (m, 2H), 3.03 (d, J=5.0 Hz, 1H), 2.88 (t, J=6.4 Hz, 2H), 2.00 (p, J=6.1 Hz, 2H), 1.80-1.50 (m, 4H), 1.12 (d, J=6.4 Hz, 3H).

Compound 3A: Preparation of 1-(6-(4-(aminomethyl)-4-methylpiperidin-1-yl)-1H-pyrazolo[3,4-b]pyrazin-3-yl)-1,2,3,4-tetrahydroquinoline-5-sulfonyl Fluoride

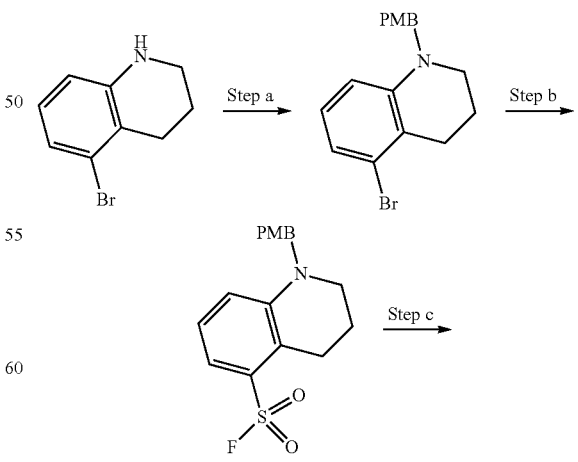

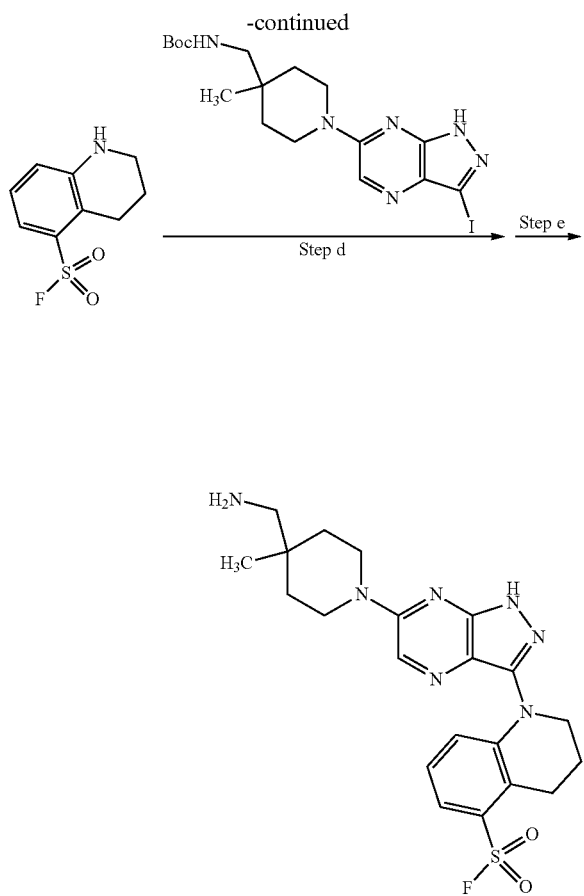

Step a: A 100-mL round-bottom flask was charged with 5-bromo-1,2,3,4-tertrahydroquinoline (1.0 g, 4.7 mmol), DMF (20 mL), PMBCl (1.1 g, 7.0 mmol), K$_2$CO$_3$ (1.3 g, 9.4 mmol), and NaI (344.5 mg, 2.3 mmol). The resulting solution was heated at 50° C. for 1.5 hours, cooled to 25° C., then quenched with water (30 mL). The resulting solution was extracted with EtOAc (3×50 mL) and the organics washed with brine (2×50 mL), dried over anhydrous sodium sulfate, filtered, concentrated under reduced pressure, and purified by silica gel chromatography (5% EtOAc/petroleum ether) to give 5-bromo-1-(4-methoxybenzyl)-1,2,3,4-tetrahydroquinoline (1.3 g, 83% yield) as a white solid. LCMS [M+H]$^+$=332.1.

Step b: A 100-mL round-bottom flask was charged with 5-bromo-1-(4-methoxybenzyl)-1,2,3,4-tetrahydroquinoline (1.3 g, 3.93 mmol), DABSO (590 mg, 2.36 mmol), Pd(Amphos)Cl$_2$ (325 mg, 0.39 mmol), Et$_3$N (1.3 g, 11.7 mmol), and iPrOH (20 mL). The resulting solution was purged with N$_2$ three times and then heated at 75° C. and stirred for 12 hours. After cooling to 25° C., N-fluorobenzenesulfonimide (NFSI, 1.9 g, 6.0 mmol) was added and the mixture was stirred for 3 hours at 25° C. Water (20 mL) was added and the resulting solution was extracted with EtOAc (3×30 mL). The organics were washed with brine (2×50 mL), dried over anhydrous sodium sulfate, filtered, concentrated under reduced pressure, and purified by reversed flash chromatography (MeCN/H$_2$O=50%) to give the 1-(4-methoxybenzyl)-1,2,3,4-tetrahydroquinoline-5-sulfonyl fluoride (810 mg, 62% yield) as a yellow solid: LCMS [M+H]$^+$=336.1.

Step c: A 100-mL round-bottom flask was charged with 1-(4-methoxybenzyl)-1,2,3,4-tetrahydroquinoline-5-sulfonyl fluoride (810 g, 2.41 mmol) and TFA (10 mL). The reaction mixture was refluxed for 30 minutes, cooled, then concentrated under reduced pressure. The residue was washed with Et$_2$O and dried under vacuum to give 1,2,3,4-tetrahydroquinoline-5-sulfonyl fluoride (460 mg, 90% yield) as a yellow solid. LCMS [M+H]$^+$=216.1.

Step d: A 50-mL round-bottom flask was charged with tert-butyl ((1-(3-iodo-1-(tetrahydro-2H-pyran-2-yl)-1H-pyrazolo[3,4-b]pyrazin-6-yl-4-methylpiperidin-4-yl)carbamate (400 mg, 0.72 mmol), 1,2,3,4-tetrahydroquinoline-5-sulfonyl fluoride (311 mg, 1.44 mmol), 1,4-dioxane (10 mL), RuPhos (67.4 mg, 0.14 mmol), 2$^{nd}$ RuPhos Precatalyst (55.9 mg, 0.072 mmol), and Cs$_2$CO$_3$ (469.4 mg, 1.44 mmol). The resulting solution was purged with N$_2$ three times then heated at 80° C. for 4 hours. After cooling to 25° C., the solution was extracted with EtOAc (3×20 mL). The organics were washed with brine (2×20 mL), dried over anhydrous sodium sulfate, filtered, concentrated under reduced pressure, and purified by silica gel chromatography (50% EtOAc/petroleum ether) to give tert-butyl ((1-(3-iodo-1-(tetrahydro-2H-pyran-2-yl)-1H-pyrazolo[3,4-b]pyrazin-6-yl-4-methylpiperidin-4-yl)carbamate (250 mg, which can be recycled) and the desired tert-butyl ((1-(3-(5-(fluorosulfonyl)-3,4-dihydroquinolin-1(2H)-yl)-1H-pyrazolo[3,4-b]pyrazin-6-yl)-4-methylpiperidin-4-yl)methyl)carbamate (30 mg, 17% yield based on the SM recycled) as a yellow solid: LCMS [M+H]$^+$=644.2.

Step e: A 50-mL round-bottom flask was charged with tert-butyl ((1-(3-(5-(fluorosulfonyl)-3,4-dihydroquinolin-1(2H)-yl)-1H-pyrazolo[3,4-b]pyrazin-6-yl)-4-methylpiperidin-4-yl)methyl)carbamate (30 mg, 0.046 mmol), and 1,4-dioxane (3 mL). A solution of 4M HCl in 1,4-dioxane (0.2 mL) was added and the reaction mixture stirred for 2 hours at 25° C. The mixture was concentrated under reduced pressure and purified by reversed phase preparative HPLC (23% B to 34% CH$_3$CN/H$_2$O, 0.1% TFA) to give 1-(6-(4-(aminomethyl)-4-methylpiperidin-1-yl)-1H-pyrazolo[3,4-b]pyrazin-3-yl)-1,2,3,4-tetrahydroquinoline-5-sulfonyl fluoride as a yellow solid (5.5 mg, 26% yield): LCMS [M+H]$^+$=460; $^1$H-NMR (400 MHz, DMSO-d$_6$) δ 12.77 (s, 1H), 8.33 (s, 1H), 7.81 (s, 3H), 7.48 (d, J=7.8 Hz, 1H), 7.38 (d, J=8.5 Hz, 1H), 7.26 (t, J=8.1 Hz, 1H), 5.76 (s, 5H), 3.99 (d, J=14.1 Hz, 2H), 3.89 (d, J=6.0 Hz, 2H), 3.52-3.46 (m, 3H), 3.16 (t, J=6.6 Hz, 2H), 2.79 (d, J=6.7 Hz, 2H), 2.08-206 (m, 2H), 1.59-1.43 (m, 4H), 1.10 (s, 3H).

The characterization of compounds disclosed herein is shown below.

| Cmpd. No. | Structure | NMR | Mass Spec. (M + H)+ |
|---|---|---|---|
| 1A | 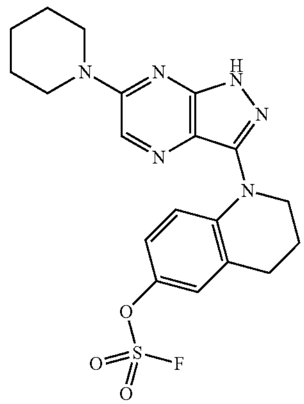 [SMILES: O=S(=O)(F)Oc1ccc2c(c1)CCCN2c1n[nH]c2nc(N3CCCCC3)cnc12] | ¹H NMR (400 MHz, DMSO-d6) δ 8.20 (s, 1H), 7.13 (s, 1H), 6.96 (d, J = 9.2 Hz, 1H), 6.87 (d, J = 9.2 Hz, 1H), 3.91 (t, J = 5.6 Hz, 2H), 3.81-3.76 (m, 4H), 2.96 (t, J = 6.4 Hz, 2H), 2.21-2.13 (m, 2H), 1.77-1.54 (m, 6H) | 433.1 |
| 2A | 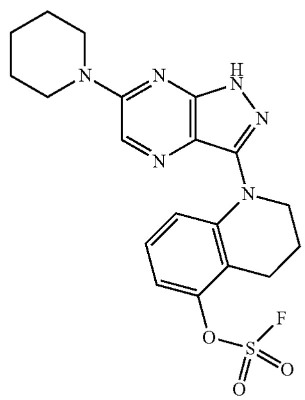 [SMILES: O=S(=O)(F)Oc1cccc2c1CCCN2c1n[nH]c2nc(N3CCCCC3)cnc12] | ¹H NMR (400 MHz, DMSO-d6) δ 12.70 (s, 1H), 8.31 (s, 1H), 7.11-7.00 (m, 2H), 6.88 (d, J = 8 Hz, 1H), 3.89 (t, J = 10.8 Hz, 2H), 3.70-3.65 (m, 4H), 2.83 (t, J = 6.2 Hz, 2H), 2.08-2.00 (m, 2H), 1.85-1.50 (m, 6H) | 433.1 |
| 3A | 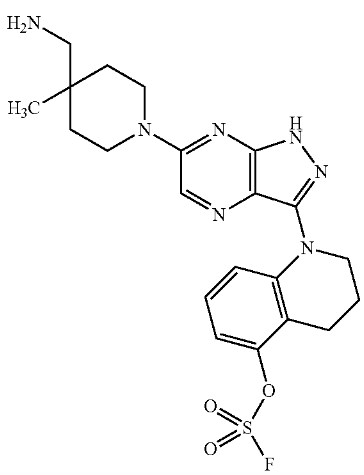 [SMILES: CC1(CN)CCN(c2cnc3c(N4CCCc5c(OS(=O)(=O)F)cccc54)n[nH]c3n2)CC1] | ¹H NMR (400 MHz, DMSO-d₆) δ ppm 8.33 (s, 1 H) 7.03-7.12 (m, 2 H) 6.89 (m, 1 H) 3.87-3.98 (m, 4 H) 3.45-3.50 (m, 2 H) 2.84-2.87 (m, 2 H) 2.51 (br s, 2 H) 2.02-2.07 (m, 2 H) 1.50-1.56 (m, 2 H) 1.35-1.39 (m, 2 H) 1.01 (s, 3 H) | 476.2 |

| Cmpd. No. | Structure | NMR | Mass Spec. (M + H)+ |
|---|---|---|---|
| 4A | 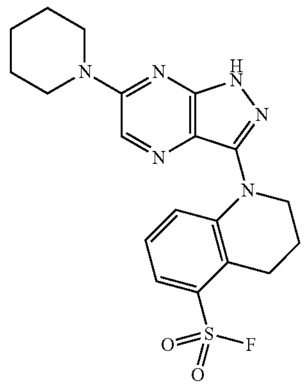 [SMILES: O=S(=O)(F)c1cccc2c1CCCN2c1n[nH]c2nc(N3CCCCC3)cnc12] | ¹H-NMR (400 MHz, CDCl₃) δ 8.14 (s, 1H), 7.60-7.58 (d, J = 7.2 Hz, 1H), 7.51-7.49 (d, J = 8.4 Hz, 1H), 7.21-7.17 (t, J = 8.4 Hz, 1H), 4.05 (m, 2H), 3.52 (m, 4H), 3.29 (m, 2H), 2.04 (m, 2H), 1.74 (m, 4H), 1.29 (m, 1H), 0.72 (m, 1H). | 417.1 |
| 5A | 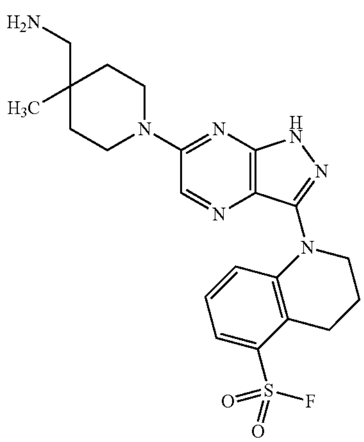 [SMILES: CC1(CN)CCN(c2cnc3c(N4CCCc5c4cccc5S(=O)(=O)F)n[nH]c3n2)CC1] | ¹H-NMR (400 MHz, DMSO-d6) δ 12.77 (s, 1H), 8.33 (s, 1H), 7.81 (s, 3H), 7.48 (d, J = 7.8 Hz, 1H), 7.38 (d, J = 8.5 Hz, 1H), 7.26 (t, J = 8.1 Hz, 1H), 5.76 (s, 5H), 3.99 (d, J = 14.1 Hz, 2H), 3.89 (d, J = 6.0 Hz, 2H), 3.52-3.46 (m, 3H), 3.16 (t, J = 6.6 Hz, 2H), 2.79 (d, J = 6.7 Hz, 2H), 2.08-206 (m, 2H), 1.59-1.43 (m, 4H) 1.10 (s, 3H) | 461.1 |
| 6A | 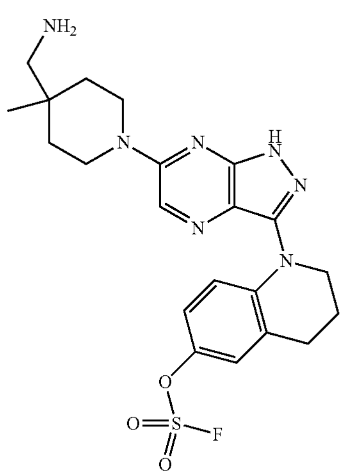 [SMILES: CC1(CN)CCN(c2cnc3c(N4CCCc5cc(OS(=O)(=O)F)ccc54)n[nH]c3n2)CC1] | ¹H NMR (400 MHz, DMSO-d6) δ 8.39 (s, 1H) 8.31-8.36 (m, 1 H) 7.12 (s, 1 H) 7.06-7.12 (m, 2 H) 3.86-3.98 (m, 4 H) 3.40-3.50 (m, 2 H) 2.87-2.90 (m, 2 H) 2.59 (br s, 2H) 1.98-2.04 (m, 2 H) 1.52-1.56 (m, 2 H) 1.48-1.52 (m, 2 H) 1.01 (s, 3 H) | |

-continued
| Cmpd. No. | Structure | NMR | Mass Spec. (M + H)+ |
|---|---|---|---|
| 7A | 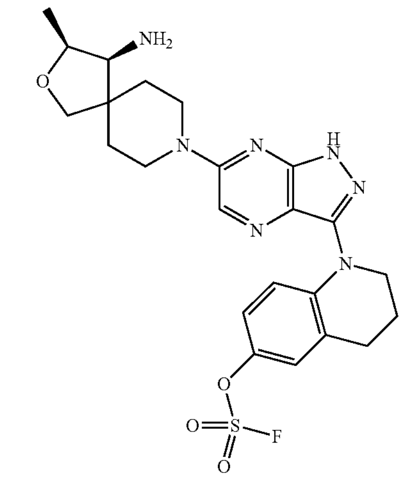 [SMILES: C[C@@H]1OCC2(CCN(c3cnc4c(N5CCCc6cc(OS(=O)(=O)F)ccc65)n[nH]c4n3)CC2)[C@@H]1N] | ¹H-NMR (400 MHz, DMSO-d6) δ 12.68 (s, 1H), 8.33 (s, 1H), 7.27 (d, J = 2.4 Hz, 1H), 7.09 (d, J = 3.3 Hz, 2H), 5.75-5.25 (m, 2H), 4.18-3.93 (m, 3H), 3.90 (t, J = 5.7 Hz, 2H), 3.74 (d, J = 8.6 Hz, 1H), 3.54 (d, J = 8.6 Hz, 1H), 3.46-3.37 (m, 2H), 3.03 (d, J = 5.0 Hz, 1H), 2.88 (t, J = 6.4 Hz, 2H), 2.00 (p, J = 6.1 Hz, 2H), 1.80-1.50 (m, 4H), 1.12 (d, J = 6.4 Hz, 3H) | |
| 8A | 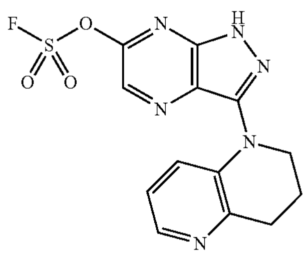 [SMILES: O=S(=O)(F)Oc1cnc2c(N3CCCc4ncccc43)n[nH]c2n1] | 1H-NMR (400 MHz, DMSO-d6) d 13.97 (s, 1H), 8.76 (s, 1H), 8.01 (s, 1H), 7.63-7.61 (d, J = 8.4 Hz, 1H), 7.04-7.01 (dd, J = 8.4, 4.4 Hz, 1H), 4.06-4.04 (t, J = 5.6 Hz, 2H), 2.99-2.96 (t, J = 6.4 Hz, 2H), 2.13-1.07 (m, 2H) | |
| 9A | 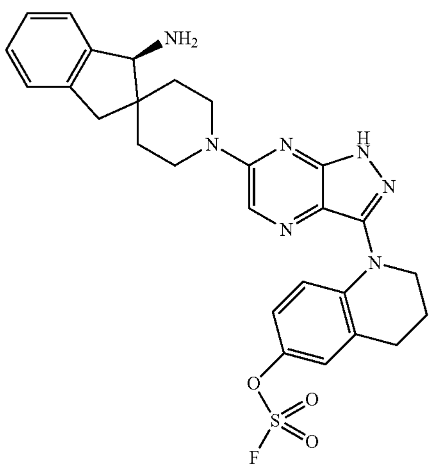 [SMILES: N[C@@H]1c2ccccc2CC12CCN(c1cnc3c(N4CCCc5cc(OS(=O)(=O)F)ccc54)n[nH]c3n1)CC2] | 1H-NMR (400 MHz, CD3OD): 8.30 (s, 1H), 7.52-7.55 (m, 1H), 7.41-7.44 (m, 2H), 7.36-7.39 (m, 1H), 7.17-7.19 (m, 1H), 6.95-7.00 (m, 2H), 4.52-4.56 (m, 1H), 4.40-4.44 (m, 2H), 3.94-3.98 (m, 2H), 3.39-3.52 (m, 2H), 3.19-3.24 (m, 2H), 2.94-2.98 (m, 2H), 2.12-2.16 (m, 2H), 1.81-1.94 (m, 3H), 1.66-1.70 (m, 1H). | 550.1 |
The compounds of Formula (Va), for example, can generally be prepared according to exemplary Scheme 3:
Scheme 3
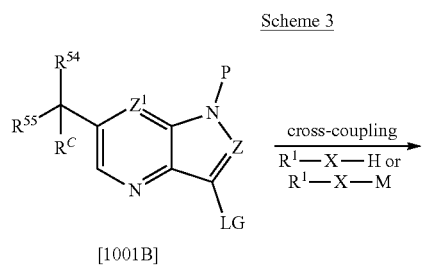
[1001B]
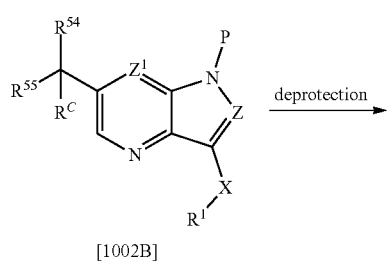
[1002B]

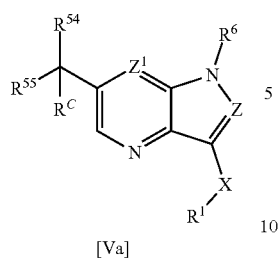

[Va]

wherein X, Z, $Z^1$, $R^1$, $R^6$, $R^{54}$, $R^{55}$ and $R^C$ are as defined as elsewhere herein, Q is independently a halogen, such as Cl, Br, I, and the like, or any other leaving group, such as $OSO_2Me$, OMs, OTs, OTf, and the like. LG is a leaving group, such as Cl, Br, I, OTs, OTf, and the like.

As shown in Scheme 3, an aryl compound such as a compound of Formula 1001B undergoes a cross-coupling reaction with a metalated or otherwise activated moiety to provide a compound of Formula 1002B. Removal of the protecting group provides a compound of Formula (I). In some embodiments, LG is I. In some embodiments, LG is $C_1$. In some embodiments, LG is OTf or OTs.

In some embodiments, the cross-coupling reaction is a Buchwald-Hartwig reaction. In some embodiments, the cross-coupling reaction is a Chan-Lam coupling reaction. In some embodiments, the cross-coupling reaction is an Ullmann reaction. In some embodiments, the cross-coupling reaction is a Suzuki reaction. In some embodiments, the cross-coupling reaction is a Stille reaction. In some embodiments, the cross-coupling reaction is a Negishi reaction. In some embodiments, the cross-coupling reaction is a Hiyama reaction. Other cross-coupling reactions may be employed as would be apparent to one of ordinary skill in the art.

In some embodiments, the protecting group is removed under acidic conditions, such as HBr in AcOH. Conditions for removal of the protecting group will depend on the nature of the protecting group. Conditions for the removal of various protecting groups can be found, e.g., in Greene et al., Protective Groups in Organic Synthesis ($4^{th}$ ed. 2006).

Compound 12B: Preparation of 2-(3-(3,4-dihydro-1,5-naphthyridin-1(2H)-yl)-1H-pyrazolo[3,4-b]pyrazin-6-yl)-2-methylpropan-1-amine

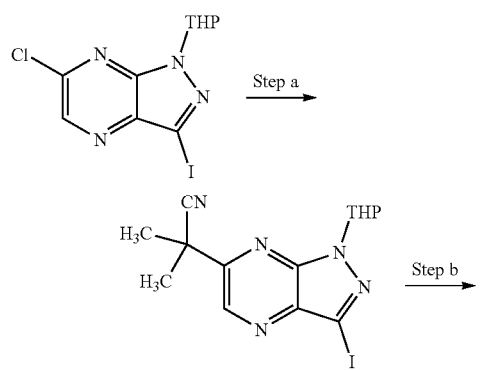

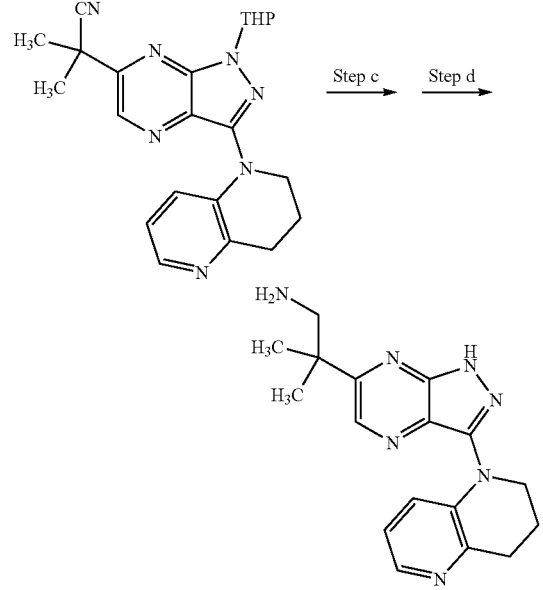

Step a: To a solution of 6-chloro-3-iodo-1-(oxan-2-yl)-1H-pyrazolo[3,4-b]pyrazine (300.0 mg, 822 µmol) and 2-methylpropanenitrile (56.8 mg, 822 µmol) in toluene (10 mL) was added NaHMDS (985.0 uL, 1.0 M, 986.0 umol) at 0° C. under $N_2$. The reaction mixture was stirred at 25° C. for 12 hrs. After this time, the solution was added into $H_2O$ (20 mL) and then extracted with EtOAc (20 mL×2). The combined organics were washed with saturated NaCl (20 mL), dried over anhydrous $Na_2SO_4$, filtered, and concentrated under reduced pressure to give crude product as orange gum. The residue was purified by flash silica gel chromatography (Ethyl acetate in petroleum ether from 0% to 15%) to give 2-[3-iodo-1-(oxan-2-yl)-1H-pyrazolo[3,4-b]pyrazin-6-yl]-2-methylpropanenitrile (210.0 mg, 64.4% yield) as yellow oil.

Step b: A solution of 2-[3-iodo-1-(oxan-2-yl)-1H-pyrazolo[3,4-b]pyrazin-6-yl]-2-methylpropanenitrile (210 mg, 528 µmol), 1,2,3,4-tetrahydro-1,5-naphthyridine (84.9 mg, 633 µmol), $Pd_2(dba)_3$ (48.3 mg, 52.8 umol), Xantphos (30.5 mg, 52.8 umol) and t-BuONa (151.0 mg, 1.58 mmol) in toluene (5.0 mL) was stirred at 110° C. for 12 hrs. After cooling, the solution was added into $H_2O$ (10.0 mL) and then extracted with EtOAc (10.0 mL×2). The combined organics were washed with saturated NaCl (20 mL), dried over anhydrous $Na_2SO_4$, filtered, and concentrated under reduced pressure to give crude product as brown gum. The residue was purified by flash silica gel chromatography (Ethyl acetate in petroleum ether from 0% to 50%) to give 2-methyl-2-[1-(oxan-2-yl)-3-(1,2,3,4-tetrahydro-1,5-naphthyridin-1-yl)-1H-pyrazolo[3,4-b]pyrazin-6-yl]propanenitrile (200 mg, 93.8% yield) as a yellow oil.

Step c: A solution of 2-methyl-2-[1-(oxan-2-yl)-3-(1,2,3,4-tetrahydro-1,5-naphthyridin-1-yl)-1H-pyrazolo[3,4-b]pyrazin-6-yl]propanenitrile (200 mg, 495 µmol), Raney Nickel (100 mg) and $NH_3$ $H_2O$ (2 mL) in MeOH (15 mL) was stirred at 25° C. for 12 hrs. under $H_2$ (15 psi). After replacing the hydrogen atmosphere with nitrogen, the reaction mixture was filtered and the filtrate concentrated under reduced pressure to give 2-methyl-2-[1-(oxan-2-yl)-3-(1,2,3,4-tetrahydro-1,5-naphthyridin-1-yl)-1H-pyrazolo[3,4-b]pyrazin-6-yl]propan-1-amine (220 mg, crude) as yellow oil. This material was used in future steps as is without further purification.

Step d: A solution of 2-methyl-2-[1-(oxan-2-yl)-3-(1,2,3,4-tetrahydro-1,5-naphthyridin-1-yl)-1H-pyrazolo[3,4-b]pyrazin-6-yl]propan-1-amine (220 mg, 539 µmol) in HCl/MeOH (5 mL) was stirred at 25° C. for 1 hr. After this time, the reaction mixture was concentrated under reduced pressure and the residue diluted with MeOH (5 mL), the pH adjusted to 9 with NH₃ H₂O, and the mixture purified by prep-HPLC (acetonitrile/aq. NH₃ H₂O) to produce 2-methyl-2-[3-(1,2,3,4-tetrahydro-1,5-naphthyridin-1-yl)-1H-pyrazolo[3,4-b]pyrazin-6-yl]propan-1-amine (77.7 mg, 49.1% yield) as a yellow solid: LCMS [M+H]$^+$=324.0; $^1$H-NMR (400 MHz, CD₃OD) δ 8.63 (s, 1H), 7.90-7.93 (m, 1H), 7.40-7.44 (m, 1H), 7.00-7.05 (m, 1H), 4.01-4.07 (m, 2H), 3.04-3.10 (m, 4H), 2.20-2.27 (m, 2H), 1.50 (s, 6H).

Compound 11B: Preparation of 2-[3-(3-chloro-2-fluorophenyl)-1H-pyrazolo[3,4-b]pyrazin-6-yl]-2-methylpropan-1-amine

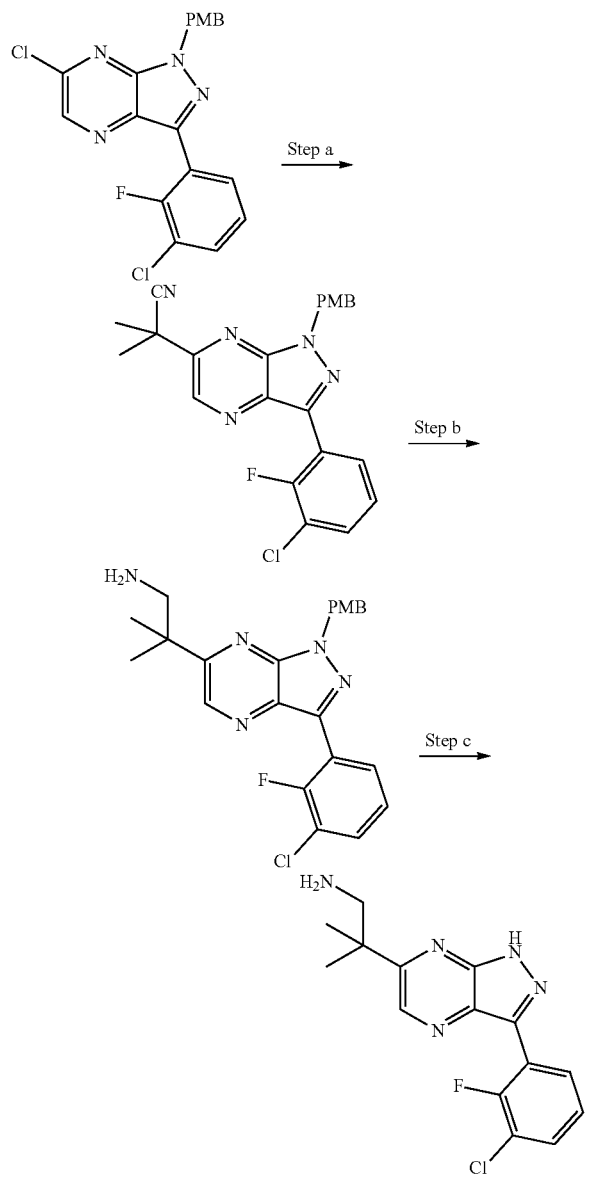

Step a: The compound of 6-chloro-3-(3-chloro-2-fluorophenyl)-1-[(4-methoxyphenyl)methyl]-1H-pyrazolo[3,4-b]pyrazine (300 mg, 0.7 mmol) and 2-methylpropanenitrile (0.07 mL, 0.8 mmol) were placed into the solvent of toluene (3.0 mL). The reaction mixture was evacuated and refilled for 3 times using N2. 1N NaHMDS (0.9 mL, 0.9 mmol) was added dropwise at 0° C. over 5 min. The reaction mixture was stirred at 0° C. for 1 hour and then stirred at 25° C. for 12 h. The reaction mixture was concentrated to give a residue. The residue was purified by flash silica gel chromatography (Ethyl acetate/Petroleum ether=0/100 to 20/100) to give the product of 2-[3-(3-chloro-2-fluorophenyl)-1-[(4-methoxyphenyl)methyl]-1H-pyrazolo[3,4-b]pyrazin-6-yl]-2-methylpropanenitrile (300 mg, 93% yield) as a white solid.

Step b: The compound of 2-[3-(3-chloro-2-fluorophenyl)-1-[(4-methoxyphenyl)methyl]-1H-pyrazolo[3,4-b]pyrazin-6-yl]-2-methylpropanenitrile (240 mg, 0.5 mmol) was dissolved in MeOH (15 mL) and THF (10 mL). Raney Ni (100 mg) and NH₃·H2O (2 mL) was added. The reaction mixture was evacuated and refilled for 3 times using H2. The reaction mixture was stirred at 25° C. for 12 hours under H2 (15 psi). The reaction mixture was filtered through a pad of celite and washed with MeOH (20 mL). The filtrate was concentrated in vacuum to give 2-[3-(3-chloro-2-fluorophenyl)-1-[(4-methoxyphenyl)methyl]-1H-pyrazolo[3,4-b]pyrazin-6-yl]-2-methylpropan-1-amine (240 mg, 99% yield) as a colorless oil.

Step c: The compound of 2-[3-(3-chloro-2-fluorophenyl)-1-[(4-methoxyphenyl)methyl]-1H-pyrazolo[3,4-b]pyrazin-6-yl]-2-methylpropan-1-amine (230 mg, 0.5 mmol) was added in the solution of TFA (2.5 mL) and TfOH (0.25 mL). The mixture was stirred at 25° C. for 2 h. The mixture was diluted with MeOH (10 mL) and concentrated to give a residue. The residue was triturated with MeOH (1 mL), adjusted to pH=8-9 with NH₃/MeOH (7 N), and a lot of precipitate formed. The mixture was filtered and the filtrate was purified by prep-HPLC (NH3·H2O) to afford the product of 2-[3-(3-chloro-2-fluorophenyl)-1H-pyrazolo[3,4-b]pyrazin-6-yl]-2-methylpropan-1-amine (150 mg, 90% yield) as a white solid. LCMS: calc. for C15H15ClFN5: 319.1, found: [M+H]$^+$ 320.2. 1HNMR (400 MHz, DMSO-d6): δ 8.83 (s, 1H), 8.17~8.22 (m, 1H), 7.67~7.71 (m, 1H), 7.40~7.45 (m, 1H), 2.91 (s, 2H), 1.39 (s, 6H).

Compound 10B: Preparation of (2-(3-(3,4-dihydro-1,5-naphthyridin-1(2H)-yl)-1H-pyrazolo[3,4-b]pyrazin-6-yl)phenyl)methanamine

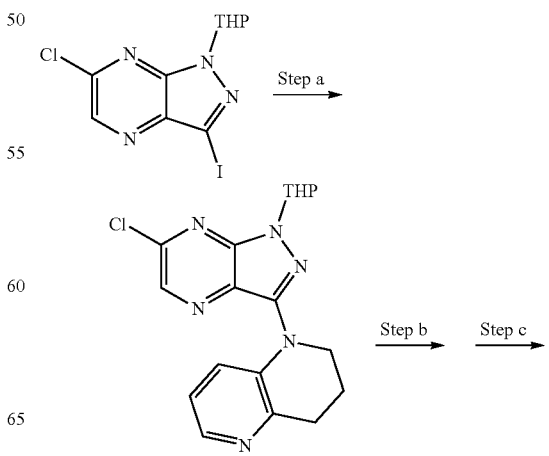

119
-continued

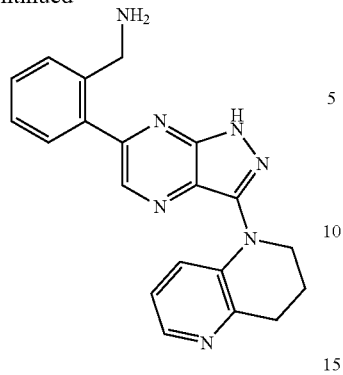

A mixture of 1,2,3,4-tetrahydro-1,5-naphthyridine (152 mg, 1.1 mmol), 6-chloro-3-iodo-1-(tetrahydro-2H-pyran-2-yl)-1H-pyrazolo[3,4-b]pyrazine (500 mg, 1.4 mmol), XantPhos (131 mg, 228 μmol), t-BuONa (219 mg, 2.3 mmol), and Pd$_2$(dba)$_3$ (104 mg, 114 μmol) in toluene (10 mL) was stirred at 120° C. for 12 hours. After cooling, the reaction mixture was concentrated under reduced pressure to give a residue which was purified by column chromatography (petroleum ether:ethyl acetate=1:2 to 0:1) to afford 1-(6-chloro-1-(tetrahydro-2H-pyran-2-yl)-1H-pyrazolo[3,4-b]pyrazin-3-yl)-1,2,3,4-tetrahydro-1,5-naphthyridine (200 mg, 47.3% yield) as a yellow solid.

A mixture of 1-(6-chloro-1-(tetrahydro-2H-pyran-2-yl)-1H-pyrazolo[3,4-b]pyrazin-3-yl)-1,2,3,4-tetrahydro-1,5-naphthyridine (200 mg, 539 μmol), (2-(aminomethyl)phenyl)boronic acid (161 mg, 1.1 mmol), Pd(dppf)C$_2$CH$_2$Cl$_2$ (87.5 mg, 107 μmol), and Cs$_2$CO$_3$ (348 mg, 1.1 mmol) in dioxane (10 mL)/H$_2$O (3 mL) was stirred at 100° C. for 12 hours. The reaction mixture was concentrated under reduced pressure to give a residue which was purified by column chromatography (DCM/methanol 10:1, 0.5% NH$_3$/H$_2$O) to afford (2-(3-(3,4-dihydro-1,5-naphthyridin-1(2H)-yl)-1-(tetrahydro-2H-pyran-2-yl)-1H-pyrazolo[3,4-b]pyrazin-6-yl)phenyl)methanamine (180 mg, 75.9% yield) as a brown solid.

A mixture of (2-(3-(3,4-dihydro-1,5-naphthyridin-1(2H)-yl)-1-(tetrahydro-2H-pyran-2-yl)-1H-pyrazolo[3,4-b]pyrazin-6-yl)phenyl)methanamine (180 mg, 407 μmol) in HCl/MeOH (4M, 5 mL) was stirred at 25° C. for 2 hours. The mixture was concentrated under reduced pressure to give a residue which was purified by prep-HPLC (acetonitrile/aq. HCl) to afford (2-(3-(3,4-dihydro-1,5-naphthyridin-1(2H)-yl)-1H-pyrazolo[3,4-b]pyrazin-6-yl)phenyl)methanamine dihydrochloride (99.2 mg, 56.6% yield) as a yellow solid: LCMS [M+H]$^+$=357.9; $^1$H-NMR (400 MHz, methanol-d$_4$) δ 8.98 (s, 1H), 8.32 (d, J=8.8 Hz, 1H), 8.14 (d, J=5.6 Hz, 1H), 7.96 (d, J=7.2 Hz, 1H), 7.75-7.65 (m, 4H), 4.33 (s, 2H), 4.28 (t, J=5.2 Hz, 2H), 3.36-3.34 (m, 2H), 2.40-2.34 (m, 2H).

Compound 9B: Preparation of (1-((3-(3-chloro-2-fluorophenyl)-1H-pyrazolo[3,4-b]pyrazin-6-yl)methyl)-1H-pyrazol-3-yl)methanamine

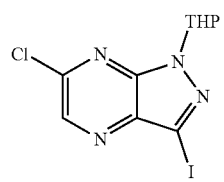

120
-continued

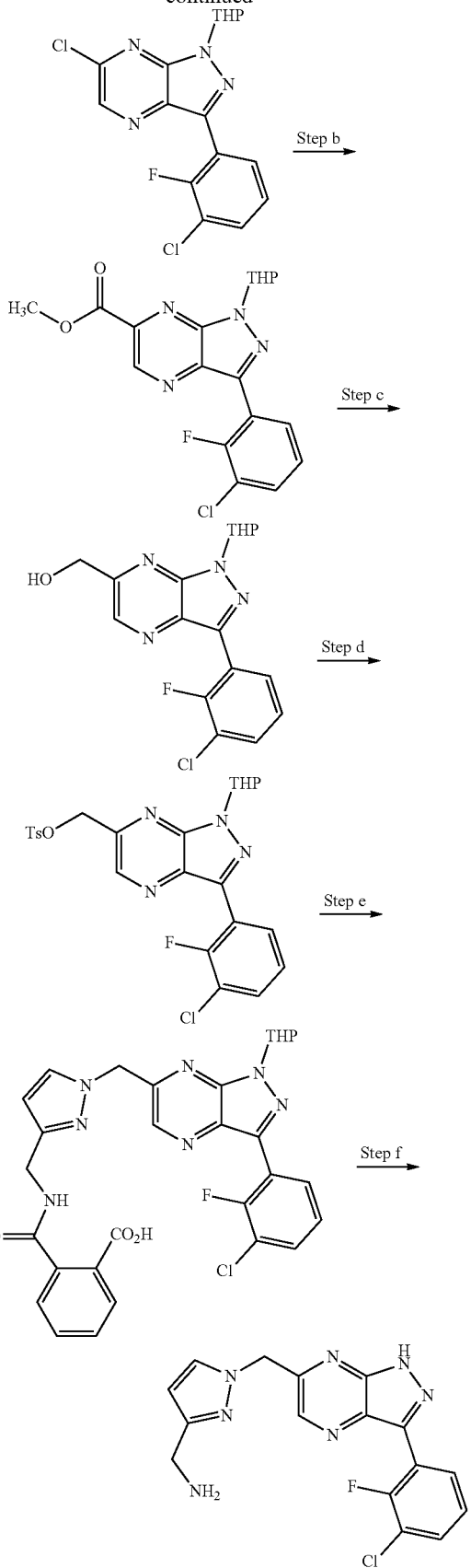

Step a: 6-Chloro-3-iodo-1-(tetrahydro-2H-pyran-2-yl)-1H-pyrazolo[3,4-b]pyrazine (300 mg, 822.0 μmol), (3-chloro-2-fluorophenyl)boronic acid (143.0 mg, 822 μmol), Pd(dppf)Cl$_2$ (60.6 mg, 82.2 μmol), and Na$_2$CO$_3$ (173 mg, 1.6 mmol) were taken up in dioxane (10 mL) and H$_2$O (1 mL) and the reaction mixture evacuated and refilled for 3 times with N$_2$. After stirring at 50° C. for 12 hours, the mixture was concentrated under reduced pressure to give a residue, which was purified by flash silica gel chromatography (petroleum ether:ethyl acetate=100:0 to 100:10) to afford 6-chloro-3-(3-chloro-2-fluorophenyl)-1-(tetrahydro-2H-pyran-2-yl)-1H-pyrazolo[3,4-b]pyrazine (800.0 mg, combined product) as a yellow solid.

Step b: 6-Chloro-3-(3-chloro-2-fluorophenyl)-1-(tetrahydro-2H-pyran-2-yl)-1H-pyrazolo[3,4-b]pyrazine (300.0 mg, 816.0 μmol), TEA (246.0 mg, 2.4 mmol), BINAP (101.0 mg, 163.0 μmol), Pd$_2$(dba)$_3$ (74.7 mg, 81.6 μmol), and KI (135 mg, 816.0 μmol) were taken up in MeOH (30.0 mL) and the reaction mixture atmosphere evacuated and refilled 3 times with CO. After stirring at 80° C. under CO (50 psi) for 12 hours, the reaction mixture was concentrated under reduced pressure to give a residue which was purified by flash silica gel chromatography (petroleum ether:ethyl acetate=100:0 to 100:20) to afford methyl 3-(3-chloro-2-fluorophenyl)-1-(tetrahydro-2H-pyran-2-yl)-1H-pyrazolo[3,4-b]pyrazine-6-carboxylate (330.0 mg, combined product) as a white solid.

Step c: Methyl 3-(3-chloro-2-fluorophenyl)-1-(tetrahydro-2H-pyran-2-yl)-1H-pyrazolo[3,4-b]pyrazine-6-carboxylate (300.0 mg, 767.0 μmol) and NaBH$_4$ (85.1 mg, 2.3 mmol) were taken up in MeOH (30.0 mL) and the reaction stirred at 25° C. for 12 hours. The mixture was concentrated under reduced pressure to give a residue which was purified by flash silica gel chromatography (DCM:MeOH=100:30) to afford (3-(3-chloro-2-fluorophenyl)-1-(tetrahydro-2H-pyran-2-yl)-1H-pyrazolo[3,4-b]pyrazin-6-yl)methanol (220.0 mg, combined product) as a yellow solid.

Step d: To a solution of (3-(3-chloro-2-fluorophenyl)-1-(tetrahydro-2H-pyran-2-yl)-1H-pyrazolo[3,4-b]pyrazin-6-yl)methanol (170 mg, 468 μmol) in THF (5.0 mL) was added NaH (33.5 mg, 1.4 mmol, 60%) and the reaction mixture stirred at 25° C. for 15 min. TsCl (106 mg, 561 μmol) was added in one portion and the reaction mixture was stirred at 25° C. for 12 hours. The mixture was quenched with saturated NH$_4$Cl (2 mL), diluted with H$_2$O (10 mL), extracted with ethyl acetate (10 mL×3), and the organics washed with brine, dried by anhydrous Na$_2$SO$_4$, filtered, and concentrated under reduced pressure to give a residue which was purified by flash silica gel chromatography (ethyl acetate:petroleum ether=0:100 to 30:100, then DCM:MeOH=10:1) to afford (3-(3-chloro-2-fluorophenyl)-1-(tetrahydro-2H-pyran-2-yl)-1H-pyrazolo[3,4-b]pyrazin-6-yl)methyl 4-methylbenzenesulfonate (50.0 mg, 20.0% yield) as a yellow solid and (3-(3-chloro-2-fluorophenyl)-1H-pyrazolo[3,4-b]pyrazin-6-yl)methyl 4-methylbenzenesulfonate (120.0 mg, 47.0% yield) as a yellow solid.

Step e: (3-(3-Chloro-2-fluorophenyl)-1H-pyrazolo[3,4-b]pyrazin-6-yl)methyl 4-methylbenzenesulfonate (120 mg, 277 μmol) was dissolved in THF (6 mL), followed by the addition of NaH (10.0 mg, 415.0 μmol). The reaction mixture was stirred at 25° C. for 15 min and 2-((1H-pyrazol-3-yl)methyl)isoindoline-1,3-dione (62.9 mg, 277 μmol) was added in one portion, followed by stirring at 25° C. for 2 hours. The reaction mixture was concentrated under reduced pressure and purified by silica gel chromatography (DCM:MeOH=10:1) to afford 2-(((1-((3-(3-chloro-2-fluorophenyl)-1H-pyrazolo[3,4-b]pyrazin-6-yl)methyl)-1H-pyrazol-3-yl)methyl)carbamoyl)benzoic acid (100.0 mg, crude product) as a yellow solid.

Step f: 2-(((1-((3-(3-Chloro-2-fluorophenyl)-1-(tetrahydro-2H-pyran-2-yl)-1H-pyrazolo[3,4-b]pyrazin-6-yl)methyl)-1H-pyrazol-3-yl)methyl)carbamoyl)benzoic acid (50 mg, 84.7 μmol) and N$_2$H$_4$·H$_2$O (6.6 mg, 84.7 μmol, 85%) were taken up in EtOH (10 mL) and the reaction mixture stirred at 90° C. for 12 hours. After cooling, the reaction mixture was concentrated under reduced pressure, diluted with MeOH (5.0 mL), and purified by prep-HPLC (acetonitrile/aq. HCl) to afford (1-((3-(3-chloro-2-fluorophenyl)-1H-pyrazolo[3,4-b]pyrazin-6-yl)methyl)-1H-pyrazol-3-yl)methanamine (1.4 mg, 4.0% yield, HCl salt) as an orange solid: LCMS [M+H]$^+$=358.0; $^1$H-NMR (400 MHz, CD$_3$OD) δ 8.56 (s, 1H), 8.10-8.07 (m, 1H), 7.97 (s, 1H), 7.65-7.59 (m, 1H), 7.38-7.33 (m, 1H), 6.48 (s, 1H), 5.73 (s, 2H), 4.14 (s, 2H).

Compound 1B: Preparation of methyl 4-(3-(3-chloro-2-fluorophenyl)-1H-pyrazolo[3,4-b]pyrazin-6-yl)piperidine-4-carboxylate

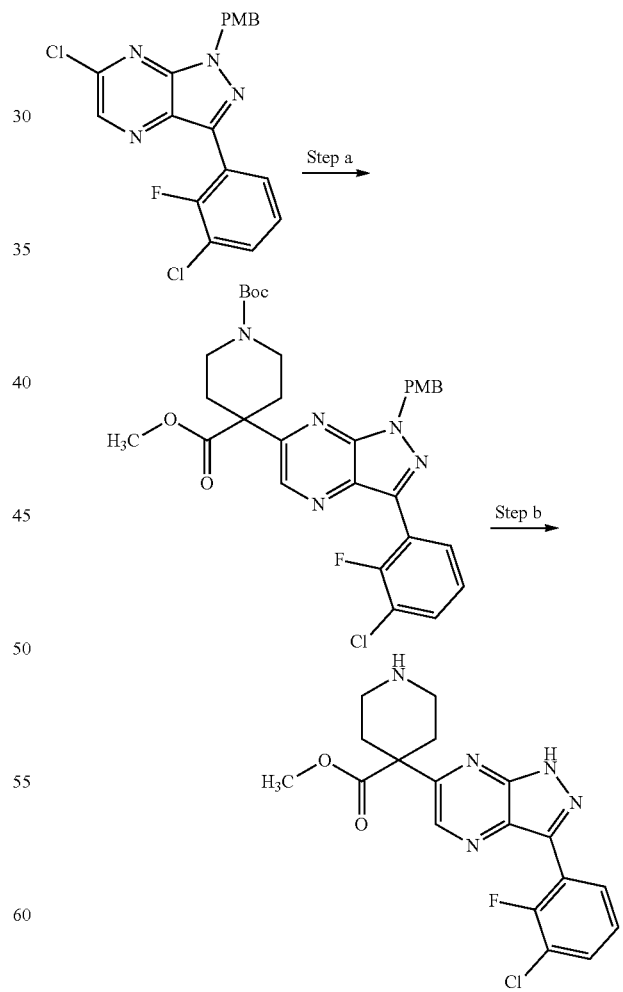

Step a: 1-tert-Butyl 4-methylpiperidine-1,4-dicarboxylate (2.82 g, 11.6 mmol) was taken up in THF (20 mL) and the mixture cooled to 5° C. Lithium diisopropylamide (11.6 mL, 11.6 mmol) was added at 5° C. and the mixture stirred for 30 min. After this time, a suspension of 6-chloro-3-(3-chloro-2-fluorophenyl)-1-(4-methoxybenzyl)-1H-pyrazolo [3,4-b]pyrazine (2.35 g, 5.82 mmol) in THF (15 mL) was added, keeping the reaction temperature at less than 10° C. The mixture was partitioned between EtOAc and water and the organics washed with brine, dried over $Na_2SO_4$, filtered, and concentrated under reduced pressure to provide a residue, which was purified by flash silica gel chromatography (10-40% EtOAc/heptane) to produce 1-(tert-butyl) 4-methyl 4-(3-(3-chloro-2-fluorophenyl)-1-(4-methoxybenzyl)-1H-pyrazolo[3,4-b]pyrazin-6-yl)piperidine-1,4-dicarboxylate as a white foam: LCMS [M−tBu]+=554.1

Step b: A microwave vial was charged with 1-tert-butyl 4-methyl 4-(3-(3-chloro-2-fluorophenyl)-1-(4-methoxybenzyl)-1H-pyrazolo[3,4-b]pyrazin-6-yl)piperidine-1,4-dicarboxylate (205 mg, 336 μmol) and TFA (4 mL). The solution was heated to 50° C. open to air (to remove Me-propene). After 30 min., the vial was sealed, and the mixture was stirred in the microwave at 100° C. for 1 hr. The mixture was cooled, the volatiles removed in vacuo, and the residue taken up in MeOH, which was also removed under reduced pressure (3×) to produce methyl 4-(3-(3-chloro-2-fluorophenyl)-1H-pyrazolo[3,4-b]pyrazin-6-yl)piperidine-4-carboxylate: LCMS [M=H]+=390.1.

Compounds 16B and 17B: Preparation of 1-[(1S)-1-methyl-4-[3-(1,2,3,4-tetrahydro-1,5-naphthyridin-1-yl)-1H-pyrazolo[3,4-b]pyrazin-6-yl]cyclohex-3-en-1-yl]methanamine and 1-[(1R)-1-methyl-4-[3-(1,2,3,4-tetrahydro-1,5-naphthyridin-1-yl)-1H-pyrazolo[3,4-b]pyrazin-6-yl]cyclohex-3-en-1-yl]methanamine

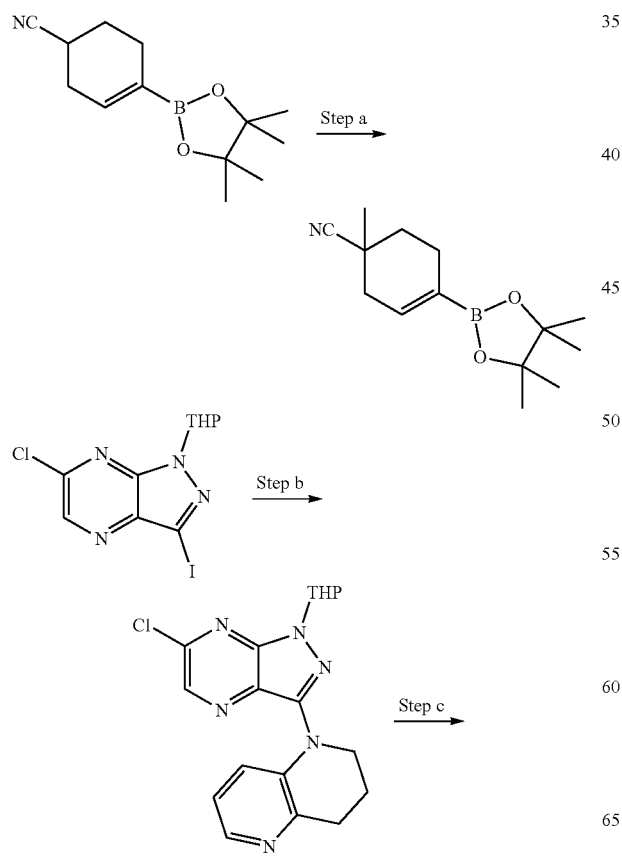

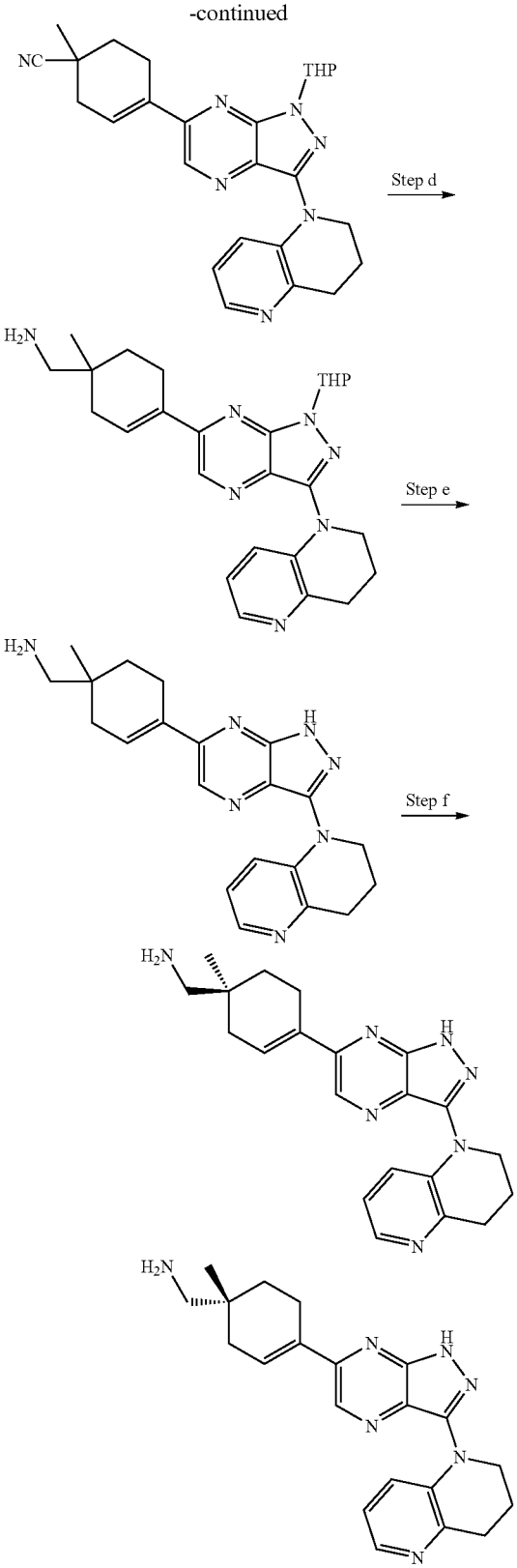

Step a: The compound of 4-(4,4,5,5-tetramethyl-1,3,2-dioxaborolan-2-yl)cyclohex-3-ene-1-carbonitrile (1 g, 4.3 mmol) was placed in THF (20 mL). The LDA (3.21 mL, 6.42 mmol, 2 M in THF) was added dropwise into the mixture at 0° C. The mixture was stirred at 0° C. for 15 min. The MeI (0.5 mL, 8.5 mmol) was added dropwise into the mixture at 0° C. The mixture was warmed to 25° C. and stirred for 2 h. The mixture was concentrated to give the product of 1-methyl-4-(4,4,5,5-tetramethyl-1,3,2-dioxaborolan-2-yl)cyclohex-3-ene-1-carbonitrile (1.2 g, crude product) as a colorless oil.

Step b: The compound of 6-chloro-3-iodo-1-(oxan-2-yl)-1H-pyrazolo[3,4-b]pyrazine (2 g, 5.5 mmol), 1,2,3,4-tetrahydro-1,5-naphthyridine (807 mg, 6.0 mmol), XantPhos-Pd-G4 (263 mg, 0.3 mmol) and Cs2CO3 (3.6 g, 10.9 mmol) were placed in PhMe (50 mL). The mixture was evacuated and refilled for 3 times using N2. The reaction mixture was stirred at 90° C. for 12 hours. The mixture was filtered and the filtrate was concentrated to give a residue. The residue was purified by silica gel column (Petroleum ether:Ethyl acetate=100:50 to 100:80) to give the product of 1-[6-chloro-1-(oxan-2-yl)-1H-pyrazolo[3,4-b]pyrazin-3-yl]-1,2,3,4-tetrahydro-1,5-naphthyridine (1.6 g, 78.8% yield) as a yellow solid.

Step c: The compound of 1-[6-chloro-1-(oxan-2-yl)-1H-pyrazolo[3,4-b]pyrazin-3-yl]-1,2,3,4-tetrahydro-1,5-naphthyridine (1.25 g, 3.4 mmol), 1-methyl-4-(4,4,5,5-tetramethyl-1,3,2-dioxaborolan-2-yl)cyclohex-3-ene-1-carbonitrile (1.0 g, 4.0 mmol), Pd(dppf)Cl2 (246 mg, 0.3 mmol) and Cs2CO3 (2.2 g, 6.7 mmol) were placed into the solvent of dioxane (50 mL) and H2O (5 mL). The reaction mixture was evacuated and refilled for 3 times using N2. The reaction mixture was stirred at 100° C. for 12 hours. The reaction mixture was concentrated and H2O (30 mL) was added, extracted with EtOAc (50 mL×3). The combined organic layers were washed with brine (50 mL), dried over anhydrous Na2SO4, filtered and concentrated to give a residue. The residue was purified by flash silica gel chromatography (Petroleum ether:Ethyl acetate=100:80 to 100:100) to afford 1-methyl-4-[1-(oxan-2-yl)-3-(1,2,3,4-tetrahydro-1,5-naphthyridin-1-yl)-1H-pyrazolo[3,4-b]pyrazin-6-yl]cyclohex-3-ene-1-carbonitrile (1.50 g, 98% yield) as a yellow solid.

Step d: The compound of 1-methyl-4-[1-(oxan-2-yl)-3-(1,2,3,4-tetrahydro-1,5-naphthyridin-1-yl)-1H-pyrazolo[3,4-b]pyrazin-6-yl]cyclohex-3-ene-1-carbonitrile (500 mg, 1.1 mmol) was dissolved in MeOH (25 mL) and THF (5 ml). Raney Ni (100 mg) and NH2NH2·H2O (4.0 mL, 109 mmol, 85%) were added. The reaction mixture was evacuated and refilled for 3 times using N2. The reaction mixture was stirred at 25° C. for 12 hours under N2. The reaction mixture was filtered through a pad of celite and washed with MeOH (20 mL). The filtrate was concentrated to give the product of 1-{1-methyl-4-[1-(oxan-2-yl)-3-(1,2,3,4-tetrahydro-1,5-naphthyridin-1-yl)-1H-pyrazolo[3,4-b]pyrazin-6-yl]cyclohexyl}methanamine (500 mg, crude product) as a yellow solid.

Step e: The compound of 1-{1-methyl-4-[1-(oxan-2-yl)-3-(1,2,3,4-tetrahydro-1,5-naphthyridin-1-yl)-1H-pyrazolo[3,4-b]pyrazin-6-yl]cyclohex-3-en-1-yl}methanamine (500 mg, 1.1 mmol) was added into HCl/MeOH (20 mL, 2M). The mixture was stirred at 25° C. for 12 h. The mixture was concentrated to give a residue. The residue was diluted with MeOH (10 mL). The pH of the mixture was adjusted to 8-9 by addition of K2CO3 (solid). The mixture was filtered and the filtrate was concentrated to give a residue. The residue was purified by flash silica gel chromatography (DCM:MeOH=100:10 to 100:30) to afford the product of 1-{1-methyl-4-[3-(1,2,3,4-tetrahydro-1,5-naphthyridin-1-yl)-1H-pyrazolo[3,4-b]pyrazin-6-yl]cyclohex-3-en-1-yl}methanamine (300 mg, 74% yield) as a yellow solid.

Step f: The compound of rac-1-{1-methyl-4-[3-(1,2,3,4-tetrahydro-1,5-naphthyridin-1-yl)-1H-pyrazolo[3,4-b]pyrazin-6-yl]cyclohex-3-en-1-yl}methanamine (200 mg, 532 μmol) was separated by Chiral-SFC (Column: DAICEL CHIRALPAK AD (250 mm*50 mm, 10 um. Condition: Ethanol (0.1% NH3/H2O). Begin B 45%, end B 45%. Flow rate: 70 mL/min.) to afford the desired product of 1-[(1S)-1-methyl-4-[3-(1,2,3,4-tetrahydro-1,5-naphthyridin-1-yl)-1H-pyrazolo[3,4-b]pyrazin-6-yl]cyclohex-3-en-1-yl]methanamine (WX-RTX-521A) (53.4 mg, 26.8% yield, Rt=2.598 min, e.e.=100%, single peak) as a yellow solid and 1-[(1R)-1-methyl-4-[3-(1,2,3,4-tetrahydro-1,5-naphthyridin-1-yl)-1H-pyrazolo[3,4-b]pyrazin-6-yl]cyclohex-3-en-1-yl]methanamine (47.1 mg, 23.6% yield, Rt=3.049 min, e.e.=100%, single peak) as a yellow solid. Note: the absolute configuration was randomly assigned. LCMS: calc. for $C_{21}H_{25}N_7$: 375.2, found: [M+H]+ 376.0. 1HNMR (400 MHz, CD3OD): δ 8.55~8.63 (m, 1H), 7.78~7.79 (m, 1H), 7.31~7.34 (m, 1H), 6.89~6.91 (m, 1H), 6.77 (s, 1H), 3.92 (s, 2H), 2.91~2.98 (m, 2H), 2.55~2.64 (m, 4H), 2.19-2.00 (m, 4H), 1.52~1.58 (m, 2H), 0.94 (s, 3H). SFC: e.e.=100.0%, Rt=2.598 min. Column: Chiralpak AD-3 100×4.6 mm I.D., 3 μm. Mobile phase: 40% of iso-propanol (0.1% ethanolamine) in CO2. Flow rate: 2.8 mL/min. Column temp: 40° C. The product of 1-[(1R)-1-methyl-4-[3-(1,2,3,4-tetrahydro-1,5-naphthyridin-1-yl)-1H-pyrazolo[3,4-b]pyrazin-6-yl]cyclohex-3-en-1-yl]methanamine (47.1 mg, 23.6% yield) was obtained as a yellow solid. LCMS: calc. for $C_{21}H_{25}N_7$: 375.2, found: [M+H]$^+$ 376.0. HPLC: 94.78% purity at 254 nm. 1HNMR (400 MHz, CD3OD): δ 8.61 (s, 1H), 7.78~7.80 (m, 1H), 7.30~7.33 (m, 1H), 6.88~6.92 (m, 1H), 6.77 (s, 1H), 3.90~3.93 (m, 2H), 2.92~2.96 (m, 2H), 2.40~2.59 (m, 4H), 2.13~2.00 (m, 4H), 1.49~1.58 (m, 2H), 0.89 (s, 3H). SFC: e.e.=100.0%, Rt=2.598 min. Column: Chiralpak AD-3 100×4.6 mm I.D., 3 m. Mobile phase: 40% of iso-propanol (0.1% ethanolamine) in CO2. Flow rate: 2.8 mL/min. Column temp: 40° C.

Compounds 14B and 15B: Preparation of 1-[(1r,4r)-1-methyl-4-[3-(1,2,3,4-tetrahydro-1,5-naphthyridin-1-yl)-1H-pyrazolo[3,4-b]pyrazin-6-yl]cyclohexyl]methanamine dihydrochloride and 1-[(1s,4s)-1-methyl-4-[3-(1,2,3,4-tetrahydro-1,5-naphthyridin-1-yl)-1H-pyrazolo[3,4-b]pyrazin-6-yl]cyclohexyl]methanamine Dihydrochloride

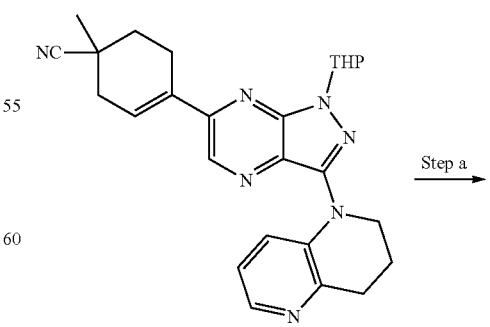

Step a →

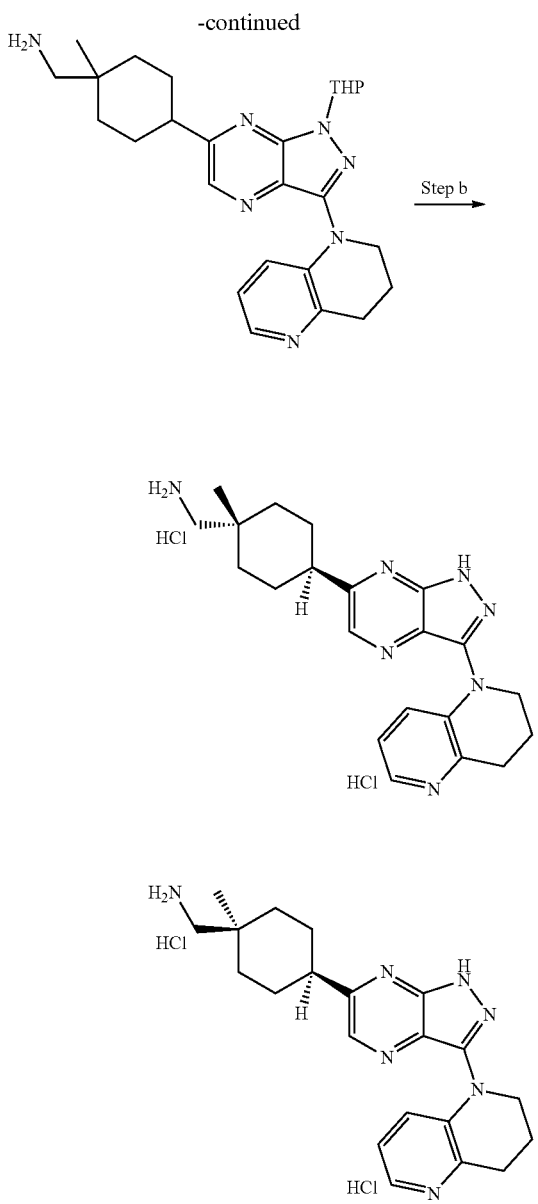

din-1-yl)-1H-pyrazolo[3,4-b]pyrazin-6-yl]cyclohexyl] methanamine dihydrochloride (24.2 mg, 2HCl salt, combined product) as an orange solid [LCMS: calc. for $C_{21}H_{27}N_7$: 377.2, found: [M+H]$^+$ 378.0. HPLC: 100% purity at 254 nm. 1HNMR (400 MHz, CD3OD): δ 8.55~8.59 (m, 1H), 8.08~8.10 (m, 1H), 7.91~7.94 (m, 1H), 7.57~7.61 (m, 1H), 4.09~4.13 (m, 2H), 3.32~3.38 (m, 2H), 2.99~3.10 (m, 1H), 2.89 (s, 2H), 2.31~2.38 (m, 2H), 1.70~2.07 (m, 6H), 1.52~1.60 (m, 2H), 1.20 (s, 3H).] and 1-[(1s,4s)-1-methyl-4-[3-(1,2,3,4-tetrahydro-1,5-naphthyridin-1-yl)-1H-pyrazolo[3,4-b]pyrazin-6-yl]cyclohexyl] methanamine dihydrochloride (11.7 mg, 2HCl salt, combined product) was obtained as a orange solid. LCMS: calc. for C21H27N7: 377.2, found: [M+H]+ 378.0. 1HNMR (400 MHz, CD3OD): δ 8.57 (s, 1H), 8.09-8.14 (m, 2H), 7.57-7.62 (m, 1H), 4.16~4.20 (m, 2H), 3.29~3.33 (m, 2H), 3.12 (s, 2H), 3.05~3.11 (m, 1H), 2.32~2.36 (m, 2H), 1.84~1.95 (m, 6H), 1.54~1.63 (m, 2H), 1.14 (s, 3H).

Compounds 18B and 19B: Preparation of (4S)-4-methyl-1-{6-[(1s,4s)-4-(aminomethyl)cyclohexyl]-1H-pyrazolo[3,4-b]pyrazin-3-yl}-1,2,3,4-tetrahydroquinoline-6-carbonitrile and (4S)-4-methyl-1-{6-[(1r,4r)-4-(aminomethyl)cyclohexyl]-1H-pyrazolo[3,4-b]pyrazin-3-yl}-1,2,3,4-tetrahydroquinoline-6-carbonitrile

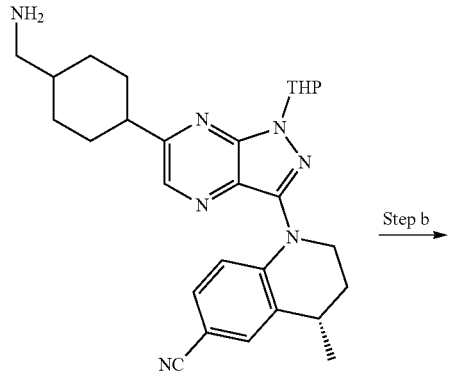

Step a: The compound of 1-methyl-4-[1-(oxan-2-yl)-3-(1,2,3,4-tetrahydro-1,5-naphthyridin-1-yl)-1H-pyrazolo[3,4-b]pyrazin-6-yl]cyclohex-3-ene-1-carbonitrile (70 mg, 0.2 mmol) was dissolved in MeOH (10 mL). Raney Ni (20 mg) and NH3·H2O (1 mL, 30%) was added. The reaction mixture was evacuated and refilled for 3 times using H2. The reaction mixture was stirred at 25° C. for 12 hours under H2 (15 psi). The reaction mixture was filtered through a pad of celite and washed with MeOH (20 mL). The filtrate was concentrated in vacuum to give 1-{1-methyl-4-[1-(oxan-2-yl)-3-(1,2,3,4-tetrahydro-1,5-naphthyridin-1-yl)-1H-pyrazolo[3,4-b]pyrazin-6-yl]cyclohexyl}methanamine (70 mg, crude product) as a yellow solid.

Step b: The compound of 1-{1-methyl-4-[1-(oxan-2-yl)-3-(1,2,3,4-tetrahydro-1,5-naphthyridin-1-yl)-1H-pyrazolo[3,4-b]pyrazin-6-yl]cyclohexyl}methanamine (70 mg, 0.2 mmol) was added into HCl/MeOH (4 mL, 2M). The mixture was stirred at 25° C. for 12 h. The mixture was concentrated and purified by prep-HPLC (HCl) to afford the product of 1-[(1r,4r)-1-methyl-4-[3-(1,2,3,4-tetrahydro-1,5-naphthyri-

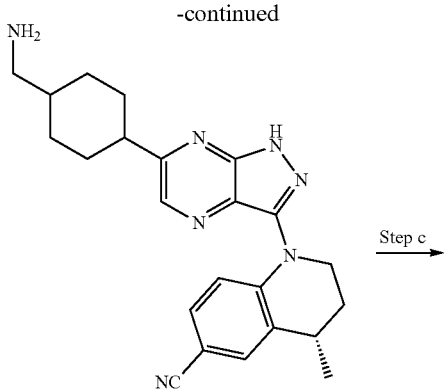

through a pad of celite and washed with MeOH (50 mL). The filtrate was concentrated to give a the product of (4S)-1-{6-[4-(aminomethyl)cyclohexyl]-1-(oxan-2-yl)-1H-pyrazolo[3,4-b]pyrazin-3-yl}-4-methyl-1,2,3,4-tetrahydroquinoline-6-carbonitrile (120 mg, crude) as a yellow oil.

Step b: The compound of (4S)-1-{6-[4-(aminomethyl)cyclohexyl]-1-(oxan-2-yl)-1H-pyrazolo[3,4-b]pyrazin-3-yl}-4-methyl-1,2,3,4-tetrahydroquinoline-6-carbonitrile (120 mg, 0.2 mmol) was added into TFA (3 mL) and DCM (3 mL). The mixture was stirred at 40° C. for 5 h. The mixture was concentrated to give a residue which was diluted with MeOH (10 mL). The mixture was adjusted to pH=9-10 by addition of NaHCO₃(s), filtered and the filtrate was concentrated to give a residue. The residue was purified by prep-HPLC (NH3·H2O) to afford the product of (4S)-1-{6-[4-(aminomethyl)cyclohexyl]-1H-pyrazolo[3,4-b]pyrazin-3-yl}-4-methyl-1,2,3,4-tetrahydroquinoline-6-carbonitrile (50.0 mg, 50.4% yield) as a yellow solid.

Step c: The compound of rac-(4S)-1-{6-[4-(aminomethyl)cyclohexyl]-1H-pyrazolo[3,4-b]pyrazin-3-yl}-4-methyl-1,2,3,4-tetrahydroquinoline-6-carbonitrile (50 mg, 124 μmol) was separated by Chiral-SFC (Column: DAICEL CHIRALPAK AS-H (250 mm*30 mm, 5 um)). Mobile phase: 50% of ethanol (0.1% NH3H2O) in CO2. Flow rate: 50 mL/min.) to afford the desired product of (4S)-4-methyl-1-{6-[(1s,4s)-4-(aminomethyl)cyclohexyl]-1H-pyrazolo[3,4-b]pyrazin-3-yl}-1,2,3,4-tetrahydroquinoline-6-carbonitrile (6.90 mg, 13.8% yield, Rt=4.333 min, single peak) as a yellow solid and (4S)-4-methyl-1-{6-[(1r,4r)-4-(aminomethyl)cyclohexyl]-1H-pyrazolo[3,4-b]pyrazin-3-yl}-1,2,3,4-tetrahydroquinoline-6-carbonitrile (10.9 mg, 21.9% yield, Rt=4.854 min, single peak) as a yellow solid.

LCMS: calc. for C23H27N7: 401.2, found: [M+H]+ 402.2. 1HNMR (400 MHz, CD3OD): δ 8.49 (s, 1H), 7.51~7.52 (m, 1H), 7.20~7.24 (m, 1H), 6.75~6.78 (m, 1H), 3.92~4.06 (m, 2H), 3.08~3.18 (m, 2H), 2.80~2.82 (m, 2H), 2.23~2.26 (m, 1H), 2.04~2.08 (m, 2H), 1.75~1.92 (m, 8H), 1.42~1.45 (m, 3H). SFC: e.e.=98.3%, Rt=4.333 min. Column: Chiralpak AS-3 100×4.6 mm I.D., 3 μm. Mobile phase A: CO2 B:ethanol (0.1% ethanolamine). Gradient: from 5% to 40% of B in 4.5 min and hold 40% for 2.5 min, then 5% of B for 1 min. Flow rate: 2.8 mL/min. Column temp: 40° C.

LCMS: calc. for C23H27N7: 401.2, found: [M+H]+ 402.3. 1HNMR (400 MHz, CD3OD): δ 8.34 (s, 1H), 7.39~7.40 (m, 1H), 7.08~7.11 (m, 1H), 6.63~6.66 (m, 1H), 3.81~3.92 (m, 2H), 2.97-2.99 (m, 1H), 2.85-2.87 (m, 1H), 2.53~2.56 (m, 2H), 1.94-2.11 (m, 1H), 1.77~1.98 (m, 6H), 1.61~1.72 (m, 2H), 1.42~1.51 (m, 2H), 1.30~1.32 (m, 3H). SFC: e.e.=97.1%, Rt=4.854 min. Column: Chiralpak AS-3 100×4.6 mm I.D., 3 μm. Mobile phase A: CO2 B:ethanol (0.1% ethanolamine). Gradient: from 5% to 40% of B in 4.5 min and hold 40% for 2.5 min, then 5% of B for 1 min. Flow rate: 2.8 mL/min. Column temp: 40° C.

The characterization of compounds disclosed herein is shown below.

Step a: The compound of (4S)-1-{6-[4-(aminomethyl)cyclohex-1-en-1-yl]-1-(oxan-2-yl)-1H-pyrazolo[3,4-b]pyrazin-3-yl}-4-methyl-1,2,3,4-tetrahydroquinoline-6-carbonitrile (120 mg, 0.2 mmol) was dissolved in MeOH (5 mL) and THF (5 mL). 10% Pd/C (20 mg, wet) was added. The reaction mixture was evacuated and refilled for 3 times using H2. The reaction mixture was stirred at 25° C. for 12 hours under H2 (15 psi). The reaction mixture was filtered

| Cmpd. No. | Structure | NMR | Mass Spec. (M + H)+ |
|---|---|---|---|
| 1B | 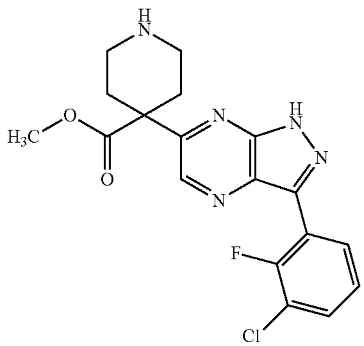 [SMILES: COC(=O)C1(c2cnc3c(-c4cccc(Cl)c4F)n[nH]c3n2)CCNCC1] | ¹H NMR (400 MHz, DMSO-d6) δ 8.86 (s, 1H), 8.16 (dt, J = 1.46, 7.08 Hz, 1H), 7.68-7.76 (m, 1H), 7.43 (t, J = 7.93 Hz, 1H), 6.53 (br s, 1H), 3.66 (s, 3H), 3.01-3.21 (m, 4H), 2.53 (br s, 2H) | 390.2 |
| 2B | 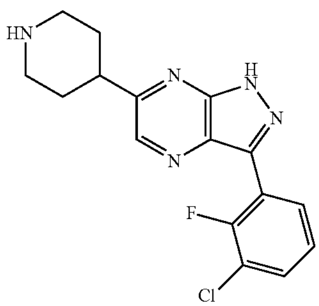 [SMILES: Fc1c(Cl)cccc1-c1n[nH]c2nc(C3CCNCC3)cnc12] | 1H NMR (400 MHz, DMSO-d6) δ 14.38 (s, 1H), 8.70 (s, 1H), 8.59-8.69 (m, 1H), 8.41 (br s, 1H), 8.11-8.20 (m, 1H), 7.67-7.75 (m, 1H), 7.42 (t, J = 7.93 Hz, 1H), 6.52 (s, 1H), 3.35-3.50 (m, 3H), 3.01-3.16 (m, 2H), 2.08-2.19 (m, 2H), 1.92-2.06 (m, 2H) | 332.1 |
| 3B | 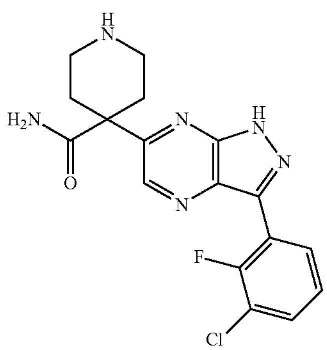 [SMILES: NC(=O)C1(c2cnc3c(-c4cccc(Cl)c4F)n[nH]c3n2)CCNCC1] | 1H NMR (400 MHz, DMSO-d6) δ 14.50 (s, 1H), 8.78 (s, 1H), 8.47 (br s, 2H), 8.11-8.19 (m, 1H), 7.67-7.76 (m, 1H), 7.35-7.48 (m, 3H), 6.52 (br s, 1H), 3.01-3.25 (m, 4H), 2.58 (br s, 1H), 2.34-2.45 (m, 2H) | 375.1 |
| 4B | 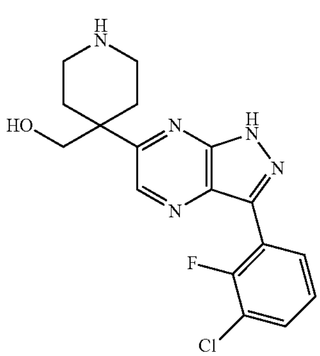 [SMILES: OCC1(c2cnc3c(-c4cccc(Cl)c4F)n[nH]c3n2)CCNCC1] | ¹H-NMR (400 MHz, DMSO-d₆) δ 14.37 (s, 1H), 8.90 (s, 1H), 8.41 (br s, 2H), 8.14-8.22 (m, 1H), 7.67-7.75 (m, 1H), 7.43 (t, J = 7.93 Hz, 1H), 6.53 (br s, 1H), 4.98 (br s, 1H), 3.57 (s, 2H), 3.26 (br d, J = 12.45 Hz, 2H), 2.88 (br d, J = 9.77 Hz, 2H), 2.58 (br d, J = 14.65 Hz, 2H), 1.91-2.04 (m, 2H) | 362.3, 364.2 |

-continued

| Cmpd. No. | Structure | NMR | Mass Spec. (M + H)+ |
|---|---|---|---|
| 5B | 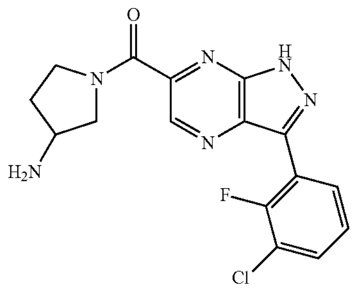 [SMILES: NC1CCN(C(=O)c2cnc3c(-c4cccc(Cl)c4F)n[nH]c3n2)C1] | 1H NMR (400 MHz, METHANOL-d4) δ ppm 1.97-2.11 (m, 1 H) 2.29-2.43 (m, 1 H) 3.63-4.27 (m, 7 H) 7.32-7.40 (m, 1 H) 7.56-7.66 (m, 1 H) 8.10-8.21 (m, 1 H) 8.48-8.56 (m, 1 H) 9.06-9.12 (m, 1 H) | 361.2 |
| 6B | 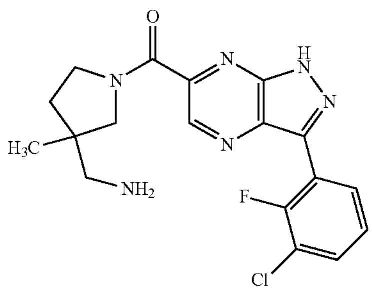 [SMILES: CC1(CN)CCN(C(=O)c2cnc3c(-c4cccc(Cl)c4F)n[nH]c3n2)C1] | $^1$H-NMR (500 MHz, methanol-$d_4$) δ ppm 1.17-1.35 (m, 3 H) 1.88-2.07 (m, 2 H) 2.94-3.10 (m, 2 H) 3.56-3.69 (m, 1 H) 3.76-3.90 (m, 2 H) 4.05-4.15 (m, 1 H) 7.32-7.40 (m, 1 H) 7.58-7.66 (m, 1 H) 8.09-8.18 (m, 1 H) 8.48-8.54 (m, 1 H) 9.03-9.11 (m, 1 H) | 389.3, 391.3 |
| 7B | 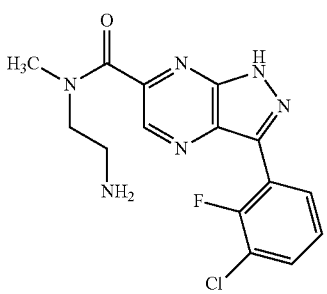 [SMILES: CN(CCN)C(=O)c1cnc2c(-c3cccc(Cl)c3F)n[nH]c2n1] | $^1$H-NMR (400 MHz, DMSO-$d_6$) δ ppm 2.35-2.43 (m, 3 H) 2.77-2.84 (m, 2 H) 3.44-3.52 (m, 4 H) 7.36-7.44 (m, 1 H) 7.61-7.70 (m, 1 H) 8.17-8.26 (m, 1 H) 8.27-8.34 (m, 1 H) 8.86-8.95 (m, 1 H) 9.13-9.21 (m, 1 H) | 349.1, 350.9 |
| 8B | 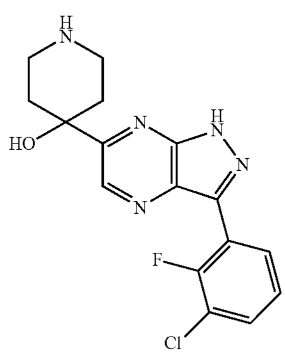 [SMILES: OC1(c2cnc3c(-c4cccc(Cl)c4F)n[nH]c3n2)CCNCC1] | ND | 348/349 |
| 9B | 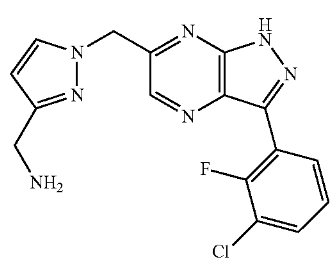 [SMILES: NCc1ccn(Cc2cnc3c(-c4cccc(Cl)c4F)n[nH]c3n2)n1] | $^1$H-NMR (400 MHz, CD$_3$OD) δ 8.56 (s, 1H), 8.10-8.07 (m, 1H), 7.97 (s, 1H), 7.65-7.59 (m, 1H), 7.38-7.33 (m, 1H), 6.48 (s, 1H), 5.73 (s, 2H), 4.14 (s, 2H) | 358.0 |

| Cmpd. No. | Structure | NMR | Mass Spec. (M + H)+ |
|---|---|---|---|
| 10B | 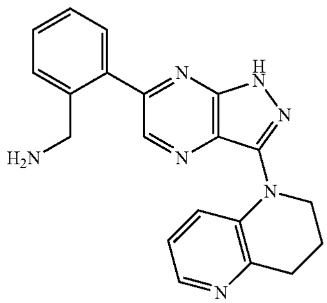 [SMILES: NCc1ccccc1-c1cnc2c(N3CCCc4ncccc43)n[nH]c2n1] | ¹H-NMR (400 MHz, methanol-d₄) δ 8.98 (s, 1H), 8.32 (d, J = 8.8 Hz, 1H), 8.14 (d, J = 5.6 Hz, 1H), 7.96 (d, J = 7.2 Hz, 1H), 7.75-7.65 (m, 4H), 4.33 (s, 2H), 4.28 (t, J = 5.2 Hz, 2H), 3.36-3.34 (m, 2H), 2.40-2.34 (m, 2H) | 357.9 |
| 11B | 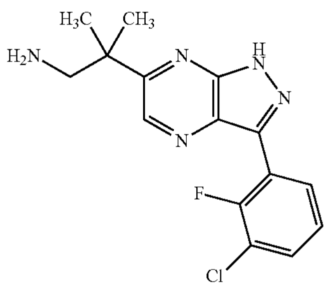 [SMILES: CC(C)(CN)c1cnc2c(-c3cccc(Cl)c3F)n[nH]c2n1] | ¹H-NMR (400 MHz, DMSO-d₆) δ 8.83 (s, 1H), 8.17~8.22 (m, 1H), 7.67~7.71 (m, 1H), 7.40~7.45 (m, 1H), 2.91 (s, 2H), 1.39 (s, 6H) | 320.2 |
| 12B | 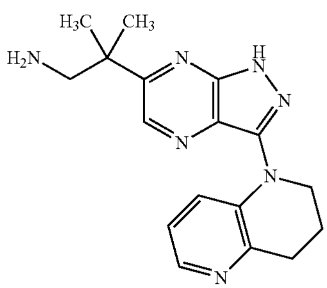 [SMILES: CC(C)(CN)c1cnc2c(N3CCCc4ncccc43)n[nH]c2n1] | ¹H-NMR (400 MHz, methanol-d₄) 8.63 (s, 1H), 7.90-7.93 (m, 1H), 7.40-7.44 (m, 1H), 7.00-7.05 (m, 1H), 4.01-4.07 (m, 2H), 3.04-3.10 (m, 4H), 2.20-2.27 (m, 2H), 1.50 (s, 6H) | 324.0 |
| 13B | 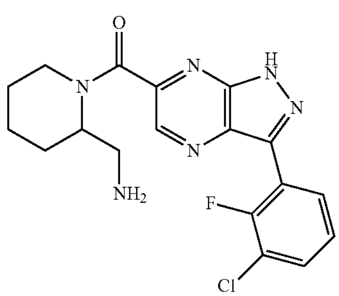 [SMILES: NCC1CCCCN1C(=O)c1cnc2c(-c3cccc(Cl)c3F)n[nH]c2n1] | ¹H NMR (500 MHz, DMSO-d₆) δ ppm 9.16 (br s, 1 H), 8.86 (br s, 1 H), 8.27 (s, 1 H), 8.18-8.26 (m, 1 H), 7.51-7.68 (m, 1 H), 7.30-7.47 (m, 1 H), 6.50-6.62 (m, 1 H), 3.32-3.43 (m, 2 H), 3.02 (br d, J = 12.51 Hz, 1 H), 2.83 (s, 1 H), 1.74 (br d, J = 5.49 Hz, 1 H), 1.59-1.69 (m, 1 H), 1.46-1.58 (m, 1 H), 1.29-1.42 (m, 2 H), 1.09-1.27 (m, 2 H) | 389.3 |
| 14B | 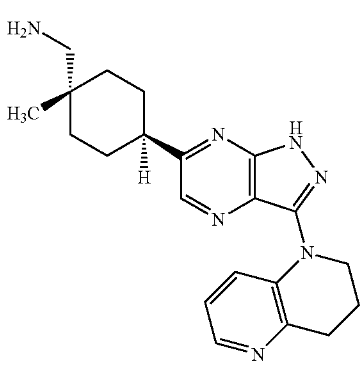 [SMILES: C[C@]1(CN)CC[C@H](c2cnc3c(N4CCCc5ncccc54)n[nH]c3n2)CC1] | ¹H-NMR (400 MHz, methanol-d₄) δ 8.55-8.59 (m, 1H), 8.08-8.10 (m, 1H), 7.91-7.94 (m, 1H), 7.57-7.61 (m, 1H), 4.09-4.13 (m, 2H), 3.32-3.38 (m, 2H), 2.99-3.10 (m, 1H), 2.89 (s, 2H), 2.31-2.38 (m, 2H), 1.70-2.07 (m, 6H), 1.52-1.60 (m, 2H), 1.20 (s, 3H) | 378.0 |

| Cmpd. No. | Structure | NMR | Mass Spec. (M + H)+ |
|---|---|---|---|
| 15B | 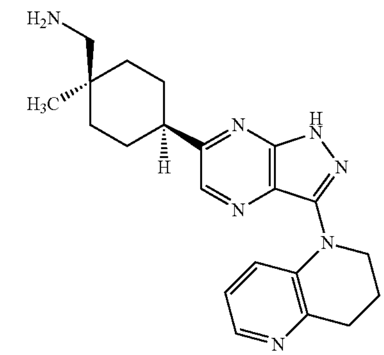 [SMILES: C[C@]1(CN)CC[C@@H](c2cnc3c(N4CCCc5ncccc54)n[nH]c3n2)CC1] | ¹H-NMR (400 MHz, methanol-d₄) δ 8.57 (s, 1H), 8.09-8.14 (m, 2H), 7.57-7.62 (m, 1H), 4.16-4.20 (m, 2H), 3.29-3.33 (m, 2H), 3.12 (s, 2H), 3.05-3.11 (m, 1H), 2.32-2.36 (m, 2H), 1.84-1.95 (m, 6H), 1.54-1.63 (m, 2H), 1.14 (s, 3H) | 378.0 |
| 16B | 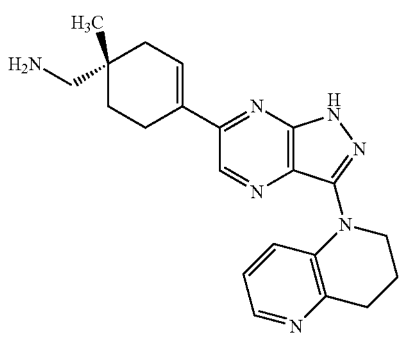 [SMILES: C[C@@]1(CN)CC=C(c2cnc3c(N4CCCc5ncccc54)n[nH]c3n2)CC1] | ¹H-NMR (400 MHz, methanol-d₄) δ 8.61 (s, 1H), 7.78~7.80 (m, 1H), 7.30~7.33 (m, 1H), 6.88~6.92 (m, 1H), 6.77 (s, 1H), 3.90~3.93 (m, 2H), 2.92~2.96 (m, 2H), 2.40~2.59 (m, 4H), 2.13-2.00 (m, 4H), 1.49~1.58 (m, 2H), 0.89 (s, 3H) | 376.0 |
| 17B | 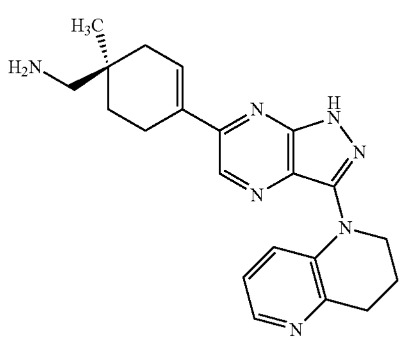 [SMILES: C[C@]1(CN)CC=C(c2cnc3c(N4CCCc5ncccc54)n[nH]c3n2)CC1] | ¹H-NMR (400 MHz, methanol-d₄) δ 8.55~8.63 (m, 1H), 7.78~7.79 (m, 1H), 7.31~7.34 (m, 1H), 6.89~6.91 (m, 1H), 6.77 (s, 1H), 3.92 (s, 2H), 2.91~2.98 (m, 2H), 2.55~2.64 (m, 4H), 2.19-2.00 (m, 4H), 1.52~1.58 (m, 2H), 0.94 (s, 3H) | 376.0 |
| 18B | 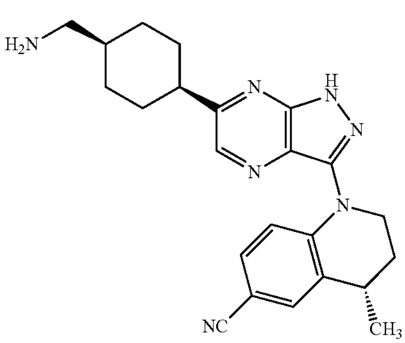 [SMILES: C[C@H]1CCN(c2n[nH]c3nc([C@H]4CC[C@@H](CN)CC4)cnc23)c2ccc(C#N)cc21] | ¹HNMR (400 MHz, CD3OD): δ 8.34 (s, 1H), 7.39~7.40 (m, 1H), 7.08~7.11 (m, 1H), 6.63-6.66 (m, 1H), 3.81-3.92 (m, 2H), 2.97-2.99 (m, 1H), 2.85~2.87 (m, 1H), 2.53~2.56 (m, 2H), 1.94-2.11 (m, 1H), 1.77~1.98 (m, 6H), 1.61~1.72 (m, 2H), 1.42~1.51 (m, 2H), 1.30~1.32 (m, 3H). | 402.3 |

| Cmpd. No. | Structure | NMR | Mass Spec. (M + H)+ |
|---|---|---|---|
| 19B | (structure) | 1HNMR (400 MHz, CD3OD): δ 8.49 (s, 1H), 7.51~7.52 (m, 1H), 7.20~7.24 (m, 1H), 6.75~6.78 (m, 1H), 3.92~4.06 (m, 2H), 3.08~3.18 (m, 2H), 2.80~2.82 (m, 2H), 2.23~2.26 (m, 1H), 2.04-2.08 (m, 2H), 1.75~1.92 (m, 8H), 1.42~1.45 (m, 3H). | 402.2 |

The compounds of Formula (VIIIa), for example, can generally be prepared according to exemplary Scheme 4:

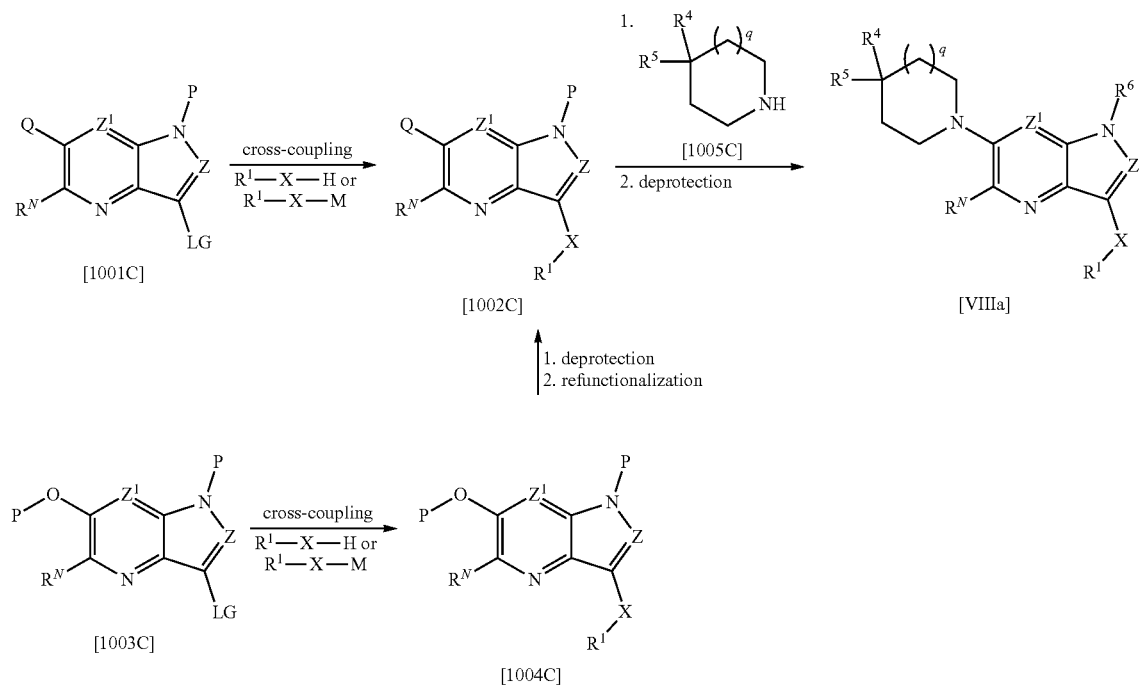

Scheme 4 wherein X, Z, Z¹, R¹, R⁶, R⁴ R⁵, Rᴺ and q are as defined as elsewhere herein, Q is independently a halogen, such as Cl, Br, I, and the like, or any other leaving group, such as OSO₂Me, OMs, OTs, OTf, and the like. LG is a leaving group, such as Cl, Br, I, OTs, OTf, and the like, and P is a protecting group, such as 4-methoxybenzyl and the like. Alternative protecting groups that can be used are described, e.g., in Greene et al., Protective Groups in Organic Synthesis (4ᵗʰ ed. 2006).

As shown in Scheme 4, an aryl compound such as a compound of Formula 1001C undergoes a cross-coupling reaction with a metalated or otherwise activated moiety to provide a compound of Formula 1002C. The compound of Formula 1002C then undergoes a substitution reaction with an amine such as Compound 1005C, followed by removal of the protecting group to provide a compound of Formula (VIIIa). In some embodiments, LG is I. In some embodiments, LG is Cl. In some embodiments, LG is OTf or OTs. Alternatively, a protected heteroaryl ether, such as a compound of Formula 1003C, undergoes a cross-coupling reaction to provide a compound of Formula 1004C. The ether protecting group is subsequently removed and the resulting hydroxyl group activated to form a Q group, such as OSO₂Me, OMs, OTs, OTf, and the like, to form a compound of Formula 1002C, which can then be carried forward to prepare compounds having the Formula (VIIIa).

Alternatively, compounds of the disclosure can generally be prepared according to exemplary Scheme 5:

Scheme 5

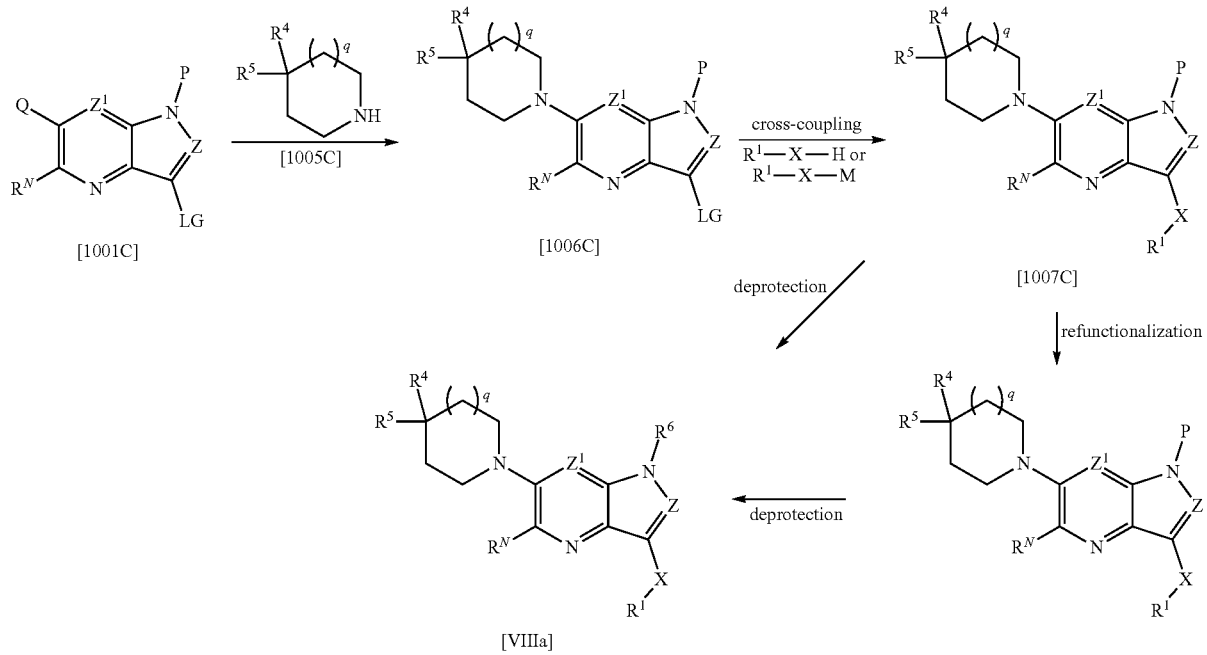

wherein X, Z, $Z^1$, $R^1$, $R^6$, $R^4$ $R^5$, $R^N$ and q are as defined as elsewhere herein, Q is independently a halogen, such as Cl, Br, I, and the like, or any other leaving group, such as $OSO_2Me$, OMs, OTs, OTf, and the like. LG is a leaving group, such as Cl, Br, I, OTs, OTf, and the like, and P is a protecting group, such as 4-methoxybenzyl and the like. Alternative protecting groups that can be used are described, e.g., in Greene et al., Protective Groups in Organic Synthesis ($4^{th}$ ed. 2006).

As shown in Scheme 5, an aryl compound such as a compound of Formula 1001C undergoes a undergoes a substitution reaction with an amine such as 1005C to provide a compound of Formula 1006C. The compound of Formula 1006C then undergoes a cross-coupling reaction with a metalated or otherwise activated moiety to provide a compound of Formula 1007C. In some embodiments, the compound of Formula 1007C can be deprotected to produce a compound of Formula (VIIIa). In other embodiments, the compound of Formula 1007C can be left protected and functional groups on the $R^1$ moiety refunctionalized by methods known to those of ordinary skill in the art.

In some embodiments, the cross-coupling reaction is a Buchwald-Hartwig reaction. In some embodiments, the cross-coupling reaction is a Chan-Lam coupling reaction. In some embodiments, the cross-coupling reaction is an Ullmann reaction. In some embodiments, the cross-coupling reaction is a Suzuki reaction. In some embodiments, the cross-coupling reaction is a Stille reaction. In some embodiments, the cross-coupling reaction is a Negishi reaction. In some embodiments, the cross-coupling reaction is a Hiyama reaction. Other cross-coupling reactions may be employed as would be apparent to one of ordinary skill in the art.

In some embodiments, the protecting group is removed under acidic conditions, such as HBr in AcOH. Conditions for removal of the protecting group will depend on the nature of the protecting group. Conditions for the removal of various protecting groups can be found, e.g., in Greene et al., Protective Groups in Organic Synthesis ($4^{th}$ ed. 2006).

Synthesis of Intermediates

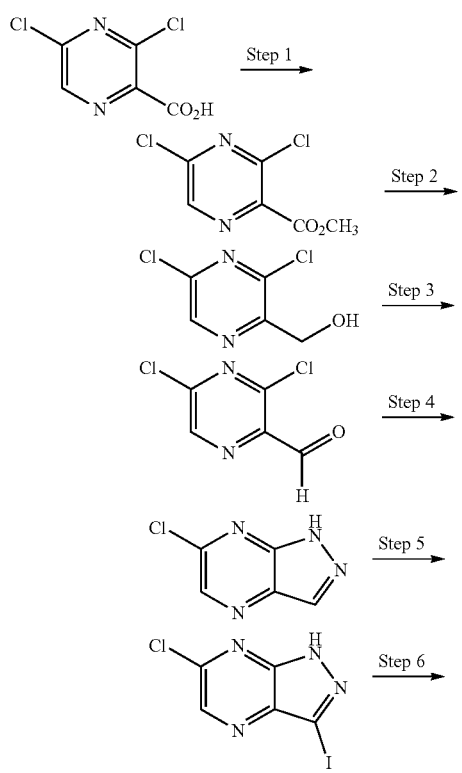

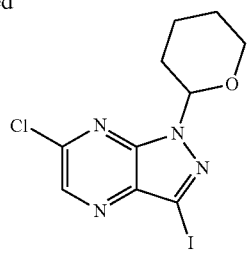

Step 1: In a 100 mL round-bottomed flask, 3,5-dichloropyrazine-2-carboxylic acid (3.65 g, 18.9 mmol) and NaHCO$_3$ (4.70 g, 22.7 mmol) were dissolved in dimethylformamide (38 mL). Iodomethane (7.14 mL, 113 mmol) was added dropwise and the resulting mixture stirred overnight at room temperature. The mixture was diluted with water (50 mL) and extracted with ethyl acetate (3×15 mL). The combined organics were washed with brine (4×10 mL), dried over anhydrous Na$_2$SO$_4$, filtered, and concentrated under reduced pressure. Methyl 3,5-dichloropyrazine-2-carboxylate (3.77 g, 96%) was obtained as a yellowish solid after drying under high vacuum for 2-3 h: $^1$H-NMR (500 MHz, CDCl$_3$) δ 8.57 (s, 1H), 4.03 (s, 3H).

Step 2: Methyl 3,5-dichloropyrazine-2-carboxylate (5.0 g, 24.2 mmol) was dissolved in a 9:1 mixture of dry tetrahydrofuran (242 mL) and methanol (27 mL). The mixture was cooled to 1.5-2° C. with an ice/water bath and stirred at this temperature for 10 min. A 2 M solution of lithium borohydride in THF (13.3 mL, 26.6 mmol) was then added carefully keeping the temperature below 4-5° C. After addition, the reaction mixture was stirred for an additional 10-15 min at 0-4° C. Methanol (120 mL) was added to the flask and the mixture stirred for 15 min at room temperature. The reaction was slowly poured into a mixture of 1 M HCl solution (100 mL) and ethyl acetate (200 mL). The resulting mixture was stirred at room temperature for 15 min. The aqueous layer was extracted with ethyl acetate (3×150 mL) and the combined organics washed with brine (2×100 mL), dried over anhydrous MgSO$_4$, filtered, and concentrated under reduced pressure. (3,5-Dichloropyrazin-2-yl)methanol (4.3 g, 99%) was obtained as a crude yellow oil after drying under high vacuum for 2 h: $^1$H-NMR (500 MHz, CDCl$_3$) δ 8.52 (s, 1H), 4.85 (s, 2H).

Step 3: (3,5-Dichloropyrazin-2-yl)methanol (4.3 g, 24 mmol) was dissolved in dichloromethane (100 mL) and MnO$_2$ (20.2 g, 240 mmol) then added in one portion. The resulting dark heterogeneous mixture was stirred for 16 h at room temperature. After this time, the reaction mixture was sonicated for 5 min. and additional MnO$_2$ (4 g) added to the reaction mixture. The resulting suspension was stirred for 2 h at room temperature, filtered over a pad of celite, and the cake washed with dichloromethane. The filtrate was concentrated under reduced pressure, affording 3,5-dichloropyrazine-2-carbaldehyde (2.36 g, 56%) as pale yellow crude oil after drying under high vacuum for 30 min: $^1$H-NMR (500 MHz, CDCl$_3$) δ 10.29 (s, 1H), 8.71 (s, 1H).

Step 4: 3,5-Dichloropyrazine-2-carbaldehyde (2.9 g, 16.4 mmol) was dissolved in N-methyl-2-pyrrolidone (16 mL) and hydrazine hydrate (0.78 mL, 49.2 mmol) added dropwise. The resulting brown suspension was stirred at 65° C. for 40 min. After this time, additional hydrazine hydrate (0.4 mL) was added and the mixture stirred at 65° C. for 2 h. The mixture was cooled to room temperature, poured into 1 M HCl solution (100 mL), and ethyl acetate (400 mL) was added. The aqueous layer was extracted with ethyl acetate (2×100 mL) and the combined organics washed with brine (300 mL), dried over anhydrous MgSO$_4$, filtered, and concentrated under reduced pressure. The yellow crude residue was purified by reversed phase chromatography (0 to 50% gradient of acetonitrile/10 mM aqueous ammonium formate) affording 6-chloro-1H-pyrazolo[3,4-b]pyrazine (800 mg, 32%) as a light brown solid after lyophilization: $^1$H-NMR (500 MHz, CD$_3$OD) δ 8.58 (s, 1H), 8.34 (s, 1H).

Step 5: 6-Chloro-1H-pyrazolo[3,4-b]pyrazine was dissolved in acetonitrile (24 mL). N-iodosuccinimide (3.43 g, 14.5 mmol) and 48% in water tetrafluoroboric acid solution (2.8 mL, 21.7 mmol) were successively added. The resulting brown/orange mixture was then stirred at reflux for 2 h. A beige/brown precipitate formed and the mixture cooled to room temperature, then placed into an ice/water bath for 5 min. The resulting solid was collected by filtration and washed with cold acetonitrile to give 6-chloro-3-iodo-1H-pyrazolo[3,4-b]pyrazine (1.81 g, 89%) as a yellow solid after drying under high vacuum: LCMS [M+H]$^+$=280.9; $^1$H-NMR (500 MHz, CDCl$_3$) δ 8.59 (s, 1H).

Step 6: 6-Chloro-3-iodo-1H-pyrazolo[3,4-b]pyrazine (850 mg, 3 mmol) was dissolved in dichloromethane (15 mL). 3,4-Dihydro-2H-pyran (0.85 mL, 9.1 mmol) and p-toluenesulfonic acid monohydrate (176 mg, 0.91 mmol) were successively added to the flask. The resulting mixture was stirred at room temperature for 10 min. The mixture became homogeneous and darkish overtime. After this time, a saturated aqueous solution of NaHCO$_3$ (20 mL) was added to the flask and the biphasic mixture stirred for 10 min. The layers were separated and organic layer washed with brine (20 mL), dried over anhydrous Na$_2$SO$_4$, filtered, and concentrated under reduced pressure. The crude residue was purified by flash chromatography (0 to 50% gradient of ethyl acetate/hexanes) to give 6-chloro-3-iodo-1-(tetrahydro-2H-pyran-2-yl)-1H-pyrazolo[3,4-b]pyrazine (1.02 g, 93%) as an off-white solid after drying under high vacuum overnight: LCMS [M+H]$^+$=364.9, [M−THP+H]$^+$=281.0; $^1$H NMR (500 MHz, CDCl$_3$) δ 8.56 (s, 1H), 5.96 (dd, J=10.4, 2.6 Hz, 1H), 4.16-4.06 (m, 1H), 3.82-3.74 (m, 1H), 2.72-2.58 (m, 1H), 2.21-2.11 (m, 1H), 2.01-1.94 (m, 1H), 1.89-1.70 (m, 2H), 1.69-1.59 (m, 1H).

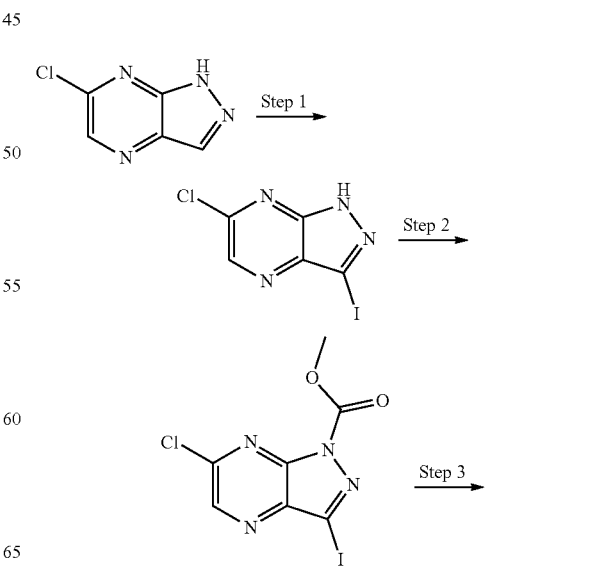

-continued

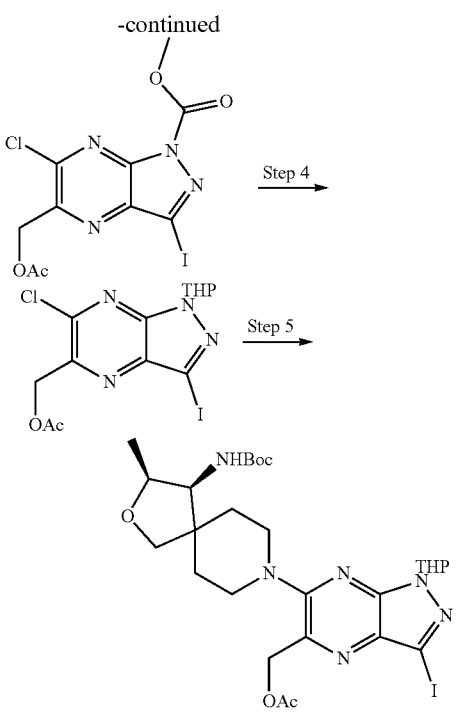

Step 1: A round bottomed flask was charged with 6-chloro-1H-pyrazolo[3,4-b]pyrazine (3.1 g, 20.0 mmol) and acetonitrile (60 mL), followed by N-iodosuccinimide (5.84 g, 26.0 mmol). The mixture was stirred at room temperature 2 h. The mixture was cooled to 0-10° C. and filtered. The precipitate was suspended in water and charged with a saturated sodium sulfite solution. The mixture was stirred for 10 min, filtered, and washed with water. The cake was air dried to afford 6-chloro-3-iodo-1H-pyrazolo[3,4-b]pyrazine (4.77 g, 17 mmol) as a tan solid. LCMS: [M+H]$^+$ 280.9.

Step 2: A round bottomed flask was charged with sodium hydride (1.28 g, 32.1 mmol) and dimethylformamide (30 mL) and cooled to 0° C. for the addition of 6-chloro-3-iodo-1H-pyrazolo[3,4-b]pyrazine (4.03 g, 14.3 mmol). Following the addition, the mixture was warmed to room temperature and stirred 1 h. The reaction was then cooled back to 0-10° C. and charged with methyl carbonochloridate (3.31 mL, 42.9 mmol). After 15 min, the reaction mixture was poured in water (250 mL), filtered, and dried to constant weight to afford methyl 6-chloro-3-iodo-1H-pyrazolo[3,4-b]pyrazine-1-carboxylate (4.78 g, 14.1 mmol) as a tan solid. LCMS: [M+H]$^+$ 338.9.

Step 3: A round bottomed flask was charged with methyl 6-chloro-3-iodo-1H-pyrazolo[3,4-b]pyrazine-1-carboxylate (525 mg, 1.55 mmol), 2-(acetyloxy)acetic acid (1.46 g, 12.4 mmol), silver nitrate (52.6 mg, 0.3100 mmol), and acetonitrile (15 mL) and water (9 mL). The reaction was heated to an internal temperature of 85° C. and a vent needle was added before the addition of ammonium persulfate (2.82 g, 12.4 mmol). The reaction was heated to 85° C. for 2 h, after which the reaction was cooled to room temperature and poured into ethyl acetate and brine. The organic layer was pre-absorbed onto silica gel and purified by column chromatography (eluting with ethyl acetate and heptanes). Product-containing fractions were pooled and concentrated in vacuo to afford methyl 5-[(acetyloxy)methyl]-6-chloro-3-iodo-1H-pyrazolo[3,4-b]pyrazole-1-carboxylate (225 mg, 0.55 mmol) as a white solid. LCMS: [M+H]$^+$ 410.9.

Step 4: A disposable reaction tube containing methyl 5-[(acetyloxy)methyl]-6-chloro-3-iodo-1H-pyrazolo[3,4-b]pyrazine-1-carboxylate (220 mg, 0.5358 mmol) in dichloromethane (4 mL) was charged with piperidine (52.9 µL, 0.5358 mmol) at room temperature. After 15 min, further piperidine (0.2 equiv) was added. After 15 min, 3,4-dihydro-2H-pyran (145 µL, 1.60 mmol) and 4-methylbenzene-1-sulfonic acid (92.2 mg, 0.5358 mmol) were added. After 30 min, the reaction mixture was pre-absorbed onto silica gel and purified by column chromatography (eluting with ethyl acetate and heptanes). Product-containing fractions were pooled and concentrated in vacuo to afford [6-chloro-3-iodo-1-(oxan-2-yl)-1H-pyrazolo[3,4-b]pyrazin-5-yl]methyl acetate as a white solid. LCMS: [M+H]$^+$ 437.0.

Step 5: A disposable reaction tube was charged with [6-chloro-3-iodo-1-(oxan-2-yl)-1H-pyrazolo[3,4-b]pyrazin-5-yl]methyl acetate (465 mg, 1.06 mmol) and dimethylformamide (6 mL) for the addition of ethylbis(propan-2-yl)amine (738 µL, 4.24 mmol) and (3S,4S)-3-methyl-2-oxa-8-azaspiro[4.5]decan-4-amine dihydrochloride (308 mg, 1.27 mmol). The vial was sealed, and the mixture was heated to 75° C. for 18 h. The reaction was charged with di-tert-butyl dicarbonate (347 mg, 1.59 mmol) and heated to 75° C. 3 h. The reaction mixture was poured into water, filtered, and the precipitate was air dried to constant weight to give (6-((3S,4S)-4-((tert-butoxycarbonyl)amino)-3-methyl-2-oxa-8-azaspiro[4.5]decan-8-yl)-3-iodo-1-(tetrahydro-2H-pyran-2-yl)-1H-pyrazolo[3,4-b]pyrazin-5-yl)methyl acetate (690 mg, 1.03 mmol) as a white solid. LCMS: [M+H]+ 671.2.

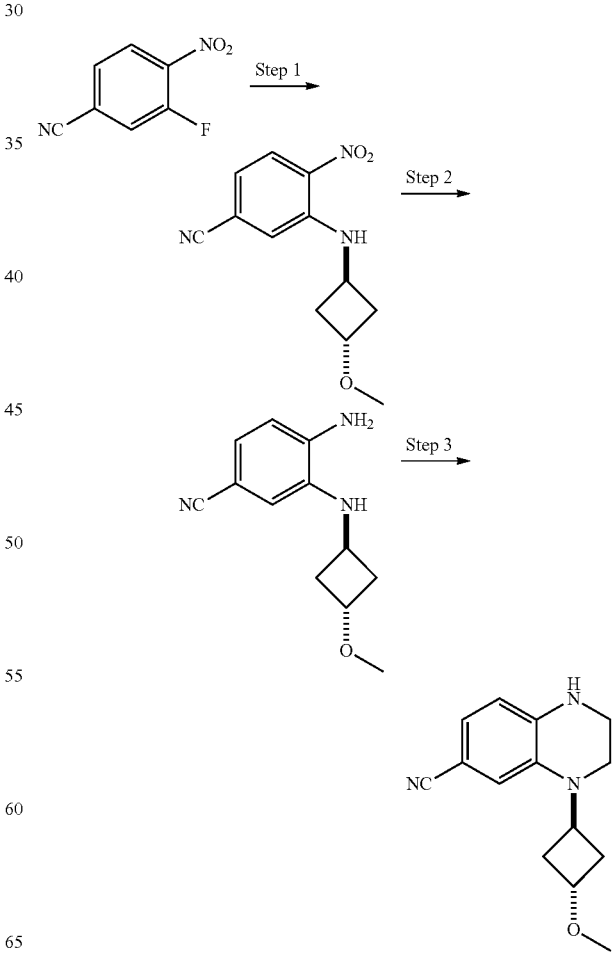

Step 1: To the mixture of 3-fluoro-4-nitrobenzonitrile (1.2 g, 7.3 mmol) and trans-3-methoxycyclobutan-1-amine hydrochloride (1.0 g, 7.3 mmol) in EtOH (30.0 mL) was added triethylamine (4.0 mL, 29.0 mmol). The mixture was stirred at 60° C. for 12 hours. TLC (Petroleum ether/EtOAc=10/1) showed a new spot formed. The mixture was concentrated in vacuum and washed with Petroleum ether/EtOAc (5/2, 40.0 mL×3). The solid was dried in vacuum to give the product of 3-[(3-methoxycyclobutyl)amino]-4-nitrobenzonitrile (2.0 g, crude) as a yellow solid.

Step 2: To the mixture of 3-[(3-methoxycyclobutyl)amino]-4-nitrobenzonitrile (2.0 g, 8.1 mmol) in THF (40.0 mL) was added 10% Pd/C (400 mg, wet). The mixture was stirred at 10° C. under $H_2$ (15 psi) for 2 hours. LCMS showed 100% desired product formed. The mixture was filtered and the filtrate was concentrated in vacuum to give the product of 4-amino-3-[(3-methoxycyclobutyl)amino]benzonitrile (1.8 g, crude) as a brown oil.

Step 3: A mixture of 4-amino-3-[(3-methoxycyclobutyl)amino]benzonitrile (1.8 g, 8.3 mmol), TBAB (5.3 g, 16.5 mmol), TEA (4.6 mL, 33.1 mmol) and 1,2-dibromoethane (1.0 mL) was stirred at 60° C. for 12 hours. LCMS showed 47.3% start material left. 1,2-dibromoethane (3.0 mL) was added to the mixture and the mixture was stirred at 60° C. for another 4 hours. LCMS showed 77.1% desired product was formed and 16.0% start material left. The mixture was poured into water (50.0 mL) and extracted with DCM (50.0 mL×3). The organic layers washed with brine and dried over anhydrous $Na_2SO_4$. The mixture was filtered and the filtrate was concentrated in vacuum to give residue. The residue was purified by flash silica gel chromatography (Petroleum ether/EtOAc=I/O to 1/1) to give the product of 4-[trans-3-methoxycyclobutyl]-1,2,3,4-tetrahydroquinoxaline-6-carbonitrile (440.0 mg, 21.8% yield) as an off-white solid. LCMS: calc. for $C_{14}H_{17}N_3O$: 243.3, found: $[M+H]^+$ 243.9. $^1$H NMR (400 MHz, $CDCl_3$): δ=7.02-6.95 (m, 2H), 6.64 (s, 1H), 6.42 (d, J=8.0 Hz, 1H), 4.09-3.98 (m, 2H), 3.59 (t, J=5.0 Hz, 2H), 3.32 (s, 3H), 3.12 (t, J=5.0 Hz, 2H), 2.46-2.32 (m, 4H).

Compound 2C: Preparation of 6-(4-amino-4-methylpiperidin-1-yl)-3-(3-chloro-2-fluorophenyl)-1H-pyrazolo[3,4-b]pyrazine-5-carboxamide

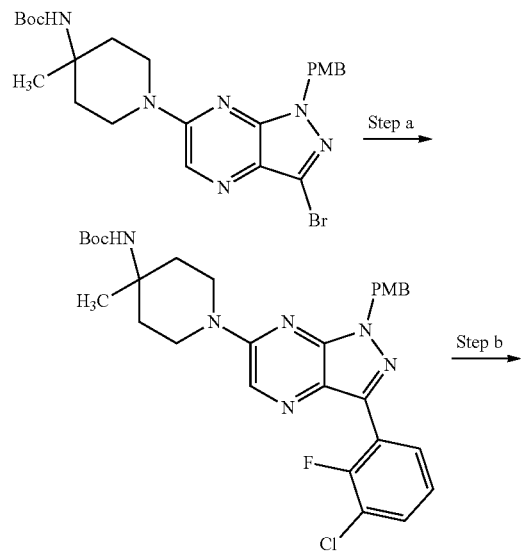

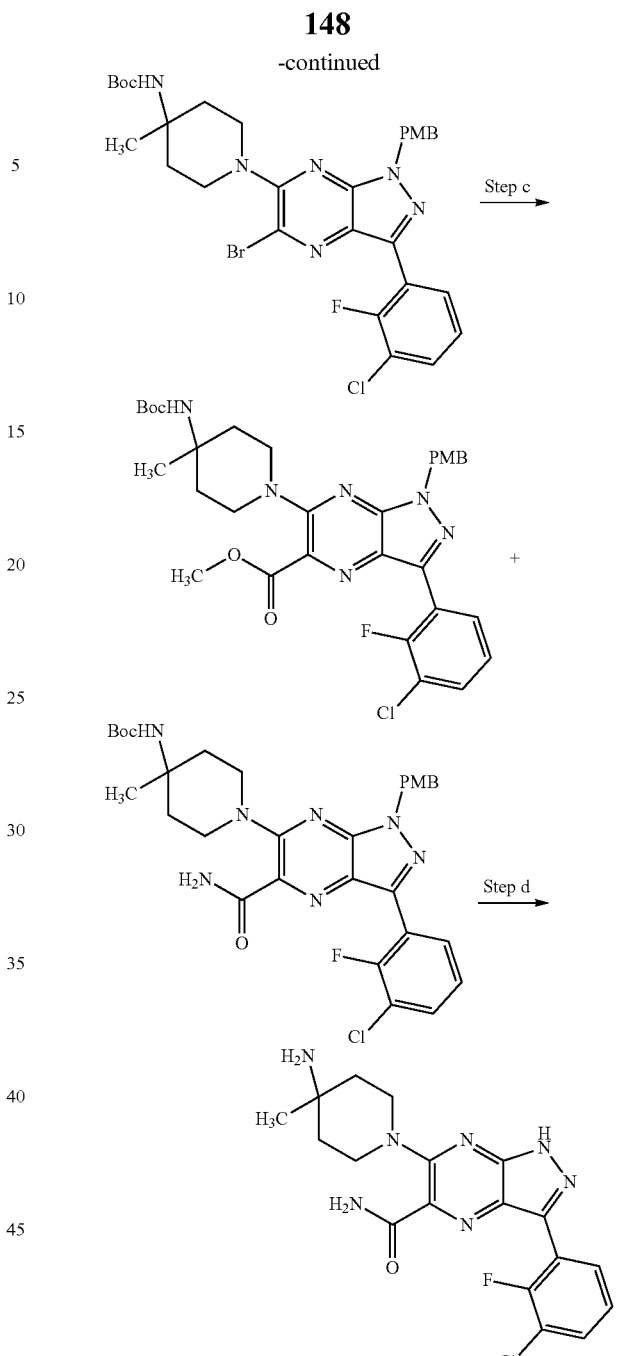

Step a: To a solution of tert-butyl (1-(3-bromo-1-(4-methoxybenzyl)-1H-pyrazolo[3,4-b]pyrazin-6-yl)-4-methylpiperidin-4-yl)carbamate (500 mg, 0.94 mmol) and (3-chloro-2-fluorophenyl)boronic acid (179 mg, 1.0 mmol) in dioxane (15 mL) and water (1.5 mL) was added Pd(dppf)Cl$_2$ (68.7 mg, 94 umol) and Cs$_2$CO$_3$ (918 mg, 2.82 mmol). The mixture was purged 3 times with N$_2$ and stirred at 100° C. for 12 hours under a nitrogen atmosphere. The mixture was concentrated under reduced pressure, the residue was diluted with water (30 mL) and extracted with DCM (30 mL×2). The combined organics were washed with water (30 mL×2), dried over anhydrous Na$_2$SO$_4$, filtered, and concentrated under reduced pressure. The residue was purified by column chromatography (0-40% EtOAc/petroleum ether) to afford tert-butyl (1-(3-(3-chloro-2-fluorophenyl)-1-(4- methoxybenzyl)-1H-pyrazolo[3,4-b]pyrazin-6-yl)-4-methylpiperidin-4-yl)carbamate (410 mg, 75% yield) as a light yellow solid.

Step b: A mixture of tert-butyl (1-(3-(3-chloro-2-fluorophenyl)-1-(4-methoxybenzyl)-1H-pyrazolo[3,4-b]pyrazin-6-yl)-4-methylpiperidin-4-yl)carbamate (340 mg, 0.58 mmol) and NBS (114 mg, 643 umol) in DMF (3 mL) was stirred at 17° C. for 1 hour. The reaction was quenched by adding water (30 mL) at 17° C. and the mixture extracted with ethyl acetate (30 mL×2). The combined organics were washed with brine (30 mL×2), dried over anhydrous Na₂SO₄, filtered, and concentrated under reduced pressure. The residue was purified by column chromatography (0-40% EtOAc/petroleum ether) to afford tert-butyl (1-(5-bromo-3-(3-chloro-2-fluorophenyl)-1-(4-methoxybenzyl)-1H-pyrazolo[3,4-b]pyrazin-6-yl)-4-methylpiperidin-4-yl) carbamate (300 mg, 77.7% yield) as a yellow gum.

Step c: To a solution of tert-butyl (1-(5-bromo-3-(3-chloro-2-fluorophenyl)-1-(4-methoxybenzyl)-1H-pyrazolo[3,4-b]pyrazin-6-yl)-4-methylpiperidin-4-yl)carbamate (350 mg, 0.53 mmol) in MeOH (5 mL) and NH₃·H₂O (0.5 mL) was added Pd(pddf)Cl₂ (38.6 mg, 52.7 umol). The mixture was evacuated and refilled for 3 times with CO and stirred at 80° C. for 20 hours under an atmosphere of CO (50 psi). After cooling, the reaction mixture was concentrated under reduced pressure and the residue was purified by column chromatography (0-50% EtOAc/petroleum ether) to afford tert-butyl (1-(5-carbamoyl-3-(3-chloro-2-fluorophenyl)-1-(4-methoxybenzyl)-1H-pyrazolo[3,4-b]pyrazin-6-yl)-4-methylpiperidin-4-yl)carbamate (60 mg, 18.1% yield) as a yellow gum and methyl 6-(4-((tert-butoxycarbonyl)amino)-4-methylpiperidin-1-yl)-3-(3-chloro-2-fluorophenyl)-1-(4-methoxybenzyl)-1H-pyrazolo[3,4-b]pyrazine-5-carboxylate (200 mg, 59.0% yield) as a yellow gum.

Step d: A solution of tert-butyl (1-(5-carbamoyl-3-(3-chloro-2-fluorophenyl)-1-(4-methoxybenzyl)-1H-pyrazolo[3,4-b]pyrazin-6-yl)-4-methylpiperidin-4-yl)carbamate (60 mg, 96 umol) in TFA (5.0 mL) and TfOH (0.5 mL) was stirred at 80° C. for 1 hour. The mixture was concentrated under reduced pressure, the residue diluted with MeOH (5.0 mL), and the pH adjusted to 10 with NH₃·H₂O. Purification by reversed phase prep-HPLC (acetonitrile/aq. NH₃) afforded 6-(4-amino-4-methylpiperidin-1-yl)-3-(3-chloro-2-fluorophenyl)-1H-pyrazolo[3,4-b]pyrazine-5-carboxamide (20.0 mg, 51.5% yield) as a yellow solid: LCMS [M+Na]⁺=426.0; ¹H-NMR (400 MHz, DMSO-d₆) δ 8.23 (t, J=7.2 Hz, 1H), 8.03 (br, 1H), 7.60-7.70 (m, 2H), 7.39 (t, J=7.6 Hz, 1H), 3.50-3.65 (m, 4H), 1.40-1.60 (m, 4H), 1.11 (s, 3H).

Compound 4C: Preparation of 6-(4-amino-4-methylpiperidin-1-yl)-3-(3-chloro-2-fluorophenyl)-1H-pyrazolo[3,4-b]pyrazine-5-carboxylic Acid

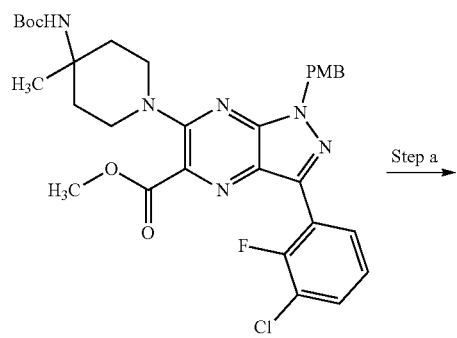

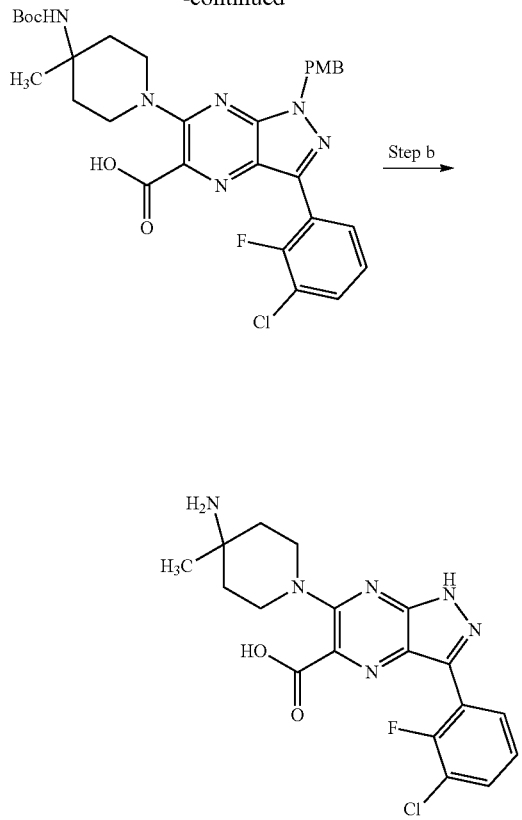

Step a: A mixture of methyl 6-(4-((tert-butoxycarbonyl)amino)-4-methylpiperidin-1-yl)-3-(3-chloro-2-fluorophenyl)-1-(4-methoxybenzyl)-1H-pyrazolo[3,4-b]pyrazine-5-carboxylate (0.2 g, 0.31 mmol) and LiOH (22.4 mg, 0.94 mmol) in MeOH (3.0 mL) and H₂O (3.0 mL) was stirred at 20° C. for 12 hours. The reaction was then stirred at 50° C. for another 30 hours. After cooling, the reaction mixture was concentrated under reduced pressure, the residue diluted with ethyl acetate (10 mL) and the pH adjusted to 6 with 1N HCl at 0° C. The mixture was extracted with ethyl acetate (30 mL) and washed with water (30 mL). The organic layer was washed with saturated brine (30 mL×2), dried over anhydrous Na₂SO₄, filtered, and concentrated under reduced pressure to give 6-(4-((tert-butoxycarbonyl)amino)-4-methylpiperidin-1-yl)-3-(3-chloro-2-fluorophenyl)-1-(4-methoxybenzyl)-1H-pyrazolo[3,4-b]pyrazine-5-carboxylic acid (220 mg, crude) was obtained as a yellow gum.

Step b: A solution of 6-(4-((tert-butoxycarbonyl)amino)-4-methylpiperidin-1-yl)-3-(3-chloro-2-fluorophenyl)-1-(4-methoxybenzyl)-1H-pyrazolo[3,4-b]pyrazine-5-carboxylic acid (0.22 g, 0.35 mmol) in TFA (5 mL) and TfOH (0.5 mL) was stirred at 50° C. for 1 hour. After cooling, the reaction mixture was concentrated under reduced pressure, the residue diluted with MeOH (10 mL), the pH adjusted to 8 with NH₃·H₂O, and the volatiles removed under reduced pressure. The residue was purified by reversed phase prep-HPLC (acetonitrile/aq. NH₃) to provide 6-(4-amino-4-methylpiperidin-1-yl)-3-(3-chloro-2-fluorophenyl)-1H-pyrazolo[3,4-b]pyrazine-5-carboxylic acid (40 mg, 28.1% yield) as a light yellow solid: LCMS [M+H]⁺=405.0; ¹H-NMR (400 MHz, DMSO-d₆+TFA) δ 8.00-8.15 (m, 1H), 7.99 (s, 2H), 7.60-7.70 (m, 1H), 7.30-7.45 (m, 1H), 3.70-3.90 (m, 2H), 3.30-3.40 (m, 2H), 1.70-1.95 (m, 4H), 1.38 (s, 3H).

Compound 13C: Preparation of (3S,4S)-8-(3-(3,4-dihydro-1,5-naphthyridin-1(2H)-yl)-5-methyl-1H-pyrazolo[3,4-b]pyrazin-6-yl)-3-methyl-2-oxa-8-azaspiro[4.5]decan-4-amine

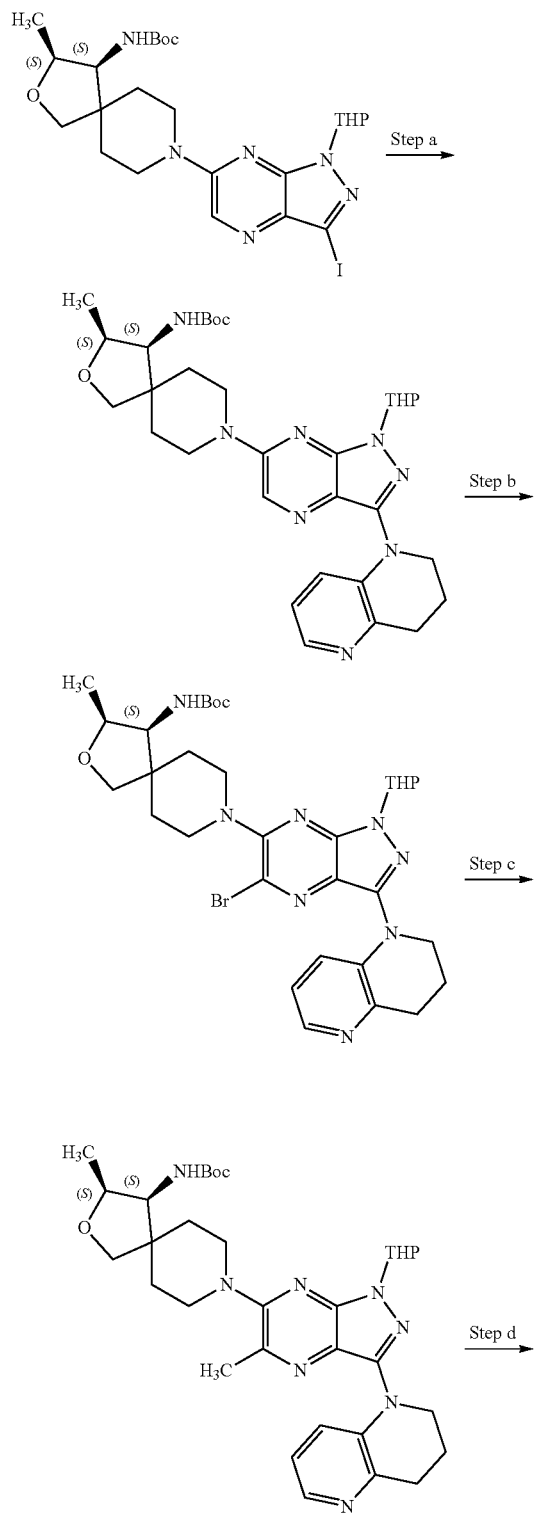

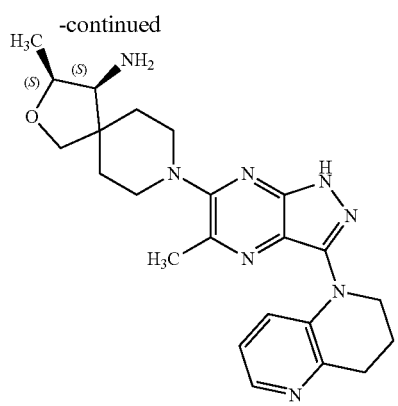

Step a: A mixture of tert-butyl N-[(3S,4S)-8-[3-iodo-1-(oxan-2-yl)-1H-pyrazolo[3,4-b]pyrazin-6-yl]-3-methyl-2-oxa-8-azaspiro[4.5]decan-4-yl]carbamate (900 mg, 1.5 mmol), 1,2,3,4-tetrahydro-1,5-naphthyridine (201 mg, 1.5 mmol), XantPhos-Pd-G4 (144 mg, 150 µmol), and Cs$_2$CO$_3$ (978 mg, 3.0 mmol) in PhMe (50 mL) was stirred at 100° C. for 12 hours under N$_2$ atmosphere. After cooling, the reaction mixture was concentrated under reduced pressure to give a residue, which was dissolved in ethyl acetate (30 mL) and washed with H$_2$O (20 mL×2). The organics were washed with brine (15 mL), dried over anhydrous Na$_2$SO$_4$, filtered, and concentrated under reduced pressure, and purified by silica gel chromatography (Ethyl acetate as eluent) to afford tert-butyl N-[(3S,4S)-3-methyl-8-[1-(oxan-2-yl)-3-(1,2,3,4-tetrahydro-1,5-naphthyridin-1-yl)-1H-pyrazolo[3,4-b]pyrazin-6-yl]-2-oxa-8-azaspiro[4.5]decan-4-yl]carbamate (490 mg, 54% yield) as a yellow solid.

Step b: To a mixture of tert-butyl N-[(3S,4S)-3-methyl-8-[1-(oxan-2-yl)-3-(1,2,3,4-tetrahydro-1,5-naphthyridin-1-yl)-1H-pyrazolo[3,4-b]pyrazin-6-yl]-2-oxa-8-azaspiro[4.5]decan-4-yl]carbamate (470 mg, 777 µmol) in MeCN (20 mL) and AcOH (20 mL) was added NBS (138 mg, 777 µmol), the resulting mixture was stirred at 25° C. for 12 hours. The reaction mixture was concentrated under reduced pressure to give a residue, which was dissolved in ethyl acetate (30 mL) and washed with sat. NaHCO$_3$ (20 mL×2). The organics were washed with brine (10 mL), dried over anhydrous Na$_2$SO$_4$, filtered, and concentrated under reduced pressure, and purified by silica gel chromatography (Ethyl acetate in petroleum ether: 75% to 85%) to afford tert-butyl N-[(3S,4S)-8-[5-bromo-1-(oxan-2-yl)-3-(1,2,3,4-tetrahydro-1,5-naphthyridin-1-yl)-1H-pyrazolo[3,4-b]pyrazin-6-yl]-3-methyl-2-oxa-8-azaspiro[4.5]decan-4-yl]carbamate (410 mg, 77% yield) as a yellow solid.

Step c: A mixture of tert-butyl N-[(3S,4S)-8-[5-bromo-1-(oxan-2-yl)-3-(1,2,3,4-tetrahydro-1,5-naphthyridin-1-yl)-1H-pyrazolo[3,4-b]pyrazin-6-yl]-3-methyl-2-oxa-8-azaspiro[4.5]decan-4-yl]carbamate (100.0 mg, 146 µmol), trimethyl-1,3,5,2,4,6-trioxatriborinane (91.6 mg, 730 µmol), Pd(dppf)Cl$_2$ (10.6 mg, 14.6 µmol), and K$_2$CO$_3$ (40.2 mg, 292 µmol) in dioxane (20 mL)/H$_2$O (2 mL) was stirred at 90° C. for 12 hours under N$_2$ atmosphere. After cooling, the reaction mixture was concentrated under reduced pressure to give a residue which was purified by silica gel chromatography (0% to 10% methanol in dichloromethane) to afford tert-butyl N-[(3S,4S)-3-methyl-8-[5-methyl-1-(oxan-2-yl)-3-(1,2,3,4-tetrahydro-1,5-naphthyridin-1-yl)-1H-pyrazolo[3,4-b]pyrazin-6-yl]-2-oxa-8-azaspiro[4.5]decan-4-yl]carbamate (80 mg, 89% yield) as a yellow solid Step d: A mixture of tert-butyl N-[(3S,4S)-3-methyl-8-[5-methyl-1-(oxan-2-yl)-3-(1,2,3,4-tetrahydro-1,5-naphthyridin-1-yl)-1H-pyrazolo[3,4-b]pyrazin-6-yl]-2-oxa-8-azaspiro[4.5]decan-4-yl]carbamate (80 mg, 129 µmol) in 4M HCl/MeOH (5 mL) was stirred at 15° C. for 1 hour. The reaction mixture was concentrated under reduced pressure then purified by reversed phase prep-HPLC (acetonitrile/aq. HCl) to afford (3S,4S)-3-methyl-8-[5-methyl-3-(1,2,3,4-tetrahydro-1,5-naphthyridin-1-yl)-1H-pyrazolo[3,4-b]pyrazin-6-yl]-2-oxa-8-azaspiro[4.5]decan-4-amine dihydrochloride (47.7 mg, 72.9% yield) as a yellow solid: LCMS [M+H]$^+$=435.1; $^1$H-NMR (400 MHz, methanol-d$_4$): δ 7.95 (d, J=5.2 Hz, 1H), 7.81 (d, J=7.2 Hz, 1H), 7.47-7.44 (m, 1H), 4.26-4.20 (m, 1H), 3.97 (t, J=5.6 Hz, 2H), 3.90 (d, J=9.2 Hz, 1H), 3.78 (d, J=9.2 Hz, 1H), 3.68-3.58 (m, 2H), 3.42 (d, J=3.9 Hz, 1H), 3.20-3.18 (m, 2H), 3.02-2.91 (m, 2H), 2.54 (s, 3H), 2.25-2.20 (m, 2H), 1.99-1.84 (m, 3H), 1.72-1.69 (m, 1H), 1.25 (d, J=6.4 Hz, 3H).

Compound 6C: 6-(4-(aminomethyl)-4-methylpiperidin-1-yl)-3-(3,4-dihydro-1,5-naphthyridin-1(2H)-yl)-1H-pyrazolo[3,4-b]pyrazin-5-ol and (1-(3-(3,4-dihydro-1,5-naphthyridin-1(2H)-yl)-5-methyl-1H-pyrazolo[3,4-b]pyrazin-6-yl)-4-methylpiperidin-4-yl)methanamine

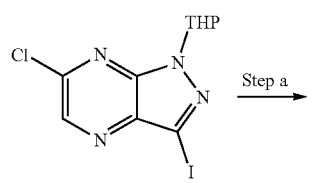

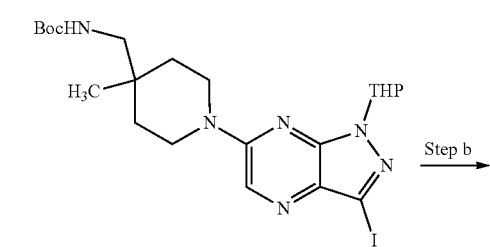

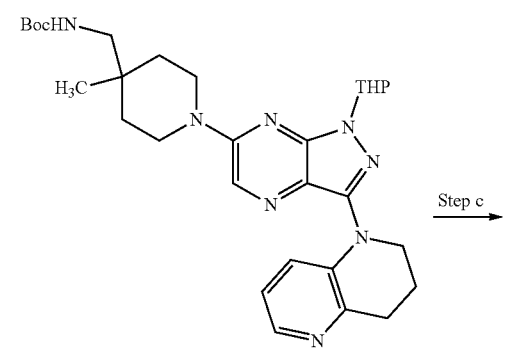

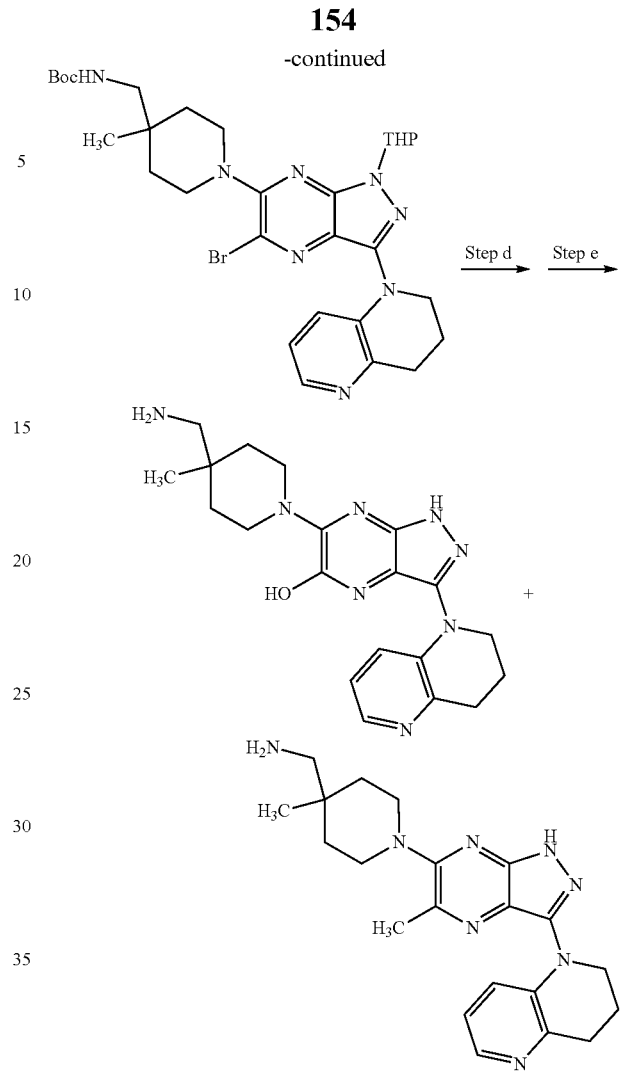

Step a: A mixture of 6-chloro-3-iodo-1-(oxan-2-yl)-1H-pyrazolo[3,4-b]pyrazine (2.0 g, 5.5 mmol), tert-butyl N-[(4-methylpiperidin-4-yl)methyl]carbamate (1.3 g, 5.5 mmol) and CsF (2.1 g, 13.7 mmol) in DMSO (50 mL) was stirred at 70° C. for 2 hours. After cooling, the reaction mixture was diluted with H$_2$O (100 mL), extracted with ethyl acetate (120 mL×2), and the combined organics washed with brine (80 mL), dried over anhydrous Na$_2$SO$_4$, filtered, and concentrated under reduced pressure and purified by silica gel chromatography (40-50% EtOAc/petroleum ether) to afford tert-butyl N-({1-[3-iodo-1-(oxan-2-yl)-1H-pyrazolo[3,4-b]pyrazin-6-yl]-4-methylpiperidin-4-yl}methyl)carbamate (3.0 g, 98% yield) as a white solid.

Step b: A mixture of tert-butyl N-({1-[3-iodo-1-(oxan-2-yl)-1H-pyrazolo[3,4-b]pyrazin-6-yl]-4-methylpiperidin-4-yl}methyl)carbamate (1.3 g, 2.3 mmol), 1,2,3,4-tetrahydro-1,5-naphthyridine (312 mg, 2.3 mmol), RuPhos (162 mg, 349 µmol), RuPhos-Pd-G4 (198 mg, 233 µmol), and Cs$_2$CO$_3$ (1.5 g, 4.7 mmol) in toluene (60 mL) was stirred at 100° C. for 12 hours under N$_2$ atmosphere. After cooling, the reaction mixture was concentrated under reduced pressure, dissolved in ethyl acetate (70 mL), and washed with H$_2$O (60 mL×2). The organics were washed with brine (40 mL), dried over anhydrous Na$_2$SO$_4$, filtered, and concentrated under reduced pressure and purified by silica gel chromatography (Ethyl acetate as eluent) to afford tert-butyl N-({4-methyl- 1-[1-(oxan-2-yl)-3-(1,2,3,4-tetrahydro-1,5-naphthyridin-1-yl)-1H-pyrazolo[3,4-b]pyrazin-6-yl]piperidin-4-yl}methyl)carbamate (610 mg, 47% yield) as a yellow solid.

Step c: A mixture of tert-butyl N-({4-methyl-1-[1-(oxan-2-yl)-3-(1,2,3,4-tetrahydro-1,5-naphthyridin-1-yl)-1H-pyrazolo[3,4-b]pyrazin-6-yl]piperidin-4-yl}methyl)carbamate (610 mg, 1.1 mmol) and NBS (191 mg, 1.1 mmol) in MeCN (30 mL) was stirred at 15° C. for 24 hours. The reaction mixture was concentrated under reduced pressure and purified by silica gel chromatography (60-80% EtOAc/petroleum ether) to afford tert-butyl N-({1-[5-bromo-1-(oxan-2-yl)-3-(1,2,3,4-tetrahydro-1,5-naphthyridin-1-yl)-1H-pyrazolo[3,4-b]pyrazin-6-yl]-4-methylpiperidin-4-yl}methyl)carbamate (170 mg, 24.5% yield) as a yellow solid.

Step d: A mixture of tert-butyl N-({1-[5-bromo-1-(oxan-2-yl)-3-(1,2,3,4-tetrahydro-1,5-naphthyridin-1-yl)-1H-pyrazolo[3,4-b]pyrazin-6-yl]-4-methylpiperidin-4-yl}methyl)carbamate (170 mg, 264 μmol), methylboronic acid (157 mg, 2.6 mmol), XPhos-Pd-G4 (68 mg, 79.1 μmol), XPhos (50 mg, 105 μmol), and $K_3PO_4 \cdot 3H_2O$ (210 mg, 792 μmol) in DMF (10 mL) was stirred at 100° C. for 12 hours under $N_2$ atmosphere. After cooling, the reaction mixture was diluted with ethyl acetate (30 mL) and washed with $H_2O$ (20 mL×2). The organics were washed with brine (10 mL), dried over anhydrous $Na_2SO_4$, filtered, and concentrated under reduced pressure to give a mixture of tert-butyl N-({4-methyl-1-[5-methyl-1-(oxan-2-yl)-3-(1,2,3,4-tetrahydro-1,5-naphthyridin-1-yl)-1H-pyrazolo[3,4-b]pyrazin-6-yl]piperidin-4-yl}methyl)carbamate and tert-butyl N-({1-[5-hydroxy-1-(oxan-2-yl)-3-(1,2,3,4-tetrahydro-1,5-naphthyridin-1-yl)-1H-pyrazolo[3,4-b]pyrazin-6-yl]-4-methylpiperidin-4-yl}methyl)carbamate (100 mg for the mixture), which was used directly in the next reaction as is.

Step e: A mixture of tert-butyl N-({4-methyl-1-[5-methyl-1-(oxan-2-yl)-3-(1,2,3,4-tetrahydro-1,5-naphthyridin-1-yl)-1H-pyrazolo[3,4-b]pyrazin-6-yl]piperidin-4-yl}methyl)carbamate, tert-butyl N-({1-[5-hydroxy-1-(oxan-2-yl)-3-(1,2,3,4-tetrahydro-1,5-naphthyridin-1-yl)-1H-pyrazolo[3,4-b]pyrazin-6-yl]-4-methylpiperidin-4-yl}methyl)carbamate (100 mg, mixture) in 4M HCl/MeOH (5 mL) was stirred at 15° C. for 0.5 hours. The reaction mixture was concentrated under reduced pressure to give a residue, which was purified by reversed phase prep-HPLC (acetonitrile/aq. $NH_3$) to afford (1-(3-(3,4-dihydro-1,5-naphthyridin-1(2H)-yl)-5-methyl-1H-pyrazolo[3,4-b]pyrazin-6-yl)-4-methylpiperidin-4-yl)methanamine (16.5 mg) as a yellow solid: LCMS $[M+H]^+$=395.0; $^1$H-NMR (400 MHz, DMSO-$d_6$) δ7.78 (d, J=3.6 Hz, 1H), 6.90-6.87 (m, 1H), 6.52 (d, J=8.0 Hz, 1H), 4.16-4.13 (m, 2H), 3.56-3.48 (m, 2H), 2.93-2.90 (m, 2H), 2.46 (s, 2H), 2.10-2.07 (m, 2H), 1.55-1.48 (m, 2H), 1.33-1.24 (m, 4H), 0.95 (s, 3H). and 1-{4-methyl-1-[5-methyl-3-(1,2,3,4-tetrahydro-1,5-naphthyridin-1-yl)-1H-pyrazolo[3,4-b]pyrazin-6-yl]piperidin-4-yl}methanamine (2.5 mg) as a yellow solid: LCMS $[M+H]^+$=393.0; H-NMR (400 MHz, DMSO-$d_6$) δ 7.89 (d, J=3.6 Hz, 1H), 7.37 (d, J=8.0 Hz, 1H), 6.97-6.94 (m, 1H), 3.96-3.93 (m, 2H), 3.56-3.52 (m, 2H), 3.14-3.09 (m, 2H), 2.97-2.94 (m, 2H), 2.53 (s, 3H), 2.11-2.07 (m, 2H), 1.64-1.59 (m, 2H), 1.44-1.24 (m, 4H), 0.97 (s, 3H).

Compound 11C: Preparation of (6-(4-(aminomethyl)-4-methylpiperidin-1-yl)-3-(3,4-dihydro-1,5-naphthyridin-1(2H)-yl)-1H-pyrazolo[3,4-b]pyrazin-5-yl)methanol

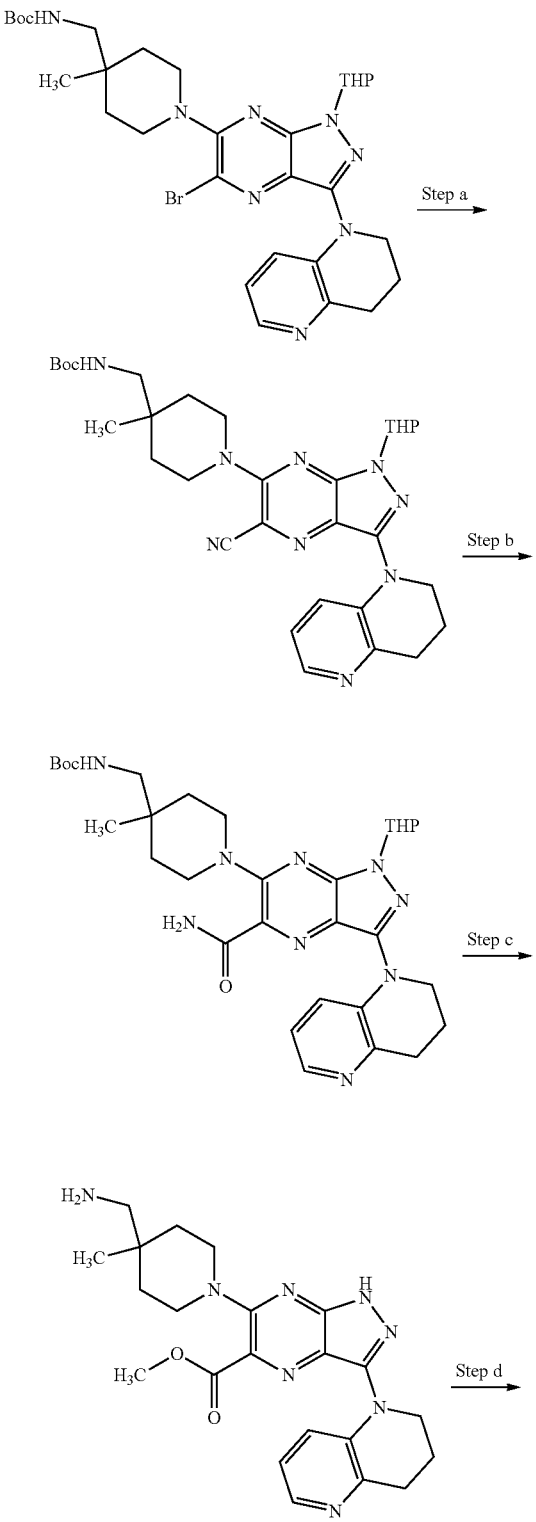

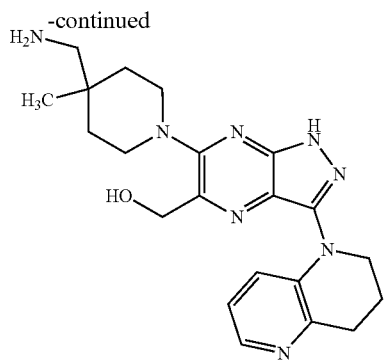

Step a: A mixture of tert-butyl N-({1-[5-bromo-1-(oxan-2-yl)-3-(1,2,3,4-tetrahydro-1,5-naphthyridin-1-yl)-1H-pyrazolo[3,4-b]pyrazin-6-yl]-4-methylpiperidin-4-yl}methyl)carbamate (610 mg, 950 μmol), Zn(CN)₂ (223 mg, 1.9 mmol), and XantPhos-Pd-G4 (91.4 mg, 95.0 μmol) in dioxane (30 mL)/H₂O (3 mL) was stirred at 80° C. for 12 hours under N₂ atmosphere. After cooling, the reaction mixture was concentrated under reduced pressure, dissolved in ethyl acetate (20 mL), and washed with H₂O (15 mL×2). The organics were washed with brine (10 mL), dried over anhydrous Na₂SO₄, filtered, concentrated under reduced pressure, and purified by silica gel chromatography (80% to 90% EtOAc/petroleum ether) to afford tert-butyl N-({1-[5-cyano-1-(oxan-2-yl)-3-(1,2,3,4-tetrahydro-1,5-naphthyridin-1-yl)-1H-pyrazolo[3,4-b]pyrazin-6-yl]-4-methylpiperidin-4-yl}methyl)carbamate (540 mg, 97% yield) as a yellow solid.

Step b: To a mixture of tert-butyl N-({1-[5-cyano-1-(oxan-2-yl)-3-(1,2,3,4-tetrahydro-1,5-naphthyridin-1-yl)-1H-pyrazolo[3,4-b]pyrazin-6-yl]-4-methylpiperidin-4-yl}methyl)carbamate (540 mg, 918 μmol) in MeOH (12 mL) was added 10% NaOH (12 mL) and the resulting mixture stirred at 90° C. for 2 hours. The reaction mixture was concentrated under reduced pressure to give a residue, which was dissolved in ethyl acetate (40 mL) and washed with H₂O (30 mL×2). The combined organics were washed with brine (15 mL), dried over anhydrous Na₂SO₄, filtered, concentrated under reduced pressure, and purified by silica gel chromatography (0% to 7% methanol in dichloromethane) to afford tert-butyl N-({1-[5-carbamoyl-1-(oxan-2-yl)-3-(1,2,3,4-tetrahydro-1,5-naphthyridin-1-yl)-1H-pyrazolo[3,4-b]pyrazin-6-yl]-4-methylpiperidin-4-yl}methyl)carbamate (450 mg, 81% yield) as a yellow solid.

Step c: To a mixture of tert-butyl N-({1-[5-carbamoyl-1-(oxan-2-yl)-3-(1,2,3,4-tetrahydro-1,5-naphthyridin-1-yl)-1H-pyrazolo[3,4-b]pyrazin-6-yl]-4-methylpiperidin-4-yl}methyl)carbamate (300 mg, 495 μmol) in MeOH (2 mL) was added conc. H₂SO₄ (2 mL) and the resulting mixture stirred at 90° C. for 4 hours. The pH was adjusted to ≥9 with solid Na₂CO₃. The resulting mixture was filtered and concentrated under reduced pressure, and purified by silica gel chromatography (0% to 10% methanol in dichloromethane, 0.5% NH₃·H₂O) to afford 6-[4-(aminomethyl)-4-methylpiperidin-1-yl]-3-(1,2,3,4-tetrahydro-1,5-naphthyridin-1-yl)-1H-pyrazolo[3,4-b]pyrazine-5-carboxylate (160 mg, 74% yield) as a yellow solid.

Step d: To a mixture of methyl 6-[4-(aminomethyl)-4-methylpiperidin-1-yl]-3-(1,2,3,4-tetrahydro-1,5-naphthyridin-1-yl)-1H-pyrazolo[3,4-b]pyrazine-5-carboxylate (130 mg, 297 μmol) in THF (10 mL) was added LiBH₄ (32.2 mg, 1.48 mmol) and the resulting mixture was stirred at 15° C. for 12 hours under N₂ atmosphere. The reaction was quenched with sat.NH₄Cl, the mixture was concentrated under reduced pressure and purified by reversed phase prep-HPLC (NH₃·H₂O) to afford (6-(4-(aminomethyl)-4-methylpiperidin-1-yl)-3-(3,4-dihydro-1,5-naphthyridin-1(2H)-yl)-1H-pyrazolo[3,4-b]pyrazin-5-yl)methanol (1.7 mg, 1.4% yield) as a yellow solid: LCMS [M+H]⁺=409.1; ¹H-NMR (400 MHz, Methanol-d₄) δ 7.90-7.89 (m, 1H), 7.45-7.42 (m, 1H), 7.05-7.01 (m, 1H), 4.72 (s, 2H), 4.05-4.03 (m, 2H), 3.60-3.55 (m, 2H), 3.31-3.28 (m, 2H), 3.06 (t, J=6.4 Hz, 2H), 2.67 (s, 2H), 2.25-2.19 (m, 2H), 1.76-1.69 (m, 2H), 1.59-1.54 (m, 2H), 1.11 (s, 3H).

Compound 12C: Preparation of (3S,4S)-8-(3-(3,4-dihydro-1,5-naphthyridin-1(2H)-yl)-5-isocyano-1H-pyrazolo[3,4-b]pyrazin-6-yl)-3-methyl-2-oxa-8-azaspiro[4.5]decan-4-amine

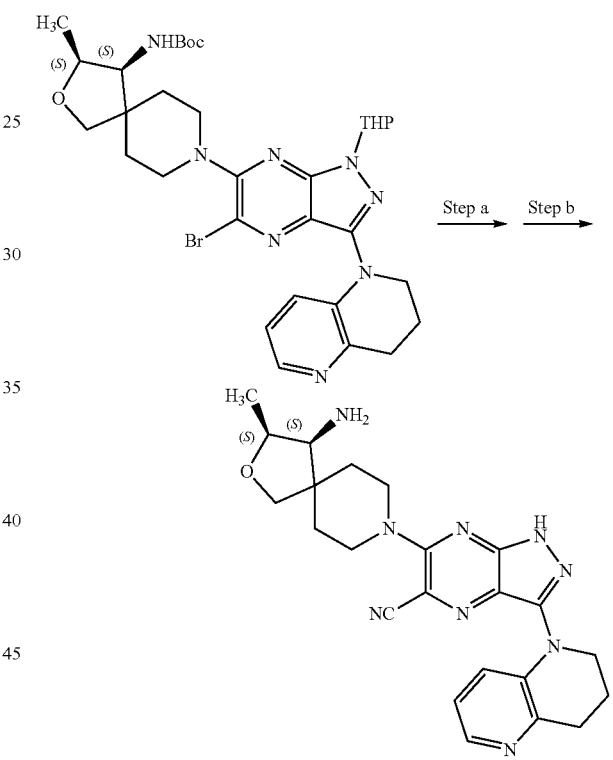

Step a: A mixture of tert-butyl N-[(3S,4S)-8-[5-bromo-1-(oxan-2-yl)-3-(1,2,3,4-tetrahydro-1,5-naphthyridin-1-yl)-1H-pyrazolo[3,4-b]pyrazin-6-yl]-3-methyl-2-oxa-8-azaspiro[4.5]decan-4-yl]carbamate (100 mg, 146 μmol), XantPhos-Pd-G₄ (14.0 mg, 14.6 μmol), and Zn(CN)₂ (34.2 mg, 292 μmol) in dioxane (10 mL)/H₂O (1 mL) was stirred at 80° C. for 12 hours under N₂ atmosphere. After cooling, the reaction mixture was concentrated under reduced pressure to give a residue, which was purified by silica gel chromatography (85-95% EtOAc/petroleum ether) to afford tert-butyl N-[(3S,4S)-8-[5-cyano-1-(oxan-2-yl)-3-(1,2,3,4-tetrahydro-1,5-naphthyridin-1-yl)-1H-pyrazolo[3,4-b]pyrazin-6-yl]-3-methyl-2-oxa-8-azaspiro[4.5]decan-4-yl]carbamate (85 mg, 92% yield) as a yellow solid.

Step b: A mixture of tert-butyl N-[(3S,4S)-8-[5-cyano-1-(oxan-2-yl)-3-(1,2,3,4-tetrahydro-1,5-naphthyridin-1-yl)-1H-pyrazolo[3,4-b]pyrazin-6-yl]-3-methyl-2-oxa-8- azaspiro[4.5]decan-4-yl]carbamate (85 mg, 134 μmol) in DCM (5 mL) and TFA (1 mL) was stirred at 20° C. for 12 hours. The pH of the reaction mixture was to 9 with solid Na$_2$CO$_3$ and the resulting mixture concentrated under reduced pressure. Purification by reversed phase prep-HPLC (acetonitrile/aq. NH$_3$) afforded 6-[(3S,4S)-4-amino-3-methyl-2-oxa-8-azaspiro[4.5]decan-8-yl]-3-(1,2,3,4-tetrahydro-1,5-naphthyridin-1-yl)-1H-pyrazolo[3,4-b]pyrazine-5-carbonitrile (27.3 mg, 45.7% yield) as a yellow solid: LCMS [M+H]$^+$=446.0; $^1$H-NMR (400 MHz, DMSO-d$_6$) δ 7.99-7.98 (m, 1H), 7.74-7.72 (m, 1H), 7.06-7.02 (m, 1H), 4.09-4.00 (m, 3H), 3.82-3.76 (m, 2H), 3.68 (d, J=8.4 Hz, 1H), 3.51-3.48 (m, 3H), 2.96-2.92 (m, 3H), 2.10-2.04 (m, 2H), 1.89-1.61 (m, 4H), 1.10-1.05 (m, 3H).

Compound 14C: Preparation of (6-((3S,4S)-4-amino-3-methyl-2-oxa-8-azaspiro[4.5]decan-8-yl)-3-(3,4-dihydro-1,5-naphthyridin-1(2H)-yl)-1H-pyrazolo[3,4-b]pyrazin-5-yl)methanol

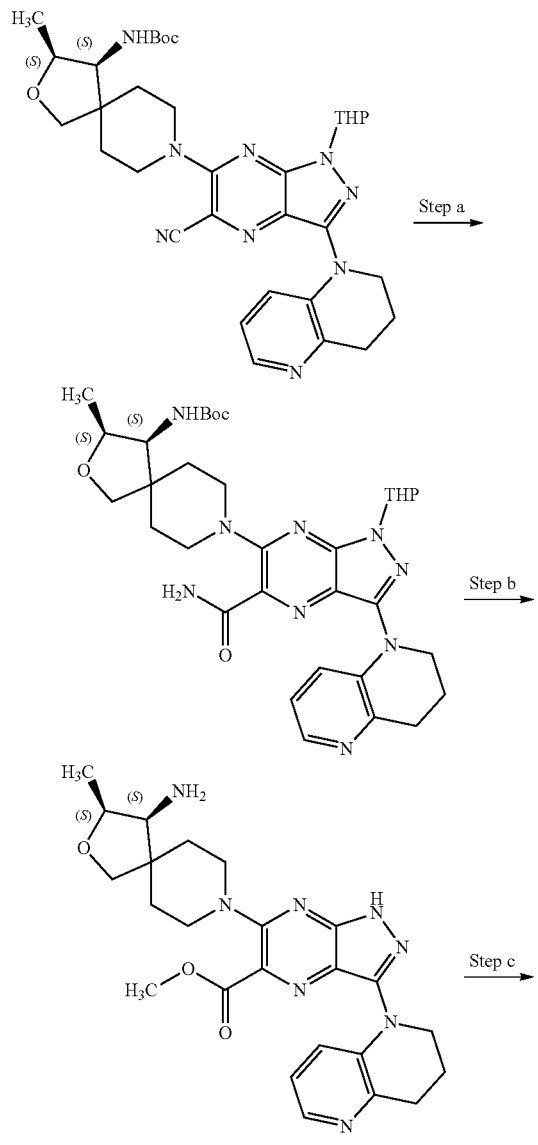

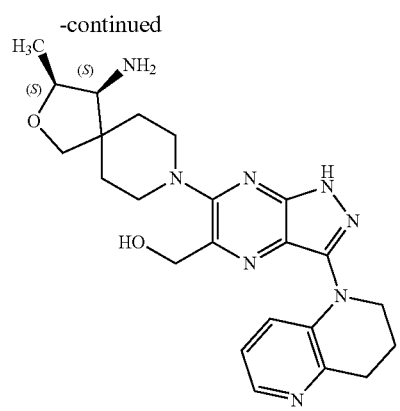

Step a: A mixture of tert-butyl N-[(3S,4S)-8-[5-cyano-1-(oxan-2-yl)-3-(1,2,3,4-tetrahydro-1,5-naphthyridin-1-yl)-1H-pyrazolo[3,4-b]pyrazin-6-yl]-3-methyl-2-oxa-8-azaspiro[4.5]decan-4-yl]carbamate (160 mg, 254 μmol) in MeOH (5 mL) and NaOH (10%, 5 mL) was stirred at 90° C. for 1 hour. The reaction mixture was concentrated under reduced pressure, dissolved in ethyl acetate (15 mL), and washed with H$_2$O (10 mL×2). The organics were washed with brine (5 mL), dried over anhydrous Na$_2$SO$_4$, filtered, concentrated under reduced pressure, and purified by silica gel chromatography (0-5% MeOH/DCM) to afford tert-butyl N-[(3S,4S)-8-[5-carbamoyl-1-(oxan-2-yl)-3-(1,2,3,4-tetrahydro-1,5-naphthyridin-1-yl)-1H-pyrazolo[3,4-b]pyrazin-6-yl]-3-methyl-2-oxa-8-azaspiro[4.5]decan-4-yl]carbamate (130 mg, 79% yield) as a yellow solid.

Step b: A mixture of tert-butyl N-[(3S,4S)-8-[5-carbamoyl-1-(oxan-2-yl)-3-(1,2,3,4-tetrahydro-1,5-naphthyridin-1-yl)-1H-pyrazolo[3,4-b]pyrazin-6-yl]-3-methyl-2-oxa-8-azaspiro[4.5]decan-4-yl]carbamate (130 mg, 200 μmol) in MeOH (1 mL) and conc. H$_2$SO$_4$ (1 mL) was stirred at 90° C. for 4 hours. The pH of the reaction mixture was adjusted to 9 with solid Na$_2$CO$_3$. The resulting mixture was filtered and concentrated in vacuum to give a residue, which was purified by silica gel chromatography (0-10% MeOH/DCM, 0.5% NH$_3$·H$_2$O) to afford methyl 6-[(3S,4S)-4-amino-3-methyl-2-oxa-8-azaspiro[4.5]decan-8-yl]-3-(1,2,3,4-tetrahydro-1,5-naphthyridin-1-yl)-1H-pyrazolo[3,4-b]pyrazine-5-carboxylate (55 mg, 57% yield) as a yellow solid.

Step c: To a solution of methyl 6-[(3S,4S)-4-amino-3-methyl-2-oxa-8-azaspiro[4.5]decan-8-yl]-3-(1,2,3,4-tetrahydro-1,5-naphthyridin-1-yl)-1H-pyrazolo[3,4-b]pyrazine-5-carboxylate (55 mg, 114 μmol) in THF (5 mL) was added LiBH$_4$ (12.4 mg, 570 mol) and the resulting mixture was stirred at 20° C. for 12 hours. The reaction was quenched with MeOH and the resulting mixture concentrated under reduced pressure to give a residue, which was purified by reversed phase prep-HPLC (acetonitrile/aq. NH$_3$) to afford (6-((3S,4S)-4-amino-3-methyl-2-oxa-8-azaspiro[4.5]decan-8-yl)-3-(3,4-dihydro-1,5-naphthyridin-1(2H)-yl)-1H-pyrazolo[3,4-b]pyrazin-5-yl)methanol (1.1 mg, 2.1% yield) as a yellow solid: LCMS [M+H]$^+$=451.1; $^1$H-NMR (400 MHz, methanol-d$_4$): δ 7.90-7.88 (m, 1H), 7.45-7.43 (m, 1H), 7.05-7.01 (m, 1H), 4.73 (s, 2H), 4.29-4.26 (m, 1H), 4.06-4.03 (m, 1H), 3.90 (d, J=8.8 Hz, 1H), 3.76 (d, J=8.8 Hz, 1H), 3.70-3.64 (m, 1H), 3.31-3.28 (m, 2H), 3.26-3.04 (m, 7H), 2.25-2.19 (m, 2H), 2.06-1.75 (m, 4H), 1.25 (d, J=6.4 Hz, 3H).

Compound 10C: Preparation of (6-((3S,4S)-4-amino-3-methyl-2-oxa-8-azaspiro[4.5]decan-8-yl)-3-(3,4-dihydro-1,5-naphthyridin-1(2H)-yl)-1H-pyrazolo[3,4-b]pyrazin-5-yl)methanol

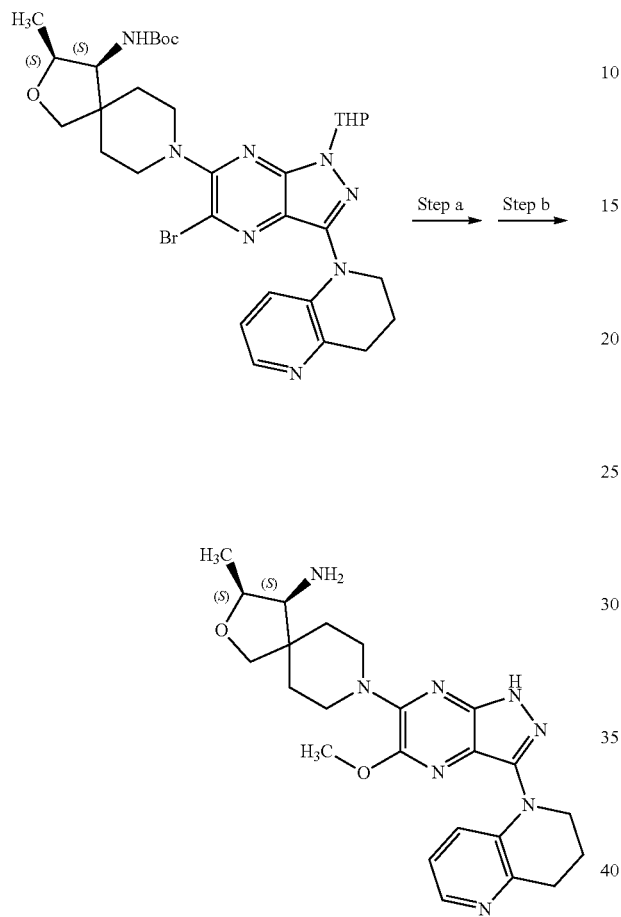

Step a: A mixture of tert-butyl N-[(3S,4S)-8-[5-bromo-1-(oxan-2-yl)-3-(1,2,3,4-tetrahydro-1,5-naphthyridin-1-yl)-1H-pyrazolo[3,4-b]pyrazin-6-yl]-3-methyl-2-oxa-8-azaspiro[4.5]decan-4-yl]carbamate (100 mg, 146 μmol) and MeONa (39.4 mg, 730 μmol) in MeOH (5 mL) was stirred at 70° C. for 12 hours. After cooling, the reaction mixture was concentrated under reduced pressure to give a residue, which was dissolved in ethyl acetate (15 mL) and washed with H₂O (10 mL×2). The organics were washed with brine (5 mL), dried over anhydrous Na₂SO₄, filtered, and concentrated under reduced pressure to afford tert-butyl N-[(3S,4S)-8-[5-methoxy-1-(oxan-2-yl)-3-(1,2,3,4-tetrahydro-1,5-naphthyridin-1-yl)-1H-pyrazolo[3,4-b]pyrazin-6-yl]-3-methyl-2-oxa-8-azaspiro[4.5]decan-4-yl]carbamate (80 mg, 86% yield) as a yellow solid.

Step b: A mixture of tert-butyl N-[(3S,4S)-8-[5-methoxy-1-(oxan-2-yl)-3-(1,2,3,4-tetrahydro-1,5-naphthyridin-1-yl)-1H-pyrazolo[3,4-b]pyrazin-6-yl]-3-methyl-2-oxa-8-azaspiro[4.5]decan-4-yl]carbamate (80 mg, 126 μmol) in 4M HCl/MeOH (5 mL) was stirred at 15° C. for 1 hour. The reaction mixture was concentrated under reduced pressure and purified by reversed phase prep-HPLC (acetonitrile/aq. HCl) to afford (3S,4S)-8-[5-methoxy-3-(1,2,3,4-tetrahydro-1,5-naphthyridin-1-yl)-1H-pyrazolo[3,4-b]pyrazin-6-yl]-3-methyl-2-oxa-8-azaspiro[4.5]decan-4-amine dihydrochloride (44.6 mg, 68% yield) as a yellow solid: LCMS [M+H]⁺+451.1; ¹H-NMR (400 MHz, methanol-d₄) δ 8.09 (d, J=9.2 Hz, 1H), 8.04 (d, J=8.8 Hz, 1H), 7.65-7.62 (m, 1H), 4.40-4.32 (m, 3H), 4.09 (t, J=5.6 Hz, 2H), 4.02 (d, J=8.8 Hz, 1H), 3.93 (s, 3H), 3.90 (d, J=9.2 Hz, 1H), 3.50 (d, J=3.6 Hz, 1H), 3.31-3.16 (m, 4H), 2.35-2.30 (m, 2H), 2.03-1.90 (m, 3H), 1.79-1.75 (m, 1H), 1.35 (d, J=6.4 Hz, 3H).

Compound 7C: Preparation of 6-[4-(aminomethyl)-4-methylpiperidin-1-yl]-3-(1,2,3,4-tetrahydro-1,5-naphthyridin-1-yl)-1H-pyrazolo[3,4-b]pyrazine-5-carbonitrile

Step a: A mixture of tert-butyl N-({1-[5-cyano-1-(oxan-2-yl)-3-(1,2,3,4-tetrahydro-1,5-naphthyridin-1-yl)-1H-pyrazolo[3,4-b]pyrazin-6-yl]-4-methylpiperidin-4-yl}methyl)carbamate (120 mg, 204 μmol) in DCM (5.0 mL) was added TFA (1.0 mL) and the reaction mixture stirred at 20° C. for 12 hours. The mixture was concentrated under reduced pressure and purified by reversed phase prep-HPLC (acetonitrile/aq. NH₃) to afford 6-[4-(aminomethyl)-4-methylpiperidin-1-yl]-3-(1,2,3,4-tetrahydro-1,5-naphthyridin-1-yl)-1H-pyrazolo[3,4-b]pyrazine-5-carbonitrile (18.0 mg, 21.8% yield) as a yellow solid: LCMS [M+H]⁺=404.1; ¹H-NMR (400 MHz, methanol-d₄) δ 7.99-7.98 (m, 1H), 7.89-7.87 (m, 1H), 7.13-7.10 (m, 1H), 4.12 (t, J=5.6 Hz, 2H), 4.02-3.96 (m, 2H), 3.59-3.52 (m, 2H), 3.05 (t, J=6.4 Hz, 2H), 2.65 (s, 2H), 2.22-2.16 (m, 2H), 1.74-1.67 (m, 2H), 1.59-1.55 (m, 2H), 1.11 (s, 3H).

Compound 8C: Preparation of 6-[4-(aminomethyl)-4-methylpiperidin-1-yl]-3-(1,2,3,4-tetrahydro-1,5-naphthyridin-1-yl)-1H-pyrazolo[3,4-b]pyrazine-5-carboxamide

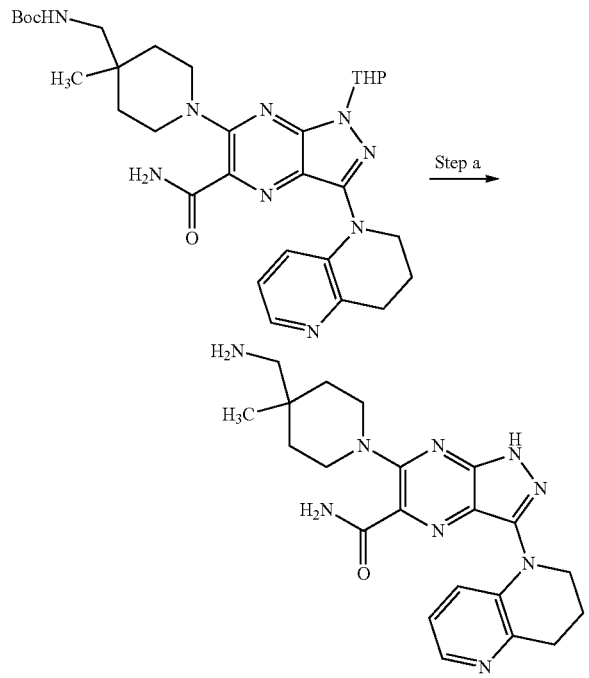

Step a: A mixture of tert-butyl N-({1-[5-carbamoyl-1-(oxan-2-yl)-3-(1,2,3,4-tetrahydro-1,5-naphthyridin-1-yl)-1H-pyrazolo[3,4-b]pyrazin-6-yl]-4-methylpiperidin-4-yl}methyl)carbamate (100 mg, 165 μmol) in 4M HCl/MeOH (5 mL) was stirred at 25° C. for 2 hours. The reaction mixture was concentrated under reduced pressure and purified by reversed phase prep-HPLC (acetonitrile/aq. HCl) to afford 6-[4-(aminomethyl)-4-methylpiperidin-1-yl]-3-(1,2,3,4-tetrahydro-1,5-naphthyridin-1-yl)-1H-pyrazolo[3,4-b]pyrazine-5-carboxamide dihydrochloride (36.0 mg, 44.1% yield) as a yellow solid: LCMS [M+H]$^+$=422.1; $^1$H-NMR (400 MHz, DMSO-d$_6$) δ 13.24 (br, 1H), 8.29 (d, J=8.4 Hz, 1H), 8.19-8.15 (m, 4H), 8.00 (s, 1H), 7.65-7.62 (m, 2H), 4.11-4.08 (m, 2H), 3.67-3.63 (m, 2H), 3.42-3.37 (m, 2H), 3.29-3.26 (m, 2H), 2.77-2.74 (m, 2H), 2.17-2.14 (m, 2H), 1.62-1.46 (m, 4H), 1.09 (s, 3H).

Compound 9C: Preparation of methyl 6-[4-(aminomethyl)-4-methylpiperidin-1-yl]-3-(1,2,3,4-tetrahydro-1,5-naphthyridin-1-yl)-1H-pyrazolo[3,4-b]pyrazine-5-carboxylate

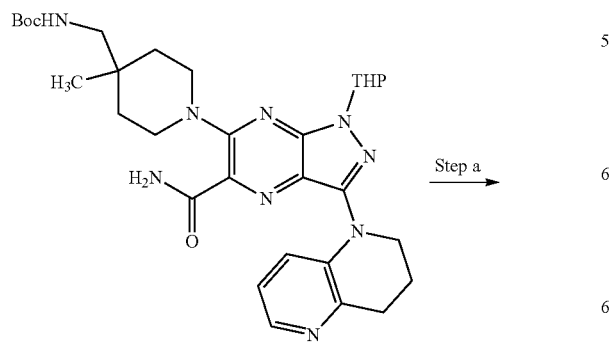

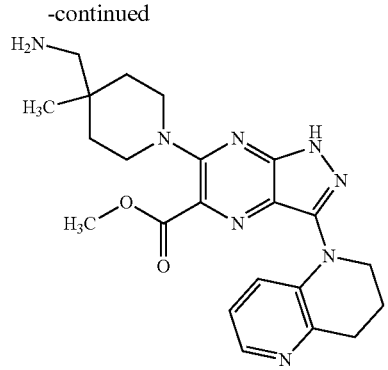

Step a: To a mixture of tert-butyl N-({1-[5-carbamoyl-1-(oxan-2-yl)-3-(1,2,3,4-tetrahydro-1,5-naphthyridin-1-yl)-1H-pyrazolo[3,4-b]pyrazin-6-yl]-4-methylpiperidin-4-yl}methyl)carbamate (150 mg, 247 μmol) in MeOH (1 mL) was added con·H$_2$SO$_4$ (1 mL) and the resulting mixture was stirred at 90° C. for 3 hours. The pH of the reaction mixture was adjusted ≥9 with solid Na$_2$CO$_3$, the mixture filtered, concentrated under reduced pressure, and purified by reversed phase prep-HPLC (acetonitrile/aq. HCl) to afford methyl 6-[4-(aminomethyl)-4-methylpiperidin-1-yl]-3-(1,2,3,4-tetrahydro-1,5-naphthyridin-1-yl)-1H-pyrazolo[3,4-b]pyrazine-5-carboxylate dihydrochloride (22.5 mg, 18.0% yield) as a yellow solid: LCMS [M+H]$^+$=437.1; $^1$H-NMR (400 MHz, DMSO-d$_6$) δ 13.41 (br, 1H), 8.25-8.17 (m, 5H), 7.64-7.60 (m, 1H), 4.07-4.04 (m, 2H), 3.87 (s, 3H), 3.58-3.54 (m, 2H), 3.37-3.26 (m, 4H), 2.77-2.74 (m, 2H), 2.17-2.14 (m, 2H), 1.60-1.46 (m, 4H), 1.10 (s, 3H).

Compound 20C: Synthesis of (3-(6-(1H-pyrazol-5-yl)-3,4-dihydro-1,5-naphthyridin-1(2H)-yl)-6-((3S,4S)-4-amino-3-methyl-2-oxa-8-azaspiro[4.5]decan-8-yl)-1H-pyrazolo[3,4-b]pyrazin-5-yl)methanol

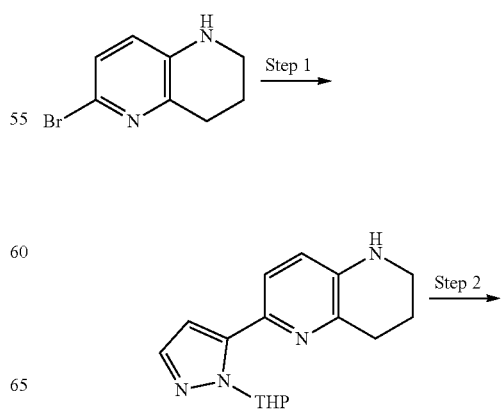

-continued

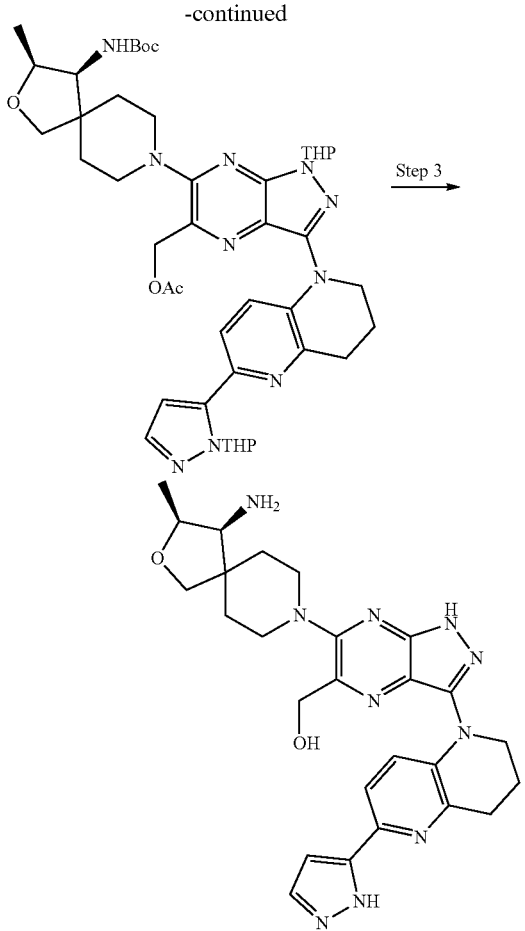

Step 1: To a solution of 6-bromo-1,2,3,4-tetrahydro-1,5-naphthyridine (4.0 g, 18.7 mmol) in dioxane (50 mL) and H₂O (5 mL) were added Cs$_2$CO$_3$ (12.1 g, 37.4 mmol), 1-(oxan-2-yl)-5-(4,4,5,5-tetramethyl-1,3,2-dioxaborolan-2-yl)-1H-pyrazole (7.8 g, 28.0 mmol) and Pd(dppf)Cl$_2$ (684 mg, 935 mmol), the mixture was stirred at 100° C. for 12 hours under N$_2$ atmosphere. LCMS indicated the reaction was consumed completely. The reaction mixture was concentrated in vacuum and purified by silica gel column (elution: Petroleum ether:ethyl acetate=1:0 to 1:3) to give 6-[1-(oxan-2-yl)-1H-pyrazol-5-yl]-1,2,3,4-tetrahydro-1,5-naphthyridine (3.7 g, 69.6% yield) as a yellow solid. LCMS: calc. for C$_{16}$H$_{20}$N$_4$O: 284.4, found: [M+H]$^+$ 284.9. HPLC: 77.8% purity at 254 nm. $^1$HNMR (400 MHz, CD$_3$OD): δ 7.55~7.54 (m, 1H), 7.25 (d, J=6.4 Hz, 1H), 6.92 (d, J=6.4 Hz, 1H), 6.48 (s, 1H), 5.94~5.90 (m, 1H), 4.04~4.00 (m, 1H), 3.61~3.60 (m, 1H), 3.34~3.32 (m, 2H), 2.94~2.92 (m, 2H), 2.48~2.41 (m, 1H), 2.12~2.08 (m, 3H), 1.92~1.90 (m, 1H), 1.78~1.48 (m, 3H).

Step 2: A disposable reaction tube was charged with {6-[(3S,4S)-4-{[(tert-butoxy)carbonyl]amino}-3-methyl-2-oxa-8-azaspiro[4.5]decan-8-yl]-3-iodo-1-(oxan-2-yl)-1H-pyrazolo[3,4-b]pyrazin-5-yl}methyl acetate (90 mg, 0.1342 mmol), 6-[1-(oxan-2-yl)-1H-pyrazol-5-yl]-1,2,3,4-tetrahydro-1,5-naphthyridine (45.7 mg, 0.1610 mmol), 9-{[5-(diphenylphosphanyl)-9,9-dimethyl-9H-xanthen-4-yl]diphenyl-?4-phosphanyl}-O-methanesulfonyl-8-methyl-8-aza-9-palladatricyclo[8.4.0.0$^2$,7]tetradeca-1(14),2,4,6,10,12-hexaene-9,9-bis(ylium)-10-uid-9-olate (12.9 mg, 0.01342 mmol), dicesiocarbonate (87.4 mg, 0.2684 mmol), and toluene (5 mL). Nitrogen was bubbled through the mixture for 10 min before the vial was sealed and heated to 95° C. for 12 h. The reaction was cooled to room temperature and pre-absorbed onto silica gel for purification by column chromatography (eluting with ethyl acetate and heptanes). The product-containing fractions were pooled and concentrated in vacuo to yield {6-[(3S,4S)-4-{[(tert-butoxy)carbonyl]amino}-3-methyl-2-oxa-8-azaspiro[4.5]decan-8-yl]-1-(oxan-2-yl)-3-{6-[1-(oxan-2-yl)-1H-pyrazol-5-yl]-1,2,3,4-tetrahydro-1,5-naphthyridin-1-yl}-1H-pyrazolo[3,4-b]pyrazin-5-yl}methyl acetate (80 mg, 0.097 mmol) as a yellow oil.

Step 3: {6-[(3S,4S)-4-{[(tert-butoxy)carbonyl]amino}-3-methyl-2-oxa-8-azaspiro[4.5]decan-8-yl]-1-(oxan-2-yl)-3-{6-[1-(oxan-2-yl)-1H-pyrazol-5-yl]-1,2,3,4-tetrahydro-1,5-naphthyridin-1-yl}-1H-pyrazolo[3,4-b]pyrazin-5-yl}methyl acetate (80 mg, 0.09673 mmol) was taken up in dichloromethane (4 mL), followed by the addition of trifluoroacetic acid (1.5 mL). The reaction was stirred at room temperature. After five hours, more trifluoroacetic acid (1 mL) was added. After 6.5 h, the reaction was charged with toluene, concentrated in vacuo, and stripped with tetrahydrofuran. The residue was taken up in tetrahydrofuran (4 mL) and charged with lithium hydroxide (23.1 mg, 0.9673 mmol) and water (0.5 mL). After 12 h, the reaction was concentrated in vacuo, dissolved in dimethylsulfoxide (5 mL) and formic acid (54.6 µL, 1.45 mmol), then purified by preparative HPLC (eluting with acetonitrile/water/formic acid). The product-containing fractions were pooled, concentrated in vacuo, and lyophilized to yield (3-(6-(1H-pyrazol-5-yl)-3,4-dihydro-1,5-naphthyridin-1(2H)-yl)-6-((3S,4S)-4-amino-3-methyl-2-oxa-8-azaspiro[4.5]decan-8-yl)-1H-pyrazolo[3,4-b]pyrazin-5-yl)methanol (31 mg, 0.060 mmol) as a yellow solid.

Compound 22C: Synthesis of (6-((3S,4S)-4-amino-3-methyl-2-oxa-8-azaspiro[4.5]decan-8-yl)-3-(quinolin-5-yl)-1H-pyrazolo[3,4-b]pyrazin-5-yl)methanol

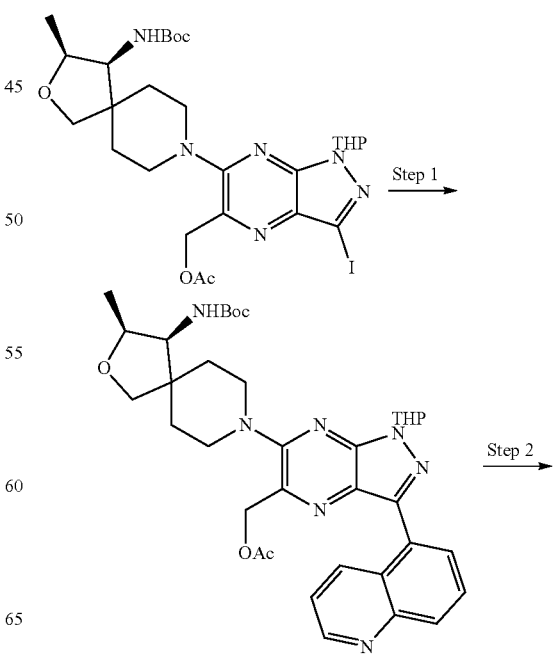

-continued

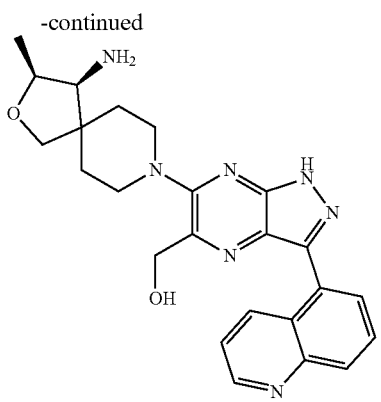

Step 1: A resealable reaction vial was charged with {6-[(3S,4S)-4-{[(tert-butoxy)carbonyl]amino}-3-methyl-2-oxa-8-azaspiro[4.5]decan-8-yl]-3-iodo-1-(oxan-2-yl)-1H-pyrazolo[3,4-b]pyrazin-5-yl}methyl acetate (100 mg, 0.1491 mmol), (quinolin-5-yl)boronic acid (38.6 mg, 0.2236 mmol), caesium carbonate (97.1 mg, 0.2982 mmol), palladium(2+) bis(cyclopenta-1,3-dien-1-yldiphenylphosphane) methylene chloride iron dichloride (12.1 mg, 0.01491 mmol). Dioxane (4 mL) and water (0.4 mL) were added, nitrogen was bubbled through the reaction mixture for 10 min, and the vessel was heated at 70° C. for 18 h. The reaction mixture was diluted with ethyl acetate and brine, the organic layer was extracted three times with ethyl acetate, and the combined organic layers were dried over sodium sulfate, filtered, and concentrated in vacuo. The crude residue was purified by column chromatography (eluting with ethyl acetate and heptanes) to afford (6-((3S,4S)-4-((tert-butoxycarbonyl)amino)-3-methyl-2-oxa-8-azaspiro[4.5]decan-8-yl)-3-(quinolin-5-yl)-1-(tetrahydro-2H-pyran-2-yl)-1H-pyrazolo[3,4-b]pyrazin-5-yl)methyl acetate (96 mg, 0.14 mmol).

Step 2: A round bottomed flask was charged with {6-[(3S,4S)-4-{[(tert-butoxy)carbonyl]amino}-3-methyl-2-oxa-8-azaspiro[4.5]decan-8-yl]-1-(oxan-2-yl)-3-(quinolin-5-yl)-1H-pyrazolo[3,4-b]pyrazin-5-yl}methyl acetate (96 mg, 0.1428 mmol), and dissolved in 2 mL DCM and 0.75 mL TFA. The reaction mixture was stirred at room temperature 6 h before the addition of further TFA (0.5 mL). After 18 h, the reaction mixture was concentrated in vacuo, and the residue was stripped with toluene and tetrahydrofuran. The residue was taken up in tetrahydrofuran (2 mL) and water (0.5 mL), followed by the addition of lithium hydroxide LiOH. The mixture was stirred 15 min before being concentrated in vacuo. The residue was purified by preparative HPLC (eluting with acetonitrile/water/formic acid), and the product-containing fractions were concentrated in vacuo and lyophilized to yield (6-((3S,4S)-4-amino-3-methyl-2-oxa-8-azaspiro[4.5]decan-8-yl)-3-(quinolin-5-yl)-1H-pyrazolo[3,4-b]pyrazin-5-yl)methanol (16 mg, 0.036 mmol) as an amorphous solid.

The characterization of compounds disclosed herein is shown below.

| Cmpd. No. | Structure | NMR | Mass Spec. (M + H)+ |
|---|---|---|---|
| 1C | (structure) | $^1$H NMR (500 MHz, DMSO-$d_6$) δ 8.10-8.00 (m, 1H), 7.74-7.65 (m, 1H), 7.42 (t, J = 7.8 Hz, 1H), 3.89-3.74 (m, 2H), 3.57-3.44 (m, 2H), 2.72-2.57 (m, 2H), 1.71-1.58 (m, 2H), 1.54-1.44 (m, 2H), 1.04 (s, 3H) | 400.0 |
| 2C | (structure) | $^1$H NMR (400 MHz, DMSO-$d_6$) δ 8.21 (t, J = 7.2 Hz, 1H), 8.04 (s, 1H), 7.64 (d, J = 7.8 Hz, 2H), 7.37 (t, J = 8.0 Hz, 1H), 3.66 (dt, J = 10.4, 4.3 Hz, 2H), 3.38-3.34 (m, 2H), 1.55-1.47 (m, 2H), 1.36-1.29 (m, 2H), 1.21 (s, 2H), 0.93 (s, 3H) | 418.3 |

-continued

| Cmpd. No. | Structure | NMR | Mass Spec. (M + H)⁺ |
|---|---|---|---|
| 3C | 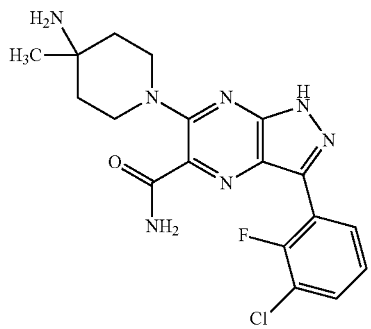 [SMILES: CC1(N)CCN(c2nc3[nH]nc(-c4cccc(Cl)c4F)c3nc2C(N)=O)CC1] | ¹H-NMR (400 MHz, DMSO-d₆) δ 8.23 (t, J = 7.2 Hz, 1H), 8.03 (br, 1H), 7.60-7.70 (m, 2H), 7.39 (t, J = 7.6 Hz, 1H), 3.50-3.65 (m, 4H), 1.40-1.60 (m, 4H), 1.11 (s, 3H) | 426.0 [M + Na]⁺ |
| 4C | 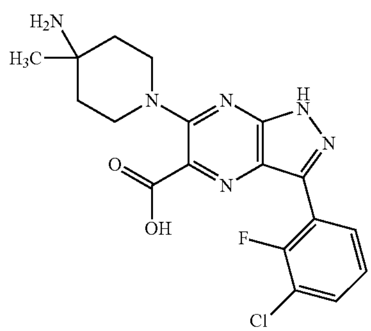 [SMILES: CC1(N)CCN(c2nc3[nH]nc(-c4cccc(Cl)c4F)c3nc2C(=O)O)CC1] | ¹H-NMR (400 MHz, DMSO-d₆) δ 8.00-8.15 (m, 1H), 7.99 (s, 2H), 7.60-7.70 (m, 1H), 7.30-7.45 (m, 1H), 3.70-3.90 (m, 2H), 3.30-3.40 (m, 2H), 1.70-1.95 (m, 4H), 1.38 (s, 3H) | 405.0 |
| 5C | 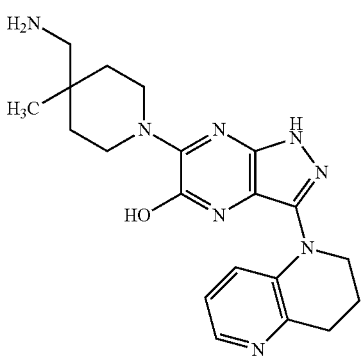 [SMILES: CC1(CN)CCN(c2nc3[nH]nc(N4CCCc5ncccc54)c3nc2O)CC1] | ¹H-NMR (400 MHz, DMSO-d₆) δ 7.78 (d, J = 3.6 Hz, 1H), 6.90-6.87 (m, 1H), 6.52 (d, J = 8.0 Hz, 1H), 4.16-4.13 (m, 2H), 3.56-3.48 (m, 2H), 2.93-2.90 (m, 2H), 2.46 (s, 2H), 2.10-2.07 (m, 2H), 1.55-1.48 (m, 2H), 1.33-1.24 (m, 4H), 0.95 (s, 3H) | 395.0 |
| 6C | 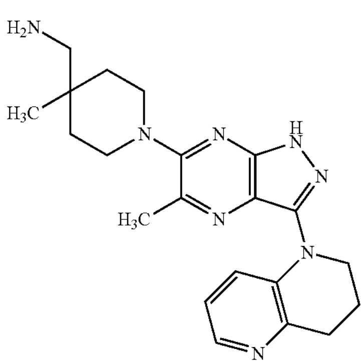 [SMILES: Cc1nc2c(N3CCCc4ncccc43)n[nH]c2nc1N1CCC(C)(CN)CC1] | ¹H-NMR (400 MHz, DMSO-d₆) δ 7.89 (d, J = 3.6 Hz, 1H), 7.37 (d, J = 8.0 Hz, 1H), 6.97-6.94 (m, 1H), 3.96-3.93 (m, 2H), 3.56-3.52 (m, 2H), 3.14-3.09 (m, 2H), 2.97-2.94 (m, 2H), 2.53 (s, 3H), 2.11-2.07 (m, 2H), 1.64-1.59 (m, 2H), 1.44-1.24 (m, 4H), 0.97 (s, 3H) | 393.0 |

| Cmpd. No. | Structure | NMR | Mass Spec. (M + H)+ |
|---|---|---|---|
| 7C | 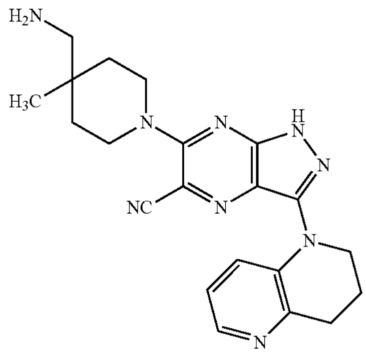 [SMILES: CC1(CN)CCN(c2nc3[nH]nc(N4CCCc5ncccc54)c3nc2C#N)CC1] | ¹H-NMR (400 MHz, methanol-d₄) δ 7.99-7.98 (m, 1H), 7.89-7.87 (m, 1H), 7.13-7.10 (m, 1H), 4.12 (t, J = 5.6 Hz, 2H), 4.02-3.96 (m, 2H), 3.59-3.52 (m, 2H), 3.05 (t, J = 6.4 Hz, 2H), 2.65 (s, 2H), 2.22-2.16 (m, 2H), 1.74-1.67 (m, 2H), 1.59-1.55 (m, 2H), 1.11 (s, 3H) | 404.1 |
| 8C | 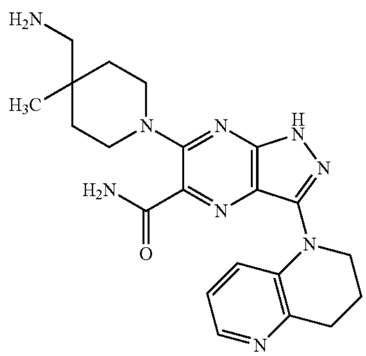 [SMILES: CC1(CN)CCN(c2nc3[nH]nc(N4CCCc5ncccc54)c3nc2C(N)=O)CC1] | ¹H-NMR (400 MHz, DMSO-d₆) δ 13.24 (br, 1H), 8.29 (d, J = 8.4 Hz, 1H), 8.19-8.15 (m, 4H), 8.00 (s, 1H), 7.65-7.62 (m, 2H), 4.11-4.08 (m, 2H), 3.67-3.63 (m, 2H), 3.42-3.37 (m, 2H), 3.29-3.26 (m, 2H), 2.77-2.74 (m, 2H), 2.17-2.14 (m, 2H), 1.62-1.46 (m, 4H), 1.09 (s, 3H) | 422.1 |
| 9C | 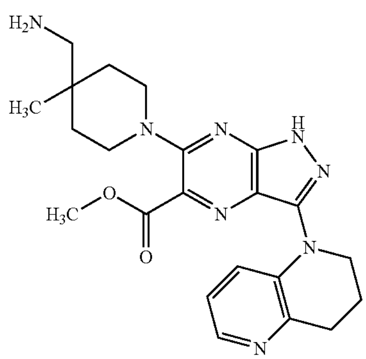 [SMILES: COC(=O)c1nc2c(N3CCCc4ncccc43)n[nH]c2nc1N1CCC(C)(CN)CC1] | ¹H-NMR (400 MHz, DMSO-d₆) δ 13.41 (br, 1H), 8.25-8.17 (m, 5H), 7.64-7.60 (m, 1H), 4.07-4.04 (m, 2H), 3.87 (s, 3H), 3.58-3.54 (m, 2H), 3.37-3.26 (m, 4H), 2.77-2.74 (m, 2H), 2.17-2.14 (m, 2H), 1.60-1.46 (m, 4H), 1.10 (s, 3H) | 437.1 |
| 10C | 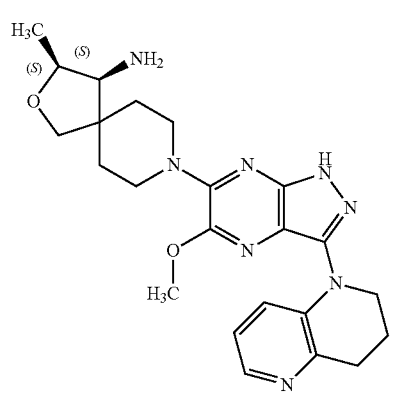 | ¹H-NMR (400 MHz, methanol-d₄) δ 8.09 (d, J = 9.2 Hz, 1H), 8.04 (d, J = 8.8 Hz, 1H), 7.65-7.62 (m, 1H), 4.40-4.32 (m, 3H), 4.09 (t, J = 5.6 Hz, 2H), 4.02 (d, J = 8.8 Hz, 1H), 3.93 (s, 3H), 3.90 (d, J = 9.2 Hz, 1H), 3.50 (d, J = 3.6 Hz, 1H), 3.31-3.16 (m, 4H), 2.35-2.30 (m, 2H), 2.03-1.90 (m, 3H), 1.79-1.75 (m, 1H), 1.35 (d, J = 6.4 Hz, 3H) | 451.1 |

-continued

| Cmpd. No. | Structure | NMR | Mass Spec. (M + H)+ |
|---|---|---|---|
| 11C | (structure) | ¹H-NMR (400 MHz, methanol-d₄) δ 7.90-7.89 (m, 1H), 7.45-7.42 (m, 1H), 7.05-7.01 (m, 1H), 4.72 (s, 2H), 4.05-4.03 (m, 2H), 3.60-3.55 (m, 2H), 3.31-3.28 (m, 2H), 3.06 (t, J = 6.4 Hz, 2H), 2.67 (s, 2H), 2.25-2.19 (m, 2H), 1.76-1.69 (m, 2H), 1.59-1.54 (m, 2H), 1.11 (s, 3H) | 409.1 |
| 12C | (structure) | ¹H-NMR (400 MHz, DMSO-d₆) δ 7.99-7.98 (m, 1H), 7.74-7.72 (m, 1H), 7.06-7.02 (m, 1H), 4.09-4.00 (m, 3H), 3.82-3.76 (m, 2H), 3.68 (d, J = 8.4 Hz, 1H), 3.51-3.48 (m, 3H), 2.96-2.92 (m, 3H), 2.10-2.04 (m, 2H), 1.89-1.61 (m, 4H), 1.10-1.05 (m, 3H) | 446.0 |
| 13C | (structure) | ¹H-NMR (400 MHz, methanol-d4) δ 7.95 (d, J = 5.2 Hz, 1H), 7.81 (d, J = 7.2 Hz, 1H), 7.47-7.44 (m, 1H), 4.26-4.20 (m, 1H), 3.97 (t, J = 5.6 Hz, 2H), 3.90 (d, J = 9.2 Hz, 1H), 3.78 (d, J = 9.2 Hz, 1H), 3.68-3.58 (m, 2H), 3.42 (d, J = 3.9 Hz, 1H), 3.20-3.18 (m, 2H), 3.02-2.91 (m, 2H), 2.54 (s, 3H), 2.25-2.20 (m, 2H), 1.99-1.84 (m, 3H), 1.72-1.69 (m, 1H), 1.25 (d, J = 6.4 Hz, 3H) | 435.1 |
| 14C | (structure) | ¹H-NMR (400 MHz, methanol-d₄) δ 7.90-7.88 (m, 1H), 7.45-7.43 (m, 1H), 7.05-7.01 (m, 1H), 4.73 (s, 2H), 4.29-4.26 (m, 1H), 4.06-4.03 (m, 1H), 3.90 (d, J = 8.8 Hz, 1H), 3.76 (d, J = 8.8 Hz, 1H), 3.70-3.64 (m, 1H), 3.31-3.28 (m, 2H), 3.26-3.04 (m, 7H), 2.25-2.19 (m, 2H), 2.06-1.75 (m, 4H), 1.25 (d, J = 6.4 Hz, 3H) | 451.1 |

-continued
| Cmpd. No. | Structure | NMR | Mass Spec. (M + H)+ |
|---|---|---|---|
| 15C | 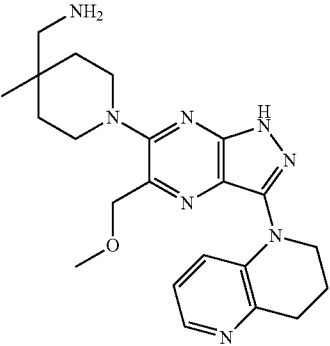 [SMILES: COCc1nc2c(N3CCCc4ncccc43)n[nH]c2nc1N1CCC(C)(CN)CC1] | ¹H NMR (400 MHz, DMSO-d6) Shift 7.91 (br dd, J = 1.34, 4.52 Hz, 1H), 7.47 (br dd, J = 1.22, 8.30 Hz, 1H), 6.95 (br dd, J = 4.52, 8.42 Hz, 1H), 4.42 (s, 2H), 3.94-4.00 (m, 2H), 3.44-3.52 (m, 2H), 3.33 (s, 3H), 3.17-3.25 (m, 2H), 2.94 (br t, J = 6.47 Hz, 2H), 2.44 (br s, 1H), 2.03-2.11 (m, 2H), 1.53-1.64 (m, 3H), 1.33-1.43 (m, 2H), 0.93 (s, 3H) | 423.3 |
| 16C | 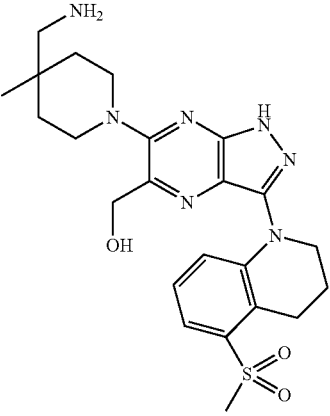 [SMILES: CC1(CN)CCN(c2nc3[nH]nc(N4CCCc5c4cccc5S(C)(=O)=O)c3nc2CO)CC1] | ¹H NMR (400 MHz, DMSO-d6) □ 7.35 (dd, J = 1.59, 7.20 Hz, 1H), 7.07-7.21 (m, 2H), 6.51 (s, 1H), 5.18-5.31 (m, 1H), 4.50 (d, J = 5.62 Hz, 2H), 3.85-3.95 (m, 2H), 3.50 (br d, J = 13.43 Hz, 3H), 3.14-3.26 (m, 8H), 2.03 (quin, J = 6.10 Hz, 2H), 1.51-1.65 (m, 2H), 1.38 (br d, J = 13.18 Hz, 2H), 0.89-1.01 (m, 3H) | 486.2 |
| 17C | 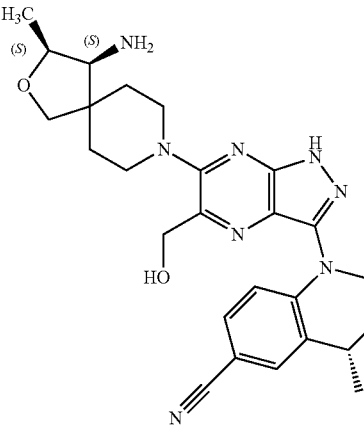 | ¹H NMR (400 MHz, DMSO-d6) □ 489.22 8.27 (s, 1H), 7.52 (d, J = 1.46 Hz, 1H), 7.26 (dd, J = 1.95, 8.54 Hz, 1H), 6.81 (d, J = 8.79 Hz, 1H), 4.52 (s, 2H), 4.08-4.20 (m, 1H), 3.83-3.95 (m, 2H), 3.77 (br d, J = 8.79 Hz, 1H), 3.60 (br d, J = 9.03 Hz, 2H), 3.18 (br d, J = 4.88 Hz, 1H), 2.93-3.12 (m, 3H), 2.53 (s, 1H), 2.00-2.12 (m, 1H), 1.65-1.89 (m, 4H), 1.59 (br d, J = 13.67 Hz, 1H), 1.30 (d, J = 7.08 Hz, 3H), 1.14 (d, J = 6.35 Hz, 3H) | |

| Cmpd. No. | Structure | NMR | Mass Spec. (M + H)+ |
|---|---|---|---|
| 18C | 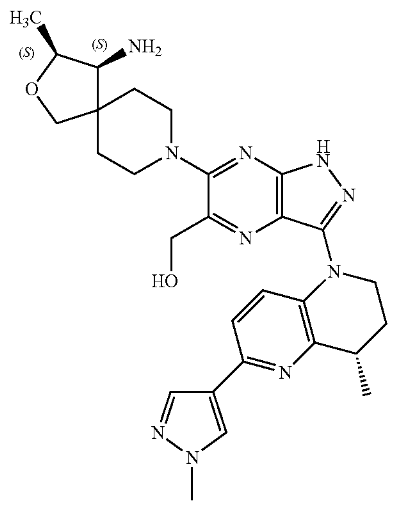 | ¹H NMR (400 MHz, DMSO-d6) ☐ 8.26 (s, 1H), 8.06 (s, 1H), 7.82 (s, 1H), 7.48 (br d, J = 8.54 Hz, 1H), 7.23 (d, J = 8.54 Hz, 1H), 4.53 (s, 2H), 4.09-4.17 (m, 1H), 3.98 (br s, 2H), 3.83 (s, 2H), 3.77 (br d, J = 8.79 Hz, 1H), 3.52-3.59 (m, 4H), 3.19 (br s, 1H), 2.88-3.11 (m, 4H), 1.99-2.12 (m, 2H), 1.77-1.92 (m, 2H), 1.70 (br d, J = 11.96 Hz, 1H), 1.59 (br d, J = 13.18 Hz, 1H), 1.14 (br d, J = 6.35 Hz, 3H) | 531.2 |
| 19C | 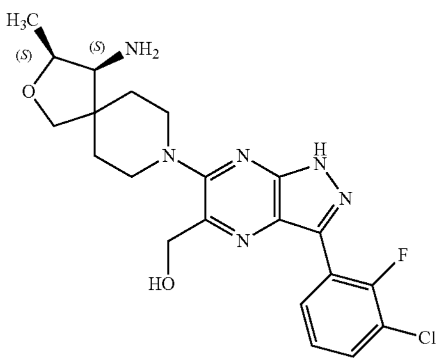 | ¹H NMR (400 MHz, DMSO-d6) Shift 8.30 (s, 1H), 8.14-8.22 (m, 1H), 7.59-7.70 (m, 1H), 7.37 (t, J = 7.93 Hz, 1H), 4.60 (s, 2H), 4.12 (td, J = 6.20, 11.78 Hz, 1H), 3.75 (br d, J = 8.79 Hz, 1H), 3.65 (br d, J = 4.88 Hz, 3H), 2.99-3.21 (m, 3H), 1.76-1.93 (m, 2H), 1.68 (br d, J = 13.67 Hz, 1H), 1.59 (br d, J = 13.43 Hz, 1H), 1.12 (d, J = 6.35 Hz, 3H) | 447.11 |
| 20C | 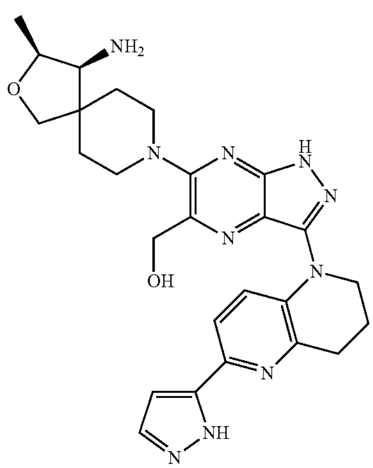 [SMILES: C[C@@H]1OCC2(CCN(c3nc4[nH]nc(N5CCCc6nc(-c7ccn[nH]7)ccc65)c4nc3CO)CC2)[C@@H]1N] | 1H NMR (400 MHz, DMSO-d6) Shift 8.27 (s, 1H), 7.62 (br s, 1H), 7.44-7.56 (m, 2H), 6.66 (d, J = 1.95 Hz, 1H), 4.53 (s, 2H), 4.06-4.19 (m, 1H), 3.91-4.05 (m, 2H), 3.67-3.77 (m, 1H), 3.54-3.66 (m, 3H), 2.94-3.17 (m, 5H), 2.10 (td, J = 6.07, 11.54 Hz, 2H), 1.74-1.94 (m, 2H), 1.52-1.71 (m, 2H), 1.12 (d, J = 6.59 Hz, 3H). | 517.2 |

-continued

| Cmpd. No. | Structure | NMR | Mass Spec. (M + H)+ |
|---|---|---|---|
| 21C | 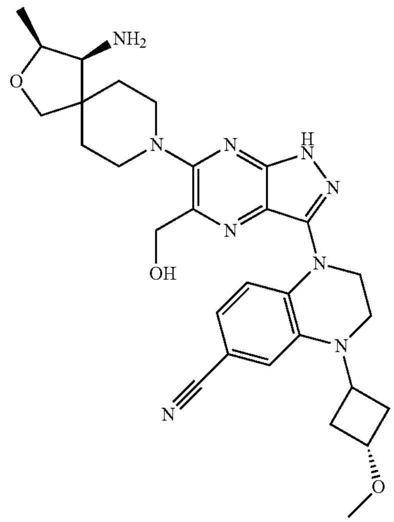 | 1H NMR (400 MHz, DMSO-d6) Shift 8.33 (s, 1H), 7.20-7.36 (m, 1H), 6.85-6.96 (m, 2H), 6.70 (s, 1H), 4.51 (s, 2H), 4.01-4.17 (m, 4H), 3.94 (tt, J = 3.48, 6.41 Hz, 1H), 3.74 (br d, J = 8.79 Hz, 1H), 3.49-3.64 (m, 3H), 3.31 (br t, J = 5.00 Hz, 2H), 3.18 (s, 3H), 2.90-3.14 (m, 3H), 2.24-2.42 (m, 4H), 1.75-1.93 (m, 2H), 1.50-1.70 (m, 2H), 1.12 (d, J = 6.35 Hz, 3H). | 560.2 |
| 22C | 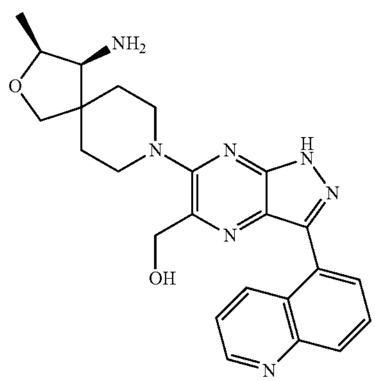 [SMILES: C[C@@H]1OCC2(CCN(c3nc4[nH]nc(-c5cccc6ncccc56)c4nc3CO)CC2)[C@@H]1N] | 1H NMR (400 MHz, DMSO-d6) & amp; #948; ppm 9.00-9.19 (m, 1 H) 8.83-8.95 (m, 1 H) 8.35 (br d, J = 6.59 Hz, 1 H) 8.10 (d, J = 8.30 Hz, 1 H) 7.82-7.97 (m, 1 H) 7.49-7.63 (m, 1 H) 4.60 (s, 2 H) 4.07-4.24 (m, 1 H) 3.58-3.73 (m, 1 H) 3.54-3.73 (m, 1 H) 3.22-3.38 (m, 1 H) 2.91-3.14 (m, 2 H) 1.83-1.98 (m, 2 H) 1.71-1.81 (m, 1 H) 1.54-1.68 (m, 1 H) 1.12-1.20 (m, 3 H). | 446.2 |
| 23C | 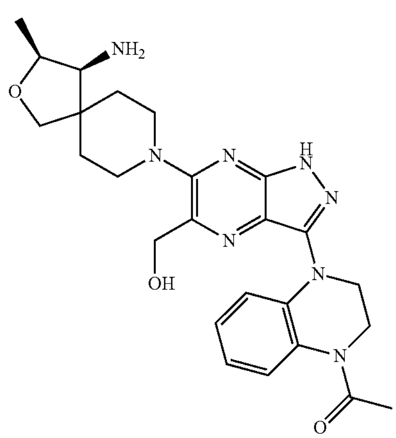 [SMILES: CC(=O)N1CCN(c2n[nH]c3nc(N4CCC5(CC4)CO[C@@H](C)[C@H]5N)c(CO)nc23)c2ccccc21] | 1H NMR (400 MHz, DMSO-d6) Shift 13.02 (br s, 1H), 7.27-7.52 (m, 2H), 7.22 (br s, 1H), 6.95 (br s, 1H), 6.78 (br t, J = 7.32 Hz, 2H), 6.46-6.59 (m, 1H), 5.29 (br s, 1H), 4.53 (br d, J = 4.39 Hz, 2H), 4.03-4.15 (m, 3H), 3.91-3.99 (m, 2H), 3.71 (br d, J = 8.79 Hz, 1H), 3.50-3.63 (m, 3H), 3.04-3.21 (m, 3H), 3.02 (br d, J = 4.88 Hz, 1H), 2.23 (s, 3H), 1.74-1.92 (m, 2H), 1.53-1.69 (m, 2H), 1.11 (d, J = 6.35 Hz, 3H) | 493.2 |

| Cmpd. No. | Structure | NMR | Mass Spec. (M + H)+ |
|---|---|---|---|
| 24C | (structure shown) | 1H NMR (500 MHz, DMSO-d6) δ ppm 8.72 (d, J = 1.30 Hz, 1 H), 8.34 (dd, J = 8.69, 1.69 Hz, 1 H), 7.99 (d, J = 2.33 Hz, 1 H), 7.70 (d, J = 8.82 Hz, 1 H), 6.94-7.14 (m, 1 H), 4.67 (s, 2 H), 4.04-4.12 (m, 1 H), 3.64-3.68 (m, 1 H), 3.51 (br d, J = 8.30 Hz, 2 H), 3.11-3.25 (m, 2 H), 3.07 (br t, J = 10.11 Hz, 1 H), 2.90 (d, J = 5.19 Hz, 1 H), 1.82-1.92 (m, 1 H), 1.73-1.81 (m, 1 H), 1.54-1.66 (m, 2 H), 1.08 (d, J = 6.48 Hz, 3 H). | 435.3 |

The compounds of Formula (XI), for example, can generally be prepared according to exemplary Scheme 6:

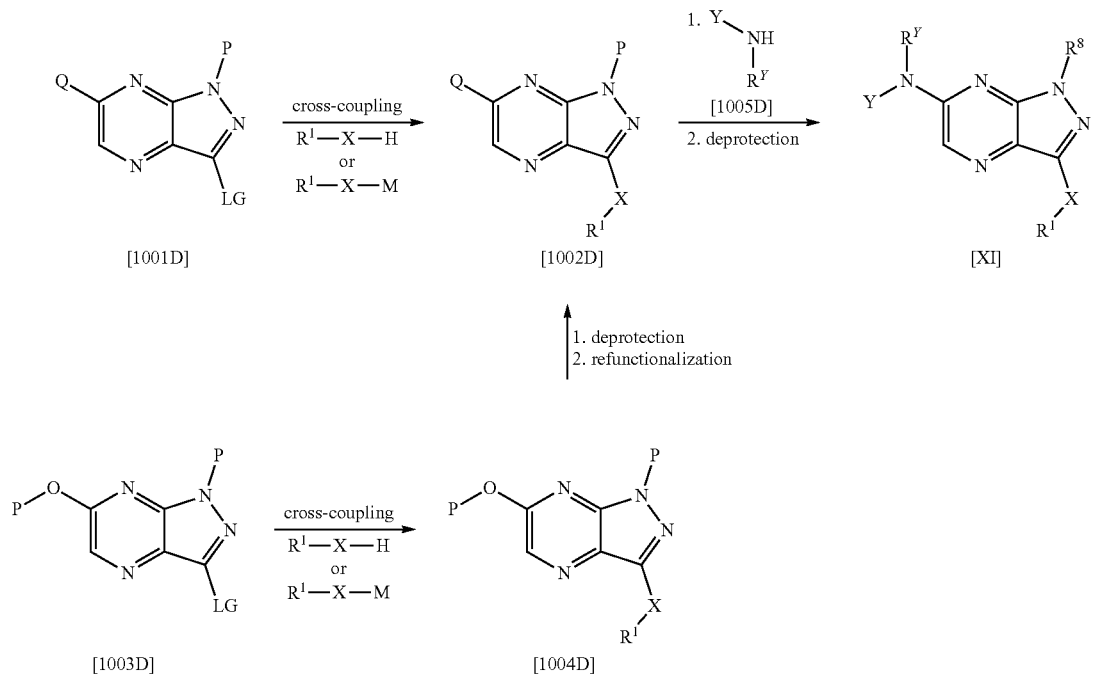

Scheme 6 wherein X, $R^1$, $R^6$, $R^Y$ and R are as defined as elsewhere herein, Q is independently a halogen, such as Cl, Br, I, and the like, or any other leaving group, such as $OSO_2Me$, OMs, OTs, OTf, and the like. LG is a leaving group, such as Cl, Br, I, OTs, OTf, and the like, and P is a protecting group, such as 4-methoxybenzyl and the like. Alternative protecting groups that can be used are described, e.g., in Greene et al., Protective Groups in Organic Synthesis (4th ed. 2006).

As shown in Scheme 6, an aryl compound such as a compound of Formula 1001D undergoes a cross-coupling reaction with a metalated or otherwise activated moiety to provide a compound of Formula 1002D. The compound of Formula 1002D then undergoes a substitution reaction with an amine such as Compound 1005D, followed by removal of the protecting group to provide a compound of Formula (XI). In some embodiments, LG is I. In some embodiments, LG is Cl. In some embodiments, LG is OTf or OTs. Alternatively, a protected heteroaryl ether, such as a compound of Formula 1003D, undergoes a cross-coupling reaction to provide a compound of Formula 1004D. The ether protecting group is subsequently removed and the resulting hydroxyl group activated to form a Q group, such as $OSO_2Me$, OMs, OTs, OTf, and the like, to form a compound of Formula 1002D, which can then be carried forward to prepare compounds having the Formula (XI).

Alternatively, compounds of the disclosure can generally be prepared according to exemplary Scheme 7:

Scheme 7

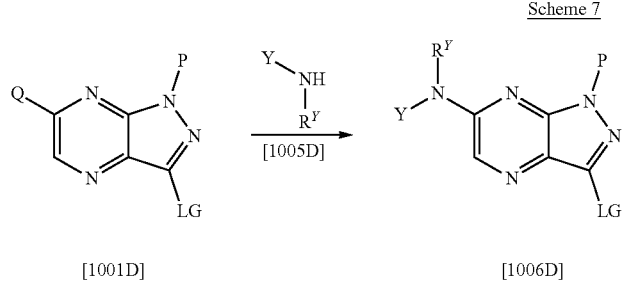

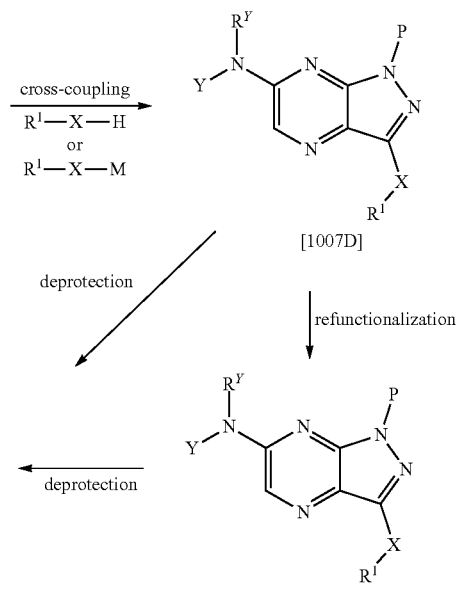

wherein X, $R^1$, $R^6$, $R^Y$ and R are as defined as elsewhere herein, Q is independently a halogen, such as Cl, Br, I, and the like, or any other leaving group, such as $OSO_2Me$, OMs, OTs, OTf, and the like. LG is a leaving group, such as Cl, Br, I, OTs, OTf, and the like, and P is a protecting group, such as 4-methoxybenzyl and the like. Alternative protecting groups that can be used are described, e.g., in Greene et al., Protective Groups in Organic Synthesis ($4^{th}$ ed. 2006).

As shown in Scheme 7, an aryl compound such as a compound of Formula 1001D undergoes a undergoes a substitution reaction with an amine such as 1005D to provide a compound of Formula 1006D. The compound of Formula 1006D then undergoes a cross-coupling reaction with a metalated or otherwise activated moiety to provide a compound of Formula 1007D. In some embodiments, the compound of Formula 1007D can be deprotected to produce a compound of Formula (XI). In other embodiments, the compound of Formula 1007D can be left protected and functional groups on the $R^1$ moiety refunctionalized by methods known to those of ordinary skill in the art.

In some embodiments, the cross-coupling reaction is a Buchwald-Hartwig reaction. In some embodiments, the cross-coupling reaction is a Chan-Lam coupling reaction. In some embodiments, the cross-coupling reaction is an Ullmann reaction. In some embodiments, the cross-coupling reaction is a Suzuki reaction. In some embodiments, the cross-coupling reaction is a Stille reaction. In some embodiments, the cross-coupling reaction is a Negishi reaction. In some embodiments, the cross-coupling reaction is a Hiyama reaction. Other cross-coupling reactions may be employed as would be apparent to one of ordinary skill in the art.

In some embodiments, the protecting group is removed under acidic conditions, such as HBr in AcOH. Conditions for removal of the protecting group will depend on the nature of the protecting group. Conditions for the removal of various protecting groups can be found, e.g., in Greene et al., Protective Groups in Organic Synthesis ($4^{th}$ ed. 2006).

Compound 6D: Preparation of N-(3-(aminomethyl)pyridin-2-yl)-3-(3-chloro-2-fluorophenyl)-N-methyl-1H-pyrazolo[3,4-b]pyrazin-6-amine

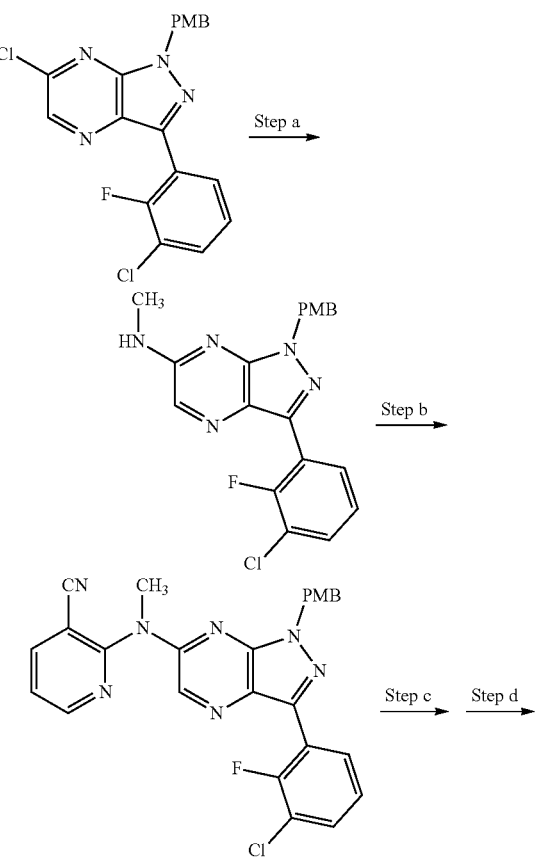

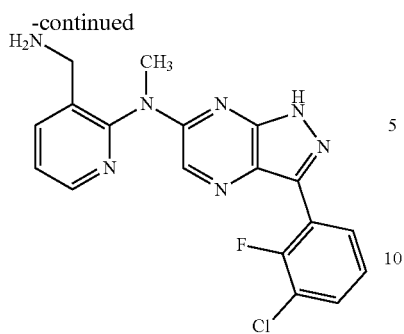

Step a: A mixture of 6-chloro-3-(3-chloro-2-fluorophenyl)-1-(4-methoxybenzyl)-1H-pyrazolo[3,4-b]pyrazine (400 mg, 991 μmol), MeNH₂ (153 mg, 4.95 mmol) was taken up in NMP (4.0 mL) in a sealed tube and heated at 100° C. for 2 hrs. The reaction mixture was cooled, diluted with EtOAc (50 mL), washed with water (30 mL×3), dried over anhydrous Na₂SO₄, filtered, and concentrated under reduced pressure to give 3-(3-chloro-2-fluorophenyl)-1-(4-methoxybenzyl)-N-methyl-1H-pyrazolo[3,4-b]pyrazin-6-amine (360 mg, 91% yield) as yellow solid: ¹HNMR (400 MHz, CDCl₃): 7.97-7.92 (m, 1H), 7.89 (s, 1H), 7.43-7.38 (m, 3H), 7.20-7.15 (m, 1H), 6.84 (d, J=8.4 Hz, 2H), 5.53 (s, 2H), 5.00 (q, J=4.8 Hz, 1H), 3.77 (s, 3H), 3.00 (d, J=4.8 Hz, 3H).

Step b: To a mixture of 3-(3-chloro-2-fluorophenyl)-1-[(4-methoxyphenyl)methyl]-N-methyl-1H-pyrazolo[3,4-b]pyrazin-6-amine (360 mg, 904 μmol), 2-chloropyridine-3-carbonitrile (249 mg, 1.80 mmol) in NMP (5.0 mL) was added Cs₂CO₃ (442 mg, 1.35 mmol) and CsF (273.0 mg, 1.80 mmol). The reaction mixture was stirred at 130° C. for 3 hrs. After cooling, the mixture was diluted with EtOAc (50 mL), washed with water (30 mL×3), dried over anhydrous Na₂SO₄, filtered, and concentrated under reduced pressure. The residue was purified by silica gel chromatography (petroleum ether/EtOAc=2/1) to give 2-{[3-(3-chloro-2-fluorophenyl)-1-[(4-methoxyphenyl)methyl]-1H-pyrazolo[3,4-b]pyrazin-6-yl](methyl)amino}pyridine-3-carbonitrile (240 mg, 53% yield) as yellow solid.

Step c: To a solution of 2-{[3-(3-chloro-2-fluorophenyl)-1-[(4-methoxyphenyl)methyl]-1H-pyrazolo[3,4-b]pyrazin-6-yl](methyl)amino}pyridine-3-carbonitrile (240 mg, 480 μmol) in THF (20 mL) was added Raney Ni (150 mg) and aqueous ammonia (2.0 mL). The reaction mixture was hydrogenated under an atmosphere of H₂ (15 psi) at 30° C. for 12 hrs. The mixture was filtered through a pad of diatomaceous earth and washed with MeOH (20 mL). The filtrate was concentrated under reduced pressure to give 3-(aminomethyl)-N-[3-(3-chloro-2-fluorophenyl)-1-[(4-methoxyphenyl)methyl]-1H-pyrazolo[3,4-b]pyrazin-6-yl]-N-methylpyridin-2-amine (235 mg, 98% yield) as yellow solid.

Step d: A solution of 3-(aminomethyl)-N-[3-(3-chloro-2-fluorophenyl)-1-[(4-methoxyphenyl)methyl]-1H-pyrazolo[3,4-b]pyrazin-6-yl]-N-methylpyridin-2-amine (220.0 mg, 436.0 μmol) in TFA/TfOH (5.0 mL/0.5 mL) was stirred at 30° C. for 12 hrs. The volatiles were removed under reduced pressure, the residue as dissolved in MeCN (5 mL), and the pH adjusted to 8.0 with 2N K₂CO₃. The mixture was filtered and purified by prep-HPLC (acetonitrile/aq. NH₃) to give N-(3-(Aminomethyl)pyridin-2-yl)-3-(3-chloro-2-fluorophenyl)-N-methyl-1H-pyrazolo[3,4-b]pyrazin-6-amine (77.0 mg, 46.1% yield) as a yellow solid: LCMS [M+H]⁺=383.9; ¹H-NMR (400 MHz, CDCl₃) δ 8.52-8.49 (m, 1H), 8.10-8.02 (m, 2H), 7.74 (s, 1H), 7.44-7.37 (m, 2H), 7.22-7.18 (m, 1H), 4.76 (br, 2H), 3.85 (s, 2H), 3.55 (s, 3H).

Compound 2D: Preparation of N-(3-(2-aminoethyl)pyridin-2-yl)-3-(3-chloro-2-fluorophenyl)-N-methyl-1H-pyrazolo[3,4-b]pyrazin-6-amine

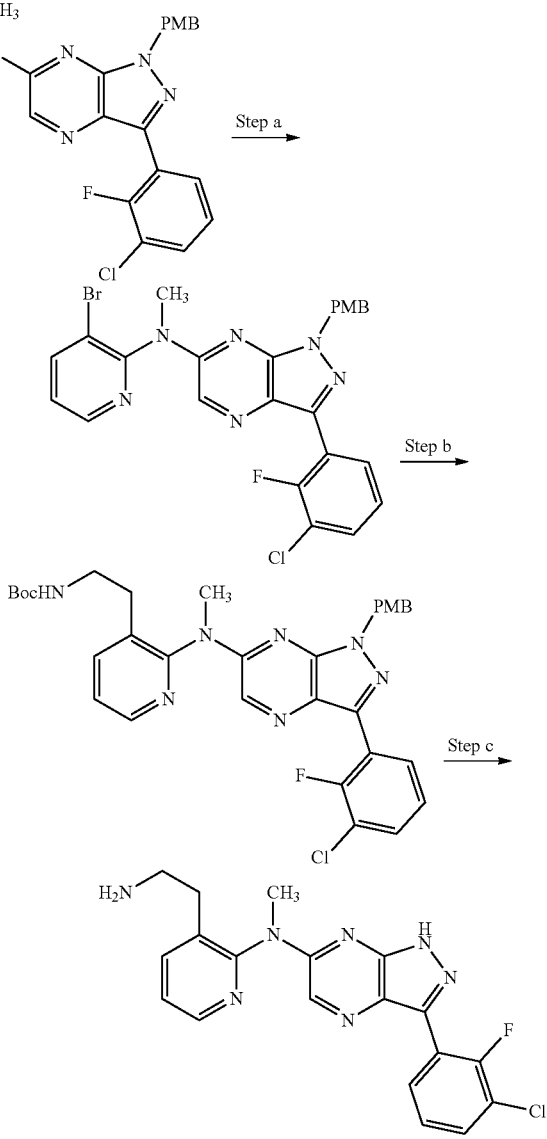

Step a: A mixture of 3-(3-chloro-2-fluorophenyl)-1-[(4-methoxyphenyl)methyl]-N-methyl-1H-pyrazolo[3,4-b]pyrazin-6-amine (250 mg, 628 μmol), 3-bromo-2-fluoropyridine (330 mg, 1.88 mmol), and Cs₂CO₃ (308.0 mg, 942.0 umol) in NMP (0.5 mL) was stirred at 150° C. for 4 hrs. The reaction mixture was cooled, poured into water (20 mL), and extracted with EtOAc (20.0 mL×2). The organics were concentrated under reduced pressure and purified by silica gel chromatography (0-30% EtOAc/petroleum ether) to give 3-bromo-N-[3-(3-chloro-2-fluorophenyl)-1-[(4-methoxyphenyl)methyl]-1H-pyrazolo[3,4-b]pyrazin-6-yl]-N-methylpyridin-2-amine (250 mg, 72% yield) as yellow solid.

Step b: A mixture of 3-bromo-N-[3-(3-chloro-2-fluorophenyl)-1-[(4-methoxyphenyl)methyl]-1H-pyrazolo[3,4-b]pyrazin-6-yl]-N-methylpyridin-2-amine (250. mg, 451 µmol), tert-butyl N-[2-(trifluoro-λ⁴-boranyl)ethyl]carbamate potassium hydride (340 mg, 1.35 mmol), Pd(dppf)Cl₂ (65.9 mg, 90.2 umol), and Cs₂CO₃ (295 mg, 902 umol) in toluene/H₂O (20 mL/4 mL) was stirred at 85° C. for 14 hrs. under N₂. After cooling, the reaction mixture was diluted with EtOAc (50 mL) and the organics washed with water (30 mL×2), dried over anhydrous Na₂SO₄, filtered, and concentrated under reduced pressure. The residue was purified by silica gel chromatographyt (0-50% EtOAc/petroleum ether) to give tert-butyl N-[2-(2-{[3-(3-chloro-2-fluorophenyl)-1-[(4-methoxyphenyl)methyl]-1H-pyrazolo[3,4-b]pyrazin-6-yl](methyl)amino}pyridin-3-yl)ethyl]carbamate (140 mg, 50% yield) as yellow solid.

Step c: A solution of tert-butyl N-[2-(2-{[3-(3-chloro-2-fluorophenyl)-1-[(4-methoxyphenyl)methyl]-1H-pyrazolo[3,4-b]pyrazin-6-yl](methyl)amino}pyridin-3-yl)ethyl]carbamate (130 mg, 210 µmol) in TFA/TfOH (5 mL, 10:1) was stirred at 25° C. for 2 hrs under N₂. The reaction mixture was cooled and the volatiles removed under reduced pressure. The residue was diluted with EtOAc (50 mL), washed with saturated NaHCO₃ (20 mL×2), and the organics dried over anhydrous Na₂SO₄, filtered, and concentrated under reduced pressure. The residue was purified by prep-HPLC (acetonitrile/aq. NH₃) to give N-(3-(2-aminoethyl)pyridin-2-yl)-3-(3-chloro-2-fluorophenyl)-N-methyl-1H-pyrazolo[3,4-b]pyrazin-6-amine (32.0 mg, 38.3% yield) as a white solid: LCMS [M+H]⁺=398.4; ¹H-NMR (400 MHz, CDCl₃) δ 8.43-8.40 (m, 1H), 8.04-8.01 (m, 1H), 7.75-7.71 (m, 1H), 7.62 (s, 1H), 7.35-7.24 (m, 2H), 7.13-7.07 (m, 1H), 3.46 (s, 3H), 2.93 (t, J=6.8 Hz, 2H), 2.69 (t, J=6.8 Hz, 2H).

Compound 3D: Preparation of N-(3-(2-aminoethyl)pyridin-2-yl)-3-(3,4-dihydro-1,5-naphthyridin-1(2H)-yl)-N-methyl-1H-pyrazolo[3,4-b]pyrazin-6-amine

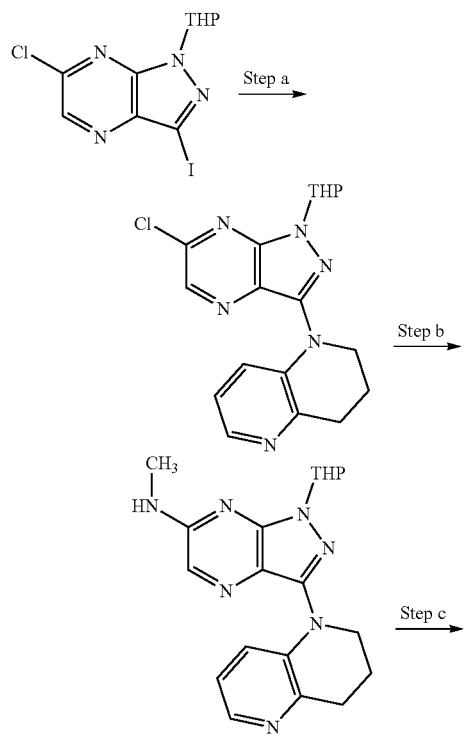

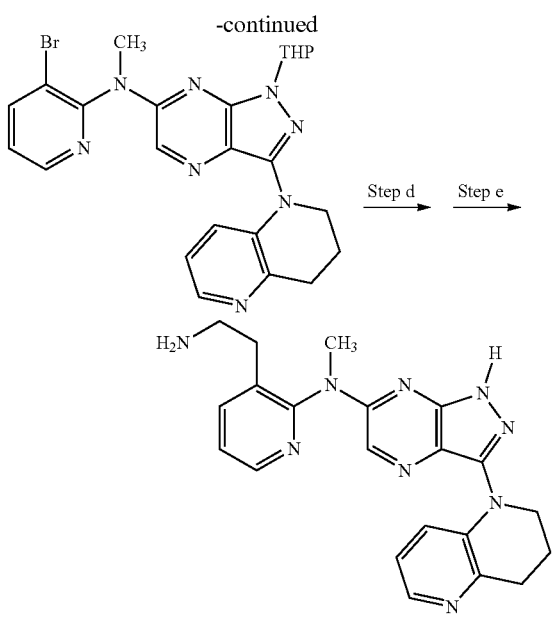

Step a: A solution of 6-chloro-3-iodo-1-(oxan-2-yl)-1H-pyrazolo[3,4-b]pyrazine (300 mg, 822 µmol), 1,2,3,4-tetrahydro-1,5-naphthyridine (121 mg, 904 umol), XantPhos (47.5 mg, 82.2 µmol), Pd₂(dba)₃ (75.2 mg, 82.2 µmol), and t-BuONa (157 mg, 1.6 mmol) in toluene (40 mL) was purged with N₂ for 3 min and stirred at 100° C. for 2 hours. After cooling, the mixture was concentrated under reduced pressure and purified by flash silica gel chromatography (50% EtOAc/petroleum ether) to afford 1-[6-chloro-1-(oxan-2-yl)-1H-pyrazolo[3,4-b]pyrazin-3-yl]-1,2,3,4-tetrahydro-1,5-naphthyridine (130 mg, 43% yield) as a yellow oil.

Step b: 1-[6-Chloro-1-(oxan-2-yl)-1H-pyrazolo[3,4-b]pyrazin-3-yl]-1,2,3,4-tetrahydro-1,5-naphthyridine (130 mg, 350 µmol) was taken up in THF (2 mL) and 2M NH₃/THF (3.5 mL) was added. The mixture stirred at 110° C. for 4 hrs. After cooling, the resulting residue was purified by silica gel chromatography (50-70% EtOAc/peptroleum ether) to give N-methyl-1-(oxan-2-yl)-3-(1,2,3,4-tetrahydro-1,5-naphthyridin-1-yl)-1H-pyrazolo[3,4-b]pyrazin-6-amine (90 mg, 71% yield) as a yellow oil.

Step c: A solution of N-methyl-1-(oxan-2-yl)-3-(1,2,3,4-tetrahydro-1,5-naphthyridin-1-yl)-1H-pyrazolo[3,4-b]pyrazin-6-amine (110 mg, 301 µmol), Cs₂CO₃ (195 mg, 602 µmol) and 3-bromo-2-fluoropyridine (211 mg, 1.2 mmol) in NMP (2 mL) was stirred at 150° C. for 6 hours. The reaction mixture was cooled, poured into water (20 mL), and extracted with EtOAc (20 mL×2). The organics were concentrated under reduced pressure and purified by silica gel column (50-100% EtOAc/peptroleum ether) to give 3-bromo-N-methyl-N-[1-(oxan-2-yl)-3-(1,2,3,4-tetrahydro-1,5-naphthyridin-1-yl)-1H-pyrazolo[3,4-b]pyrazin-6-yl]pyridin-2-amine (70 mg, 45%) as a yellow solid.

Step d: A mixture of 3-bromo-N-methyl-N-[1-(oxan-2-yl)-3-(1,2,3,4-tetrahydro-1,5-naphthyridin-1-yl)-1H-pyrazolo[3,4-b]pyrazin-6-yl]pyridin-2-amine (120 mg, 230 µmol), potassium tert-butyl N-[2-(difluoroboranyl)ethyl]carbamate fluoride (173 mg, 690 µmol), Cs2CO₃ (149 mg, 460 µmol), and Pd(dppf)Cl₂ (16.8 mg, 23.0 µmol) in toluene/H₂O (5 mL/1 mL) was stirred at 85° C. for 14 hours under N₂. The reaction mixture was cooled, diluted with EtOAc (50 mL), and washed with water (30 mL×2). The organics were dried over anhydrous Na₂SO₄, filtered, concentrated under reduced pressure, and purified by silica gel chromatography (50-100% EtOAc/peptroleum ether) to give tert-butyl N-[2-(2-{methyl[1-(oxan-2-yl)-3-(1,2,3,4-tetrahydro-1,5-naphthyridin-1-yl)-1H-pyrazolo[3,4-b]pyrazin-6-yl]amino}pyridin-3-yl)ethyl]carbamate (45 mg, 34% yield) as a yellow solid.

Step e: To a solution of tert-butyl N-[2-(2-{methyl[1-(oxan-2-yl)-3-(1,2,3,4-tetrahydro-1,5-naphthyridin-1-yl)-1H-pyrazolo[3,4-b]pyrazin-6-yl]amino}pyridin-3-yl)ethyl]carbamate (45 mg, 76.8 μmol) in MeOH (1 mL) at 0° C. was added 4M HCl/MeOH (2 mL) and the mixture stirred at 20° C. for 6 hours. After cooling, the reaction mixture was concentrated under reduced pressure and purified by prep-HPLC (acetonitrile/aq. HCl) to afford N-(3-(2-aminoethyl)pyridin-2-yl)-3-(3,4-dihydro-1,5-naphthyridin-1(2H)-yl)-N-methyl-1H-pyrazolo[3,4-b]pyrazin-6-amine hydrochloride (16.6 mg, 49% yield) as a yellow solid: LCMS [M+H]⁺=402.0; ¹H-NMR (400 MHz, methanol-d₄) δ 8.75-8.72 (m, 1H), 8.68-8.62 (m, 1H), 8.31~8.27 (m, 2H), 8.14~8.11 (m, 1H), 7.92~7.90 (m, 1H), 7.62~7.60 (m, 1H), 4.19~4.16 (m, 2H), 3.72 (s, 3H), 3.30~3.24 (m, 4H), 3.15~3.12 (m, 2H), 2.28~2.22 (m, 2H).

The characterization of compounds disclosed herein is shown below.

| Cmpd. No. | Structure | NMR | Mass Spec. (M + H)⁺ |
|---|---|---|---|
| 1D | 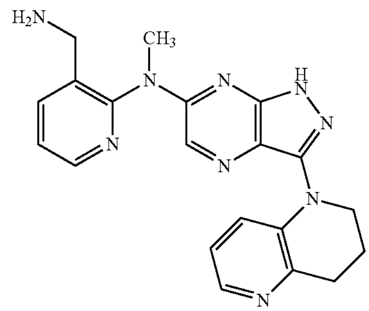 [SMILES: CN(c1cnc2c(N3CCCc4ncccc43)n[nH]c2n1)c1ncccc1CN] | ¹H-NMR (400 MHz, CDCl₃) δ 8.52-8.49 (m, 1H), 8.10-8.02 (m, 2H), 7.74 (s, 1H), 7.44-7.37 (m, 2H), 7.22-7.18 (m, 1H), 4.76 (br, 2H), 3.85 (s, 2H), 3.55 (s, 3H) | 383.9 |
| 2D | 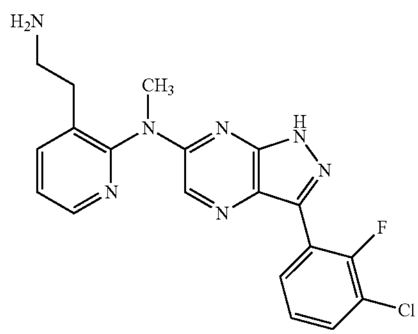 [SMILES: CN(c1cnc2c(-c3cccc(Cl)c3F)n[nH]c2n1)c1ncccc1CCN] | ¹H-NMR (400 MHz, CDCl₃) δ 8.43-8.40 (m, 1H), 8.04-8.01 (m, 1H), 7.75-7.71 (m, 1H), 7.62 (s, 1H), 7.35-7.24 (m, 2H), 7.13-7.07 (m, 1H), 3.46 (s, 3H), 2.93 (t, J = 6.8 Hz, 2H), 2.69 (t, J = 6.8 Hz, 2H). | 398.4 |
| 3D | 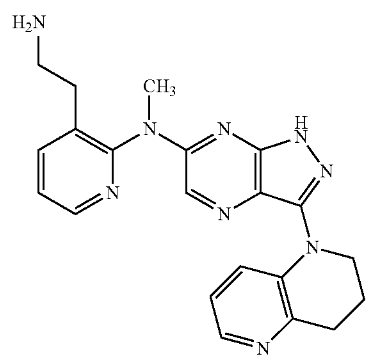 [SMILES: CN(c1cnc2c(N3CCCc4ncccc43)n[nH]c2n1)c1ncccc1CCN] | ¹H-NMR (400 MHz, methanol-d₄): δ 8.75~8.72 (m, 1H), 8.68~8.62 (m, 1H), 8.31~8.27 (m, 2H), 8.14~8.11 (m, 1H), 7.92~7.90 (m, 1H), 7.62~7.60 (m, 1H), 4.19~4.16 (m, 2H), 3.72 (s, 3H), 3.30~3.24 (m, 4H), 3.15~3.12 (m, 2H), 2.28~2.22 (m, 2H). | 402.0 |

-continued

| Cmpd. No. | Structure | NMR | Mass Spec. (M + H)+ |
|---|---|---|---|
| 4D | 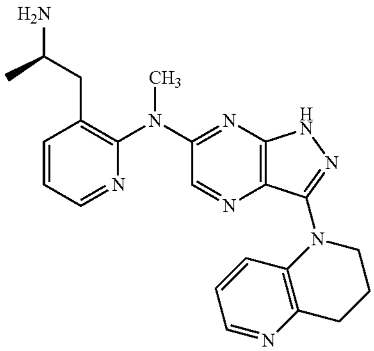 [SMILES: C[C@@H](N)Cc1cccnc1N(C)c1cnc2c(N3CCCc4ncccc43)n[nH]c2n1] | | 412.1 |
| 5D | 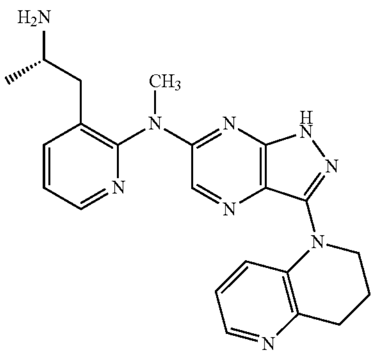 [SMILES: C[C@H](N)Cc1cccnc1N(C)c1cnc2c(N3CCCc4ncccc43)n[nH]c2n1] | | 412.1 |

SPH2 Allosteric Inhibition Assay and Binding.

SHP2 is allosterically activated through binding of bis-tyrosyl-phosphorylated peptides to its Src Homology 2 (S12) domains. The latter activation step leads to the release of the auto-inhibitory interface of SHP2, which in turn renders the SH1P2 protein tyrosine phosphatase (PTP) active and available for substrate recognition and reaction catalysis. The catalytic activity of SHP2 was monitored using the surrogate substrate DiFMIP in a prompt fluorescence assay format.

More specifically, the phosphatase reactions were performed at room temperature in 96-well black polystyrene plate, flat bottom, low flange, non-binding surface (Corning, Cat #3575) using a final reaction volume of 50 µl and the following assay buffer conditions: 60 mM HEPES, pH 7.2, 75 mM NaCl, 75 mM KCl, 1 mM EDTA 0.005% Brij-35, 5 mM DTT.

The inhibition of SHP2 by compounds of the disclosure (concentrations varying from 0.003-100 µM) was monitored using an assay in which 0.25 nM of SH1P2 was incubated with of 0.5 µM of peptide IRS1_pY1172(dPEG8)pY1222 (sequence: H2N-LN(pY)IDLDLV(dPEG8)LST(pY)AS-INFQK-amide) (SEQ ID NO: 4). After 30-60 minutes incubation at 25° C., the surrogate substrate DiFMUP (Invitrogen, cat #D6567, 100 µM final) was added to the reaction and the conversion of DiFMUP to 6,8-difluoro-7-hydroxyl-4-methylcoumarin (DiFMU) was monitored continuously for 10 minutes with excitation at 355 nm and emission at 460 nm using a microplate reader (PolarStar, BMG). The inhibitor dose response curves were analyzed using normalized $IC_{50}$ regression curve fitting with control based normalization.

Biochemical assay results for compounds of the disclosure are shown in Table 1. In Table 1, A means an $IC_{50}$ of less than 1 µM; B means an $IC_{50}$ equal to 1 µM but less than 10 µM; and C means an $IC_{50}$ of 10 µM or more. The FIGURE shows the binding of compound 6A with SHP2.

TABLE 1

| SHP2 $IC_{50}$ Assay Results | |
|---|---|
| Compound No. | $IC_{50}$ |
| 1A | C |
| 2A | C |
| 3A | A |
| 4A | C |
| 5A | A |
| 6A | A |
| 7A | A |
| 8A | C |

Biochemical assay results for compounds of the disclosure are shown in Table 2. In Table 2, A means an $IC_{50}$ of less than 1 µM; B means an $IC_{50}$ equal to 1 µM but less than 10 µM; and C means an $IC_{50}$ of 10 µM or more.

TABLE 2

| SHP2 $IC_{50}$ Assay Results | |
|---|---|
| Compound No. | $IC_{50}$ |
| 1B | A |
| 2B | A |
| 3B | A |
| 4B | A |

TABLE 2-continued

SHP2 IC$_{50}$ Assay Results

| Compound No. | IC$_{50}$ |
| --- | --- |
| 5B | B |
| 6B | C |
| 7B | C |
| 8B | A |
| 9B | C |
| 10B | C |
| 11B | C |
| 12B | C |
| 13B | C |
| 14B | A |
| 15B | B |
| 16B | A |
| 17B | B |
| 18B | A |
| 19B | B |

Biochemical assay results for compounds of the disclosure are shown in Table 3. In Table 3, A means an IC$_{50}$ of less than 1 μM; B means an IC$_{50}$ equal to 1 μM but less than 10 μM; and C means an IC$_{50}$ of 10 μM or more

TABLE 3

SHP2 IC$_{50}$ Assay Results

| Compound No. | IC$_{50}$ |
| --- | --- |
| 1C | A |
| 2C | A |
| 3C | A |
| 4C | B |
| 5C | A |
| 6C | A |
| 7C | A |
| 8C | A |
| 9C | A |
| 10C | A |
| 11C | A |
| 12C | A |
| 13C | A |
| 14C | A |
| 15C | A |
| 16C | A |
| 17C | A |
| 18C | A |
| 19C | A |
| 20C | A |
| 21C | A |
| 22C | A |
| 23C | A |
| 24C | A |

Biochemical assay results for compounds of the disclosure are shown in Table 4. In Table 4, A means an IC$_{50}$ of less than 1 μM; B means an IC$_{50}$ equal to 1 μM but less than 10 μM; and C means an IC$_{50}$ of 10 μM or more

TABLE 4

SHP2 IC$_{50}$ Assay Results

| Compound No. | IC$_{50}$ |
| --- | --- |
| 1D | A |
| 2D | A |
| 3D | B |
| 4D | A |
| 5D | A |

INCORPORATION BY REFERENCE

All publications and patents mentioned herein are hereby incorporated by reference in their entirety for all purposes as if each individual publication or patent was specifically and individually incorporated by reference. In case of conflict, the present application, including any definitions herein, will control.

EQUIVALENTS

While specific embodiments of the subject disclosure have been discussed, the above specification is illustrative and not restrictive. Many variations of the present disclosure will become apparent to those skilled in the art upon review of this specification. The full scope of the disclosure should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present disclosure.

What is claimed is:

1. A compound having Formula i, ii, iii, or iv, or a pharmaceutically acceptable salt or stereoisomer thereof:

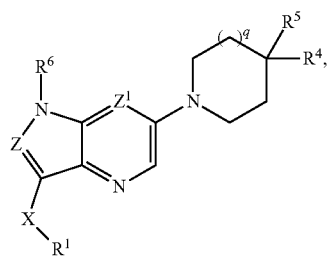

(i)

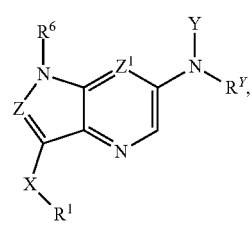

(ii)

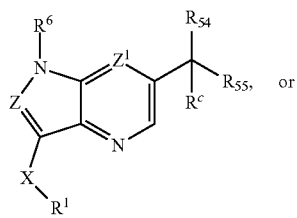

(iii)

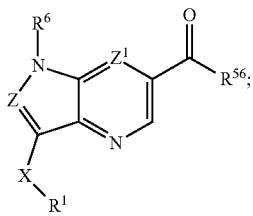

(iv)

wherein:

$Z^1$ is N or CH;

Z is N or CH;

X is selected from the group consisting of a bond, —O—, —NR$^{X1}$—, and —S(O)$_w$—;

w is 0, 1 or 2;

R$^{X1}$ is selected from the group consisting of hydrogen, —(C$_1$-C$_6$)alkyl and phenyl;

R$^1$ is a ring moiety selected from the group consisting of a 8-12 membered bicyclic heteroaryl, a 11-15 membered tricyclic heteroaryl, phenyl, a 5-7 membered monocyclic heteroaryl, and a 4-7 membered heterocyclyl, wherein the ring moiety is substituted with —O—S(O)2-F or —S(O)2-F, and wherein the ring moiety may additionally and optionally be further substituted with one, two or more substituents each independently selected from the group consisting of R$^{10}$, —OR$^{10}$, —S(O)$_w$R$^{10}$, —C$_{1-6}$alkyl-S(O)$_w$—C$_{1-3}$alkyl, —N(R$^{10}$)$_2$, —N(CO)R$^{10}$, —N—S(O)$_w$—R$^{10}$, —OS(O)$_w$—R$^{10}$, —S(O)$_w$—N(R$^{10}$)$_2$, —S(O)(NH)R$^{10}$, —N(H)—SO$_2$—C$_{1-3}$alkyl, —N(SO$_2$—C$_{1-3}$alkyl)$_2$, P(O)(R$^{10}$)$_2$, —C(O)R$^{10}$, —C(O)OR$^{10}$, —C(O)N(R$^{10}$)$_2$, oxo, halogen, hydroxyl, cyano, nitro, —C(=N—OR$^a$)—C$_{1-3}$alkyl, —C(=N—OR$^a$)—H, —S(O)(NR$^a$)—C$_{1-3}$alkyl, phenyl (optionally substituted with one, two or three halogen, —O-phenyl, C$_{1-3}$alkyl or C$_{1-3}$haloalkyl), C$_{1-3}$alkyl, C$_{2-6}$alkynyl, C$_{1-3}$haloalkyl, C$_{3-6}$cycloalkyl, heterocyclyl (optionally substituted with one, two or three halogen, oxo, C$_{1-3}$alkyl or C$_{1-3}$haloalkyl), and heteroaryl (optionally substituted with one, two or three halogen, —C(O)N(R$^{10}$)$_2$, C$_{1-3}$alkyl, C$_{1-3}$alkyl-O—C$_{1-3}$alkyl, C$_{1-3}$alkyl-OH, or C$_{1-3}$haloalkyl);

R$^{10}$ is independently selected from the group consisting of hydrogen, C$_{1-6}$alkyl, C$_{2-6}$ alkenyl, C$_{2-6}$alkynyl, C$_{3-6}$cycloalkyl, C$_{5-6}$cycloalkenyl, C$_{2-6}$heteroalkyl, heterocycloalkyl, aryl, and heteroaryl; wherein C$_{1-6}$alkyl, C$_{2-6}$alkenyl, C$_{2-6}$alkynyl, C$_{3-6}$cycloalkyl, C$_{5-6}$cycloalkenyl, C$_{2-6}$ heteroalkyl, heterocycloalkyl, aryl, and heteroaryl is optionally substituted by one, two, three or more substituents each independently selected from the group consisting of halogen, hydroxyl, —NR$^a$C(O)—R$^{20}$, —C(O)—R$^{20}$, —C(NR$^a$)—R$^b$, —NR$^a$R$^b$, C$_{1-6}$alkyl, C$_{1-6}$haloalkyl and C$_{1-6}$alkoxy;

R$^{20}$ is selected from the group consisting of hydrogen, hydroxyl, halogen, —NR$^a$R$^b$, C$_{1-6}$alkyl and C$_{1-6}$alkoxy;

R$^a$ and R$^b$ are each independently selected from the group consisting of hydrogen and C$_{1-3}$alkyl;

R$^6$ is independently for each occurrence selected from the group consisting of H, —(C$_{1-6}$)alkyl, —C(O)OC$_{1-4}$alkyl, and phenyl;

q is 0 or 1;

R$^Y$ is selected from the group consisting of hydrogen and —(C$_1$-C$_6$)alkyl;

Y is selected from the group consisting of a 3-7 membered saturated carbocycle, a 4-7 membered saturated heterocycle, phenyl, and a 5-6 membered monocyclic heteroaryl; wherein Y is optionally substituted with one or more substituents each independently selected from the group consisting of (C$_1$-C$_6$)alkyl, —C(O)N(R$^6$)$_2$, —N(R$^6$)$_2$, halogen, and cyano, wherein said —(C$_1$-C$_6$) alkyl is optionally substituted with one or more substituents selected from the group consisting of —OH, —N(R$^6$)$_2$, oxo, and halogen;

R$^{55}$ is selected from the group consisting of —C$_{1-4}$alkyl-N(R$^6$)$_2$, —N(R$^6$)$_2$, and heteroaryl (optionally substituted by one, two, or three substituent each independently selected from halogen, hydroxyl, cyano, —(C$_1$-C$_6$)alkyl, and —O(C$_1$-C$_6$) alkyl, —C(O)N(R$^6$)$_2$, —N(R$^6$)$_2$, and —(C$_1$-C$_6$)alkyl-N(R$^6$)$_2$);

R$^{54}$ is selected from the group consisting of H, and C$_{1-2}$alkyl, or

R$^{54}$ and R$^{55}$ taken together with the carbon to which they are attached form a ring selected from the group consisting of C$_{3-6}$cycloalkyl and heterocyclyl, wherein the ring is optionally substituted on a carbon by one, two or three substituents each independently selected from the group consisting of R$^4$ and R$^5$ and on a nitrogen if present by R$^6$;

R$^C$ is selected from the group consisting of H, OH, —(C$_1$-C$_6$)alkyl, —C(O)—O—C$_{1-6}$(alkyl), —C(O)—C$_{1-6}$(alkyl), and heterocyclyl, wherein C$_{1-6}$(alkyl) is optionally substituted by one two or three substituents each selected from the group consisting of halogen, hydroxyl and N(R$_6$)$_2$; or wherein R$^C$ is absent and R$^{54}$ and R$^{55}$ taken together with the carbon to which they are attached form a ring selected from C$_{5-6}$cyclalkenyl and phenyl; wherein the ring is optionally substituted on a carbon by one, two or three substituents each independently selected from the group consisting of R$^4$ and R$^5$;

R$^{56}$ is N(R$_6$)$_2$ or heterocycle (optionally substituted by one, two or three substituents each independently selected from halogen, hydroxyl, N(R$_6$)$_2$, —(C$_1$-C$_6$) alkyl, —C(O)—O—C$_{1-6}$(alkyl), —C(O)—C$_{1-6}$(alkyl), wherein C$_{1-6}$(alkyl) is optionally substituted by one two or three substituents each selected from the group consisting of: halogen, hydroxyl or N(R$_6$)$_2$);

R$^4$ and R$^5$ are each independently selected from the group consisting of H, —OH, —(C$_1$-C$_6$)alkyl, —O(C$_1$-C$_6$) alkyl, —(C$_1$-C$_6$)alkyl-O—R$^6$, —C(O)N(R$^6$)$_2$, —N(R$^6$)$_2$, halogen, —(C$_1$-C$_6$)alkyl-N(R$^6$)$_2$, and cyano, wherein said —(C$_1$-C$_6$)alkyl, —O(C$_1$-C$_6$)alkyl, —(C$_1$-C$_6$)alkyl-O—R$^6$, or —(C$_1$-C$_6$)alkyl-N(R$^6$)$_2$ is optionally substituted with one or more substituents selected from the group consisting of —OH, —NH$_2$, oxo, and halogen;

or R$^4$ and R$^5$, taken together with the carbon to which they are attached, form a 4-6 membered carbocyclic heterocylic ring B; which ring B is optionally substituted with one or or two substitutes each independently selected from the group consisting of (C$_1$-C$_6$)alkyl, —O(C$_1$-C$_6$) alkyl, —N(R$^6$)$_2$, —C(O)N(R$^6$)$_2$, halogen, oxo, and cyano.

2. The compound of claim 1, wherein X is a bond, R$^1$ is a nitrogen containing ring moiety and R$^1$ is bound through the nitrogen.

3. The compound of claim 1, wherein R$^1$ is selected from the group consisting of 1,2,3,4-tetrahydroquinolin-1-yl, 1,2,3,4-tetrahydro-1,5-naphthyridin-1-yl, 1,2,3,4-tetrahydroquinolin-1-yl, 1,2,3,4-tetrahydroquinoxalin-1-yl, 1,2,3,4-tetrahydropyrido[2,3-b]pyrazin-1-yl, 1H-benzo[d]imidazol-1-yl, indolin-1-yl, 2,3-dihydro-1H-pyrrolo[3,2-b]pyridin-1-yl, 2,3-dihydro-1H-pyrrolo[3,2-c]pyridin-1-yl, isoindolin-2-yl, 2,3,4,5-tetrahydrobenzo[f][1,4]oxazepin-4-yl, 2-(3,4-dihydroisoquinolin-1(2H)-one), 2-(3,4-dihydroisoquinolin-1 (2H)-one), 2,3-dihydro-1H-pyrido[2,3-b][1,4]oxazin-1-yl, piperidin-1-yl, 1-(1,2,3,4-tetrahydro-6H-pyrido[1,2-a]pyrimidin-6-one), 1,2,3,4-tetrahydro-1,8-naphthyridin-1-yl, 1-(3,4-dihydro-1,5-naphthyridin-2(1H)-one), 2,3,4,5-tetrahydro-1H-benzo[b]azepin-1-yl, 1-(2,3-dihydroquinolin-4 (1H)-one), 2,3-dihydro-1H-pyrido[2,3-b][1,4]oxazin-1-yl, 1,2,3,4-tetrahydro-1,6-naphthyridin-1-yl, 5,6,7,8-tetrahydro-4H-pyrazolo[1,5-a][1,3]diazepin-4-yl, 3,4-dihydroquinoxalin-1-yl-2(1H)-one, 2,3,4,6-tetrahydro-1,6-naphthyridin-1-yl-5(1H)-one, 1,2,3,4-tetrahydroisoquinolin-2-yl, 1,2,3,4-tetrahydro-2,7-naphthyridin-2-yl, 1,2,3,4-tetrahydro-2,6-naphthyridin-2-yl, 3,4-dihydro-2H-benzo[b][1,4]thiazin-4-yl 1 1-dioxide, 1,2,3,4-tetrahydropyrazino[2,3-d]pyridazin-1-yl, 1,4-dihydropyrido[3,4-b]pyrazin-1-yl-3 (2H)-one, 5,6,7,8-tetrahydro-1,6-naphthyridin-6-yl, 5,6,7,8-tetrahydro-1,7-naphthyridin-7-yl, 1,2,3,4-tetrahydropyrido[3,4-b]pyrazin-1-yl, 5,8-dihydropteridin-5-yl-7(6H)-one, 4,5,6,7-tetrahydrothieno[3,2-b]pyridin-4-yl, or 5,6,7,8-tetrahydropyrazino[2,3-c]pyridazin-5-yl wherein a nitrogen ring moiety of R$^1$ may be optionally further substituted with one or two substituents each independently selected from the group consisting of Cl, F, —CN, C$_{1-4}$alkyl, —OC$_{1-4}$alkyl, C$_{2-6}$alkenyl, C$_{2-4}$alkynyl, C$_{3-6}$cycloalkyl, C$_{5-6}$cycloalkenyl, —C(H)=N—OCH$_3$, —C(H)=N—OH, —C(CH$_3$)=N—OH, —(CH$_2$)$_{0-1}$C(O)NH$_2$, —(CH$_2$)$_{0-1}$C(O)NHC$_{1-4}$alkyl, —(CH$_2$)$_{0-1}$C(O)N(C$_{1-4}$alkyl)$_2$, —(CH$_2$)$_{0-1}$C(O)OC$_{1-4}$alkyl, —(CH$_2$)$_{0-1}$C(O)OH, —S(O)$_2$C$_{1-4}$alkyl, —(CH$_2$)$_{0-1}$NH$_2$, —(CH$_2$)$_{0-1}$NHC$_{1-4}$alkyl, —(CH$_2$)$_{0-1}$(C$_{1-4}$alkyl)$_2$, —(CH$_2$)$_{0-1}$NH(CO)C$_{1-4}$alkyl, phenyl, optionally substituted heteroaryl and optionally substituted heterocyclyl, wherein $C_{1-4}$alkyl or $C_{3-6}$cycloalkyl may be optionally substituted with one, two or three fluorine atoms, one or two hydroxyl groups, or one or two —$OC_{1-2}$alkyl groups.

4. The compound of claim 1, wherein $R^1$ is a 1,2,3,4-tetrahydroquinoline moiety or a 1,2,3,4-tetrahydro-1,5-naphthyridine moiety optionally further substituted with one, two, or three halo, —$C(O)N(R^{10})_2$, $C_{1-3}$alkyl, $C_{1-3}$haloalkyl, or heteroaryl (optionally substituted with one, two, or three halogen, —$C(O)N(R^{10})_2$, $C_{1-3}$alkyl, $C_{1-3}$alkyl-O—$C_{1-3}$alkyl, $C_{1-3}$alkyl-OH, or $C_{1-3}$haloalkyl).

5. The compound of claim 1, represented by:

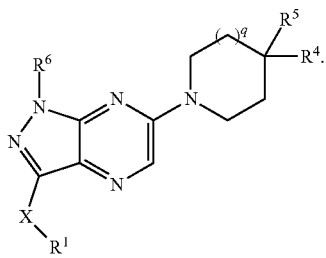

6. The compound of claim 1, wherein $R^4$ and $R^5$ are each independently selected from the group consisting of H, —OH, —$(C_1-C_6)$alkyl, —$O(C_1-C_6)$alkyl, —$(C_1-C_6)$alkyl-O—$R^6$, —$C(O)N(R^6)_2$, —$N(R^6)_2$, halogen, —$(C_1-C_6)$alkyl-$N(R^6)_2$, and cyano, wherein said —$(C_1-C_6)$alkyl, —$O(C_1-C_6)$alkyl, —$(C_1-C_6)$alkyl-O—$R^6$, or —$(C_1-C_6)$alkyl-$N(R^6)_2$ is optionally substituted with one or more substituents selected from the group consisting of —OH, —$NH_2$, oxo, and halogen.

7. The compound of claim 1, wherein $R^4$ and $R^5$, taken together with the carbon to which they are attached, form a 4-6 membered carbocyclic or heterocyclic ring, which ring is optionally substituted with one or two substituents each independently selected from the group consisting of $(C_1-C_6)$alkyl, —$O(C_1-C_6)$alkyl, —$N(R^6)_2$, —$C(O)N(R^6)_2$, halogen, oxo, and cyano.

8. The compound of claim 7, wherein $R^4$ and $R^5$ taken together, are selected from the group consisting of:

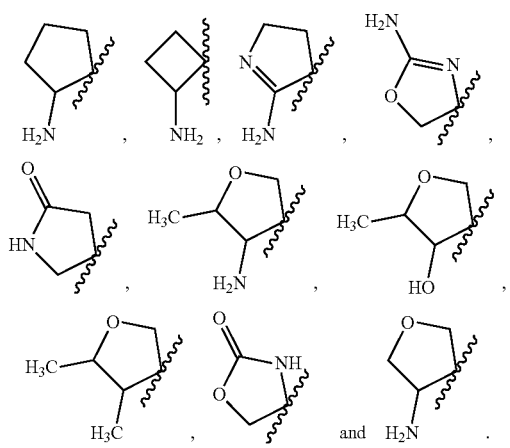

9. A compound of claim 1 having Formula IIa or IIb, or a pharmaceutically acceptable salt or stereoisomer thereof:

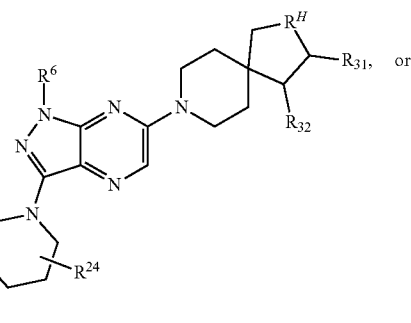

(IIa)

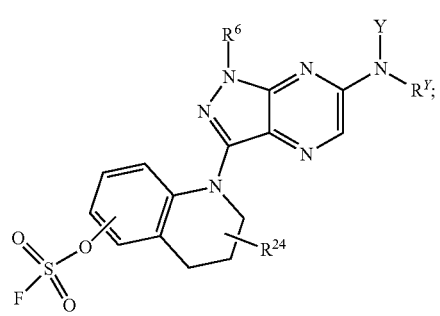

(IIb)

wherein:
$R^H$ is O or $C(R^{25})_2$;
$R^{31}$ is hydrogen or $C_{1-6}$alkyl;
$R^{32}$ is $N(R^6)_2$;
$R^{24}$ is selected from the group consisting of hydrogen, halogen, and $C_1$-$C_6$alkyl;
$R^{25}$ is independently selected for each occurrence from the group consisting of hydrogen, hydroxyl, halogen, and $C_1$-$C_6$alkyl (optionally substituted by hydroxyl or halogen);
$R^6$ is independently for each occurrence selected from the group consisting of H, —$(C_1-C_6)$alkyl, —$C(O)OC_{1-4}$alkyl, and phenyl;
Y is selected from the group consisting of a 3-7 membered saturated carbocycle, a 4-7 membered saturated heterocycle, phenyl, and a 5-6 membered monocyclic heteroaryl; wherein Y is optionally substituted with one or more substituents each independently selected from the group consisting of $(C_1-C_6)$alkyl, —$C(O)N(R^6)_2$, —$N(R^6)_2$, halogen, and cyano, wherein said —$(C_1-C_6)$alkyl is optionally substituted with one or more substituents selected from the group consisting of —OH, —$N(R^6)_2$, oxo, and halogen; and
$R^Y$ is selected from the group consisting of hydrogen and —$(C_1-C_6)$alkyl.

10. A compound of claim 9 having Formula IIIa or IIIb, or a pharmaceutically acceptable salt or stereoisomer thereof:

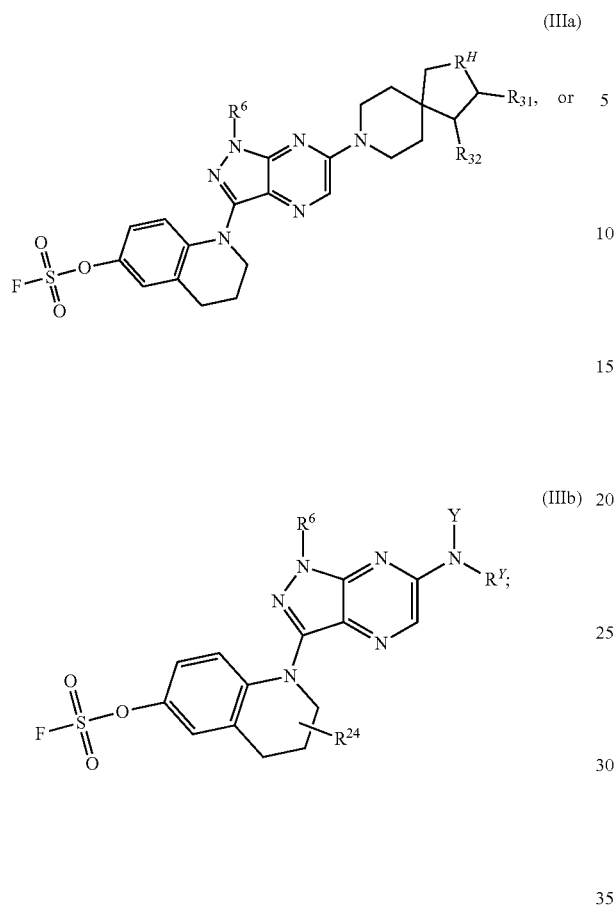
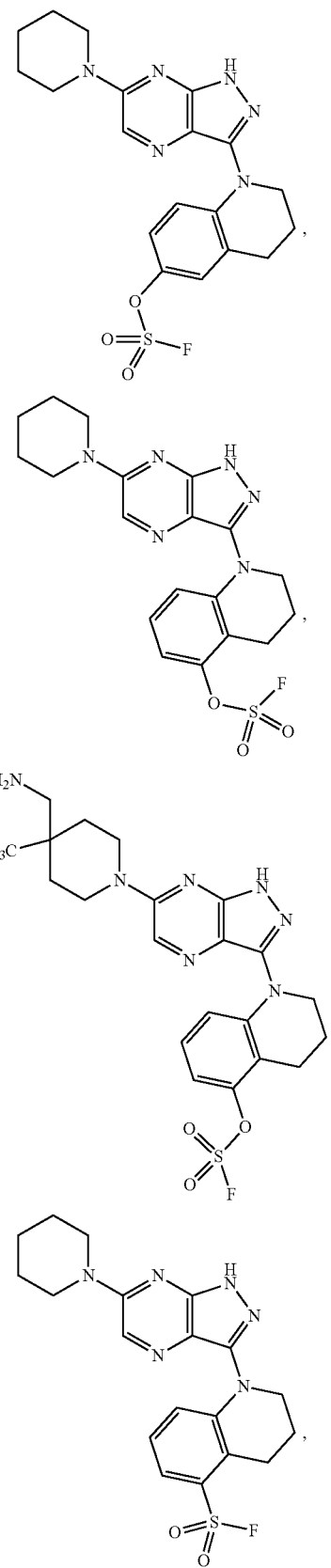

wherein:
R$^H$ is O or C(R$^{25}$)$_2$;
R$^{31}$ is hydrogen or C$_{1-6}$alkyl;
R$^{32}$ is N(R$^6$)$_2$;
R$^{24}$ is selected from the group consisting of hydrogen, halogen, and C$_1$-C$_6$alkyl;
R$^{25}$ is independently selected for each occurrence from the group consisting of hydrogen, hydroxyl, halogen, and C$_1$-C$_6$alkyl (optionally substituted by hydroxyl or halogen);
R$^6$ is independently selected, for each occurrence, from the group consisting of hydrogen, —(C$_1$-C$_6$)alkyl and phenyl;
Y is selected from the group consisting of a 3-7 membered saturated carbocycle, a 4-7 membered saturated heterocycle, phenyl, and a 5-6 membered monocyclic heteroaryl; wherein Y is optionally substituted with one or more substituents each independently selected from the group consisting of (C$_1$-C$_6$)alkyl, —C(O)N(R$^6$)$_2$, —N(R$^6$)$_2$, halogen, and cyano, wherein said —(C$_1$-C$_6$)alkyl is optionally substituted with one or more substituents selected from the group consisting of —OH, —N(R$^6$)$_2$, oxo, and halogen; and
R$^Y$ is selected from the group consisting of hydrogen and —(C$_1$-C$_6$)alkyl.

11. The compound of claim 1 selected from the group consisting of:

211
-continued

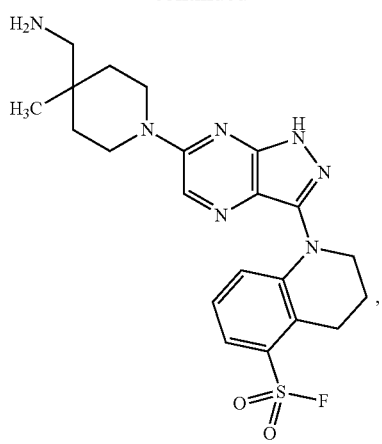

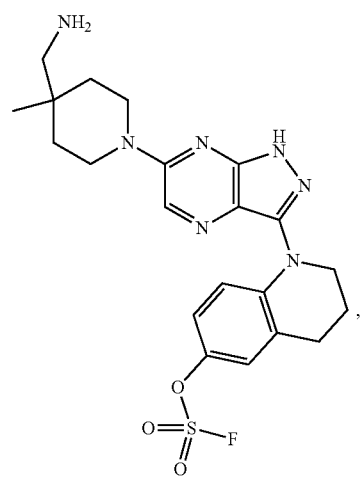

212
-continued

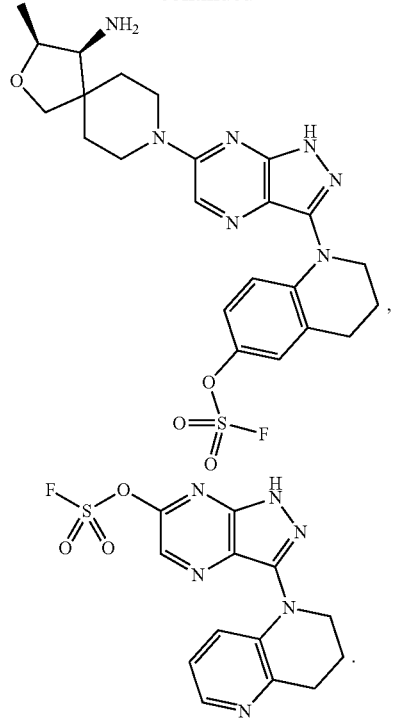

12. A pharmaceutical composition comprising a compound of claim 1 and a pharmaceutically acceptable carrier.

13. A method of inhibiting SHP2 phosphatase activity in a subject comprising administration of a therapeutically effective amount of the compound of claim 1 to a subject in need thereof.

14. A method of treating a disorder mediated by SHP2 in a subject having the disorder, the method comprising administration of a therapeutically effective amount of the compound of claim 1 to a subject in need thereof.

15. The method of claim 14, wherein the disorder is selected from the group consisting of Noonan syndrome, neutropenia, diabetes, neuroblastoma, melanoma, acute myeloid leukemia, juvenile leukemia, or juvenile myelomonocytic leukemia.

16. The method of claim 14, wherein the disorder is selected from the group consisting of breast cancer, lung cancer, or colorectal cancer.

* * * * *

SEQUENCE LISTING

```
<160> NUMBER OF SEQ ID NOS: 4

<210> SEQ ID NO 1
<211> LENGTH: 597
<212> TYPE: PRT
<213> ORGANISM: Homo sapiens

<400> SEQUENCE: 1

Met Thr Ser Arg Arg Trp Phe His Pro Asn Ile Thr Gly Val Glu Ala
1               5                   10                  15

Glu Asn Leu Leu Leu Thr Arg Gly Val Asp Gly Ser Phe Leu Ala Arg
            20                  25                  30
```

-continued

```
Pro Ser Lys Ser Asn Pro Gly Asp Phe Thr Leu Ser Val Arg Arg Asn
            35                  40                  45

Gly Ala Val Thr His Ile Lys Ile Gln Asn Thr Gly Asp Tyr Tyr Asp
 50                  55                  60

Leu Tyr Gly Gly Glu Lys Phe Ala Thr Leu Ala Glu Leu Val Gln Tyr
 65                  70                  75                  80

Tyr Met Glu His His Gly Gln Leu Lys Glu Lys Asn Gly Asp Val Ile
                 85                  90                  95

Glu Leu Lys Tyr Pro Leu Asn Cys Ala Asp Pro Thr Ser Glu Arg Trp
            100                 105                 110

Phe His Gly His Leu Ser Gly Lys Glu Ala Glu Lys Leu Leu Thr Glu
        115                 120                 125

Lys Gly Lys His Gly Ser Phe Leu Val Arg Glu Ser Gln Ser His Pro
130                 135                 140

Gly Asp Phe Val Leu Ser Val Arg Thr Gly Asp Asp Lys Gly Glu Ser
145                 150                 155                 160

Asn Asp Gly Lys Ser Lys Val Thr His Val Met Ile Arg Cys Gln Glu
                165                 170                 175

Leu Lys Tyr Asp Val Gly Gly Gly Glu Arg Phe Asp Ser Leu Thr Asp
            180                 185                 190

Leu Val Glu His Tyr Lys Lys Asn Pro Met Val Glu Thr Leu Gly Thr
        195                 200                 205

Val Leu Gln Leu Lys Gln Pro Leu Asn Thr Thr Arg Ile Asn Ala Ala
210                 215                 220

Glu Ile Glu Ser Arg Val Arg Glu Leu Ser Lys Leu Ala Glu Thr Thr
225                 230                 235                 240

Asp Lys Val Lys Gln Gly Phe Trp Glu Glu Phe Glu Thr Leu Gln Gln
                245                 250                 255

Gln Glu Cys Lys Leu Leu Tyr Ser Arg Lys Glu Gly Gln Arg Gln Glu
            260                 265                 270

Asn Lys Asn Lys Asn Arg Tyr Lys Asn Ile Leu Pro Phe Asp His Thr
        275                 280                 285

Arg Val Val Leu His Asp Gly Asp Pro Asn Glu Pro Val Ser Asp Tyr
290                 295                 300

Ile Asn Ala Asn Ile Ile Met Pro Glu Phe Glu Thr Lys Cys Asn Asn
305                 310                 315                 320

Ser Lys Pro Lys Lys Ser Tyr Ile Ala Thr Gln Gly Cys Leu Gln Asn
                325                 330                 335

Thr Val Asn Asp Phe Trp Arg Met Val Phe Gln Glu Asn Ser Arg Val
            340                 345                 350

Ile Val Met Thr Thr Lys Glu Val Glu Arg Gly Lys Ser Lys Cys Val
        355                 360                 365

Lys Tyr Trp Pro Asp Glu Tyr Ala Leu Lys Glu Tyr Gly Val Met Arg
370                 375                 380

Val Arg Asn Val Lys Glu Ser Ala Ala His Asp Tyr Thr Leu Arg Glu
385                 390                 395                 400

Leu Lys Leu Ser Lys Val Gly Gln Ala Leu Leu Gln Gly Asn Thr Glu
                405                 410                 415

Arg Thr Val Trp Gln Tyr His Phe Arg Thr Trp Pro Asp His Gly Val
            420                 425                 430

Pro Ser Asp Pro Gly Gly Val Leu Asp Phe Leu Glu Glu Val His His
        435                 440                 445

Lys Gln Glu Ser Ile Met Asp Ala Gly Pro Val Val Val His Cys Ser
```

```
                    450                 455                 460

Ala Gly Ile Gly Arg Thr Gly Thr Phe Ile Val Ile Asp Ile Leu Ile
465                 470                 475                 480

Asp Ile Ile Arg Glu Lys Gly Val Asp Cys Asp Ile Asp Val Pro Lys
                    485                 490                 495

Thr Ile Gln Met Val Arg Ser Gln Arg Ser Gly Met Val Gln Thr Glu
                500                 505                 510

Ala Gln Tyr Arg Phe Ile Tyr Met Ala Val Gln His Tyr Ile Glu Thr
                515                 520                 525

Leu Gln Arg Arg Ile Glu Glu Gln Lys Ser Lys Arg Lys Gly His
530                 535                 540

Glu Tyr Thr Asn Ile Lys Tyr Ser Leu Ala Asp Gln Thr Ser Gly Asp
545                 550                 555                 560

Gln Ser Pro Leu Pro Pro Cys Thr Pro Thr Pro Pro Cys Ala Glu Met
                565                 570                 575

Arg Glu Asp Ser Ala Arg Val Tyr Glu Asn Val Gly Leu Met Gln Gln
                580                 585                 590

Gln Lys Ser Phe Arg
            595

<210> SEQ ID NO 2
<211> LENGTH: 593
<212> TYPE: PRT
<213> ORGANISM: Homo sapiens

<400> SEQUENCE: 2

Met Thr Ser Arg Arg Trp Phe His Pro Asn Ile Thr Gly Val Glu Ala
1               5                   10                  15

Glu Asn Leu Leu Leu Thr Arg Gly Val Asp Gly Ser Phe Leu Ala Arg
            20                  25                  30

Pro Ser Lys Ser Asn Pro Gly Asp Phe Thr Leu Ser Val Arg Arg Asn
        35                  40                  45

Gly Ala Val Thr His Ile Lys Ile Gln Asn Thr Gly Asp Tyr Tyr Asp
    50                  55                  60

Leu Tyr Gly Gly Glu Lys Phe Ala Thr Leu Ala Glu Leu Val Gln Tyr
65                  70                  75                  80

Tyr Met Glu His His Gly Gln Leu Lys Glu Lys Asn Gly Asp Val Ile
                85                  90                  95

Glu Leu Lys Tyr Pro Leu Asn Cys Ala Asp Pro Thr Ser Glu Arg Trp
            100                 105                 110

Phe His Gly His Leu Ser Gly Lys Glu Ala Glu Lys Leu Leu Thr Glu
        115                 120                 125

Lys Gly Lys His Gly Ser Phe Leu Val Arg Glu Ser Gln Ser His Pro
130                 135                 140

Gly Asp Phe Val Leu Ser Val Arg Thr Gly Asp Asp Lys Gly Glu Ser
145                 150                 155                 160

Asn Asp Gly Lys Ser Lys Val Thr His Val Met Ile Arg Cys Gln Glu
                165                 170                 175

Leu Lys Tyr Asp Val Gly Gly Gly Glu Arg Phe Asp Ser Leu Thr Asp
            180                 185                 190

Leu Val Glu His Tyr Lys Lys Asn Pro Met Val Glu Thr Leu Gly Thr
        195                 200                 205

Val Leu Gln Leu Lys Gln Pro Leu Asn Thr Thr Arg Ile Asn Ala Ala
    210                 215                 220
```

```
Glu Ile Glu Ser Arg Val Arg Glu Leu Ser Lys Leu Ala Glu Thr Thr
225                 230                 235                 240

Asp Lys Val Lys Gln Gly Phe Trp Glu Glu Phe Glu Thr Leu Gln Gln
            245                 250                 255

Gln Glu Cys Lys Leu Leu Tyr Ser Arg Lys Glu Gly Gln Arg Gln Glu
            260                 265                 270

Asn Lys Asn Lys Asn Arg Tyr Lys Asn Ile Leu Pro Phe Asp His Thr
            275                 280                 285

Arg Val Val Leu His Asp Gly Asp Pro Asn Glu Pro Val Ser Asp Tyr
290                 295                 300

Ile Asn Ala Asn Ile Ile Met Pro Glu Phe Glu Thr Lys Cys Asn Asn
305                 310                 315                 320

Ser Lys Pro Lys Lys Ser Tyr Ile Ala Thr Gln Gly Cys Leu Gln Asn
            325                 330                 335

Thr Val Asn Asp Phe Trp Arg Met Val Phe Gln Glu Asn Ser Arg Val
            340                 345                 350

Ile Val Met Thr Thr Lys Glu Val Glu Arg Gly Lys Ser Lys Cys Val
            355                 360                 365

Lys Tyr Trp Pro Asp Glu Tyr Ala Leu Lys Glu Tyr Gly Val Met Arg
370                 375                 380

Val Arg Asn Val Lys Glu Ser Ala Ala His Asp Tyr Thr Leu Arg Glu
385                 390                 395                 400

Leu Lys Leu Ser Lys Val Gly Gln Gly Asn Thr Glu Arg Thr Val Trp
            405                 410                 415

Gln Tyr His Phe Arg Thr Trp Pro Asp His Gly Val Pro Ser Asp Pro
            420                 425                 430

Gly Gly Val Leu Asp Phe Leu Glu Glu Val His His Lys Gln Glu Ser
            435                 440                 445

Ile Met Asp Ala Gly Pro Val Val His Cys Ser Ala Gly Ile Gly
450                 455                 460

Arg Thr Gly Thr Phe Ile Val Ile Asp Ile Leu Ile Asp Ile Ile Arg
465                 470                 475                 480

Glu Lys Gly Val Asp Cys Asp Ile Asp Val Pro Lys Thr Ile Gln Met
            485                 490                 495

Val Arg Ser Gln Arg Ser Gly Met Val Gln Thr Glu Ala Gln Tyr Arg
            500                 505                 510

Phe Ile Tyr Met Ala Val Gln His Tyr Ile Glu Thr Leu Gln Arg Arg
            515                 520                 525

Ile Glu Glu Glu Gln Lys Ser Lys Arg Lys Gly His Glu Tyr Thr Asn
530                 535                 540

Ile Lys Tyr Ser Leu Ala Asp Gln Thr Ser Gly Asp Gln Ser Pro Leu
545                 550                 555                 560

Pro Pro Cys Thr Pro Thr Pro Cys Ala Glu Met Arg Glu Asp Ser
            565                 570                 575

Ala Arg Val Tyr Glu Asn Val Gly Leu Met Gln Gln Lys Ser Phe
            580                 585                 590

Arg
```

<210> SEQ ID NO 3
<211> LENGTH: 460
<212> TYPE: PRT
<213> ORGANISM: Homo sapiens

<400> SEQUENCE: 3

-continued

```
Met Thr Ser Arg Arg Trp Phe His Pro Asn Ile Thr Gly Val Glu Ala
 1               5                  10                  15

Glu Asn Leu Leu Leu Thr Arg Gly Val Asp Gly Ser Phe Leu Ala Arg
             20                  25                  30

Pro Ser Lys Ser Asn Pro Gly Asp Phe Thr Leu Ser Val Arg Arg Asn
             35                  40                  45

Gly Ala Val Thr His Ile Lys Ile Gln Asn Thr Gly Asp Tyr Tyr Asp
         50                  55                  60

Leu Tyr Gly Gly Glu Lys Phe Ala Thr Leu Ala Glu Leu Val Gln Tyr
 65                  70                  75                  80

Tyr Met Glu His His Gly Gln Leu Lys Glu Lys Asn Gly Asp Val Ile
                 85                  90                  95

Glu Leu Lys Tyr Pro Leu Asn Cys Ala Asp Pro Thr Ser Glu Arg Trp
             100                 105                 110

Phe His Gly His Leu Ser Gly Lys Glu Ala Glu Lys Leu Leu Thr Glu
             115                 120                 125

Lys Gly Lys His Gly Ser Phe Leu Val Arg Glu Ser Gln Ser His Pro
     130                 135                 140

Gly Asp Phe Val Leu Ser Val Arg Thr Gly Asp Asp Lys Gly Glu Ser
145                 150                 155                 160

Asn Asp Gly Lys Ser Lys Val Thr His Val Met Ile Arg Cys Gln Glu
                 165                 170                 175

Leu Lys Tyr Asp Val Gly Gly Gly Glu Arg Phe Asp Ser Leu Thr Asp
             180                 185                 190

Leu Val Glu His Tyr Lys Lys Asn Pro Met Val Glu Thr Leu Gly Thr
             195                 200                 205

Val Leu Gln Leu Lys Gln Pro Leu Asn Thr Thr Arg Ile Asn Ala Ala
     210                 215                 220

Glu Ile Glu Ser Arg Val Arg Glu Leu Ser Lys Leu Ala Glu Thr Thr
225                 230                 235                 240

Asp Lys Val Lys Gln Gly Phe Trp Glu Glu Phe Glu Thr Leu Gln Gln
                 245                 250                 255

Gln Glu Cys Lys Leu Leu Tyr Ser Arg Lys Glu Gly Gln Arg Gln Glu
             260                 265                 270

Asn Lys Asn Lys Asn Arg Tyr Lys Asn Ile Leu Pro Phe Asp His Thr
             275                 280                 285

Arg Val Val Leu His Asp Gly Asp Pro Asn Glu Pro Val Ser Asp Tyr
     290                 295                 300

Ile Asn Ala Asn Ile Ile Met Pro Glu Phe Glu Thr Lys Cys Asn Asn
305                 310                 315                 320

Ser Lys Pro Lys Lys Ser Tyr Ile Ala Thr Gln Gly Cys Leu Gln Asn
                 325                 330                 335

Thr Val Asn Asp Phe Trp Arg Met Val Phe Gln Glu Asn Ser Arg Val
             340                 345                 350

Ile Val Met Thr Thr Lys Glu Val Glu Arg Gly Lys Ser Lys Cys Val
             355                 360                 365

Lys Tyr Trp Pro Asp Glu Tyr Ala Leu Lys Glu Tyr Gly Val Met Arg
     370                 375                 380

Val Arg Asn Val Lys Glu Ser Ala Ala His Asp Tyr Thr Leu Arg Glu
385                 390                 395                 400

Leu Lys Leu Ser Lys Val Gly Gln Gly Asn Thr Glu Arg Thr Val Trp
                 405                 410                 415

Gln Tyr His Phe Arg Thr Trp Pro Asp His Gly Val Pro Ser Asp Pro
```

```
                    420                 425                 430
Gly Gly Val Leu Asp Phe Leu Glu Glu Val His His Lys Gln Glu Ser
            435                 440                 445

Ile Met Asp Ala Gly Pro Val Val His Cys Arg
       450                 455             460

<210> SEQ ID NO 4
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (13)..(13)
<223> OTHER INFORMATION: PHOSPHORYLATION
<220> FEATURE:
<221> NAME/KEY: MOD_RES
<222> LOCATION: (20)..(20)
<223> OTHER INFORMATION: AMIDATION

<400> SEQUENCE: 4

Leu Asn Tyr Ile Asp Leu Asp Leu Val Leu Ser Thr Tyr Ala Ser Ile
1               5                   10                  15

Asn Phe Gln Lys
            20
```